(12) United States Patent
Anderson et al.

(10) Patent No.: US 9,227,917 B2
(45) Date of Patent: Jan. 5, 2016

(54) AMINE-CONTAINING LIPIDOIDS AND USES THEREOF

(71) Applicant: Massachusetts Institute of Technology, Cambridge, MA (US)

(72) Inventors: Daniel Griffith Anderson, Framingham, MA (US); Kathryn Ann Whitehead, Pittsburgh, PA (US); Joseph R. Dorkin, Somerville, MA (US); Arturo Jose Vegas, Cambridge, MA (US); Yunlong Zhang, Cambridge, MA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/089,603

(22) Filed: Nov. 25, 2013

(65) Prior Publication Data

US 2014/0161830 A1    Jun. 12, 2014

Related U.S. Application Data

(63) Continuation of application No. 13/966,136, filed on Aug. 13, 2013, now abandoned.

(60) Provisional application No. 61/682,468, filed on Aug. 13, 2012.

(51) Int. Cl.

| | |
|---|---|
| C07C 229/26 | (2006.01) |
| A61K 31/4965 | (2006.01) |
| A61K 31/445 | (2006.01) |
| A61K 31/40 | (2006.01) |
| A61K 31/357 | (2006.01) |
| A61K 31/24 | (2006.01) |
| A61K 31/225 | (2006.01) |
| A61K 31/4985 | (2006.01) |
| A61K 9/51 | (2006.01) |
| C07D 319/18 | (2006.01) |
| C07C 229/12 | (2006.01) |
| C07C 229/14 | (2006.01) |
| C07D 487/04 | (2006.01) |
| C07D 207/09 | (2006.01) |
| C07D 211/14 | (2006.01) |
| C07D 211/26 | (2006.01) |
| C07D 295/13 | (2006.01) |
| C12N 15/11 | (2006.01) |
| C12N 15/88 | (2006.01) |
| A61K 45/06 | (2006.01) |
| C07C 229/24 | (2006.01) |
| C07C 229/28 | (2006.01) |
| C07C 229/34 | (2006.01) |
| C07D 211/34 | (2006.01) |
| C07D 241/04 | (2006.01) |
| C07D 295/15 | (2006.01) |

(Continued)

(52) U.S. Cl.
CPC ............. *C07C 229/26* (2013.01); *A61K 9/1272* (2013.01); *A61K 9/5123* (2013.01); *A61K 31/225* (2013.01); *A61K 31/24* (2013.01); *A61K 31/357* (2013.01); *A61K 31/40* (2013.01); *A61K 31/445* (2013.01); *A61K 31/495* (2013.01); *A61K 31/4965* (2013.01); *A61K 31/4985* (2013.01); *A61K 31/573* (2013.01); *A61K 31/704* (2013.01); *A61K 31/713* (2013.01); *A61K 45/06* (2013.01); *A61K 47/48038* (2013.01); *A61K 47/48046* (2013.01); *A61K 47/48869* (2013.01); *C07C 229/12* (2013.01); *C07C 229/14* (2013.01); *C07C 229/24* (2013.01); *C07C 229/28* (2013.01); *C07C 229/34* (2013.01); *C07D 207/09* (2013.01); *C07D 211/14* (2013.01); *C07D 211/26* (2013.01); *C07D 211/34* (2013.01); *C07D 241/04* (2013.01); *C07D 295/13* (2013.01); *C07D 295/15* (2013.01); *C07D 319/16* (2013.01); *C07D 319/18* (2013.01); *C07D 487/04* (2013.01); *C12N 15/111* (2013.01); *C12N 15/88* (2013.01); *A61K 47/18* (2013.01); *C07C 2101/14* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 2,647,121 A | 7/1953 | Jacoby | |
| 2,717,909 A | 9/1955 | Kosmin | |

(Continued)

FOREIGN PATENT DOCUMENTS

| | | |
|---|---|---|
| CA | 2518132 A1 | 3/2006 |
| CN | 100 569 877 C | 12/2009 |

(Continued)

OTHER PUBLICATIONS

Extended European Search Report for European Application No. 06784878.8, mailed Jun. 29, 2009.

(Continued)

*Primary Examiner* — Thomas S Heard
(74) *Attorney, Agent, or Firm* — Wolf, Greenfield & Sacks, P.C.

(57) ABSTRACT

Provided herein are lipidoids that may be prepared from the conjugate addition of alkylamines to acrylates. In some embodiments, provided lipidoids are biodegradable and may be used in a variety of drug delivery systems. Given the amino moiety of the lipidoids, they are well-suited for the delivery of polynucleotides, in addition to other agents. Nanoparticles containing the inventive lipidoids and polynucleotides have been prepared and have been shown to be effective in delivering siRNA.

27 Claims, 30 Drawing Sheets

(51) Int. Cl.
*C07D 319/16* (2006.01)
*A61K 31/495* (2006.01)
*A61K 31/573* (2006.01)
*A61K 31/704* (2006.01)
*A61K 31/713* (2006.01)
*A61K 9/127* (2006.01)
*A61K 47/48* (2006.01)
*A61K 47/18* (2006.01)

(56) References Cited

U.S. PATENT DOCUMENTS

| | | |
|---|---|---|
| 2,844,629 A | 7/1958 | William et al. |
| 3,096,560 A | 7/1963 | Liebig |
| 3,350,325 A | 10/1967 | Ashby et al. |
| 3,535,289 A | 10/1970 | Yoshihara et al. |
| 3,805,301 A | 4/1974 | Liebig |
| 3,945,052 A | 3/1976 | Liebig |
| 4,013,507 A | 3/1977 | Rembaum |
| 4,180,068 A | 12/1979 | Jacobsen et al. |
| 4,182,833 A | 1/1980 | Hicks |
| 4,308,085 A | 12/1981 | Horhold et al. |
| 4,323,525 A | 4/1982 | Bornat |
| 4,339,369 A | 7/1982 | Hicks et al. |
| 4,475,972 A | 10/1984 | Wong |
| 4,720,517 A | 1/1988 | Ravichandran et al. |
| 4,762,915 A | 8/1988 | Kung et al. |
| 4,878,908 A | 11/1989 | Martin et al. |
| 4,897,355 A | 1/1990 | Eppstein et al. |
| 4,946,857 A | 8/1990 | Kanehira et al. |
| 4,966,945 A | 10/1990 | Drawert et al. |
| 5,025,005 A | 6/1991 | Nomura et al. |
| 5,047,540 A | 9/1991 | Kamata et al. |
| 5,138,067 A | 8/1992 | Kamata et al. |
| 5,171,678 A | 12/1992 | Behr et al. |
| 5,201,998 A | 4/1993 | Topfl et al. |
| 5,330,768 A | 7/1994 | Park et al. |
| 5,334,761 A | 8/1994 | Gebeyehu et al. |
| 5,395,619 A | 3/1995 | Zalipsky et al. |
| 5,455,352 A | 10/1995 | Huellmann et al. |
| 5,464,924 A | 11/1995 | Silvis et al. |
| 5,503,852 A | 4/1996 | Steiner et al. |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,700,437 A | 12/1997 | Fujii et al. |
| 5,705,188 A | 1/1998 | Junichi et al. |
| 5,736,573 A | 4/1998 | Galat |
| 5,776,747 A | 7/1998 | Schinstine et al. |
| 5,817,873 A | 10/1998 | Meyer et al. |
| 5,874,105 A | 2/1999 | Watkins et al. |
| 5,885,613 A | 3/1999 | Holland et al. |
| 5,976,569 A | 11/1999 | Milstein |
| 6,090,384 A | 7/2000 | Ra et al. |
| 6,120,799 A | 9/2000 | McDonald et al. |
| 6,204,297 B1 | 3/2001 | Tracy et al. |
| 6,271,209 B1 | 8/2001 | Smith et al. |
| 6,335,199 B1 | 1/2002 | Bischoff et al. |
| 6,696,424 B1 | 2/2004 | Wheeler |
| 6,756,055 B2 | 6/2004 | McDonald et al. |
| 6,821,530 B2 | 11/2004 | Koob et al. |
| 6,998,115 B2 | 2/2006 | Langer et al. |
| 7,022,214 B2 | 4/2006 | Olech |
| 7,084,303 B2 | 8/2006 | Watanabe et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,972,435 B2 | 7/2011 | Bury et al. |
| 7,977,452 B2 | 7/2011 | Tomalia et al. |
| 8,071,082 B2 | 12/2011 | Zugates et al. |
| RE43,612 E | 8/2012 | Anderson et al. |
| 8,287,849 B2 | 10/2012 | Langer et al. |
| 8,361,555 B2 | 1/2013 | Paquet, Jr. |
| 8,450,298 B2 | 5/2013 | Mahon et al. |
| 8,557,231 B2 | 10/2013 | Langer et al. |
| 8,562,966 B2 | 10/2013 | Zugates et al. |
| 8,808,681 B2 | 8/2014 | Anderson et al. |
| 8,969,353 B2 | 3/2015 | Mahon et al. |
| 9,006,487 B2 | 4/2015 | Anderson et al. |
| 2002/0193622 A1 | 12/2002 | Watanabe et al. |
| 2003/0215395 A1 | 11/2003 | Yu et al. |
| 2004/0235982 A1 | 11/2004 | Rabasco et al. |
| 2005/0069590 A1 | 3/2005 | Buehler et al. |
| 2005/0143332 A1 | 6/2005 | Monahan et al. |
| 2005/0148786 A1 | 7/2005 | Ikeda et al. |
| 2005/0244961 A1 | 11/2005 | Short et al. |
| 2006/0223939 A1 | 10/2006 | Lange et al. |
| 2006/0228404 A1 | 10/2006 | Anderson et al. |
| 2007/0275923 A1 | 11/2007 | Chen et al. |
| 2008/0145338 A1 | 6/2008 | Anderson et al. |
| 2008/0242626 A1 | 10/2008 | Zugates et al. |
| 2009/0023673 A1 | 1/2009 | Manoharan et al. |
| 2009/0221684 A1 | 9/2009 | Grinstaff et al. |
| 2010/0036084 A1 | 2/2010 | Langer et al. |
| 2010/0178699 A1 | 7/2010 | Gao et al. |
| 2010/0331234 A1 | 12/2010 | Mahon et al. |
| 2011/0009641 A1 | 1/2011 | Anderson et al. |
| 2011/0293703 A1 | 12/2011 | Mahon et al. |
| 2012/0009222 A1 | 1/2012 | Nguyen et al. |
| 2012/0065358 A1 | 3/2012 | Langer et al. |
| 2012/0128760 A1 | 5/2012 | Manoharan et al. |
| 2012/0251560 A1 | 10/2012 | Dahlman et al. |
| 2013/0158021 A1 | 6/2013 | Dong et al. |
| 2013/0302401 A1 | 11/2013 | Ma et al. |
| 2014/0094399 A1 | 4/2014 | Langer et al. |
| 2014/0329884 A1 | 11/2014 | Dong et al. |

FOREIGN PATENT DOCUMENTS

| | | |
|---|---|---|
| CN | 101 863 544 B | 9/2011 |
| DE | 2430998 A1 | 1/1975 |
| DE | 2520814 A1 | 11/1976 |
| EP | 0 673 637 A1 | 9/1995 |
| EP | 0 959 092 A1 | 11/1999 |
| EP | 1 912 679 A2 | 4/2008 |
| EP | 2 045 251 A1 | 4/2009 |
| EP | 2 476 756 A1 | 7/2012 |
| EP | 2 532 649 | 12/2012 |
| FR | 1 378 382 | 11/1964 |
| FR | 2235112 A | 1/1975 |
| GB | 1072118 A | 6/1967 |
| GB | 1 602 085 A | 11/1981 |
| JP | S48-022365 A | 3/1973 |
| JP | S49-127908 A | 12/1974 |
| JP | 50-24216 A | 3/1975 |
| JP | S51-023537 A | 2/1976 |
| JP | 51-125144 | 11/1976 |
| JP | S52-010847 A | 1/1977 |
| JP | 63-125144 A | 5/1988 |
| JP | 63-154788 A | 6/1988 |
| JP | 4-108173 | 4/1992 |
| JP | H07-053535 A | 2/1995 |
| JP | H09-505593 A | 2/1995 |
| JP | H10-197978 A | 7/1998 |
| JP | 11-005786 A | 1/1999 |
| JP | 11-080142 A | 3/1999 |
| JP | 2001-523215 A | 11/2001 |
| JP | 2002-167368 A | 6/2002 |
| JP | 2003-519199 A | 6/2003 |
| JP | 2008-247749 A | 10/2008 |
| JP | 2014172827 A | 9/2014 |
| WO | WO 93/18229 A1 | 9/1993 |
| WO | WO 93/18754 A1 | 9/1993 |
| WO | WO 95/11004 A1 | 4/1995 |
| WO | WO 95/14651 A1 | 6/1995 |
| WO | WO 96/26179 A1 | 8/1996 |
| WO | WO 96/36314 A2 | 11/1996 |
| WO | WO 97/23457 A1 | 7/1997 |
| WO | WO 98/16202 A1 | 4/1998 |
| WO | WO 00/03044 A1 | 1/2000 |
| WO | WO 01/15726 A2 | 3/2001 |
| WO | WO 02/22709 A1 | 3/2002 |
| WO | WO 02/31025 A2 | 4/2002 |
| WO | WO 03/040288 A2 | 5/2003 |

(56) References Cited

FOREIGN PATENT DOCUMENTS

| WO | WO 03/070735 A2 | 8/2003 |
|---|---|---|
| WO | WO 2004/043588 A2 | 5/2004 |
| WO | WO 2004/048345 A2 | 6/2004 |
| WO | WO 2004/106411 | 12/2004 |
| WO | WO 2005/028619 A2 | 3/2005 |
| WO | WO 2005/121348 A1 | 12/2005 |
| WO | WO 2006/065266 A2 | 6/2006 |
| WO | WO 2006/082088 A1 | 8/2006 |
| WO | WO 2006/105043 A2 | 10/2006 |
| WO | WO 2006/138380 A2 | 12/2006 |
| WO | WO 2007/143659 | 12/2007 |
| WO | WO 2008/011561 | 1/2008 |
| WO | WO 2008/036168 A2 | 3/2008 |
| WO | WO 2008/113364 A2 | 9/2008 |
| WO | WO 2008/119741 A2 | 10/2008 |
| WO | WO 2009/046220 A2 | 4/2009 |
| WO | WO 2010/042877 A1 | 4/2010 |
| WO | WO 2010/045512 A2 | 4/2010 |
| WO | WO 2010/053572 A2 | 5/2010 |
| WO | WO 2010/099387 A1 | 9/2010 |
| WO | WO 2010/114789 A1 | 10/2010 |
| WO | WO 2010/129709 A1 | 11/2010 |
| WO | WO 2011/012746 A2 | 2/2011 |
| WO | WO 2011/068810 A1 | 6/2011 |
| WO | WO 2012/027675 A2 | 3/2012 |
| WO | WO 2012/133737 A1 | 10/2012 |
| WO | WO 2012/135025 A2 | 10/2012 |
| WO | WO 2012/170889 A1 | 12/2012 |
| WO | WO 2012/170930 A1 | 12/2012 |
| WO | WO 2013/063468 A1 | 5/2013 |
| WO | WO 2014/028487 A1 | 2/2014 |
| WO | WO 2014/179562 A1 | 11/2014 |
| WO | WO 2014/210356 A1 | 12/2014 |

OTHER PUBLICATIONS

Extended European Search Report for European Application No. 11186795.8, mailed Jun. 19, 2012.
International Search Report and Written Opinion for PCT/US2006/023171, mailed May 29, 2008.
International Preliminary Report on Patentability for PCT/US2006/023171, mailed Jul. 3, 2008.
Invitation to Pay Additional Fees for PCT/US2013/054726, mailed Oct. 31, 2013.
International Search Report and Written Opinion for PCT/US2013/054726, mailed Jan. 7, 2014.
Akinc et al., A combinatorial library of lipid-like materials for delivery of RNAi therapeutics. *Nat Biotechnol.* May 2008;26(5):561-9. doi: 10.1038/nbt1402. Epub Apr. 27, 2008.
Braun et al., Structure/function relationships of polyamidoamine/DNA dendrimers as gene delivery vehicles. *J Pharm Sci.* Feb. 2005;94(2):423-36.
Li et al., Reverse Atom Transfer Radical Polymerization in Miniemulsion. *Macromolecules* 2003;36(16):6028-6035.
Martell et al., The Preparation and the Properties of Some N,N'-Disubstituted-ethylenediaminedipropionic Acids. *J Am Chem Soc.* 1950;72:5357-61.
Swali et al., Solid-Phase Dendrimer Synthesis and the Generation of Super-High-Loading Resin Beads for Combinatorial Chemistry. *J Org Chem Am Chem Soc.* 1997;62:4902-03.
Tsvetkov et al., [Neoglycoconjugates based on dendrimeric poly(aminoamides)]. *Bioorg Khim.* Nov.-Dec.;28(6):518-34. Russian. Published in English in *Russian Journal of Bioorganic Chemistry*, 2002:28(6):470-86.
Invitation to Pay Additional Fees for PCT/US2012/062222, mailed Dec. 14, 2012.
International Search Report and Written Opinion for PCT/US2012/062222, mailed Mar. 27, 2013.
Extended European Search Report for European Application No. 09825132.5, dated Jul. 16, 2013.
International Search Report and Written Opinion for PCT/US2009/006018, mailed May 25, 2010.

International Preliminary Report on Patentability for PCT/US2009/006018, mailed May 19, 2011.
International Search Report and Written Opinion for PCT/US2009/005810, mailed Jun. 16, 2010.
International Preliminary Report on Patentability for PCT/US2009/005810, mailed May 12, 2011.
International Search Report and Written Opinion for PCT/US2011/049360, mailed Mar. 20, 2012.
International Preliminary Report on Patentability for PCT/US2011/049360, mailed Mar. 7, 2013.
Invitation to Pay Additional Fees for PCT/US2012/030349, mailed on Jul. 24, 2012.
International Search Report and Written Opinion for PCT/US2012/030349, mailed on Oct. 5, 2012.
International Preliminary Report on Patentability for PCT/US2012/030349, mailed on Oct. 10, 2013.
Adami et al., An amino acid-based amphoteric liposomal delivery system for systemic administration of siRNA. Mol Ther. Jun. 2011;19(6):1141-51.
Akinc et al., Exploring polyethylenimine-mediated DNA transfection and the proton sponge hypothesis. J Gene Med. May 2005;7(5):657-63.
Alshamsan et al., The induction of tumor apoptosis in B16 melanoma following STAT3 siRNA delivery with a lipid-substituted polyethylenimine. Biomaterials. Feb. 2010;31(6):1420-8. Epub Nov. 13, 2009.
Anderson et al., Nanoliter-scale synthesis of arrayed biomaterials and application to human embryonic stem cells. Nat Biotechnol. Jul. 2004;22(7):863-6. Epub Jun. 13, 2004.
Anderson, Biological Responses to Materials. Annu Rev Mater Res. 2001;31:81-110.
Anderson, Human gene therapy. Nature. Apr. 30, 1998;392(6679 Suppl):25-30. Review.
Asokan et al., Cytosolic delivery of macromolecules. 3. Synthesis and characterization of acid-sensitive bis-detergents. Bioconjug Chem. Nov.-Dec. 2004;15(6):1166-73.
Bajaj et al., Synthesis and gene transfection efficacies of PEI-cholesterol-based lipopolymers. Bioconjug Chem. Aug. 2008;19(8):1640-51. Epub Jul. 11, 2008.
Behr, Synthetic gene-transfer vectors. Acc Chem Res. 1993;26:274-278.
Berge et al., Pharmaceutical salts. J Pharm Sci. Jan. 1977;66(1):1-19.
Bossle et al., Synthesis and biological activity of new 2-substituted analogs of fluphenazine. J Med Chem. Mar. 1, 1976;19(3):370-3.
Boussif et al., A versatile vector for gene and oligonucleotide transfer into cells in culture and in vivo: polyethylenimine. Proc Natl Acad Sci U S A. Aug. 1, 1995;92(16):7297-301.
Bratlie et al., Rapid biocompatibility analysis of materials via in vivo fluorescence imaging of mouse models. PLoS One. Apr. 6, 2010;5(4):e10032.
Breunig et al., Breaking up the correlation between efficacy and toxicity for nonviral gene delivery. Proc Natl Acad Sci U S A. Sep. 4, 2007;104(36):14454-9. Epub Aug. 28, 2007.
Breunig et al., Mechanistic investigation of poly(ethylene imine)-based siRNA delivery: disulfide bonds boost intracellular release of the cargo. J Control Release. Aug. 25, 2008;130(1):5763. Epub May 24, 2008.
Brodbeck et al., Biomaterial surface chemistry dictates adherent monocyte/macrophage cytokine expression in vitro. Cytokine. Jun. 21, 2002;18(6):311-9.
Byk et al., Synthesis, activity, and structure—activity relationship studies of novel cationic lipids for DNA transfer. J Med Chem. Jan. 15, 1998;41(2):224-35.
Chakraborty, Potentiality of Small Interfering RNAs (siRNA) as Recent Therapeutic Targets for Gene-Silencing. Curr Drug Targets. 2007;8:469-82.
Chan et al., Triplex DNA: fundamentals, advances, and potential applications for gene therapy. J Mol Med (Berl). Apr. 1997;75(4):267-82.
Chang, Therapeutic applications of polymeric artificial cells. Nat Rev Drug Discov. Mar. 2005;4(3):221-35.
Chen et al., Polymeric growth factor delivery strategies for tissue engineering. Pharm Res. Aug. 2003;20(8):1103-12.

(56) References Cited

OTHER PUBLICATIONS

Chen et al., Rapid discovery of potent siRNA-containing lipid nanoparticles enabled by controlled microfluidic formulation. J Am Chem Soc. Apr. 25, 2012;134(16):6948-51. doi: 10.1021/ja301621z. Epub Apr. 10, 2003.
Cotton et al., Receptor-mediated transport of DNA into eukaryotic cells. Methods Enzymol. 1993;217:618-44.
Creusat et al., Proton sponge trick for pH-sensitive disassembly of polyethylenimine-based siRNA delivery systems. Bioconjug Chem. May 19, 2010;21(5):994-1002.
Crooke et al., Evaluating the mechanism of action of antiproliferative antisense drugs. Antisense Nucleic Acid Drug Dev. Apr. 2000;10(2):123-6.
Crooke, Molecular mechanisms of action of antisense drugs. Biochim Biophys Acta. Dec. 10, 1999;1489(1):31-44.
Crystal, Transfer of genes to humans: early lessons and obstacles to success. Science. Oct. 20, 1995;270(5235):404-10. Review.
Davis et al., Evidence of RNAi in humans from systemically administered siRNA via targeted nanoparticles. Nature. Apr. 15, 2010;464(7291):1067-70. Epub Mar. 21, 2010.
Decher, Fuzzy Nanoassemblies: Toward Layered Polymeric Multicomposites. Science. 1997;277;1232-37.
Deshmukh et al., Liposome and polylysine mediated gene therapy. New J Chem. 1997;21:113124.
Discher et al., Polymer vesicles. Science. Aug. 9, 2002;297(5583):967-73. Review.
Discher et al., Polymersomes: tough vesicles made from diblock copolymers. Science. May 14, 1994;284(5417):1143-6.
Elbashir et al., Duplexes of 21-nucleotide RNAs mediate RNA interference in cultured mammalian cells. Nature. May 24, 2011;411(6836):494-8.
Elbashir et al., RNA interference is mediated by 21- and 22-nucleotide RNAs. Genes Dev. 2001;15:188-200.
Ewert et al., Cationic lipid-DNA complexes for gene therapy: understanding the relationship between complex structure and gene delivery pathways at the molecular level. Curr Med Chem. Jan. 2004;11(2):133-49.
Fire et al., Potent and specific genetic interference by double-stranded RNA in Caenorhabditis elegans. Nature. Feb. 19, 1998;391(6669):806-11.
Frank-Kamenetsky et al., Therapeutic RNAi targeting PCSK9 acutely lowers plasma cholesterol in rodents and LDL cholesterol in nonhuman primates. Proc Natl Acad Sci U S A. Aug. 19, 2008;105(33):11915-20. doi: 10.1073/pnas.0805434105. Epub Aug. 11, 2008.
Furgeson et al., Modified linear polyethylenimine-cholesterol conjugates for DNA complexation. Bioconjug Chem. Jul.-Aug. 2003;14(4):840-7.
Furgeson et al., Novel water insoluble lipoparticulates for gene delivery. Pharm Res. Apr. 2002;19(4):382-90.
Geisbert et al., Postexposure protection of non-human primates against a lethal Ebola virus challenge with RNA interference: a proof-of-concept study. Lancet. May 29, 2010;375(9729):1896-905. doi:10.1016/S0140-6736(10)60357-1.
Geng et al., Hydrolytic degradation of poly(ethylene oxide)-block-polycaprolactone worm micelles. J Am Chem Soc. Sep. 21, 2005;127(37):12780-1.
Godbey et al., Size matters: molecular weight affects the efficiency of poly(ethylenimine) as a gene delivery vehicle. J Biomed Mater Res. Jun. 5, 1999;45(3):268-75.
Gonzalez et al., New class of polymers for the delivery of macromolecular therapeutics. Bioconjug Chem. Nov.-Dec. 1999;10(6):1068-74.
Grayson et al., Biophysical and structural characterization of polyethylenimine-mediated siRNA delivery in vitro. Pharm Res. Aug. 2006;23(8):1868-76.
Grunlan et al., Synthesis of 1,9-bis[glycidyloxypropyl]penta(1'H, 1'H, 2'H, 2'H-perfluoroalkylmethylsiloxane)s and copolymerization with piperazine. Polymer. 2004;45:2517-23.
Grzelinski et al., RNA interference-mediated gene silencing of pleiotrophin through polyethylenimine-complexed small interfering RNAs in vivo exerts antitumoral effects in glioblastoma xenografts. Hum Gene Ther. Jul. 2006;17(7):751-66.
Gunatillake et al., Recent developments in biodegradable synthetic polymers. Biotechnol Annu Rev. 2006;12:301-47.
Haensler et al., Polyamidoamine cascade polymers mediate efficient transfection of cells in culture. Bioconjug Chem. Sep.-Oct. 1993;4(5):372-9.
Heyes et al., Cationic lipid saturation influences intracellular delivery of encapsulated nucleic acids. J Control Release. Oct. 3, 2005;107(2):276-87.
Hofland et al., Formation of stable cationic lipid/DNA complexes for gene transfer. Proc Natl Acad Sci U S A. Jul. 9, 1996;93(14):7305-9.
Hope et al., Cationic Lipids, Phosphatidylethanolamine and the Intracellular Delivery of Polymeric, Nucleic Acid-Based Drugs. Molecular Membrane Technology. 1998;15:1-14.
Howard, Delivery of RNA interference therapeutics using polycation-based nanoparticles. Adv Drug Deliv Rev. Jul. 25, 2009;61(9):710-20. Epub Apr. 5, 2009.
Hunt et al., Effect of biomaterial surface charge on the inflammatory response: evaluation of cellular infiltration and TNF alpha production. J Biomed Mater Res. May 1996;31(1):139-44.
Ichimaru et al., Synthesis and characterization of new piperazine-type inhibitors for mitochondrial NADH-ubiquinone oxidoreductase (complex I). Biochemistry. Oct. 7, 2008;47(40):10816-26. Epub Sep. 10, 2008.
Incani et al., Lipid and hydrophobic modification of cationic carriers on route to superior gene vectors. Soft Matter. 2010;6:2124-38.
Jayaraman et al., Maximizing the potency of siRNA lipid nanoparticles for hepatic gene silencing in vivo. Angew Chem Int Ed Engl. Aug. 20, 2012;51(34):8529-33. doi: 10.1002/anie.201203263. Epub Jul. 10, 2012.
Jiang et al., Electrochemically controlled release of lipid/DNA complexes: a new tool for synthetic gene delivery system. Electrochem Commun. 2004;6:576-82.
Jiang et al., Hyaluronic acid-polyethyleneimine conjugate for target specific intracellular delivery of siRNA. Biopolymers. Jul. 2008;89(7):635-42.
Jiang et al., Ultralow-fouling, functionalizable, and hydrolyzable zwitterionic materials and their derivatives for biological applications. Adv Mater. Mar. 5, 2010;22(9):920-32.
John et al. Effective RNAi-mediated gene silencing without interruption of the endogenous microRNA pathway. Nature. Oct. 11, 2007;449(7163):745-7. Epub Sep. 26, 2007.
Jolck et al., Solid-phase synthesis of PEGylated lipopeptides using click chemistry. Bioconjug Chem. May 19, 2010;21(5):807-10.
Jon et al., Degradable poly(amino alcohol esters) as potential DNA vectors with low cytotoxicity. Biomacromolecules. Nov.-Dec. 2003;4(6):1759-62.
Kabanov et al., DNA complexes with polycations for the delivery of genetic material into cells. Bioconjug Chem. Jan.-Feb. 1995;6(1):7-20.
Kamath et al., Surface chemistry influences implant-mediated host tissue responses. J Biomed Mater Res A. Sep. 2008;86(3):617-26.
Kaur et al., A delineation of diketopiperazine self-assembly processes: understanding the molecular events involved in Nepsilon-(fumaroyl)diketopiperazine of L-Lys (FDKP) interactions. Mol Pharm. Mar.-Apr. 2008;5(2):294-315.
Kim et al., Comparative evaluation of target-specific GFP gene silencing efficiencies for antisense ODN, synthetic siRNA, and siRNA plasmid complexed with PEI-PEG-FOL conjugate. Bioconjug Chem. Jan.-Feb. 2006;17(1):241-4.
Kim et al., Efficient siRNA delivery using water soluble lipopolymer for anti-angiogenic gene therapy. J Control Release. Apr. 23, 2007;118(3):357-63. Epub Jan. 9, 2007.
Kim et al., Local and systemic delivery of VEGF siRNA using polyelectrolyte complex micelles for effective treatment of cancer. J Control Release. Jul. 14, 2008;129(2):107-16. Epub Mar. 14, 2008.
Kukowska-Latallo et al., Efficient transfer of genetic material into mammalian cells using Starburst polyamidoamine dendrimers. Proc Natl Acad Sci USA. May 14, 1996;93(10):4897-902.

(56) References Cited

OTHER PUBLICATIONS

Kwon et al., Application of an HIV gp41-derived peptide for enhanced intracellular trafficking of synthetic gene and siRNA delivery vehicles. Bioconjug Chem. Apr. 2008;19(4):920-7. Epub Apr. 1, 2008.

Langer, Perspectives and challenges in tissue engineering and regenerative medicine. Adv Mater. Sep. 4, 2009;21(32-33):3235-6.

Lee et al., Stability and cellular uptake of polymerized siRNA (poly-siRNA)/polyethylenimine (PEI) complexes for efficient gene silencing. J Control Release. Feb. 15, 2010;141(3):339-46. Epub Oct. 14, 2009.

Leuschner et al., Therapeutic siRNA silencing in inflammatory monocytes in mice. Nat Biotechnol. Oct. 9, 2011;29(11):1005-10. doi: 10.1038/nbt.1989.

Lim, et al., A self-destroying polycationic polymer: biodegradable poly(4-hydroxy-l-proline ester. J. Am. Chem. Soc. 1999;121:5633-5639.

Love, et al., Lipid-like materials for low-dose, in vivo gene silencing. Proc Natl Acad Sci U S A. Feb. 2, 2010;107(5):1864-9. doi: 10.1073/pnas.0910603106. Epub Jan. 11, 2010.

Lukyanov et al., Micelles from lipid derivatives of water-soluble polymers as delivery systems for poorly soluble drugs. Adv Drug Deliv Rev. May 7, 2004;56(9):1273-89.

Luo et al., Synthetic DNA delivery systems. Nat Biotechnol. Jan. 2000;18(1):33-7. Review.

Ma et al., Developlment of Cationic Polymer Coatings to Regulate Foreign Body Responses. Adv Mater. 2011;23:H189-94.

Mathiowitz et al., Novel microcapsules for delivery systems. Reactive Polymers. Oct. 1987;6(2-3):275-83.

Mathiowitz et al., Polyanhydride microspheres as drug carriers. I. Hot melt microencapsulation. J Control Release. 1987;5:13-22.

Mathiowitz et al., Polyanhydride microspheres as drug carriers. II. Microencapsulation by solvent removal. J Appl Polymer Sci. Feb. 20, 1988;35(3):755-74.

Miller, Cationic Liposomes for Gene Therapy. Angew. Chem. Int. Ed. 1998;37:1769-1785.

Mintzer et al., Nonviral vectors for gene delivery. Chem Rev. Feb. 2009;109(2):259-302.

Morris et al., Lentiviral-mediated delivery of siRNAs for antiviral therapy. Gene Ther. 2006;13:553-58.

Narang et al., Cationic lipids with increased DNA binding affinity for nonviral gene transfer in dividing and nondividing cells. Bioconjug Chem. Jan.-Feb. 2005;16(1):156-68.

Navarro et al., Phospholipid-polyethylenimine conjugate-based micelle-like nanoparticles for siRNA delivery. Drug Deliv and Trans Res. 2011; 25-33.

Neamnark et al., Aliphatic lipid substitution on 2 kDa polyethylenimine improves plasmid delivery and transgene expression. Mol Pharm. 2009 Nov.-Dec.;6(6):1798-815.

Nguyen et al., Drug delivery-mediated control of RNA immunostimulation. Mol Ther. Sep. 2009;17(9):1555-62. Epub Jul. 7, 2009.

Novobrantseva et al., Systemic RNAi-mediated Gene Silencing in Nonhuman Primate and Rodent Myeloid Cells. Mol Ther Nucleic Acids. Jan. 24, 2012;1:e4. doi: 10.1038/mtna.2011.3.

Parrish et al., Five- and six-membered ring opening of pyroglutamic diketopiperazine. J Org Chem. Mar. 22, 2002;67(6):1820-6.

Peer et al., Nanocarriers as an emerging platform for cancer therapy. Nat Nanotechnol. Dec. 2007;2(12):751-60.

Philipp et al., Hydrophobically modified oligoethylenimines as highly efficient transfection agents for siRNA delivery. Bioconjug Chem. Nov. 2009;20(11):2055-61.

Phillips et al., Enhanced antibody response to liposome-associated protein antigens: preferential stimulation of IgG2a/b production. Vaccine. 1992;10(3):151-8.

Pollard et al., Ether amino alcohols. II. J Org Chem. 1952;17:1-3.

Prata et al., Lipophilic peptides for gene delivery. Bioconjug Chem. Feb. 2008;19(2):418-20.

Putnam, Polymers for gene delivery across length scales. Nat Mater. Jun. 2006;5(6):439-51.

Ratner et al., Biomaterials: where we have been and where we are going. Annu Rev Biomed Eng. 2004;6:41-75.

Ryng et al., Synthesis and Structure Elucidation of 5-Aminomethinimino-3-methyl-4-isoxazolecarboxylic Acid Phenylamides and Their Immunological Activity. Archiv der Pharmazie Jan. 1, 1997;330(11):319-26.

Sahay et al., Endocytosis of nanomedicines. J Control Release. Aug. 3, 2010;145(3):182-95. Epub Mar. 10, 2010.

Sakiyama-Elbert et al., Functional Biomaterials: Design of Novel Biomaterials. Ann Rev Mater Res. 2001;31:183-201.

Saltzman, Chapter 19. Cell Interactions with Polymers. In: Principles of Tissue Engineering, 2d ed., 2000:221-35.

Sanford, The biolistic process. Trends Biotechnol. 1988;6:299-302.

Sato et al., Resolution of liver cirrhosis using vitamin A-coupled liposomes to deliver siRNA against a collagen-specific chaperone. Nat Biotechnol. Apr. 2008;26(4):431-42. doi: 10.1038/nbt1396. Epub Mar. 30, 2008.

Semple et al., Rational design of cationic lipids for siRNA delivery. Nat Biotechnol. Feb. 2010;28(2):172-6. doi:10.1038/nbt.1602. Epub Jan. 17, 2010.

Staubli et al., Hydrolytically degradable amino acid containing polymers. J Am Chem Soc. 1990;45:4419-24.

Suh et al., Ionization of Poly(ethylenimine) and Poly(allylamine) at Various PHS. Bioorg Chem. 1994;22:318-27.

Szoka et al., Comparative properties and methods of preparation of lipid vesicles (liposomes). Annu Rev Biophys Bioeng. 1980;9:467-508.

Tang et al., In vitro gene delivery by degraded polyamidoamine dendrimers. Bioconjug Chem. Nov.-Dec. 1996;7(6):703-14.

Tarcha et al., Synthesis and characterization of chemically condensed oligoethylenimine containing beta-aminopropionamide linkages for siRNA delivery. Biomaterials. Sep. 2007;28(25):3731-40. Epub May 3, 2007.

Tranchant et al., Physicochemical optimisation of plasmid delivery by cationic lipids. J Gene Med. Feb. 2004;6 Suppl 1:S24-35.

Urban-Klein et al., RNAi-mediated gene-targeting through systemic application of polyethylenimine (PEI)-complexed siRNA in vivo. Gene Ther. Mar. 2005;12(5):461-6.

Van Balen et al., Liposome/water lipophilicity: methods, information content, and pharmaceutical applications. Med Res Rev. May 2004;24(3):299-324.

Van Dijkhuizen-Radersma et al., Biocompatibility and degradation of poly(ether-ester) microspheres: in vitro and in vivo evaluation. Biomaterials. Dec. 2002;23(24):4719-29.

Vandenbroucke et al., Prolonged gene silencing in hepatoma cells and primary hepatocytes after small interfering RNA delivery with biodegradable poly(beta-amino esters). J Gene Med. Jul. 2008;10(7):783-94.

Von Harpe et al., Characterization of commercially available and synthesized polyethylenimines for gene delivery. J Control Release. Nov. 3, 2000;69(2):309-22.

Walde, Preparation of vesicles (liposomes). Encyclopedia of Nanoscience and Nanotechnology, Nalwa, Ed. American Scientific Publishers: Los Angeles. 2004;9:43-79.

Werth et al., A low molecular weight fraction of polyethylenimine (PEI) displays increased transfection efficiency of DNA and siRNA in fresh or lyophilized complexes. J Control Release. May 15, 2006;112(2):257-70. Epub Mar. 6, 2006.

Whitehead et al., In vitro-in vivo translation of lipid nanoparticles for hepatocellular siRNA delivery. ACS Nano. Aug. 28, 2012;6(8):6922-9. doi: 10.1021/nn301922x. Epub Jul. 6, 2012.

Whitehead et al., Knocking down barriers: advances in siRNA delivery. Nat Rev Drug Discov. Feb. 2009;8(2):129-38. doi: 10.1038/nrd2742.

Williams, On the mechanisms of biocompatibility. Biomaterials. Jul. 2008;29(20):2941-53. Epub Apr. 28, 2008.

Wintermantel et al., Blocked polyurethane prepolymers as component A in reactive adhesives. STN International HCAPLUS Database. 2006. Accession No. 2006:215601.

Wu et al., Cationic lipid polymerization as a novel approach for constructing new DNA delivery agents. Bioconjug Chem. Mar.-Apr. 2001;12(2):251-7.

(56) References Cited

OTHER PUBLICATIONS

Yoshioka et al., Epoxy-based Electroactive Polymer Gels. Experimental Mechanics. 2002;42:404-08.
Zagridullin et al., Monobasic amines. II. Cycloalkylation and hydroxyalkylation of cyclic and acyclic di- and polyamines.. Zhurnal Organicheskoi Khimii. 1990;26(1):184-88. Russian.
Zaugg et al., 3-Carboxy-2,5-piperazinedione and Derivatives. J Amer Chem Soc. Jun. 5, 1956;78(11):2626-2631.
Zhang et al., Ionization behavior of amino lipids for siRNA delivery: determination of ionization constants, SAR, and the impact of lipid pKa on cationic lipid-biomembrane interactions. Langmuir. Mar. 1, 2011;27(5):1907-14. doi: 10.1021/1a104590k. Epub Jan. 20, 2011.
Zintchenko et al., Simple modifications of branched Pei lead to highly efficient siRNA carriers with low toxicity. Bioconjug Chem. Jul. 2008;19(7):1448-55. Epub Jun. 14, 2008.
International Preliminary Report on Patentability for PCT/US2012/062222, mailed May 8, 2014.
Invitation to Pay Additional Fees for PCT/US2004/016521, mailed Sep. 29, 2004.
International Search Report and Written Opinion for PCT/US2004/016521, mailed Dec. 8, 2004.
International Preliminary Report on Patentability for PCT/US2004/016521, mailed Dec. 15, 2005.
Extended European Search Report for EP 07013193.3, mailed Jan. 28, 2008.
International Search Report for PCT/US2001/031270, mailed May 22, 2002.
Written Opinion for PCT/US2001/031270, mailed Jan. 2, 2003.
International Preliminary Examination Report for PCT/US2001/031270, mailed Aug. 19, 2003.
International Search Report and Written Opinion for PCT/US2007/073976, mailed Sep. 29, 2008.
International Preliminary Report on Patentability for PCT/US2007/073976, mailed Feb. 5, 2009.
Extended European Search Report for Ep 07813156.2, mailed Oct. 5, 2009.
International Search Report and Written Opinion for PCT/US2007/070430, mailed Dec. 13, 2007.
International Preliminary Report on Patentability for PCT/US2007/070430, mailed Dec. 24, 2008.
Extended European Search Report for EP 07798132.2, mailed Jul. 18, 2011.
Partial Supplementary European Search Report for European Application No. 11820727.3, mailed Nov. 26, 2014.
Extended European Search Report for European Application No. 11820727.3, mailed Apr. 22, 2015.
International Preliminary Report on Patentability for PCT/US2013/054726, mailed Feb. 26, 2015.
International Search Report and Written Opinion for PCT/US2014/036355, mailed Aug. 5, 2014.
International Search Report and Written Opinion for PCT/US2014/044408, mailed Oct. 24, 2014.
Akinc et al., Development of lipidoid-siRNA formulations for systemic delivery to the liver. Mol Ther. May 2009;17(5):872-9. doi: 10.1038/mt.2009.36. Epub Mar. 3, 2009.
Akinc et al., Parallel synthesis and biophysical characterization of a degradable polymer library for gene delivery. J Am Chem Soc. May 7, 2013;125(18):5316-23.
Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.
Anderson et al., Structure/property studies of polymeric gene delivery using a library of poly(beta-amino esters). Mol Ther. Mar. 2005;11(3):426-34.
Behr et al., Efficient gene transfer into mammalian primary endocrine cells with lipopolyaminecoated Dna. Proc Natl Acad Sci U S a. 1989 Sep;86(18):6982-6.
Brey et al., Controlling poly(beta-amino ester) network properties through macromer branching. Acta Biomater. Mar. 2008;4(2):207-17. Epub Oct. 22, 2007.
Brey et al., Influence of macromer molecular weight and chemistry on poly(beta-amino ester) network properties and initial cell interactions. J Biomed Mater Res A. Jun. 1, 2008;85(3):731-41.
Burnett et al., Current progress of siRNA/shRNA therapeutics in clinical trials. Biotechnol J. Sep. 2011;6(9):1130-46. doi: 10.1002/biot.201100054. Epub Jul. 11, 2011.
Castanotto et al.,. The promises and pitfalls of RNA-interference-based therapeutics. Nature. Jan. 22, 2009;457(7228):426-33. doi: 10.1038/nature07758.
Chen et al., Tumor-targeted delivery of siRNA by non-viral vector: safe and effective cancer therapy. Expert Opin Drug Deliv. Dec. 2008;5(12):1301-11. doi: 10.1517/17425240802568505.
Chiang et al., Synthesis, characterization and properties of novel self-extinguishing organic-inorganic nanocomposites containing nitrogen, silicon and phosphorus via sol-gel method. Composite Science and Technology. 2008;68(14):2849-57.
Damen et al., Delivery of DNA and siRNA by novel gemini-like amphiphilic peptides. J Control Release. Jul. 1, 2010;145(1):33-9. doi: 10.1016/j.jconrel.2010.03.028. Epub Apr. 8, 2010.
Davis, The first targeted delivery of siRNA in humans via a self-assembling, cyclodextrin polymer-based nanoparticle: from concept to clinic. Mol Pharm. May-Jun. 2009;6(3):659-68. doi: 10.1021/mp900015y.
Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014.
Felgner et al., Lipofection: a highly efficient, lipid-mediated DNA-transfection procedure. Proc Natl Acad Sci U S A. Nov. 1987;84(21):7413-7.
Fenske et al., Liposomal nanomedicines. Expert Opin Drug Deliv. Jan. 2008;5(1):25-44.
Ferruti et al., A novel modification of poly(1-lysine) leading to a soluble cationic polymer with reduced toxicity and with potential as a transfection agent. Macromol Chem Phys 1998;199:2565-75.
Ferruti et al., Linear amino polymers: Synthesis, protonation and complex formation. Advances in Polymer Science. 1984;58:55-92.
Gademann et al., The fourth helical secondary structure of beta-peptides: the (P)-28-helix of a beta-hexapeptide consisting of (2R,3S)-3-amino-2-hydroxy acid residues. Angew Chem Int Ed Engl. Apr. 4, 2003;42(13):1534-7.
Giuliani et al., Beyond natural antimicrobial peptides: multimeric peptides and other peptidomimetic approaches. Cell Mol Life Sci. Jul. 2011;68(13):2255-66. doi: 10.1007/s00018-011-0717-3. Epub May 20, 2011.
Gupta et al., A review of in vitro-in vivo investigations on dendrimers: the novel nanoscopic drug carriers. Nanomedicine. Jun. 2006;2(2):66-73.
Hill et al., In vitro cytotoxicity of poly(amidoamine)s: relevance to DNA delivery. Biochim Biophys Acta. Apr. 19, 1999;1427(2):161-74.
Ikeda et al., Role of micafungin in the antifungal armamentarium. Curr Med Chem. 2007;14(11):1263-75.
Juliano et al., Biological barriers to therapy with antisense and siRNA oligonucleotides. Mol Pharm. May-Jun. 2009;6(3):686-95. doi:10.1021/mp900093r.
Kim et al., Synthesis of biodegradable cross-linked poly(beta-amino ester) for gene delivery and its modification, inducing enhanced transfection efficiency and stepwise degradation. Bioconjug Chem. Sep.-Oct. 2005;16(5):1140-8.
Klibanov et al., Amphipathic polyethyleneglycols effectively prolong the circulation time of liposomes. FEBS Lett. Jul. 30, 1990;268(1):235-7.
Lynn et al., Accelerated discovery of synthetic transfection vectors: parallel synthesis and screening of a degradable polymer library. J Am Chem Soc. Aug. 22, 2001;123(33):8155-6.
Lynn et al., Degradable Poly((β-amino esters): Synthesis, Characterization, and Self-Assembly with Plasmid DNA. J. Am. Chem. Soc. 2000;122 (44): 10761-8.

(56) References Cited

OTHER PUBLICATIONS

Lynn et al., pH-Responsive Polymer Microspheres: Rapid Release of Encapsulated Material within the Range of Intracellular pH. Angew Chem Int Ed Engl. May 4, 2001;40(9):1707-10.

Margus et al., Cell-penetrating peptides as versatile vehicles for oligonucleotide delivery. Mol Ther. Mar. 2012;20(3):525-33. doi: 10.1038/mt.2011.284. Epub Jan. 10, 2012.

SEN, Surfactin: biosynthesis, genetics and potential applications. Adv Exp Med Biol. 2010;672:316-23.

Shchori, Poly(secondary Amine)s from Diacrylates and Diamines. J Polym Sci Polymer. Jun. 1983;21(6):413-15.

Siegwart et al., Combinatorial synthesis of chemically diverse core-shell nanoparticles for intracellular delivery. Proc Natl Acad Sci U S A. Aug. 9, 2011;108(32):12996-3001. doi: 10.1073/pnas. 1106379108. Epub Jul. 22, 2011.

Tan et al., Engineering Nanocarriers for siRNA Delivery. Small. Apr. 4, 2011;7(7):841-56. doi: 10.1002/smll.201001389. Epub Feb. 25, 2011.

Thiel et al., Therapeutic applications of DNA and RNA aptamers. Oligonucleotides. Sep. 2009;19(3):209-22. doi: 10.1089/oli.2009. 0199.

Van De Wetering et al., Structure-activity relationships of water-soluble cationic methacrylate/methacrylamide polymers for nonviral gene delivery. Bioconjug Chem. Jul.-Aug. 1999;10(4):589-97.

Weinstein et al., RNAi nanomedicines: challenges and opportunities within the immune system. Nanotechnology. Jun. 11, 2010;21(23):232001. doi: 10.1088/0957-4484/21/23/232001. Epub May 13, 2010.

Zamora et al., RNA interference therapy in hung transplant patients infected with respiratory syncytial virus. Am J Respir Crit Care Med. Feb. 15, 2011;183(4):531-8. doi: 10.1164/rccm.201003-04220C. Epub Sep. 17, 2010.

a b c d a b c a d e

AMINE-CONTAINING LIPIDOIDS AND USES THEREOF

RELATED REFERENCES

The present application is a continuation of and claims priority under 35 U.S.C. §120 to U.S. patent application, U.S. Ser. No. 13/966,136, filed Aug. 13, 2013, which claims priority under 35 U.S.C. §119(e) to U.S. provisional application, U.S. Ser. No. 61/682,468, filed Aug. 13, 2012, which is incorporated herein by reference.

GOVERNMENT SUPPORT

This invention was made with U.S. Government support under Grant No.5-F32-EB009623-02 awarded by the National Institutes of Health. The U.S. Government has certain rights in this invention.

BACKGROUND OF THE INVENTION

The discovery of RNA interference (RNAi) in mammalian cells (Fire, et al. *Nature* 391:806-811 (1998)) has allowed for the development of short interfering RNA (siRNA) therapeutics (Elbashir, et al. *Nature* 411:494-8 (2001)), which have the potential to treat a wide variety of human diseases, including viral infections and cancer, through genetic modulation. Theoretically, siRNA can be used to alter the expression of nearly any gene in the body through the silencing of complementary messenger RNA. Such precise genetic control offers a broad therapeutic potential that is typically not attainable using conventional small molecule drugs. siRNA delivery vehicles must negotiate a number of obstacles in vivo prior to delivering their payload to target cells. In addition to escorting therapeutic cargo through the bloodstream and extracellular matrix, delivery vehicles must mediate siRNA transport across the cellular membrane of the target cell as well as to facilitate endosomal escape prior to lysosomal digestion (Akinc, et al. *J. Gene. Med.* 7:657-63 (2005)). It is only once these barriers have been breached that siRNA can interact with the RNAi machinery within the cytoplasm and trigger the gene silencing process (Whitehead, et al. *Nature Rev. Drug Discov.* 8:129-38 (2009)).

A select number of delivery systems have previously been reported to deliver siRNA for the treatment of a variety of disease targets in vivo, including hypercholesterolemia (Frank-Kamenetsky, et al. *Proc. Natl. Acad. Sci. USA* 107:1864-9 (2010); Love, et al. *Proc. Natl. Acad. Sci. USA* 26:431-42 (2008)), liver cirrhosis (Sato, et al. *Nature Biotechnol.* 26:431-42 (2008)), Ebola virus (Geisbert, et al. *Lancet* 375:1896-1905 (2010)), and cancer (Huang, et al. *Proc. Natl. Acad. Sci. USA* 106:3426-30 (2009)). Unfortunately, RNAi success in vivo has not consistently translated to success in the clinic. Because siRNA must be dosed repeatedly to achieve therapeutic effect, ideal delivery vehicles will offer a substantial therapeutic window in order to ensure the broadest clinical application. Although some materials have been identified that allow for potent gene silencing at siRNA doses as low as 0.01 mg/kg (Love, et al. *Proc. Natl. Acad. Sci. USA* 107:1864-9 (2010)), their clinical potential has been limited due to a lack of delivery vehicle degradability. There exists a continuing need for non-toxic, biodegradable, biocompatible lipids that can be used to transfect nucleic acids and other therapeutic agents. Such lipids would have several uses, including the delivery of siRNA.

SUMMARY OF THE INVENTION

The compounds described herein, known as lipidoids for their lipid-like tails, may be prepared by the addition of a primary or secondary amine to an acrylate via a Michael addition reaction. The lipidoids described herein may be used in the delivery of therapeutic agents to a subject. The inventive lipidoids are particularly useful in delivering negatively charged agents. For example, lipidoids described herein may be used to deliver DNA, RNA, or other polynucleotides to a subject or to a cell. In certain embodiments, lipidoids of the present invention are used to deliver siRNA. In certain embodiments, lipidoids described herein are useful as reagents.

In one aspect, the present invention provides a compound of the Formula (I):

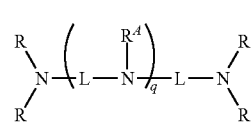

I or a salt thereof, wherein L, R, $R^A$, and q are as defined herein. In certain embodiments, a provided compound is of the Formula (I-a), (I-b), (I-c), (I-d), or (I-e):

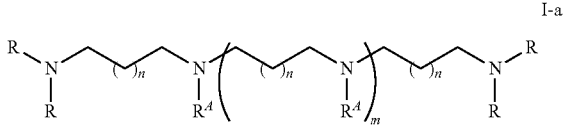

I-a

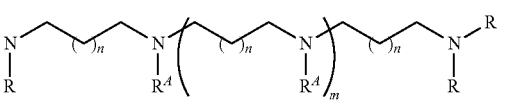

I-b

I-c

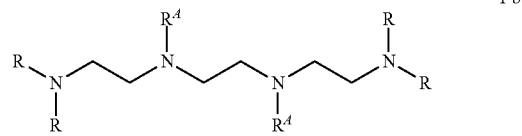

I-d

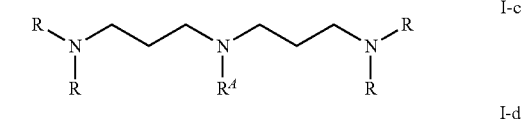

I-e

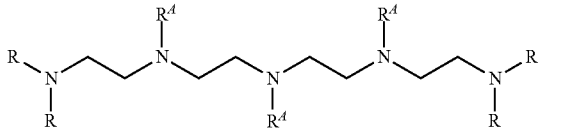

or a salt thereof, wherein m, n, R, and $R^A$ are as defined herein.

In another aspect, the present invention provides a compound of the Formula (II):

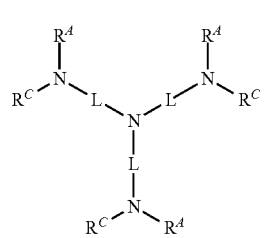

II or a salt thereof, wherein L, $R^C$, and $R^A$ are as defined herein. In certain embodiments, a provided compound is of the Formula (II-a), (II-b), (II-c), (II-d), (II-e), or (II-f):

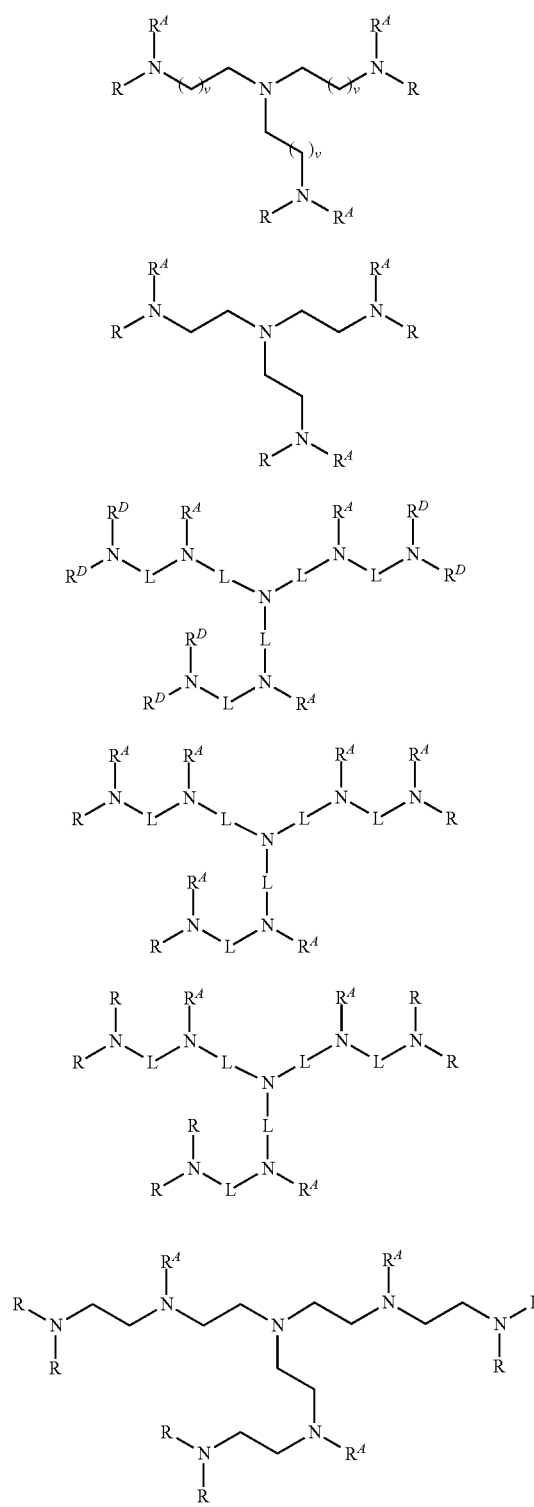

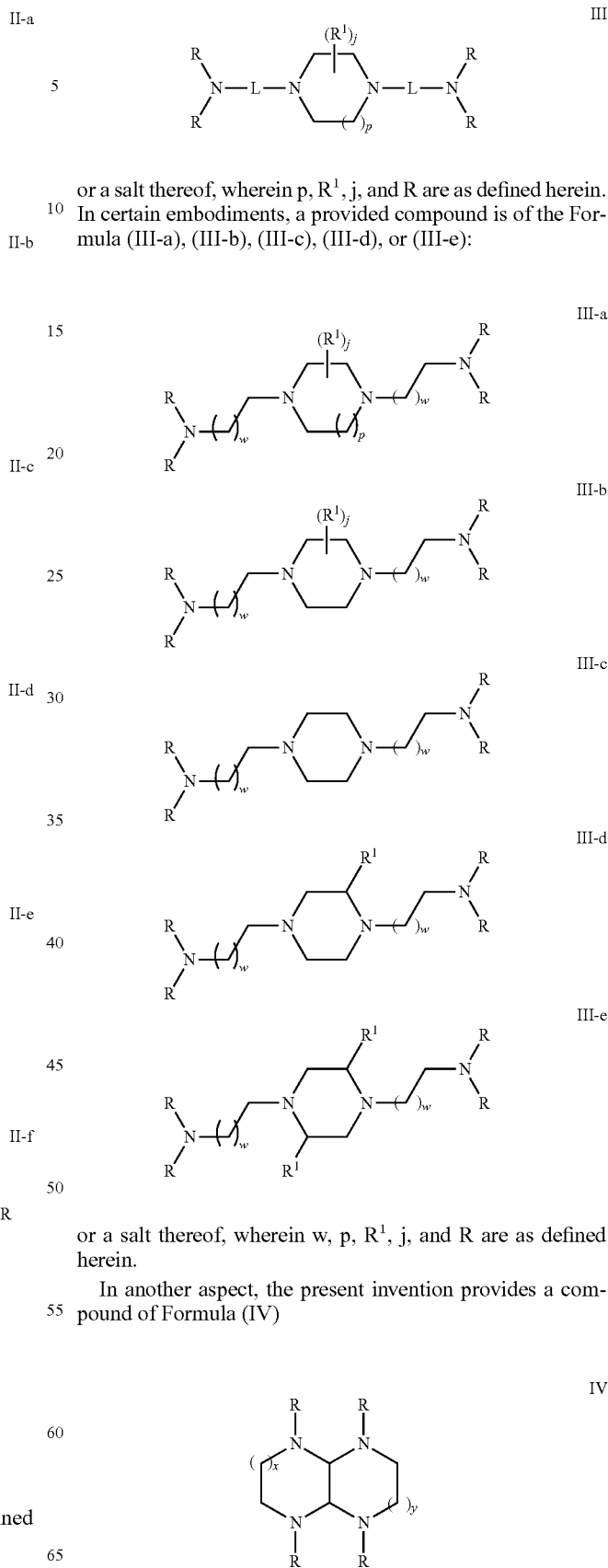

or a salt thereof, wherein v, L, R, $R^D$, and $R^A$ are as defined herein.

In another aspect, the present invention provides a compound of the Formula (III):

or a salt thereof, wherein p, $R^1$, j, and R are as defined herein. In certain embodiments, a provided compound is of the Formula (III-a), (III-b), (III-c), (III-d), or (III-e):

or a salt thereof, wherein w, p, $R^1$, j, and R are as defined herein.

In another aspect, the present invention provides a compound of Formula (IV)

or a salt thereof, wherein R, x, and y are as defined herein. In certain embodiments, a provided compound is of the Formula (IV-a):

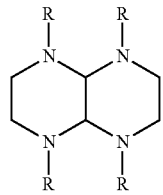

IV-a or a salt thereof, wherein R is as defined herein.

In another aspect, the present invention provides a compound of Formula (V):

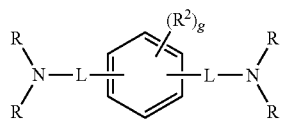

V or a salt thereof, wherein L, $R^2$, g, and R are as defined herein. In certain embodiments, a provided compound is of the Formula (V-a), (V-b), (V-c), or (V-d):

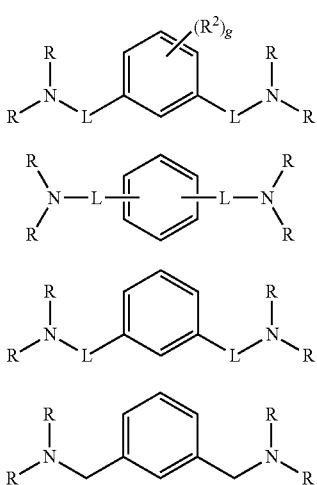

V-a

V-b

V-c

V-d or a salt thereof, wherein L, $R^2$, g, and R are as defined herein.

In another aspect, the present invention provides a compound of formula

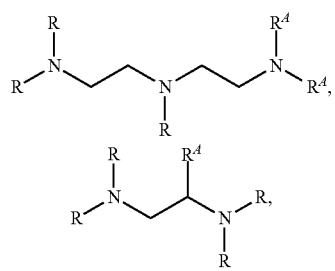

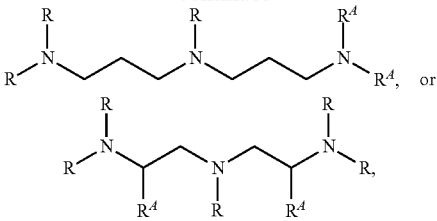

or a salt thereof, wherein R and $R^A$ are as defined herein.

In another aspect, the present invention provides lipidoids having certain features. In some embodiments, a lipidoid of the present invention is prepared from an alkylamine starting material that has at least one tertiary amine. In some embodiments, a lipidoid of the present invention has three or more lipid-like tails. In some embodiments, the lipid-like tails on a lipidoid of the present invention are between $C_{12}$-$C_{14}$ in length, e.g., $C_{13}$ (e.g., derived from the $O_{13}$ acrylate shown in FIG. 1). In certain embodiments, a provided lipidoid is prepared from an alkylamine starting material that has at least one tertiary amine and has three or more $C_{13}$ tails.

In another aspect, the inventive lipidoids are combined with an agent to form nanoparticles, microparticles, liposomes, or micelles. The agent to be delivered by the nanoparticles, microparticles, liposomes, or micelles may be in the form of a gas, liquid, or solid, and the agent may be, for example, a polynucleotide, protein, peptide, or small molecule. In certain embodiments, inventive lipidoids may be combined with other lipids, polymers, surfactants, cholesterol, carbohydrates, proteins, etc. to form the particles. In certain embodiments, the particles may be combined with an excipient to form pharmaceutical or cosmetic compositions.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The term "aliphatic," as used herein, includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups. As will be appreciated by one of ordinary skill in the art, "aliphatic" is intended herein to include alkyl, alkenyl, alkynyl, cycloalkyl, and cycloalkenyl moieties.

The term "alkyl" as used herein refers to saturated, straight- or branched-chain hydrocarbon radicals derived from a hydrocarbon moiety containing between one and twenty carbon atoms by removal of a single hydrogen atom. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

In certain embodiments, the alkyl groups employed in the inventive lipidoids contain 1-20 aliphatic carbon atoms. In certain other embodiments, the alkyl groups employed in the inventive lipidoids contain 1-10 aliphatic carbon atoms. In yet other embodiments, the alkyl groups contain 1-8 aliphatic carbon atoms. In still other embodiments, the alkyl groups employed in the invention contain 1-6 aliphatic carbon atoms. In yet other embodiments, the alkyl groups contain 1-4 carbon atoms. Illustrative alkyl groups thus include, but are not limited to, for example, methyl, ethyl, n-propyl, isopropyl, n-butyl, sec-butyl, isobutyl, tert-butyl, n-pentyl, sec-pentyl, isopentyl, tert-pentyl, n-hexyl, and sec-hexyl.

The terms "alkenyl" and "alkynyl" are given their ordinary meaning in the art and refer to unsaturated aliphatic groups analogous in length and possible substitution to the alkyls described above, but that contain at least one double or triple bond respectively.

The term "cycloalkyl", as used herein, refers saturated, cyclic hydrocarbon radicals derived from a hydrocarbon moiety containing between three and seven carbon atoms by removal of a single hydrogen atom. Suitable cycloalkyls include cyclopropyl, cyclobutyl, cyclopentyl, cyclohexyl, and cycloheptyl.

The term "cycloalkylalkyl," as used herein, refers to a cycloalkyl group attached via a straight chain or branched alkyl group. Suitable cycloalkylalkyl groups include, but are not limited to, —CH$_2$(cyclopropyl), —CH$_2$CH$_2$(cyclopropyl), —CH$_2$(cyclobutyl), —CH$_2$CH$_2$(cyclobutyl), —CH$_2$(cyclopentyl), —CH$_2$CH$_2$(cyclopentyl), —CH$_2$(cyclohexyl), —CH$_2$CH$_2$(cyclohexyl), —CH$_2$(cycloheptyl), and —CH$_2$CH$_2$(cycloheptyl).

The term "alkylene" as used herein refers to a bivalent alkyl group. An "alkylene" group is a polymethylene group, i.e., —(CH$_2$)$_k$—, wherein k is a positive integer, e.g., from 1 to 20, from 1 to 10, from 1 to 6, from 1 to 4, from 1 to 3, from 1 to 2, or from 2 to 3. In some embodiments, one or more hydrogens on an alkylene group is replaced by a substituent (e.g., fluoro).

The following are more general terms used throughout the present application:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. In certain embodiments, compounds are "biocompatible" if their addition to cells in vitro at a minimum therapeutically effective dose results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant long-term toxic effect on the cells. In certain embodiments, the components do not induce inflammation or other adverse effects in vivo. In certain embodiments, the chemical reactions relied upon to break down the biodegradable compounds are uncatalyzed.

"Peptide" or "protein": According to the present invention, a "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guano sine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, sulfonamides, dexamethasone, and doxorubicin.

BRIEF DESCRIPTION OF THE DRAWINGS

FIG. 11A shows acidic hydrolysis condition, and FIG. 11B shows basic hydrolysis condition.

DETAILED DESCRIPTION OF CERTAIN EMBODIMENTS

Figure 1:
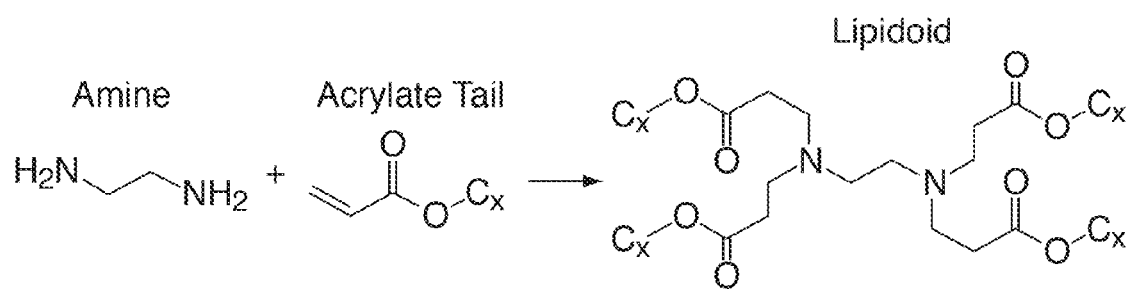
FIG. 1 displays a subset of the large library of biodegradable lipidoids that were synthesized combinatorially through the conjugate addition of alkylamines (in red) to alkyl-acrylate tails (in blue). The rest of the alkylamines used in lipidoid library synthesis are shown in FIG. 2.
Figure 1:
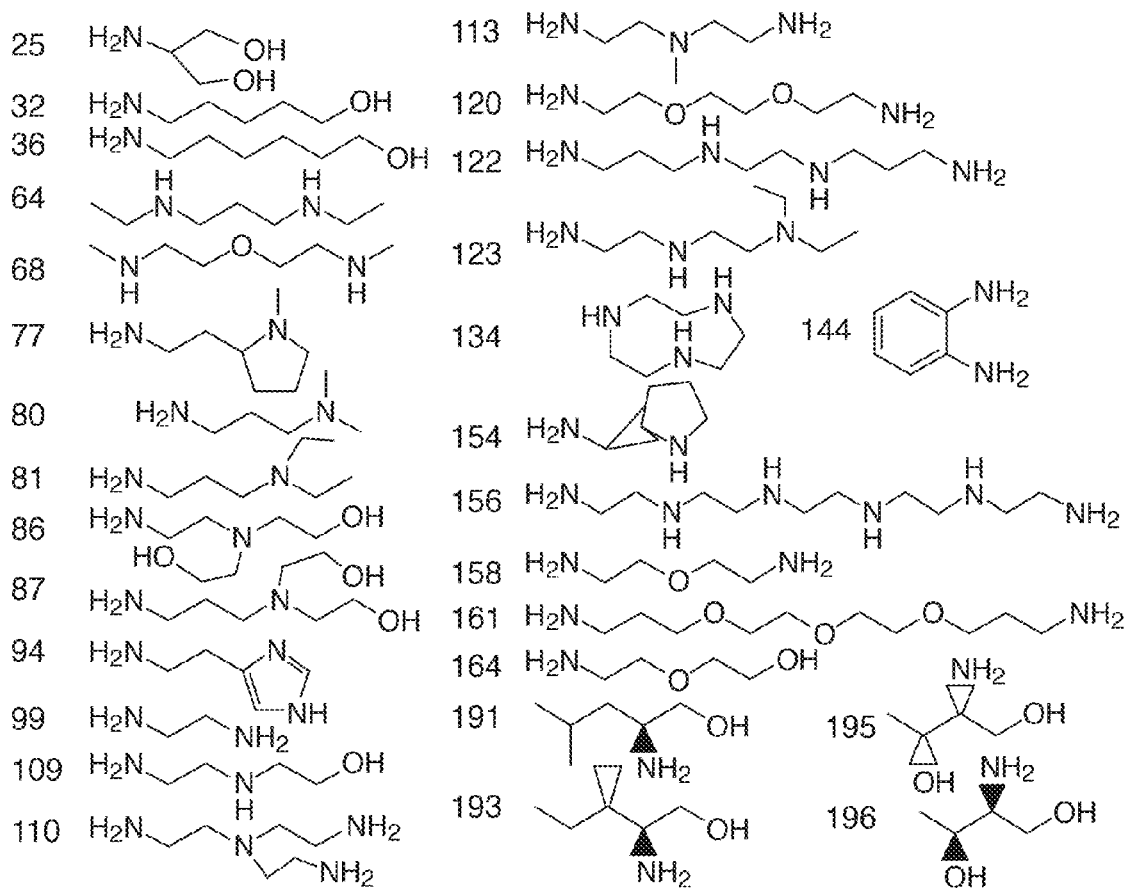
Figure 1:
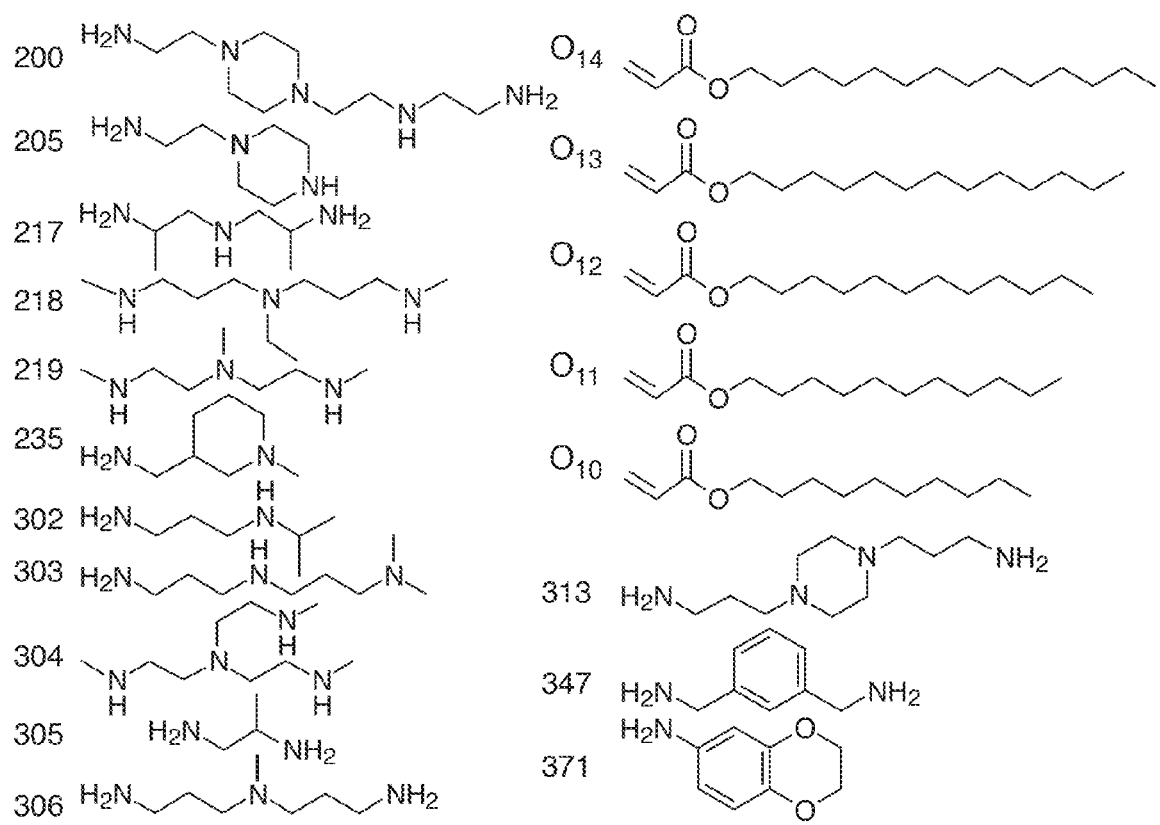

The present invention provides lipidoids and lipidoid-based delivery systems. The systems described herein may be used in the pharmaceutical/drug delivery arts to delivery polynucleotides, proteins, small molecules, peptides, antigen, drugs, etc. to a patient, tissue, organ, cell, etc.

The lipidoids of the present invention provide for several different uses in the drug delivery art. The lipidoids with their amine-containing hydrophilic portion may be used to complex polynucleotides and thereby enhance the delivery of polynucleotides and prevent their degradation. The lipidoids may also be used in the formation of nanoparticles, microparticles, liposomes, and micelles containing the agent to be delivered. In certain embodiments, the lipids are biocompatible and biodegradable, and particles formed therefrom are also biodegradable and biocompatible and may be used to provide controlled, sustained release of the agent. Provided lipidoids and their corresponding particles may also be responsive to pH changes given that these lipids are protonated at lower pH.

Lipidoids

The lipidoids of the present invention contain primary, secondary, or tertiary amines and salts thereof. In certain embodiments, the inventive lipidoids are biodegradable. In certain embodiments, inventive lipidoids are effective at delivering an agent (e.g., RNA) to a cell.

In certain embodiments, a lipidoid of the present invention is prepared from an alkylamine starting material that has at least one tertiary amine. In some embodiments, a lipidoid of the present invention has three or more lipid-like tails. In some embodiments, the lipid-like tails on a lipidoid of the present invention are between $C_{10}$-$C_{14}$ in length, e.g., $C_{12}$-$C_{14}$, e.g., $C_{13}$. In certain embodiments, a provided lipidoid is prepared from an alkylamine starting material that has at least one tertiary amine and the lipidoid formed therefrom has three or more $C_{13}$ tails. In certain embodiments, a provided lipidoid is prepared from an alkylamine starting material that has at least one tertiary amine, provided that the amine is not amine 110, amine 113, or amine 115, and the lipidoid formed therefrom has three or more $C_{13}$ tails.

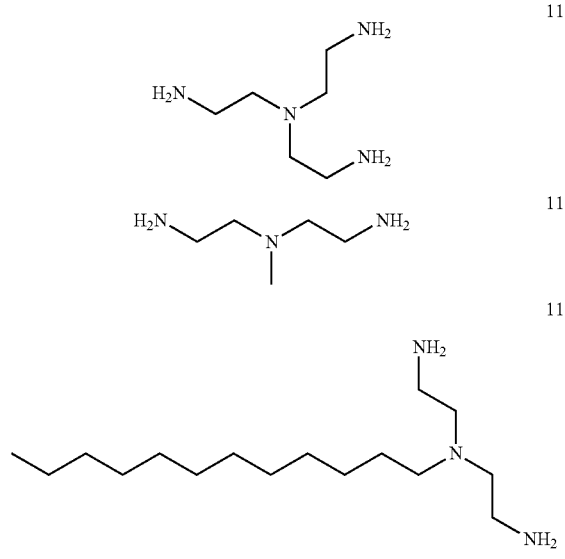

In certain embodiments, a lipidoid of the present invention is of the Formula (I):

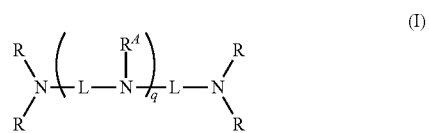

or a salt thereof, wherein each L is, independently, branched or unbranched $C_{1-6}$ alkylene, wherein L is optionally substituted with one or more fluorine radicals;

each $R^A$ is, independently, branched or unbranched $C_{1-6}$ alkyl, $C_{3-7}$ cycloalkyl, or branched or unbranched $C_{4-12}$ cycloalkylalkyl, wherein $R^A$ is optionally substituted with one or more fluorine radicals;

each R is, independently, hydrogen or —$CH_2CH_2C(=O)OR^B$;

each $R^B$ is, independently, $C_{10-14}$ alkyl, wherein $R^B$ is optionally substituted with one or more fluorine radicals; and q is 1, 2, or 3.

In certain embodiments, a lipidoid of formula (I) is not

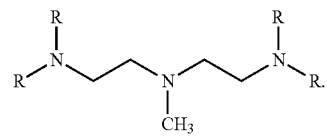

As defined generally above, each L is, independently, branched or unbranched $C_{1-6}$ alkylene, wherein L is optionally substituted with one or more fluorine radicals. In some embodiments, L is substituted with one or more fluorine radicals. In other embodiments, L is unsubstituted. In some embodiments, L is branched. In other embodiments, L is unbranched. In certain embodiments, L is $C_{1-4}$ alkylene. In certain embodiments, L is methylene, ethylene, or propylene.

As defined generally above, each $R^A$ is, independently, branched or unbranched $C_{1-6}$ alkyl, $C_{3-7}$ cycloalkyl, or branched or unbranched $C_{4-12}$ cycloalkylalkyl, wherein $R^A$ is optionally substituted with one or more fluorine radicals. In some embodiments, $R^A$ is substituted with one or more fluorine radicals. For example, when $R^A$ is methyl, it may be substituted with one, two, or three fluorine radicals to give —$CH_2F$, —$CHF_2$, or —$CF_3$. In other embodiments, $R^A$ is unsubstituted. In some embodiments, all $R^A$ groups are the same. In other embodiments, the $R^A$ groups are different. In some embodiments, $R^A$ is branched or unbranched $C_{1-6}$ alkyl. In certain embodiments, $R^A$ is branched $C_{1-6}$ alkyl. In certain embodiments, $R^A$ is unbranched $C_{1-6}$ alkyl. In certain embodiments, $R^A$ is $C_{1-3}$ alkyl. In certain embodiments, $R^A$ is methyl, ethyl, or propyl. In certain embodiments, $R^A$ is $C_{3-7}$ cycloalkyl. In certain embodiments, $R^A$ is cyclohexyl. In certain embodiments, $R^A$ is cyclopropyl, cyclobutyl, or cyclopentyl. In certain embodiments, $R^A$ is cycloheptyl. In some embodiments, $R^A$ is branched or unbranched $C_{4-12}$ cycloalkylalkyl.

As defined generally above, each R is, independently, hydrogen or —$CH_2CH_2C(=O)OR^B$. In some embodiments, at least three R groups are —$CH_2CH_2C(=O)OR^B$. In some embodiments, at least four R groups are —$CH_2CH_2C(=O)OR^B$. In some embodiments, all R groups are —$CH_2CH_2C(=O)OR^B$.

As defined generally above, each $R^B$ is, independently, $C_{10-14}$ alkyl, wherein $R^B$ is optionally substituted with one or more fluorine radicals. In some embodiments, $R^B$ is substituted with one or more fluorine radicals. For example, in some embodiments, $R^B$ may be substituted with one fluoro, or in other embodiments, may be perfluorinated. In other embodiments, $R^B$ is unsubstituted. In some embodiments, all $R^B$ groups are the same. In certain embodiments, $R^B$ is $C_{10}$ alkyl. In some embodiments, $R^B$ is n-decyl. In certain embodiments, $R^B$ is $C_{11}$ alkyl. In some embodiments, $R^B$ is n-undecyl. In certain embodiments, $R^B$ is $C_{12}$ alkyl. In some embodiments, $R^B$ is n-dodecyl. In certain embodiments, $R^B$ is $C_{13}$ alkyl. In some embodiments, $R^B$ is n-tridecyl. In certain embodiments, $R^B$ is $C_{14}$ alkyl. In some embodiments, $R^B$ is n-tetradecyl.

As defined generally above, q is 1, 2, or 3. In some embodiments, q is 1. In some embodiments, q is 2. In some embodiments, q is 3.

In some embodiments, a lipidoid of the present invention is of the Formula (I-a):

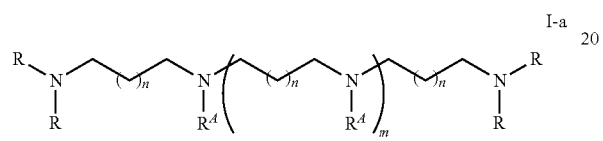

or a salt thereof,
wherein R and $R^A$ are as defined above and described herein;
    each n is, independently, 0, 1, or 2; and
    m is 0, 1, or 2.

In some embodiments, m is 0. In some embodiments, m is 1. In some embodiments, m is 2.

In some embodiments, n is 0. In some embodiments, n is 1. In some embodiments, n is 2.

In some embodiments, m is 0, and n is 0. In some embodiments, m is 1, and n is 0. In some embodiments, m is 2, and n is 0. In some embodiments, m is 0, and n is 1. In some embodiments, m is 0, and n is 2. In some embodiments, m is 1, and n is 1.

In some embodiments, a lipidoid of the present invention is of the Formula (I-b):

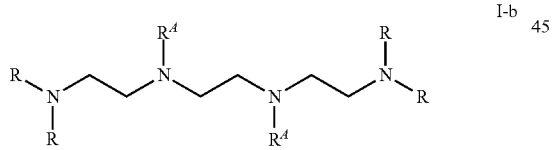

or a salt thereof, wherein R and $R^A$ are as defined above and described herein.

In some embodiments, a lipidoid of the present invention is of the Formula (I-c):

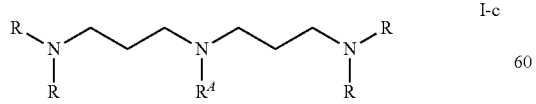

or a salt thereof, wherein R and $R^A$ are as defined above and described herein.

In some embodiments, a lipidoid of the present invention is of the Formula (I-d):

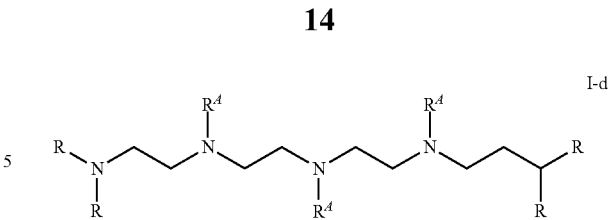

or a salt thereof, wherein R and $R^A$ are as defined above and described herein.

In some embodiments, a lipidoid of the present invention is of the Formula (I-e):

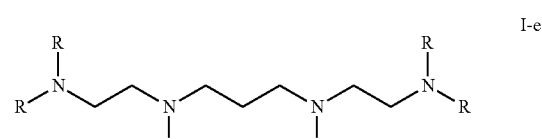

or a salt thereof, wherein R and $R^A$ are as defined above and described herein.

In some embodiments, a lipidoid of the present invention is of one of the following formulae:

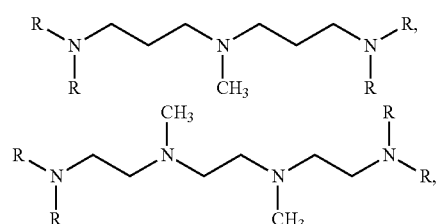

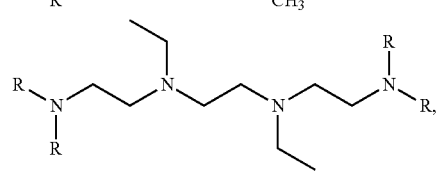

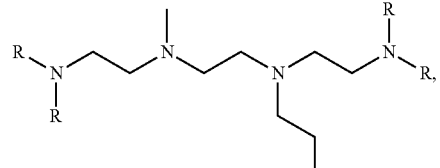

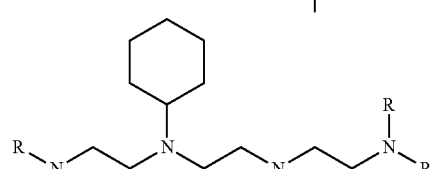

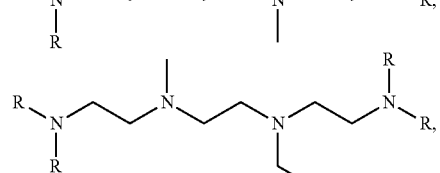

In certain embodiments, a lipidoid of the present invention is of the Formula (II):

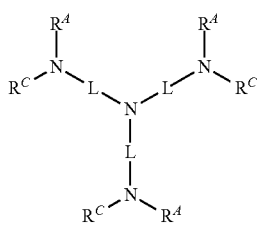

or a salt thereof,
wherein each L is, independently, branched or unbranched $C_{1-6}$ alkylene, wherein L is optionally substituted with one or more fluorine radicals;

each $R^A$ is, independently, branched or unbranched $C_{1-6}$ alkyl, $C_{3-7}$ cycloalkyl, or branched or unbranched $C_{4-12}$ cycloalkylalkyl, wherein $R^A$ is optionally substituted with one or more fluorine radicals;

each $R^C$ is, independently, -L-N($R^D$)$_2$ or —R;

each R is, independently, hydrogen or —CH$_2$CH$_2$C(=O)OR$^B$;

each $R^D$ is, independently, —$R^A$ or —R; and each $R^B$ is, independently, $C_{10-14}$ alkyl, wherein $R^B$ is optionally substituted with one or more fluorine radicals.

As defined generally above, each L is, independently, branched or unbranched $C_{1-6}$ alkylene, wherein L is optionally substituted with one or more fluorine radicals. In some embodiments, L is substituted with one or more fluorine radicals. In other embodiments, L is unsubstituted. In some embodiments, L is branched. In other embodiments, L is unbranched. In certain embodiments, L is $C_{1-4}$ alkylene. In certain embodiments, L is methylene, ethylene, or propylene.

As defined generally above, each $R^A$ is, independently, branched or unbranched $C_{1-6}$ alkyl, $C_{3-7}$ cycloalkyl, or branched or unbranched $C_{4-12}$ cycloalkylalkyl, wherein $R^A$ is optionally substituted with one or more fluorine radicals. In some embodiments, $R^A$ is substituted with one or more fluorine radicals. For example, when $R^A$ is methyl, it may be substituted with one, two, or three fluorine radicals to give —CH$_2$F, —CHF$_2$, or —CF$_3$. In other embodiments, $R^A$ is unsubstituted. In some embodiments, all $R^A$ groups are the same. In other embodiments, the $R^A$ groups are different. In some embodiments, $R^A$ is branched or unbranched $C_{1-6}$ alkyl. In certain embodiments, $R^A$ is branched $C_{1-6}$ alkyl. In certain embodiments, $R^A$ is unbranched $C_{1-6}$ alkyl. In certain embodiments, $R^A$ is $C_{1-3}$ alkyl. In certain embodiments, $R^A$ is methyl, ethyl, or propyl. In certain embodiments, $R^A$ is $C_{3-7}$ cycloalkyl. In certain embodiments, $R^A$ is cyclohexyl. In certain embodiments, $R^A$ is cyclopropyl, cyclobutyl, or cyclopentyl. In certain embodiments, $R^A$ is cycloheptyl. In some embodiments, $R^A$ is branched or unbranched $C_{4-12}$ cycloalkylalkyl.

As defined generally above, each $R^C$ is, independently, -L-N($R^D$)$_2$ or —R. In some embodiments, all $R^C$ groups are —R. In some embodiments, $R^C$ is -L-N($R^D$)$_2$.

As defined generally above, each $R^D$ is, independently, —$R^A$ or —R. In some embodiments, all $R^D$ groups are —R. In some embodiments, one $R^D$ on a nitrogen is —R, and the other is —$R^A$.

As defined generally above, each R is, independently, hydrogen or —CH$_2$CH$_2$C(=O)OR$^B$. In some embodiments, at least one R group is —CH$_2$CH$_2$C(=O)OR$^B$. In some embodiments, at least two R groups are —CH$_2$CH$_2$C(=O)OR$^B$. In some embodiments, at least three R groups are —CH$_2$CH$_2$C(=O)OR$^B$. In some embodiments, at least four R groups are —CH$_2$CH$_2$C(=O)OR$^B$. In some embodiments, all R groups are —CH$_2$CH$_2$C(=O)OR$^B$.

As defined generally above, each $R^B$ is, independently, $C_{10-14}$ alkyl, wherein $R^B$ is optionally substituted with one or more fluorine radicals. In some embodiments, $R^B$ is substituted with one or more fluorine radicals. For example, in some embodiments, $R^B$ may be substituted with one fluoro, or in other embodiments, may be perfluorinated. In other embodiments, $R^B$ is unsubstituted. In some embodiments, all $R^B$ groups are the same. In certain embodiments, $R^B$ is $C_{10}$ alkyl. In some embodiments, $R^B$ is n-decyl. In certain embodiments, $R^B$ is $C_{11}$ alkyl. In some embodiments, $R^B$ is n-undecyl. In certain embodiments, $R^B$ is $C_{12}$ alkyl. In some embodiments, $R^B$ is n-dodecyl. In certain embodiments, $R^B$ is $C_{13}$ alkyl. In some embodiments, $R^B$ is n-tridecyl. In certain embodiments, $R^B$ is $C_{14}$ alkyl. In some embodiments, $R^B$ is n-tetradecyl.

In certain embodiments, a lipidoid of the present invention is of the Formula (II-a):

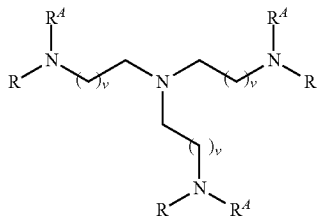

or a salt thereof,
wherein
    each v is, independently, 1, 2, or 3.
In certain embodiments, v is 1. In certain embodiments, v is 2. In certain embodiments, v is 3.
In certain embodiments, a lipidoid of the present invention is of the Formula (II-b):

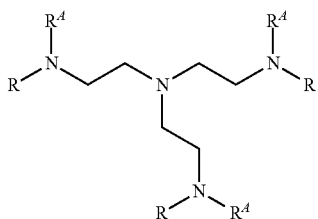

or a salt thereof, wherein $R^A$ and $R^B$ are as defined above and described herein.
In certain embodiments, a lipidoid of the present invention is of the formula:

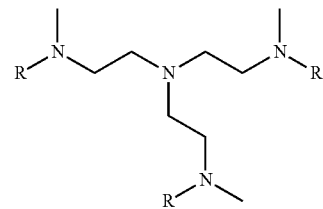

or a salt thereof, wherein $R^B$ is as defined above and described herein.
In certain embodiments, a lipidoid of the present invention is of the Formula (II-c):

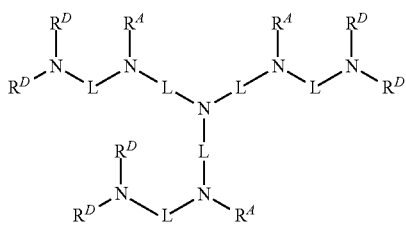

or a salt thereof, wherein L, $R^A$, and $R^D$ are as defined above and described herein.

In certain embodiments, a lipidoid of the present invention is of the Formula (II-d):

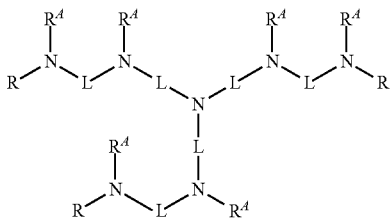

or a salt thereof, wherein L, $R^A$, and R are as defined above and described herein.
In certain embodiments, a lipidoid of the present invention is of the Formula (II-e):

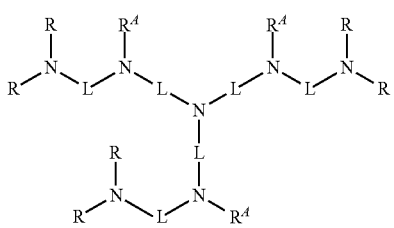

or a salt thereof, wherein L, $R^A$, and R are as defined above and described herein.
In certain embodiments, a lipidoid of the present invention is of the Formula (II-f):

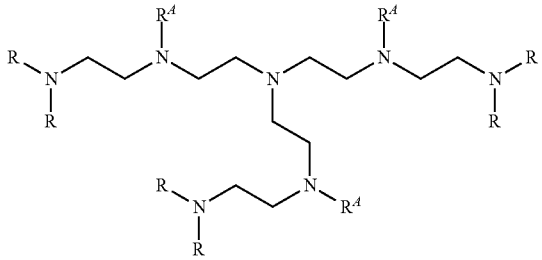

or a salt thereof, wherein $R^A$ and R are as defined above and described herein.
In certain embodiments, a lipidoid of the present invention is of the formula:

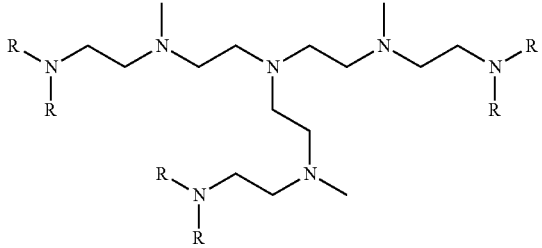

or a salt thereof, wherein R is as defined above and described herein.

In certain embodiments, a lipidoid of the present invention is of the Formula (III):

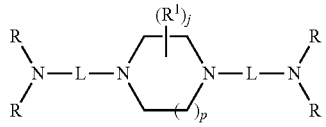

III or a salt thereof,
wherein
each L is, independently, branched or unbranched $C_{1-6}$ alkylene, wherein L is optionally substituted with one or more fluorine radicals;
each R is, independently, hydrogen or —$CH_2CH_2C(=O)OR^B$;
each $R^B$ is, independently, $C_{10-14}$ alkyl, wherein $R^B$ is optionally substituted with one or more fluorine radicals;
each $R^1$ is, independently, fluoro or $C_{1-6}$ alkyl optionally substituted with one or more fluorine radicals;
j is 0, 1, 2, 3, or 4; and
p is 1 or 2.

In certain embodiments, at least three R groups of formula (III) are —$CH_2CH_2C(=O)OR^B$.

As defined generally above, each L is, independently, branched or unbranched $C_{1-6}$ alkylene, wherein L is optionally substituted with one or more fluorine radicals. In some embodiments, L is substituted with one or more fluorine radicals. In other embodiments, L is unsubstituted. In some embodiments, L is branched. In other embodiments, L is unbranched. In certain embodiments, L is $C_{1-4}$ alkylene. In certain embodiments, L is methylene, ethylene, or propylene.

As defined generally above, each R is, independently, hydrogen or —$CH_2CH_2C(=O)OR^B$. In some embodiments, at least three R groups are —$CH_2CH_2C(=O)OR^B$. In some embodiments, at least four R groups are —$CH_2CH_2C(=O)OR^B$. In some embodiments, all R groups are —$CH_2CH_2C(=O)OR^B$.

As defined generally above, each $R^B$ is, independently, $C_{10-14}$ alkyl, wherein $R^B$ is optionally substituted with one or more fluorine radicals. In some embodiments, $R^B$ is substituted with one or more fluorine radicals. For example, in some embodiments, $R^B$ may be substituted with one fluoro, or in other embodiments, may be perfluorinated. In other embodiments, $R^B$ is unsubstituted. In some embodiments, all $R^B$ groups are the same. In certain embodiments, $R^B$ is $C_{10}$ alkyl. In some embodiments, $R^B$ is n-decyl. In certain embodiments, $R^B$ is $C_{11}$ alkyl. In some embodiments, $R^B$ is n-undecyl. In certain embodiments, $R^B$ is $C_{12}$ alkyl. In some embodiments, $R^B$ is n-dodecyl. In certain embodiments, $R^B$ is $C_{13}$ alkyl. In some embodiments, $R^B$ is n-tridecyl. In certain embodiments, $R^B$ is $C_{14}$ alkyl. In some embodiments, $R^B$ is n-tetradecyl.

In certain embodiments, p is 1. In certain embodiments, p is 2.

As defined generally above, each $R^1$ is, independently, fluoro or $C_{1-6}$ alkyl optionally substituted with one or more fluorine radicals. In some embodiments, $R^1$ is fluoro. In some embodiments, $R^1$ is $C_{1-6}$ alkyl optionally substituted with one or more fluorine radicals. In some embodiments, $R^1$ is unsubstituted $C_{1-6}$ alkyl. In some embodiments, $R^1$ is methyl or ethyl. In some embodiments, $R^1$ is —$CF_3$.

In some embodiments, j is 0. In some embodiments, j is 1. In some embodiments, j is 2. In some embodiments, j is 3. In some embodiments, j is 4.

In certain embodiments, a lipidoid of the present invention is of the Formula (III-a):

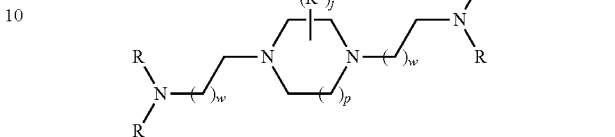

III-a or a salt thereof,
wherein p, $R^1$, j, and R are as defined above and described herein, and
each w is, independently, 1, 2, or 3.

In certain embodiments, w is 1. In certain embodiments, w is 2. In certain embodiments, w is 3.

In certain embodiments, a lipidoid of the present invention is of the Formula (III-b):

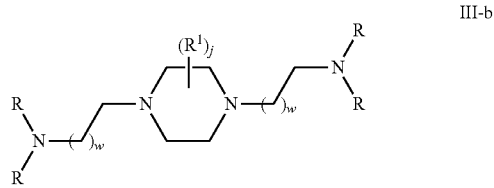

III-b or a salt thereof, wherein $R^1$, j, w, and R are as defined above and described herein.

In certain embodiments, a lipidoid of the present invention is of the Formula (III-c):

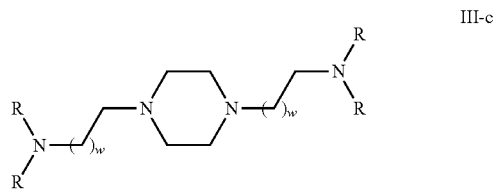

III-c wherein w and R are as defined above and described herein.

In certain embodiments, a lipidoid of the present invention is of the Formula (III-d):

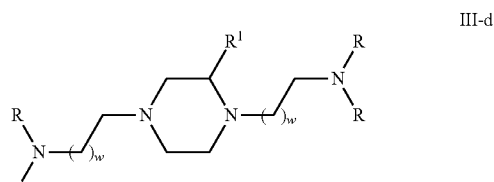

III-d wherein w, $R^1$, and R are as defined above and described herein.

In certain embodiments, a lipidoid of the present invention is of the Formula (III-e):

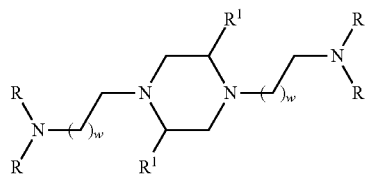

wherein w, $R^1$, and R are as defined above and described herein.

In certain embodiments, a lipidoid of the present invention is of the formula:

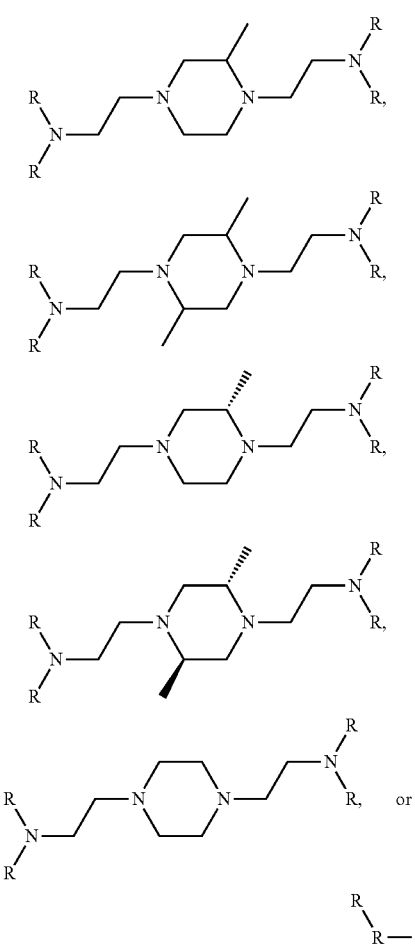

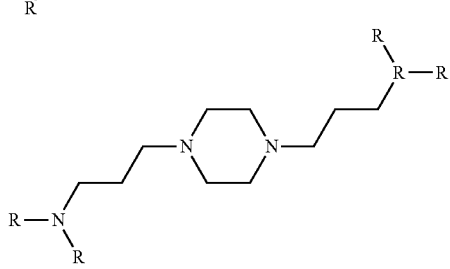

wherein R is as defined above and described herein.

In certain embodiments, a lipidoid of the present invention is of the Formula (IV):

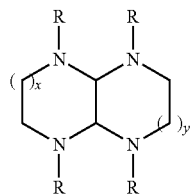

or a salt thereof, wherein each R is, independently, hydrogen or —$CH_2CH_2C(=O)OR^B$;

each $R^B$ is, independently, $C_{10-14}$ alkyl, wherein $R^B$ is optionally substituted with one or more fluorine radicals;

x is 1 or 2; and y is 1 or 2.

As defined generally above, each R is, independently, hydrogen or —$CH_2CH_2C(=O)OR^B$. In some embodiments, at least one R group is —$CH_2CH_2C(=O)OR^B$. In some embodiments, at least two R groups are —$CH_2CH_2C(=O)OR^B$. In some embodiments, at least three R groups are —$CH_2CH_2C(=O)OR^B$. In some embodiments, at least four R groups are —$CH_2CH_2C(=O)OR^B$. In some embodiments, all R groups are —$CH_2CH_2C(=O)OR^B$.

As defined generally above, each $R^B$ is, independently, $C_{10-14}$ alkyl, wherein $R^B$ is optionally substituted with one or more fluorine radicals. In some embodiments, $R^B$ is substituted with one or more fluorine radicals. For example, in some embodiments, $R^B$ may be substituted with one fluoro, or in other embodiments, may be perfluorinated. In other embodiments, $R^B$ is unsubstituted. In some embodiments, all $R^B$ groups are the same. In certain embodiments, $R^B$ is $C_{10}$ alkyl. In some embodiments, $R^B$ is n-decyl. In certain embodiments, $R^B$ is $C_{11}$ alkyl. In some embodiments, $R^B$ is n-undecyl. In certain embodiments, $R^B$ is $C_{12}$ alkyl. In some embodiments, $R^B$ is n-dodecyl. In certain embodiments, $R^B$ is $C_{13}$ alkyl. In some embodiments, $R^B$ is n-tridecyl. In certain embodiments, $R^B$ is $C_{14}$ alkyl. In some embodiments, $R^B$ is n-tetradecyl.

In some embodiments, x is 1. In some embodiments, x is 2. In some embodiments, y is 1. In some embodiments, y is 2. In some embodiments, x is 1 and y is 1. In some embodiments, x is 2 and y is 2.

In certain embodiments, a lipidoid of the present invention is of the Formula (IV-a):

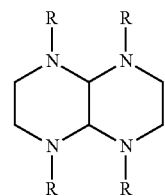

or a salt thereof, wherein R is as defined above and described herein.

In certain embodiments, a lipidoid of the present invention is of the Formula (V):

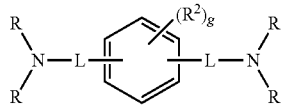

V or a salt thereof, wherein each L is, independently, branched or unbranched $C_{1-6}$ alkylene, wherein L is optionally substituted with one or more fluorine radicals;

each $R^2$ is, independently, halo, $C_{1-6}$ aliphatic optionally substituted with one or more fluorine radicals, —$OR^x$, —$N(R^y)_2$, —$SR^x$, —CN, —C(=Z)$R^y$, —C(=Z)Z$R^y$, or —ZC(=Z)Z$R^y$;

Z is O or N;

each $R^x$ is, independently, $C_{1-6}$ aliphatic;

each $R^y$ is, independently, hydrogen or $C_{1-6}$ aliphatic;

g is 0, 1, 2, 3, or 4;

each R is independently hydrogen or —$CH_2CH_2C(=O)OR^B$; and each $R^B$ is independently $C_{10-14}$ alkyl, wherein $R^B$ is optionally substituted with one or more fluorine radicals.

As defined generally above, each L is, independently, branched or unbranched $C_{1-6}$ alkylene, wherein L is optionally substituted with one or more fluorine radicals. In some embodiments, L is substituted with one or more fluorine radicals. In other embodiments, L is unsubstituted. In some embodiments, L is branched. In other embodiments, L is unbranched. In certain embodiments, L is $C_{1-4}$ alkylene. In certain embodiments, L is methylene, ethylene, or propylene.

As defined generally above, each R is, independently, hydrogen or —$CH_2CH_2C(=O)OR^B$. In some embodiments, at least one R group is —$CH_2CH_2C(=O)OR^B$. In some embodiments, at least two R groups are —$CH_2CH_2C(=O)OR^B$. In some embodiments, at least three R groups are —$CH_2CH_2C(=O)OR^B$. In some embodiments, at least four R groups are —$CH_2CH_2C(=O)OR^B$. In some embodiments, all R groups are —$CH_2CH_2C(=O)OR^B$.

As defined generally above, each $R^B$ is, independently, $C_{10-14}$ alkyl, wherein $R^B$ is optionally substituted with one or more fluorine radicals. In some embodiments, $R^B$ is substituted with one or more fluorine radicals. For example, in some embodiments, $R^B$ may be substituted with one fluoro, or in other embodiments, may be perfluorinated. In other embodiments, $R^B$ is unsubstituted. In some embodiments, all $R^B$ groups are the same. In certain embodiments, $R^B$ is $C_{10}$ alkyl. In some embodiments, $R^B$ is n-decyl. In certain embodiments, $R^B$ is $C_{11}$ alkyl. In some embodiments, $R^B$ is n-undecyl. In certain embodiments, $R^B$ is $C_{12}$ alkyl. In some embodiments, $R^B$ is n-dodecyl. In certain embodiments, $R^B$ is $C_{13}$ alkyl. In some embodiments, $R^B$ is n-tridecyl. In certain embodiments, $R^B$ is $C_{14}$ alkyl. In some embodiments, $R^B$ is n-tetradecyl.

As defined generally above, each $R^2$ is, independently, halo, $C_{1-6}$ aliphatic optionally substituted with one or more fluorine radicals, —$OR^x$, —$N(R^y)_2$, —$SR^x$, —CN, —C(=Z)$R^y$, —C(=Z)Z$R^y$, —ZC(=Z)Z$R^y$; wherein Z is O or N; each $R^x$ is, independently, $C_{1-6}$ aliphatic; and each $R^y$ is, independently, hydrogen or $C_{1-6}$ aliphatic. In some embodiments, $R^2$ is halo. In some embodiments, $R^2$ is fluoro. In some embodiments, $R^2$ is $C_{1-6}$ aliphatic optionally substituted with one or more fluorine radicals. In some embodiments, $R^2$ is $C_{1-6}$ alkyl.

In some embodiments, g is 0. In some embodiments, g is 1. In some embodiments, g is 2. In some embodiments, g is 3. In some embodiments, g is 4.

In certain embodiments, a lipidoid of the present invention is of Formula (V-a):

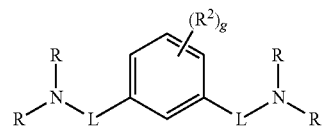

V-a or a salt thereof, wherein L, $R^2$, g, and R are as defined above and described herein.

In certain embodiments, a lipidoid of the present invention is of Formula (V-b):

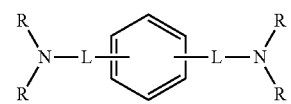

V-b or a salt thereof, wherein L and R are as defined above and described herein.

In certain embodiments, a lipidoid of the present invention is of Formula (V-c):

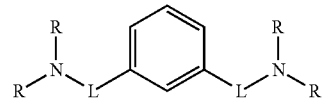

V-c or a salt thereof, wherein L and R are as defined above and described herein.

In certain embodiments, a lipidoid of the present invention is of Formula (V-d):

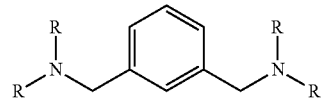

V-d or a salt thereof, wherein R is as defined above and described herein.

In certain embodiments, a lipidoid of the present invention is of the formula:

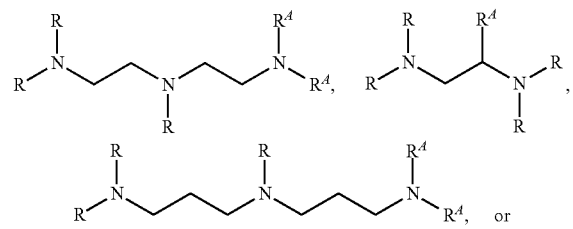

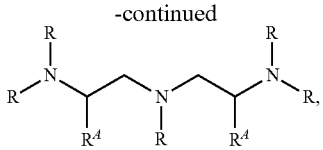

or a salt thereof, wherein each $R^A$ is, independently, branched or unbranched $C_{1-6}$ alkyl, $C_{3-7}$ cycloalkyl, or branched or unbranched $C_{4-12}$ cycloalkylalkyl, wherein $R^A$ is optionally substituted with one or more fluorine radicals;

each R is, independently, hydrogen or —CH$_2$CH$_2$C(=O)OR$^B$; and each $R^B$ is, independently, $C_{10-14}$ alkyl, wherein $R^B$ is optionally substituted with one or more fluorine radicals.

As defined generally above, each $R^A$ is, independently, branched or unbranched $C_{1-6}$ alkyl, $C_{3-7}$ cycloalkyl, or branched or unbranched $C_{4-12}$ cycloalkylalkyl, wherein $R^A$ is optionally substituted with one or more fluorine radicals. In some embodiments, $R^A$ is substituted with one or more fluorine radicals. For example, when $R^A$ is methyl, it may be substituted with one, two, or three fluorine radicals to give —CH$_2$F, —CHF$_2$, or —CF$_3$. In other embodiments, $R^A$ is unsubstituted. In some embodiments, all $R^A$ groups are the same. In other embodiments, the $R^A$ groups are different. In some embodiments, $R^A$ is branched or unbranched $C_{1-6}$ alkyl. In certain embodiments, $R^A$ is branched $C_{1-6}$ alkyl. In certain embodiments, $R^A$ is unbranched $C_{1-6}$ alkyl. In certain embodiments, $R^A$ is $C_{1-3}$ alkyl. In certain embodiments, $R^A$ is methyl, ethyl, or propyl. In certain embodiments, $R^A$ is $C_{3-7}$ cycloalkyl. In certain embodiments, $R^A$ is cyclohexyl. In certain embodiments, $R^A$ is cyclopropyl, cyclobutyl, or cyclopentyl. In certain embodiments, $R^A$ is cycloheptyl. In some embodiments, $R^A$ is branched or unbranched $C_{4-12}$ cycloalkylalkyl.

As defined generally above, each R is, independently, hydrogen or —CH$_2$CH$_2$C(=O)OR$^B$. In some embodiments, at least one R group is —CH$_2$CH$_2$C(=O)OR$^B$. In some embodiments, at least two R groups are —CH$_2$CH$_2$C(=O)OR$^B$. In some embodiments, at least three R groups are —CH$_2$CH$_2$C(=O)OR$^B$. In some embodiments, at least four R groups are —CH$_2$CH$_2$C(=O)OR$^B$. In some embodiments, all R groups are —CH$_2$CH$_2$C(=O)OR$^B$.

As defined generally above, each $R^B$ is, independently, $C_{10-14}$ alkyl, wherein $R^B$ is optionally substituted with one or more fluorine radicals. In some embodiments, $R^B$ is substituted with one or more fluorine radicals. For example, in some embodiments, $R^B$ may be substituted with one fluoro, or in other embodiments, may be perfluorinated. In other embodiments, $R^B$ is unsubstituted. In some embodiments, all $R^B$ groups are the same. In certain embodiments, $R^B$ is $C_{10}$ alkyl. In some embodiments, $R^B$ is n-decyl. In certain embodiments, $R^B$ is $C_{11}$ alkyl. In some embodiments, $R^B$ is n-undecyl. In certain embodiments, $R^B$ is $C_{12}$ alkyl. In some embodiments, $R^B$ is n-dodecyl. In certain embodiments, $R^B$ is $C_{13}$ alkyl. In some embodiments, $R^B$ is n-tridecyl. In certain embodiments, $R^B$ is $C_{14}$ alkyl. In some embodiments, $R^B$ is n-tetradecyl.

In certain embodiments, a lipidoid of the present invention is of the formula:

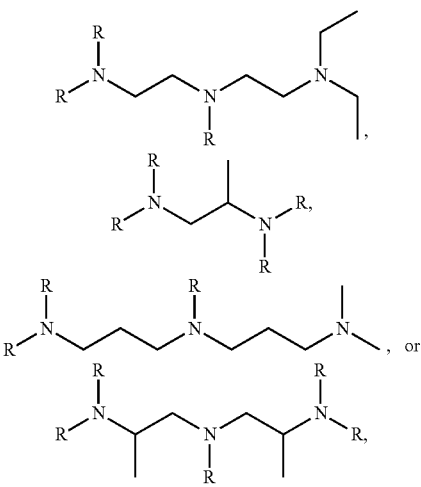

or a salt thereof, wherein R is as defined above and described herein.

Figure 2:
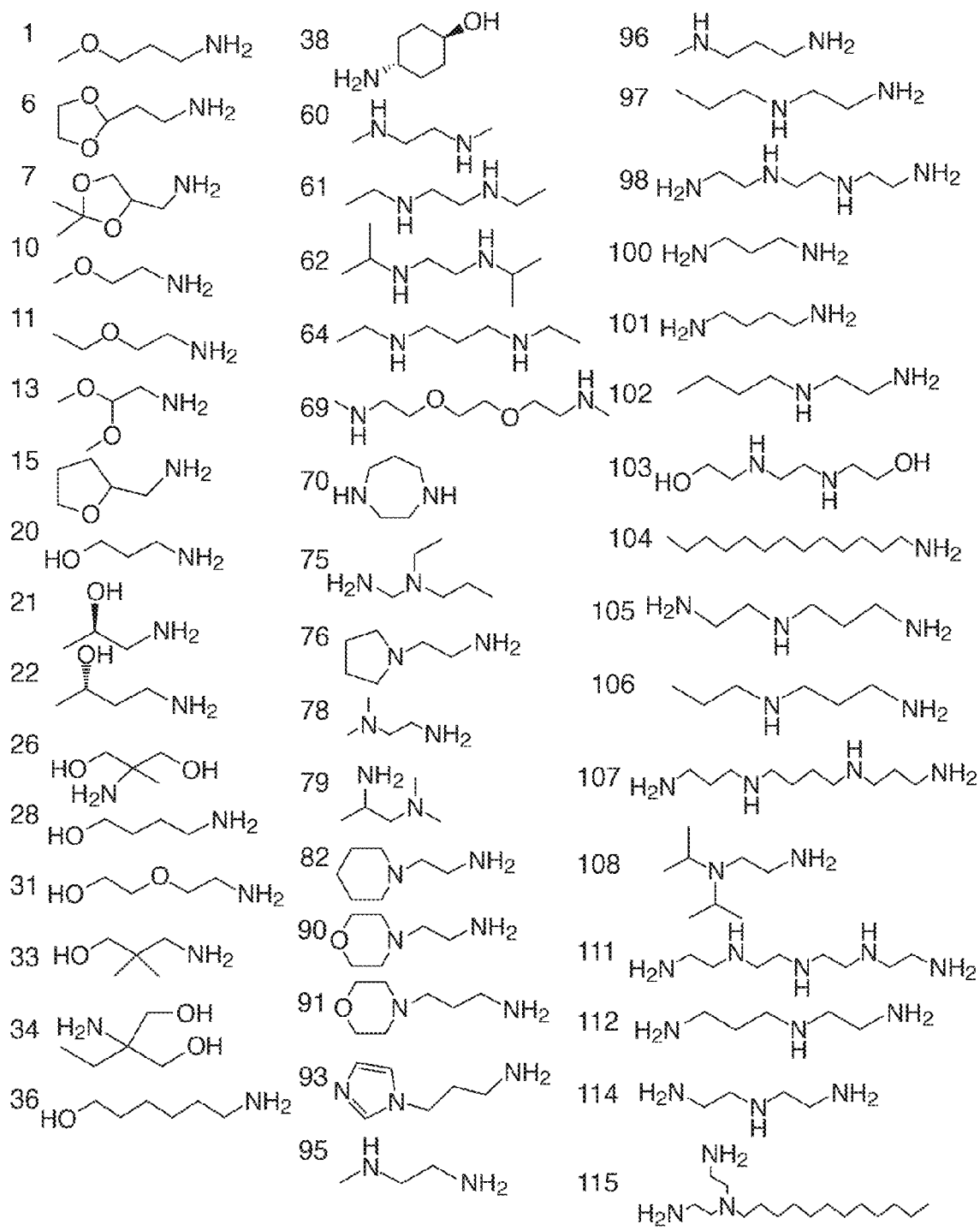
FIG. 2 shows additional alkylamines used in the lipidoid library.
Figure 2:
Figure 2:
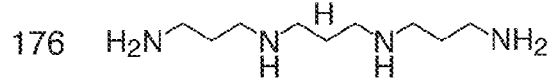
Figure 2:
Figure 2:
Figure 2:
Figure 2:
Figure 2:
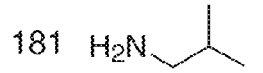
Figure 2:
Figure 2:
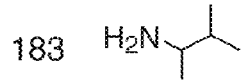
Figure 2:
Figure 2:
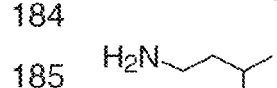
Figure 2:
Figure 2:
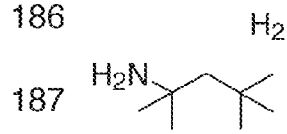
Figure 2:
Figure 2:
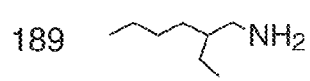
Figure 2:
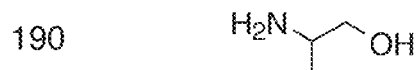
Figure 2:
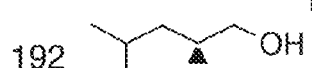
Figure 2:
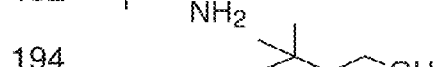
Figure 2:
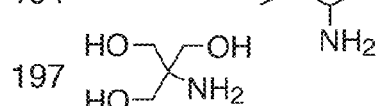
Figure 2:
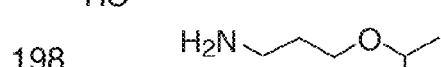
Figure 2:
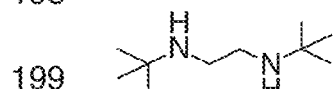
Figure 2:
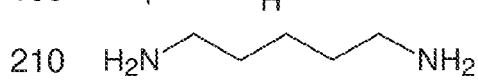
Figure 2:
Figure 2:
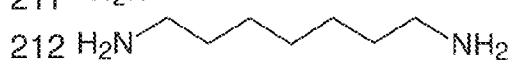
Figure 2:
Figure 2:
Figure 2:
Figure 2:
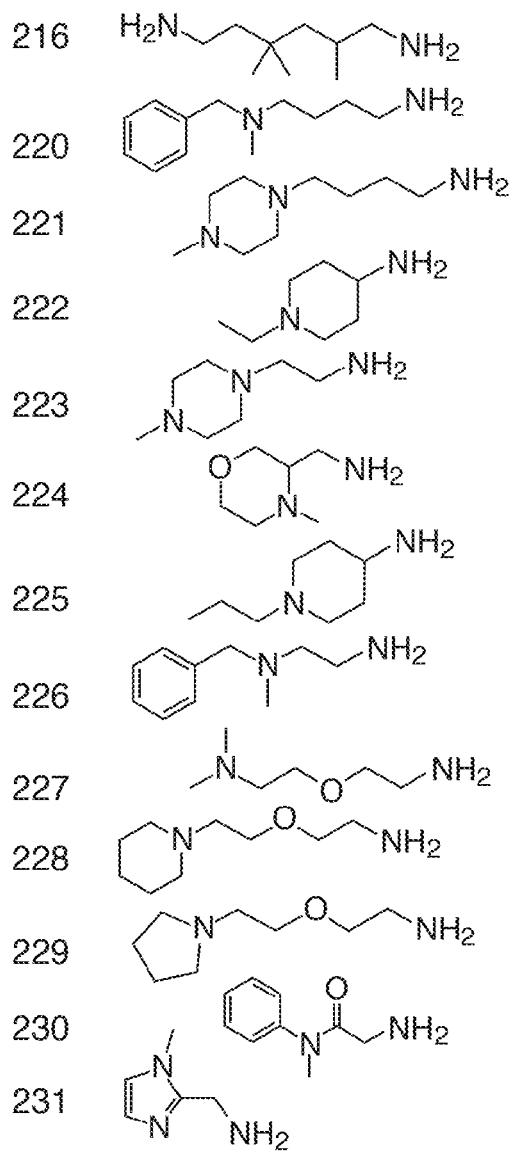
Figure 2:
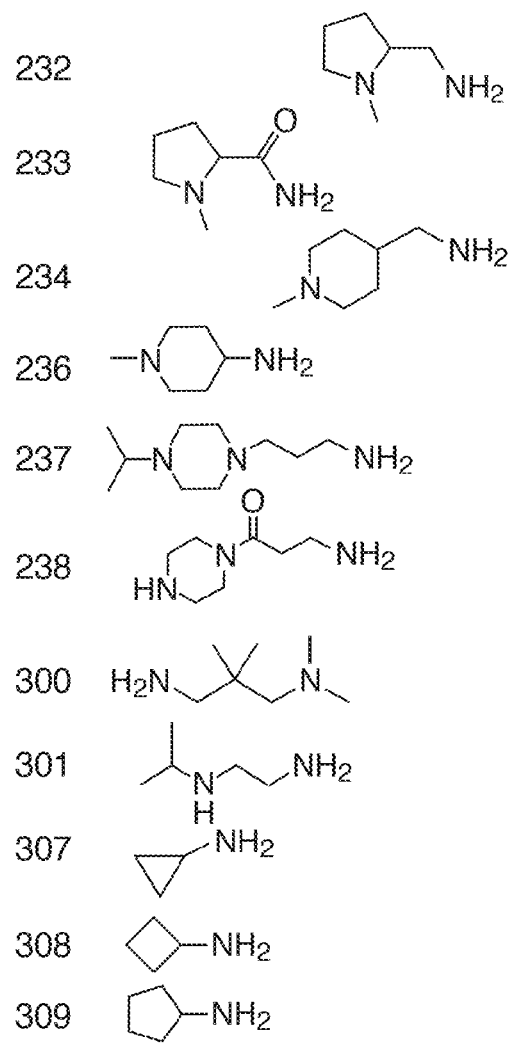
Figure 2:
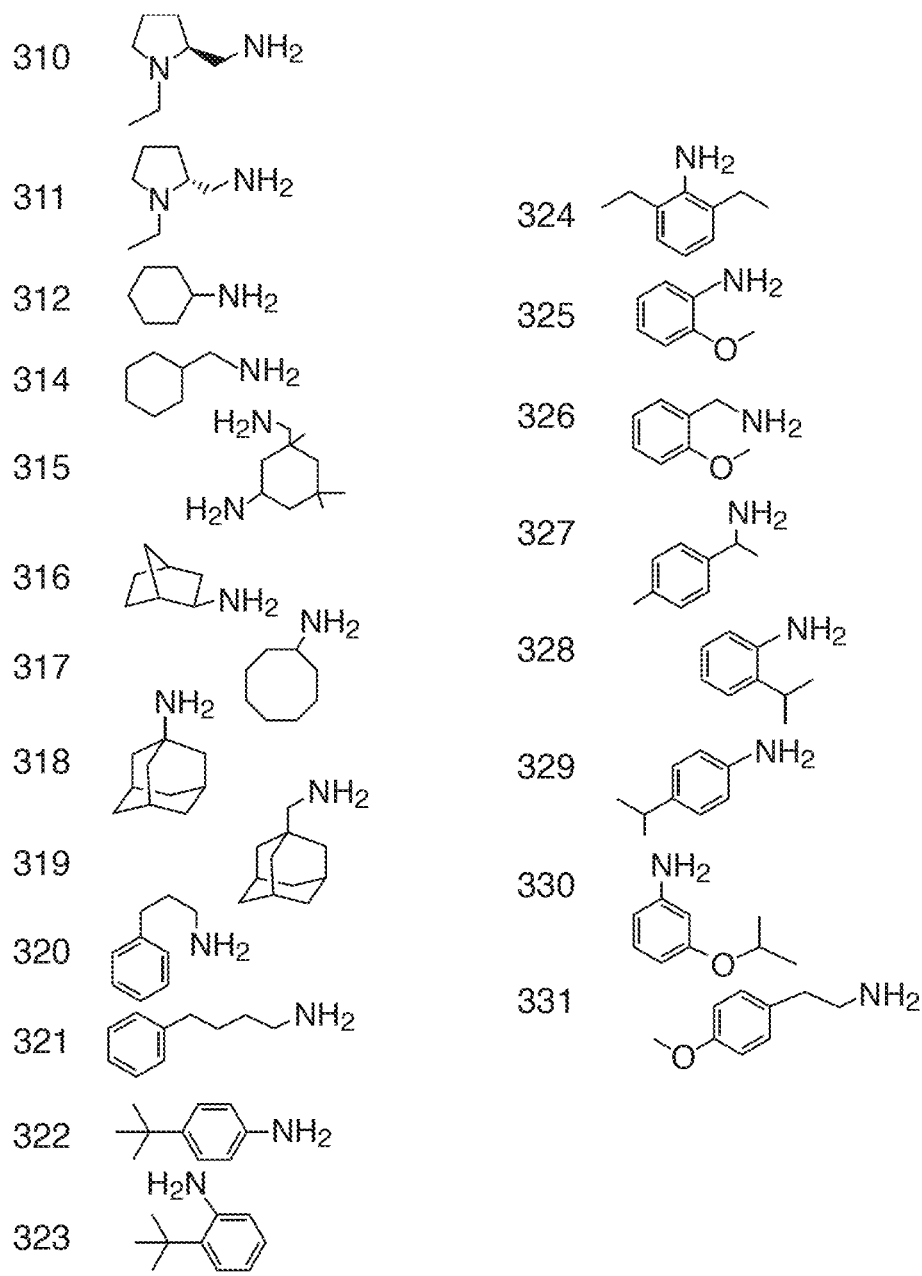
Figure 2:
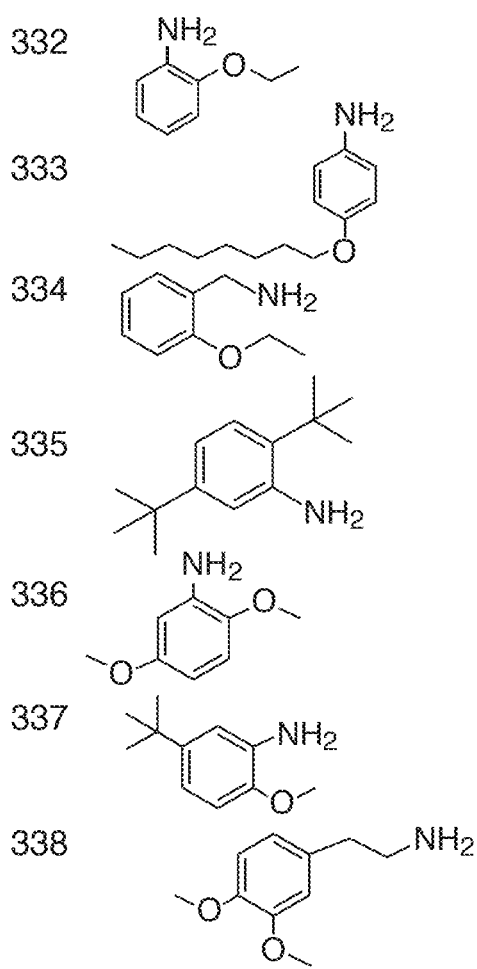
Figure 2:
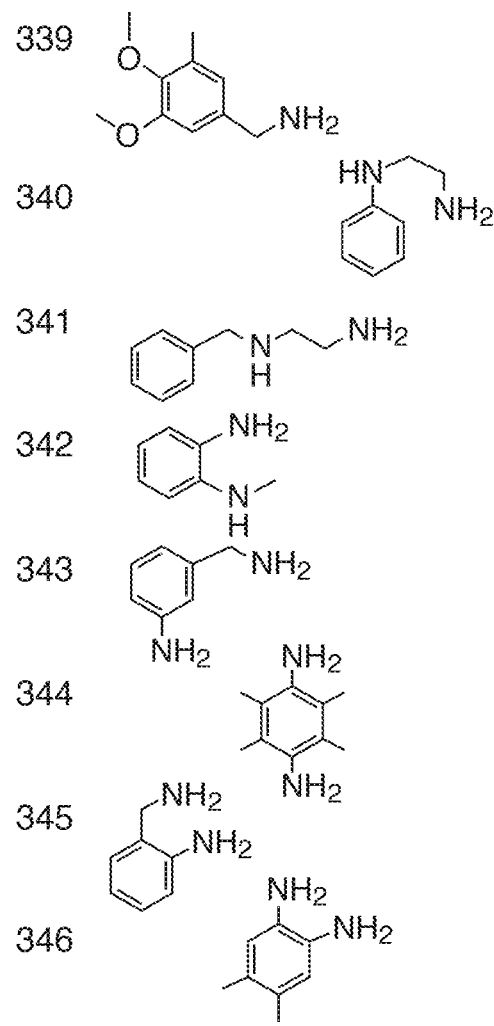
Figure 2:
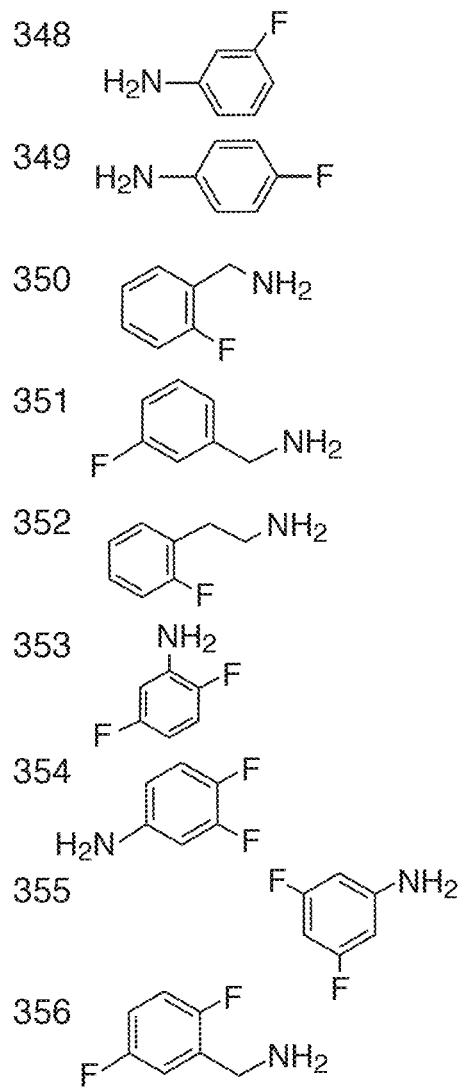
Figure 2:
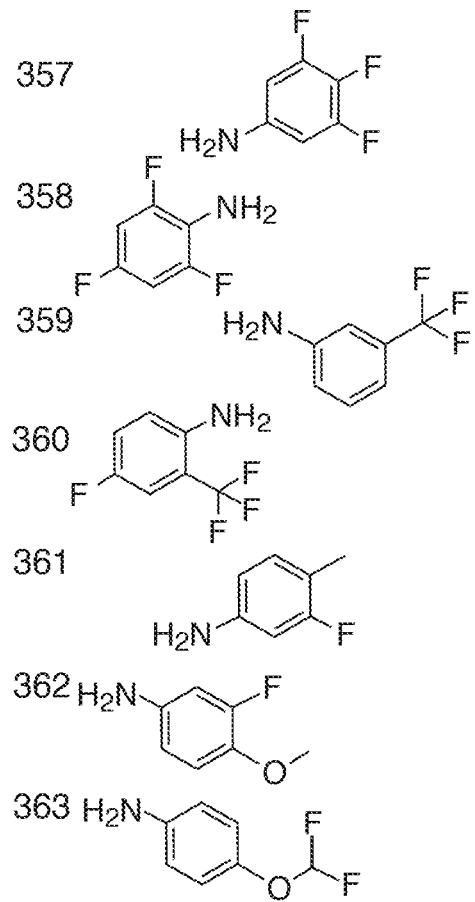
Figure 2:
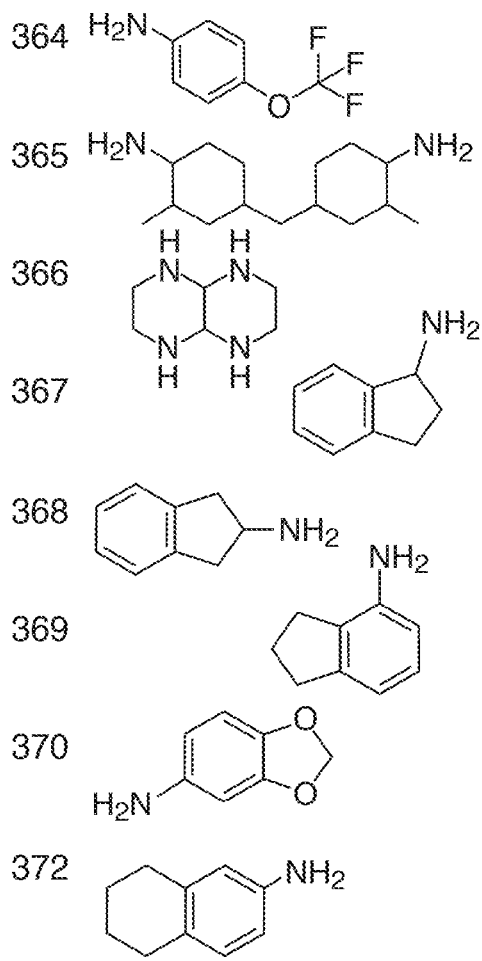
Figure 2:
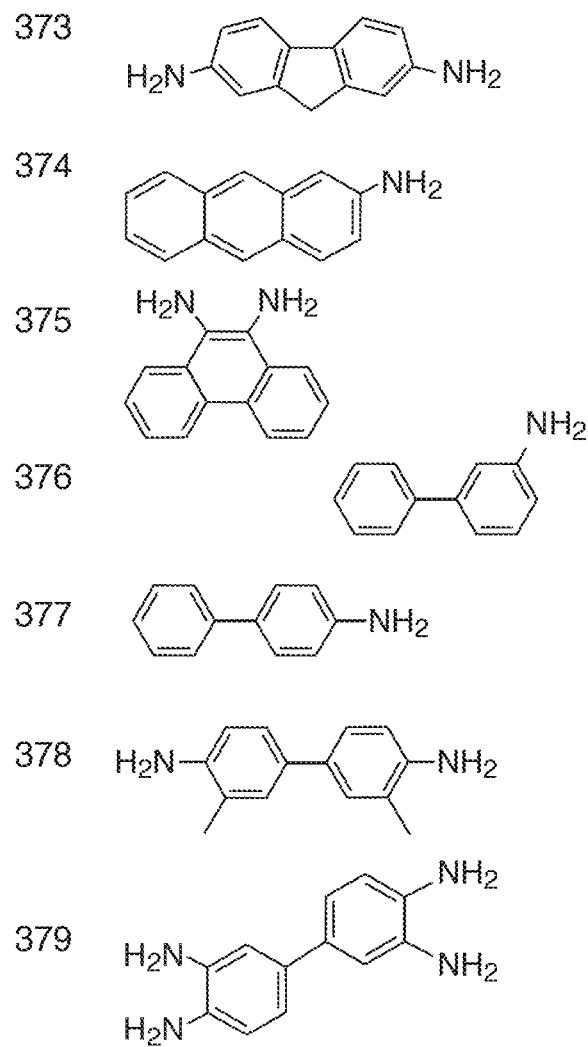
Figure 2:
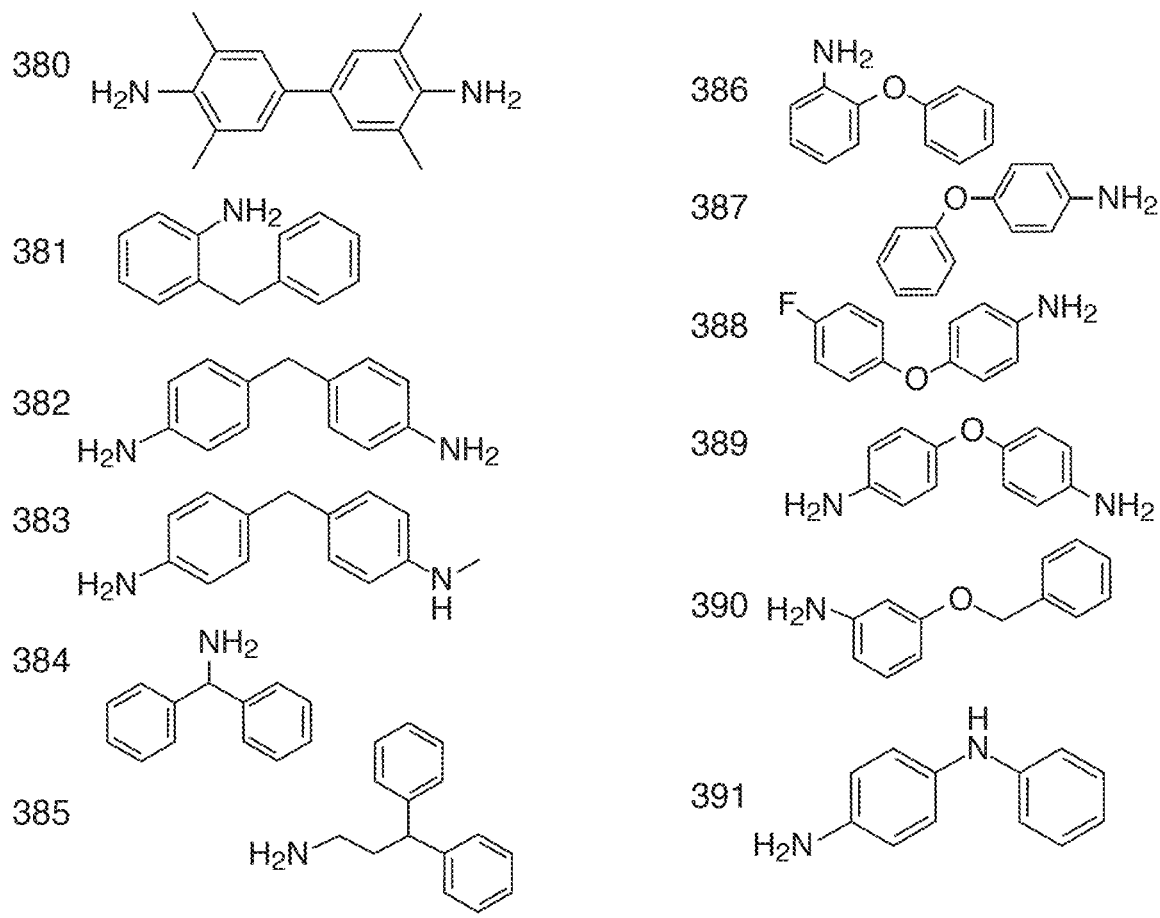
Figure 2:
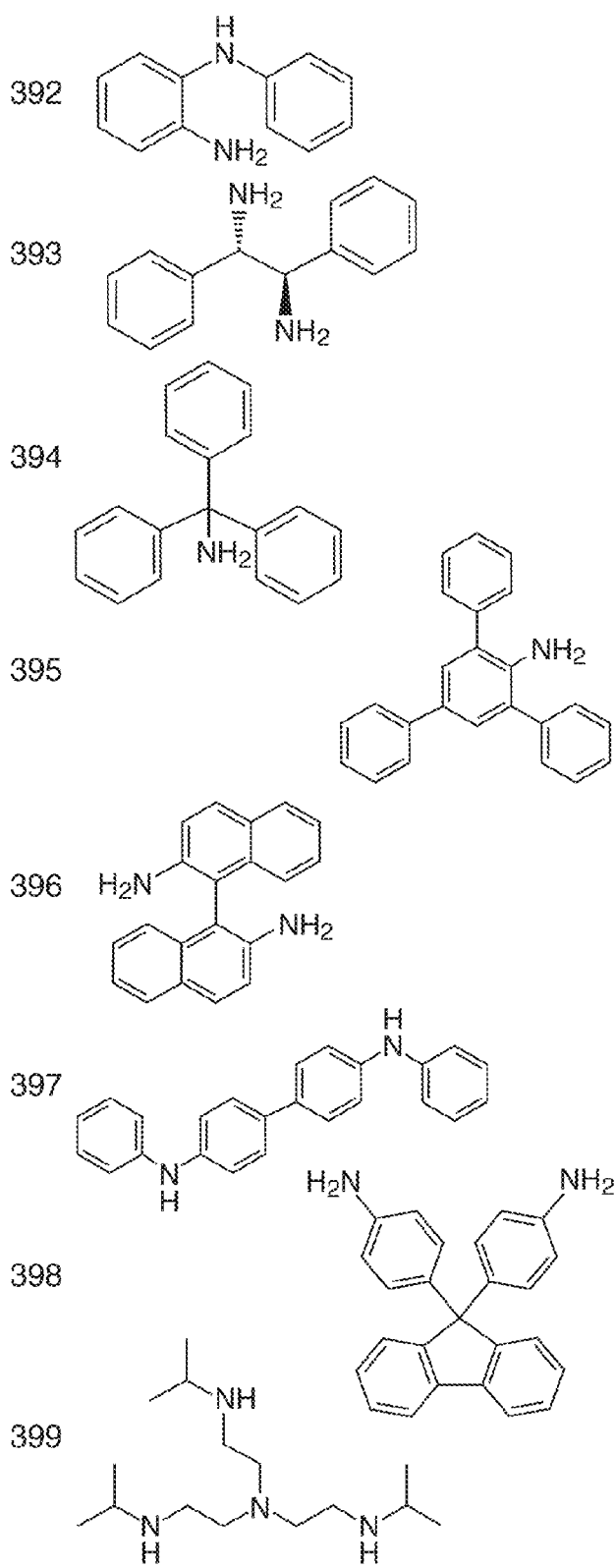

In some embodiments, a lipidoid of the present invention is a compound resulting from a Michael addition between any one of the amines shown in FIG. 1 or FIG. 2 and an acrylate shown in FIG. 1. In certain embodiments, the number of equivalents of acrylate can be controlled to obtain the desired number of lipid tails on the inventive lipidoid.

In certain embodiments, an inventive lipidoid is prepared by reacting amine 113 with acrylate $O_{10}$, $O_{11}$, $O_{12}$, $O_{13}$, or $O_{14}$ to form compound 113$O_{10}$, 113$O_{11}$, 113$O_{12}$, 113$O_{13}$, or 113$O_{14}$. In certain embodiments, an inventive lipidoid is of one of the formulae below:

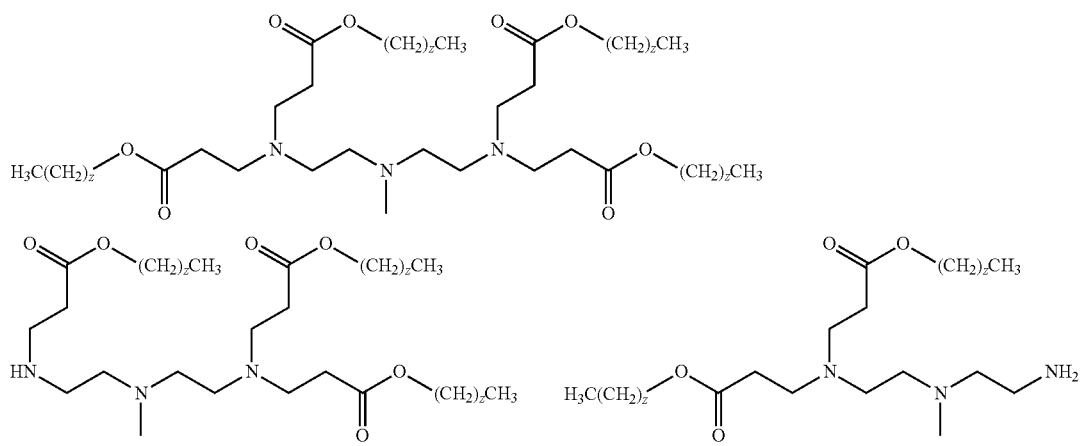

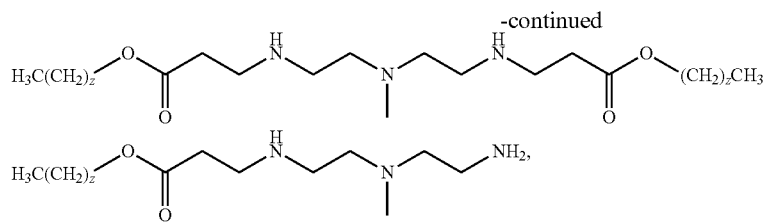

wherein z is 11 or 12.

In some embodiments, the present invention provides a composition of one or more of the above lipidoids. In certain embodiments, an inventive lipidoid is of the formula:

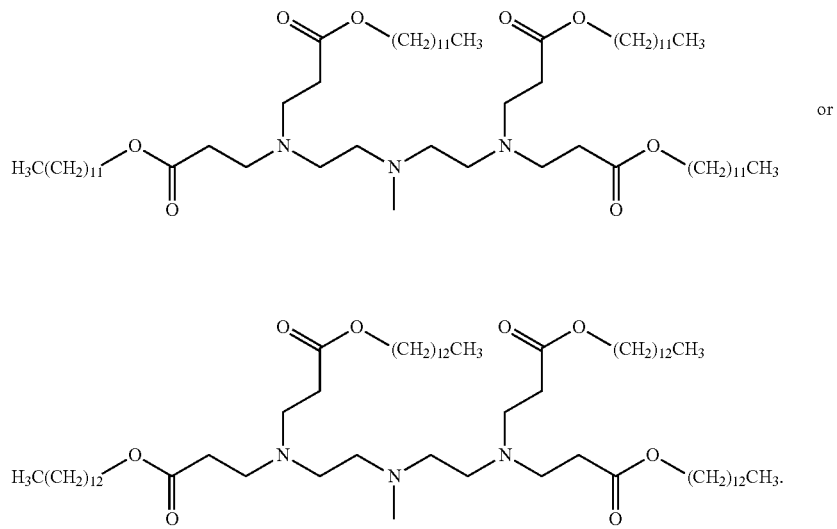

or

In certain embodiments, an inventive lipidoid is prepared by reacting amine 123 with acrylate $O_{10}$, $O_{11}$, $O_{12}$, $O_{13}$, or $O_{14}$ to form compound $123O_{10}$, $123O_{11}$, $123O_{12}$, $123O_{13}$, or $123O_{14}$. In certain embodiments, an inventive lipidoid is of one of the formulae below:

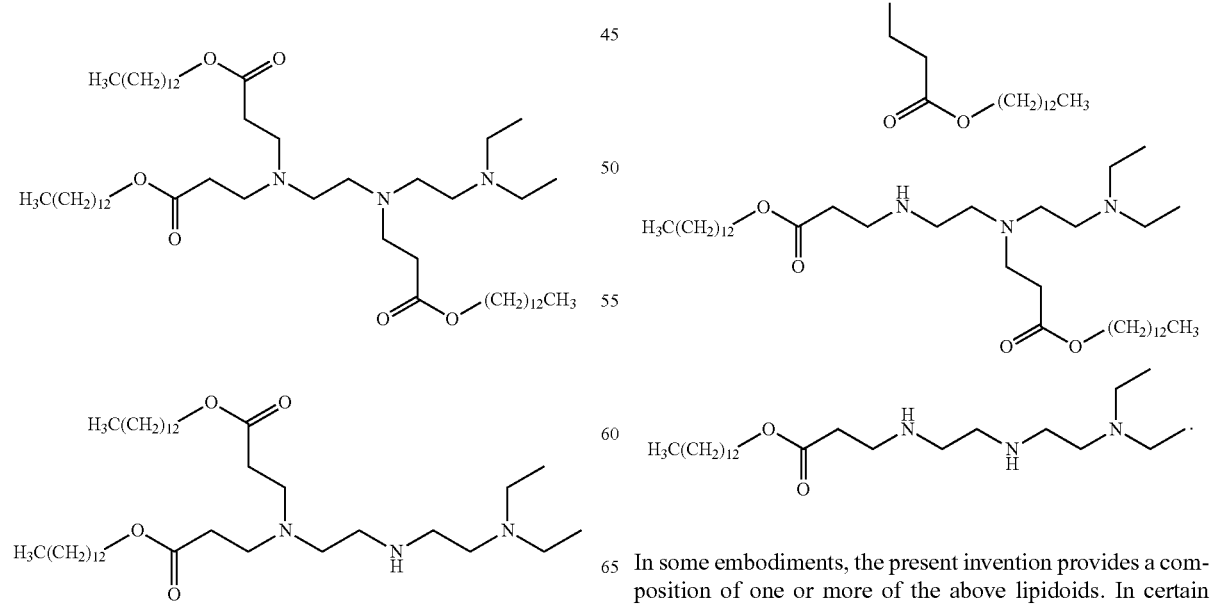

In some embodiments, the present invention provides a composition of one or more of the above lipidoids. In certain embodiments, an inventive lipidoid is of the formula:

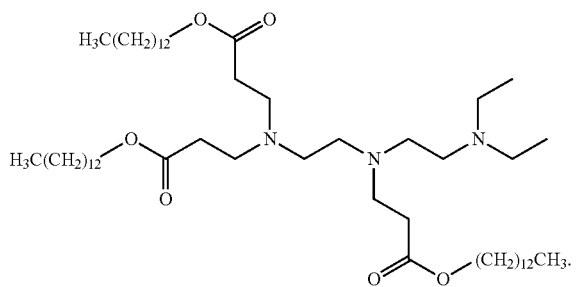

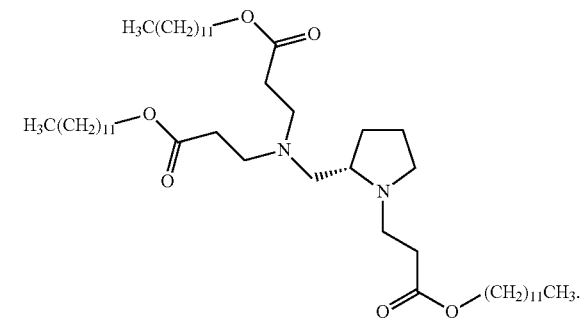

In certain embodiments, an inventive lipidoid is prepared by reacting amine 154 with acrylate $O_{10}$, $O_n$, $O_{12}$, $O_{13}$, or $O_{14}$ to form compound $154O_{10}$, $154O_{11}$, $154O_{12}$, $154O_{13}$, or $154O_{14}$. In certain embodiments, an inventive lipidoid is of one of the formulae below:

In certain embodiments, an inventive lipidoid is prepared by reacting amine 191 with acrylate $O_{10}$, $O_{11}$, $O_{12}$, $O_{13}$, or $O_{14}$ to form compound $191O_{10}$, $191O_{11}$, $191O_{12}$, $191O_{13}$, or $191O_{14}$. In certain embodiments, an inventive lipidoid is of one of the formulae below:

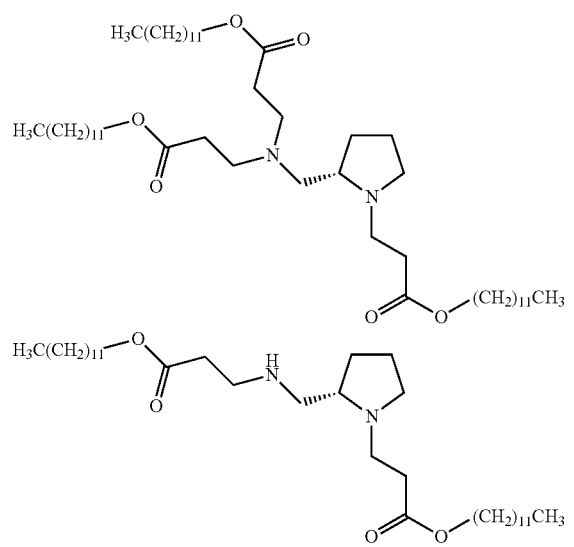

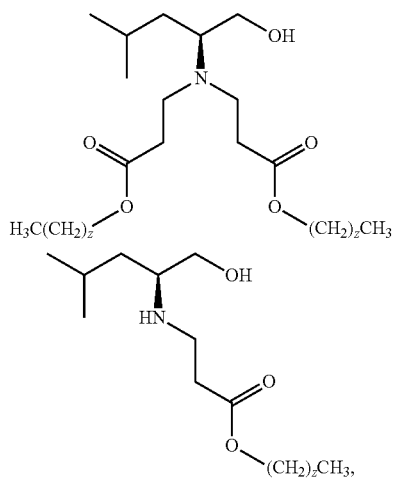

wherein z is 10, 11, or 13.

In some embodiments, the present invention provides a composition of one or more of the above lipidoids. In certain embodiments, an inventive lipidoid is of the formula:

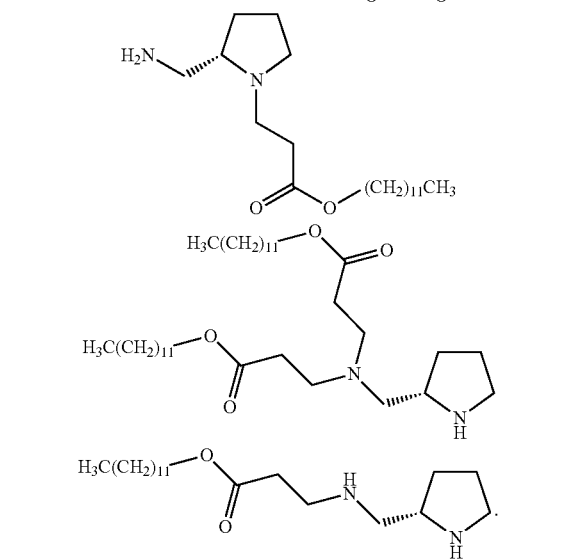

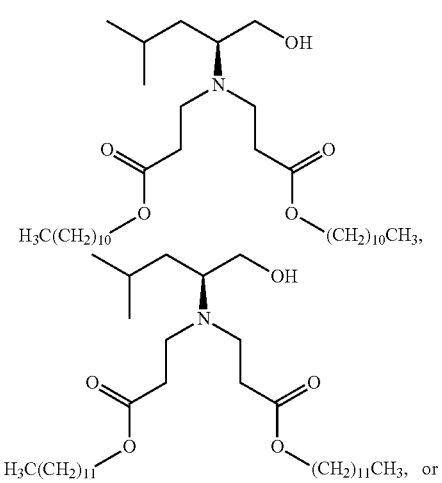

In some embodiments, the present invention provides a composition of one or more of the above lipidoids. In certain embodiments, an inventive lipidoid is of the formula:

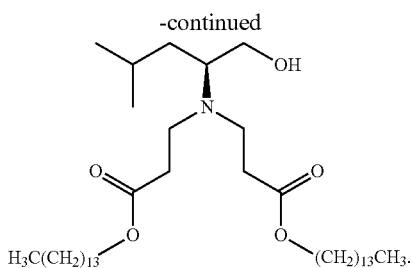

In certain embodiments, an inventive lipidoid is prepared by reacting amine 192 with acrylate $O_{10}$, $O_n$, $O_{12}$, $O_{13}$, or $O_{14}$ to form compound $192O_{10}$, $192O_{11}$, $192O_{12}$, $192O_{13}$, or $192O_{14}$. In certain embodiments, an inventive lipidoid is of one of the formulae below:

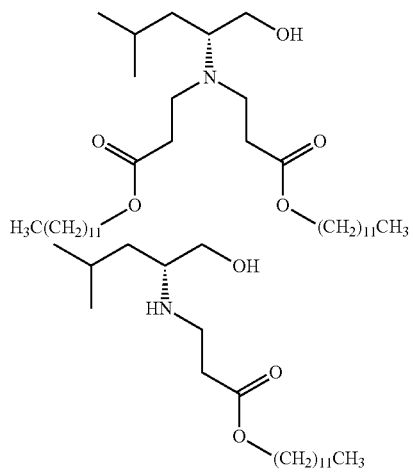

In some embodiments, the present invention provides a composition of one or more of the above lipidoids. In certain embodiments, an inventive lipidoid is of the formula:

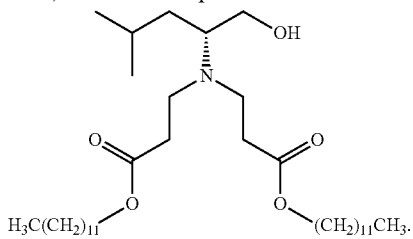

In certain embodiments, an inventive lipidoid is prepared by reacting amine 193 with acrylate $O_{10}$, $O_{11}$, $O_{12}$, $O_{13}$, or $O_{14}$ to form compound $193O_{10}$, $193O_{11}$, $193O_{12}$, $193O_{13}$, or $193O_{14}$. In certain embodiments, an inventive lipidoid is of one of the formulae below:

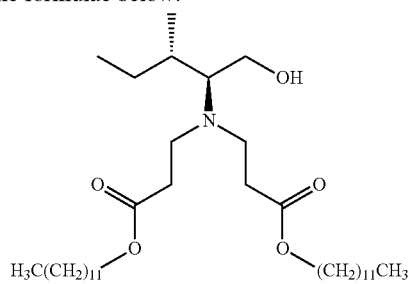

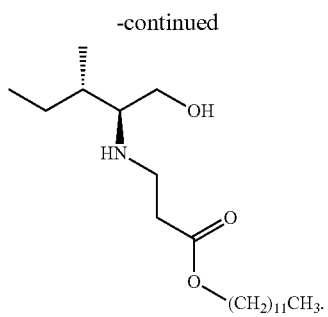

In some embodiments, the present invention provides a composition of one or more of the above lipidoids. In certain embodiments, an inventive lipidoid is of the formula:

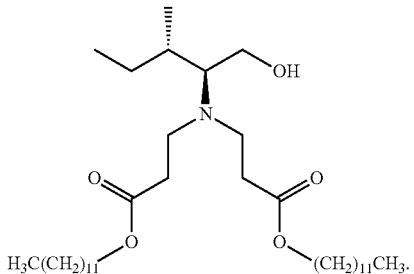

In certain embodiments, an inventive lipidoid is prepared by reacting amine 195 with acrylate $O_{10}$, $O_{11}$, $O_{12}$, $O_{13}$, or $O_{14}$ to form compound $195O_{10}$, $195O_{11}$, $195O_{12}$, $195O_{13}$, or $195O_{14}$ In certain embodiments, an inventive lipidoid is of one of the formulae below:

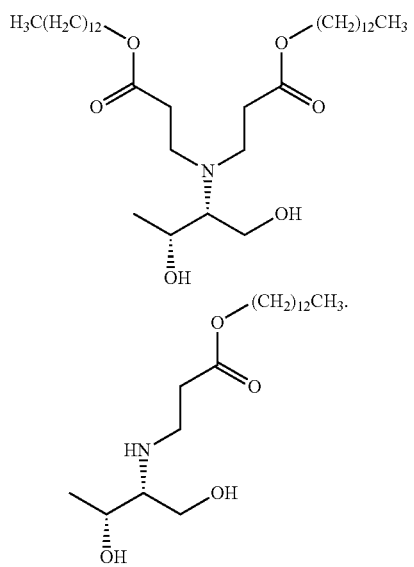

In some embodiments, the present invention provides a composition of one or more of the above lipidoids. In certain embodiments, an inventive lipidoid is of the formula:

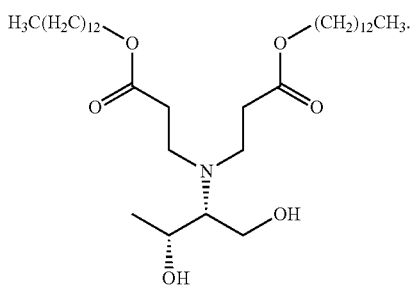

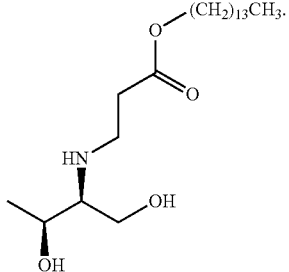

-continued

In some embodiments, the present invention provides a composition of one or more of the above lipidoids. In certain embodiments, an inventive lipidoid is of the formula:

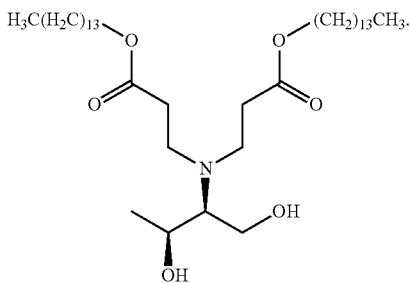

In certain embodiments, an inventive lipidoid is prepared by reacting amine 196 with acrylate $O_{10}$, $O_{11}$, $O_{12}$, $O_{13}$, or $O_{14}$ to form compound $196O_{10}$, $196O_{11}$, $196O_{12}$, $196O_{13}$, or $196O_{14}$. In certain embodiments, an inventive lipidoid is of one of the formulae below:

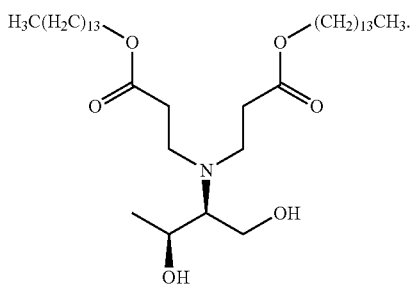

In certain embodiments, an inventive lipidoid is prepared by reacting amine 200 with acrylate $O_{10}$, $O_{11}$, $O_{12}$, $O_{13}$, or $O_{14}$ to form compound $200O_{10}$, $200O_{11}$, $200O_{12}$, $200O_{13}$, or $200O_{14}$. In certain embodiments, an inventive lipidoid is of one of the formulae below:

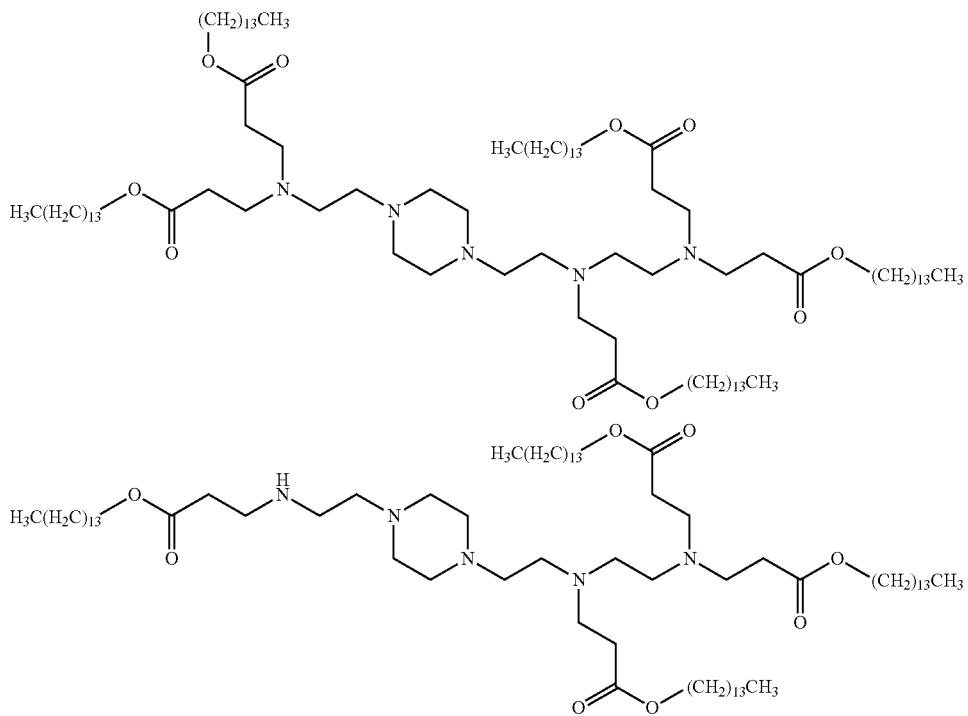

-continued
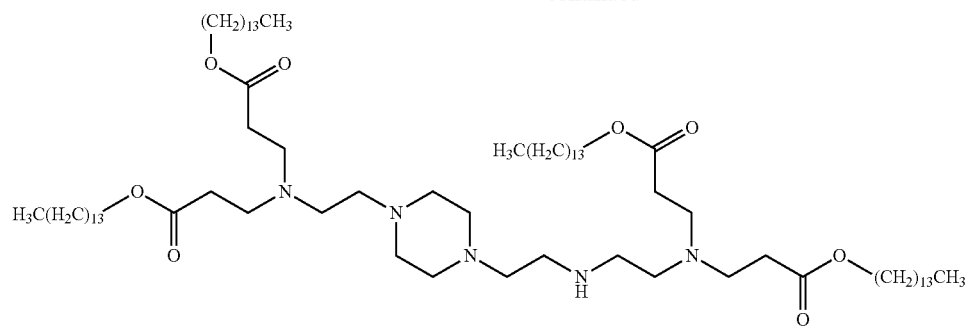
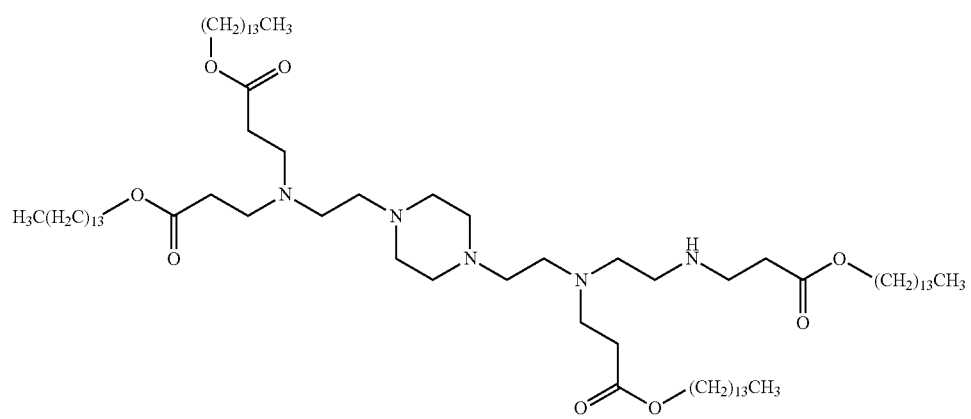
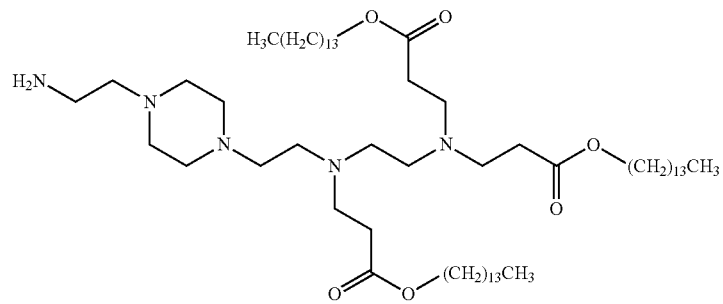
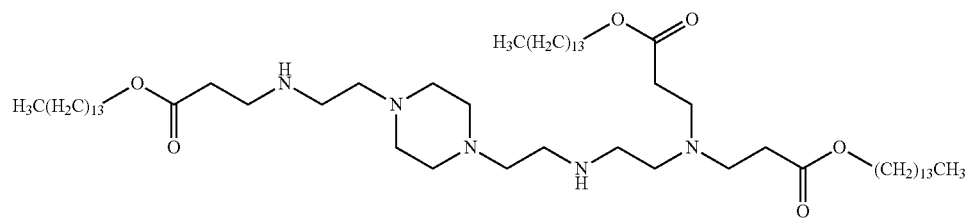
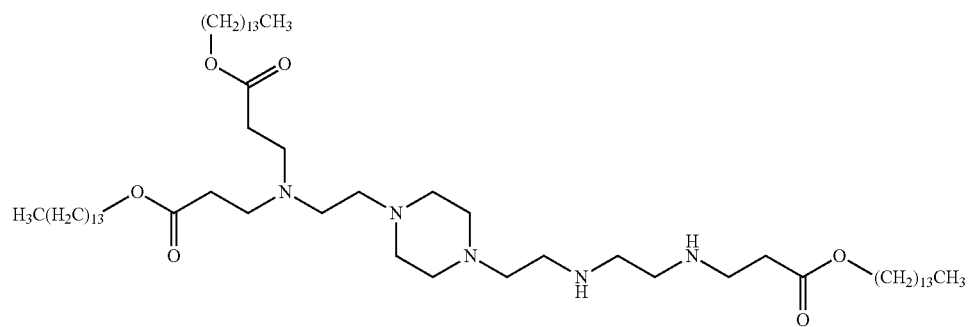

-continued
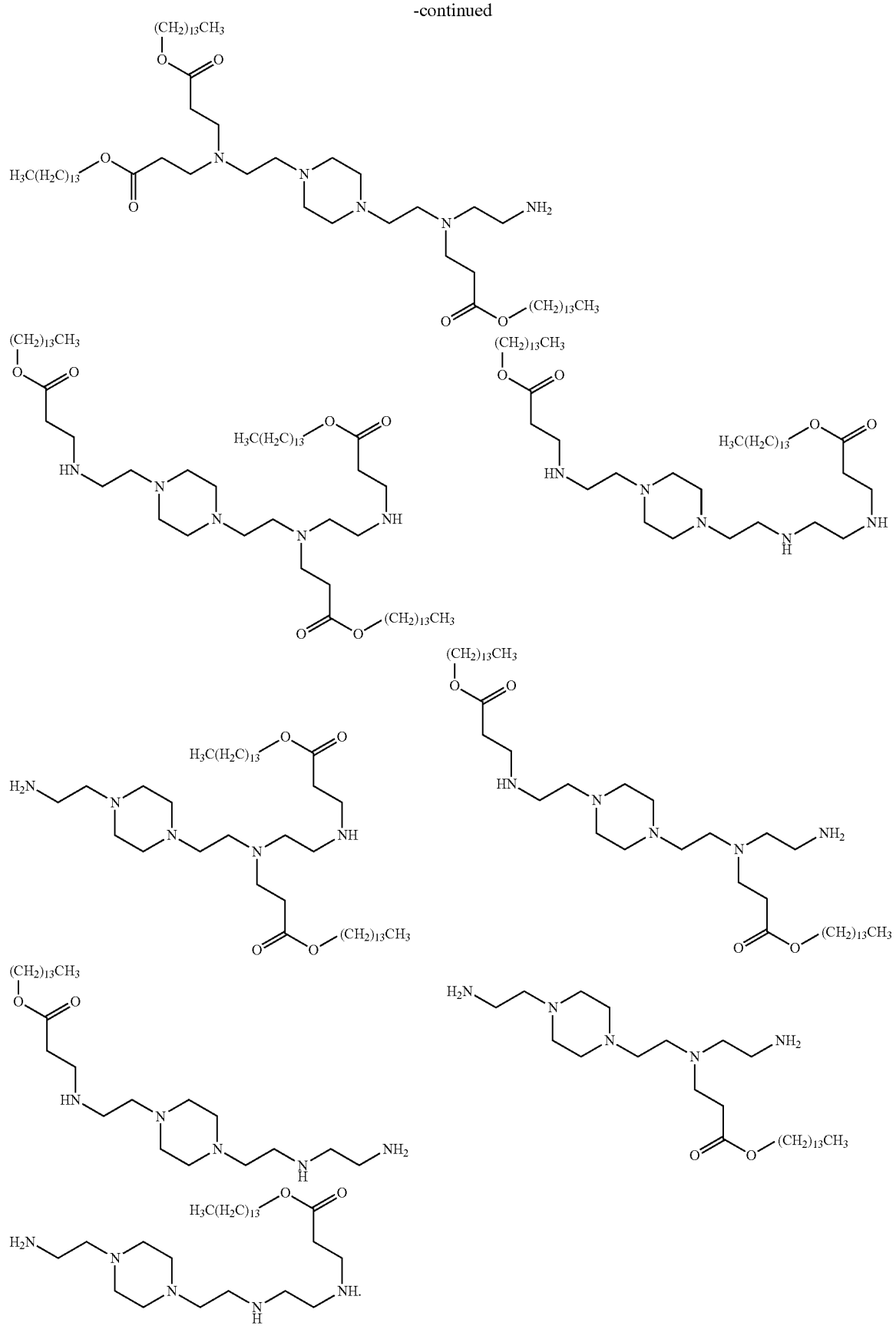

In some embodiments, the present invention provides a composition of one or more of the above lipidoids. In certain embodiments, an inventive lipidoid is of the formula:

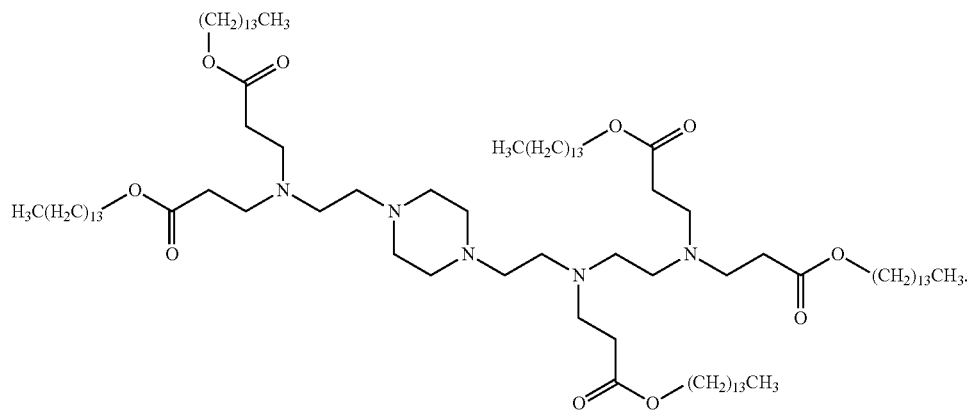

In certain embodiments, an inventive lipidoid is prepared by reacting amine 205 with acrylate $O_{10}$, $O_{11}$, $O_{12}$, $O_{13}$, or $O_{14}$ to form compound $205O_{10}$, $205O_{11}$, $205O_{12}$, $205O_{13}$, or $205O_{14}$. In certain embodiments, an inventive lipidoid is of one of the formulae below:

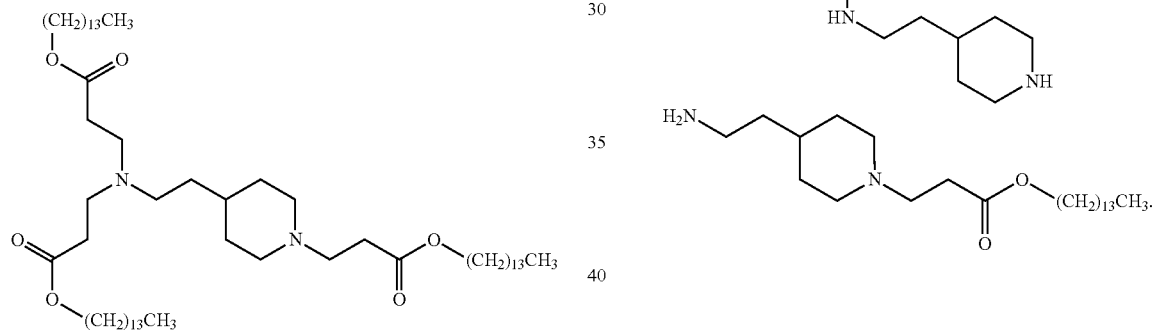

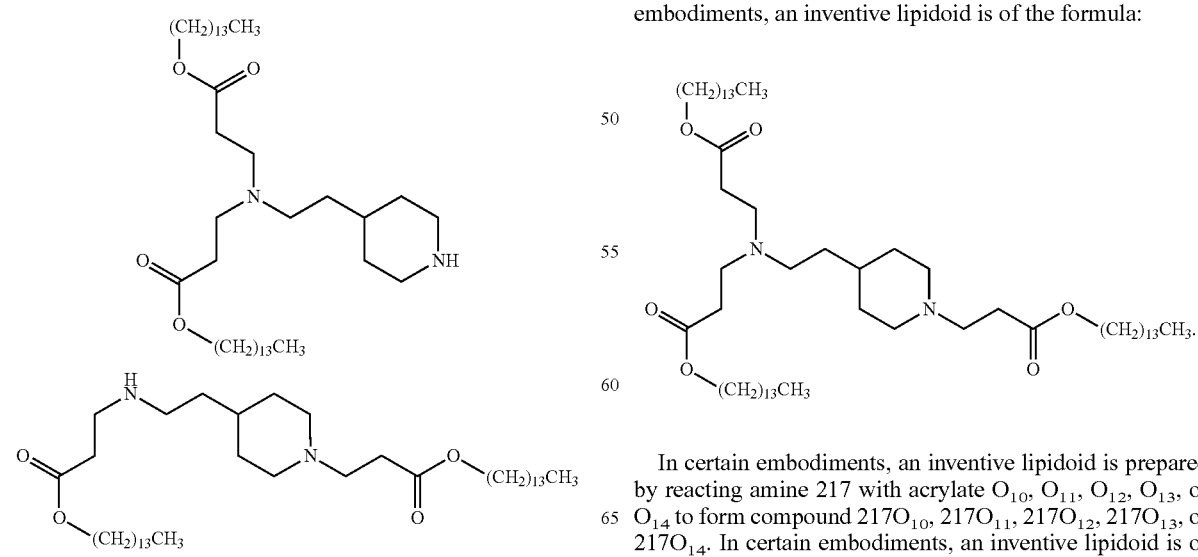

In some embodiments, the present invention provides a composition of one or more of the above lipidoids. In certain embodiments, an inventive lipidoid is of the formula:

In certain embodiments, an inventive lipidoid is prepared by reacting amine 217 with acrylate $O_{10}$, $O_{11}$, $O_{12}$, $O_{13}$, or $O_{14}$ to form compound $217O_{10}$, $217O_{11}$, $217O_{12}$, $217O_{13}$, or $217O_{14}$. In certain embodiments, an inventive lipidoid is of one of the formulae below:

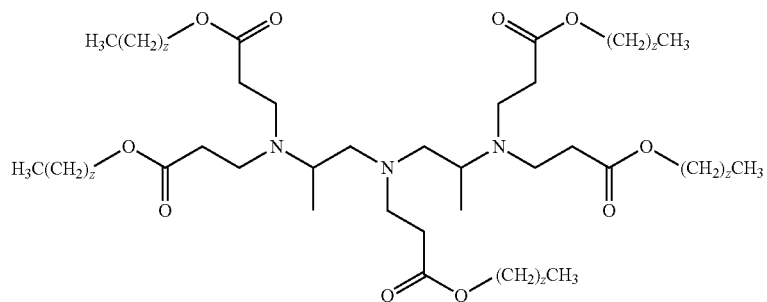
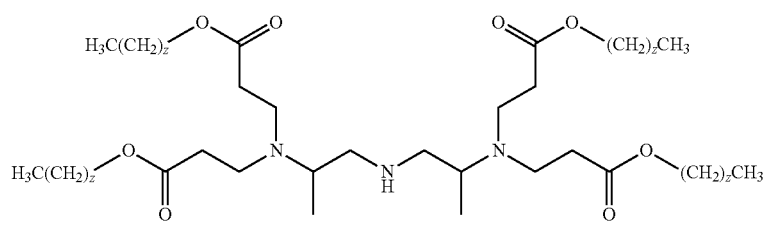
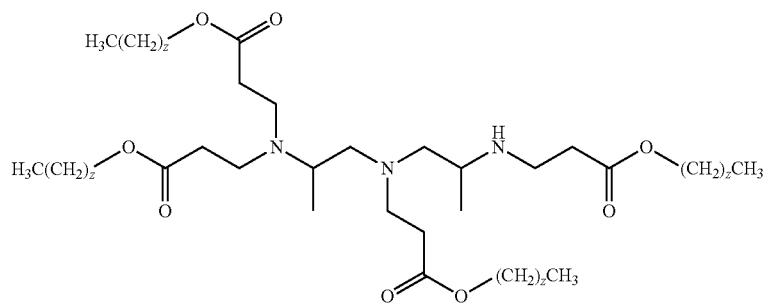
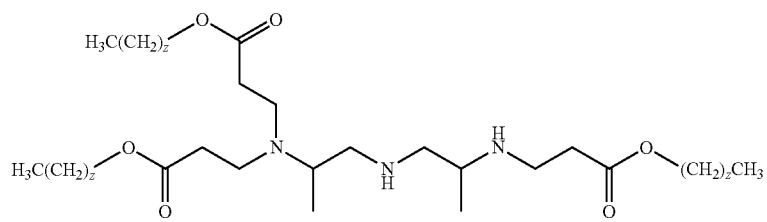
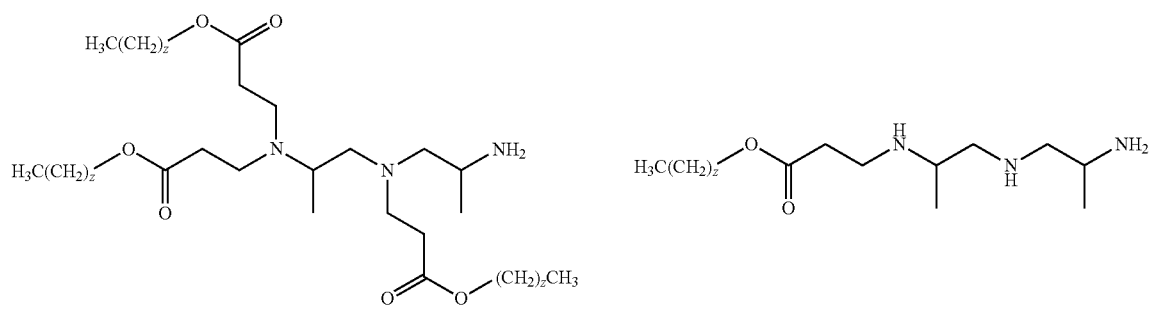
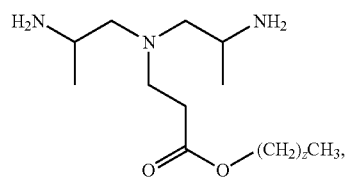
wherein z is 11 or 12.

In some embodiments, the present invention provides a composition of one or more of the above lipidoids. In certain embodiments, an inventive lipidoid is of the formula:

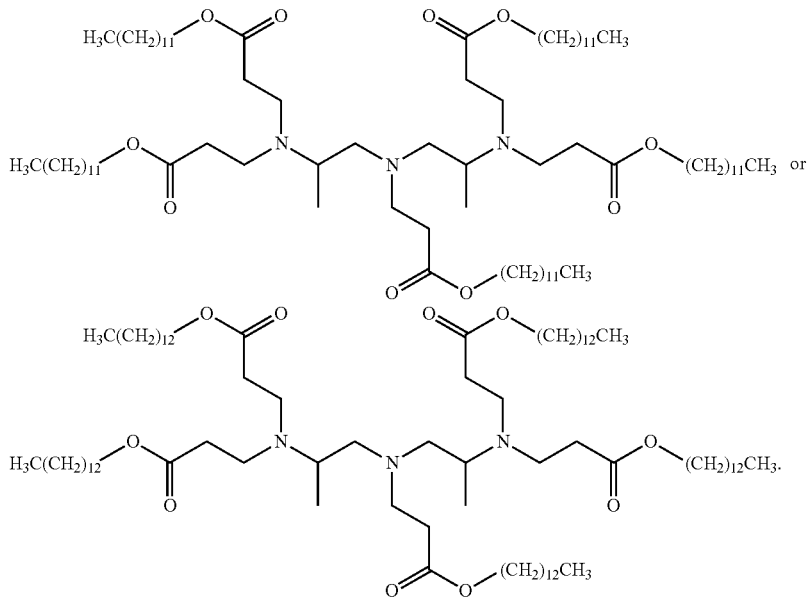

In certain embodiments, an inventive lipidoid is prepared by reacting amine 218 with acrylate $O_{10}$, $O_{11}$, $O_{12}$, $O_{13}$, or $O_{14}$ to form compound $218O_{10}$, $218O_{11}$, $218O_{12}$, $218O_{13}$, or $218O_{14}$. In certain embodiments, an inventive lipidoid is of one of the formulae below:

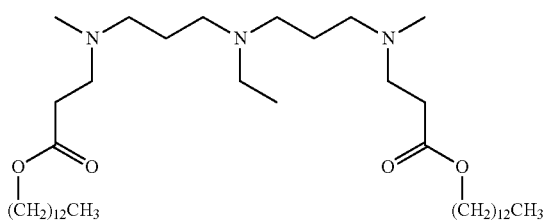

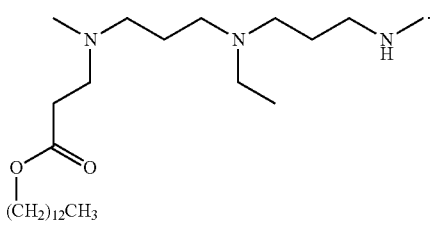

In certain embodiments, an inventive lipidoid is prepared by reacting amine 232 with acrylate $O_{10}$, $O_n$, $O_{12}$, $O_{13}$, or $O_{14}$ to form compound $232O_{10}$, $232O_{11}$, $232O_{12}$, $232O_{13}$, or $232O_{14}$. In certain embodiments, an inventive lipidoid is of one of the formulae below:

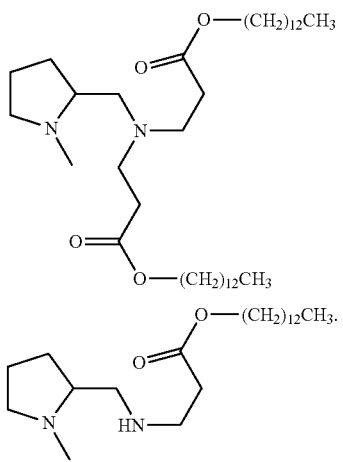

In some embodiments, the present invention provides a composition of one or more of the above lipidoids. In certain embodiments, an inventive lipidoid is of the formula:

In some embodiments, the present invention provides a composition of one or more of the above lipidoids. In certain embodiments, an inventive lipidoid is of the formula:

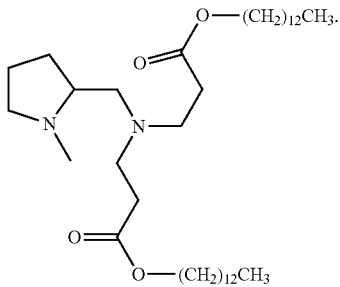

In certain embodiments, an inventive lipidoid is prepared by reacting amine 235 with acrylate $O_{10}$, $O_n$, $O_{12}$, $O_{13}$, or $O_{14}$ to form compound $235O_{10}$, $235O_{11}$, $235O_{12}$, $235O_{13}$, or $235O_{14}$. In certain embodiments, an inventive lipidoid is of one of the formulae below:

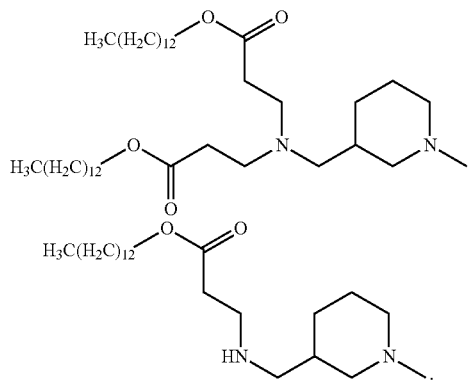

In some embodiments, the present invention provides a composition of one or more of the above lipidoids. In certain embodiments, an inventive lipidoid is of the formula:

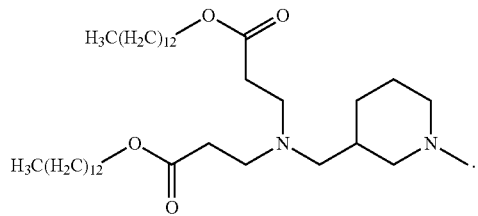

In certain embodiments, an inventive lipidoid is prepared by reacting amine 302 with acrylate $O_{10}$, $O_{11}$, $O_{12}$, $O_{13}$, or $O_{14}$ to form compound $302O_{10}$, $302O_{11}$, $302O_{12}$, $302O_{13}$, or $302O_{14}$. In certain embodiments, an inventive lipidoid is of one of the formulae below:

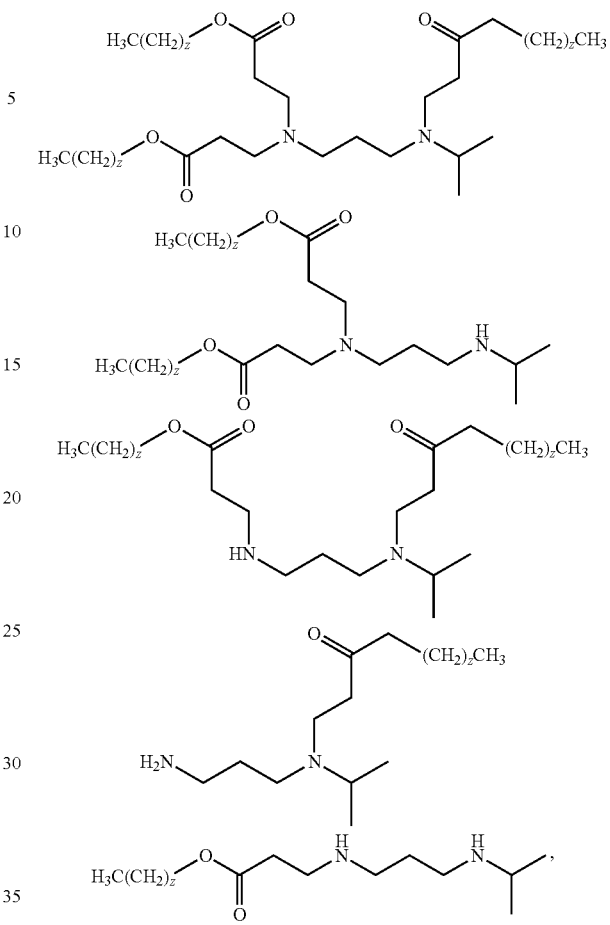

wherein z is 12 or 13.

In some embodiments, the present invention provides a composition of one or more of the above lipidoids. In certain embodiments, an inventive lipidoid is of the formula:

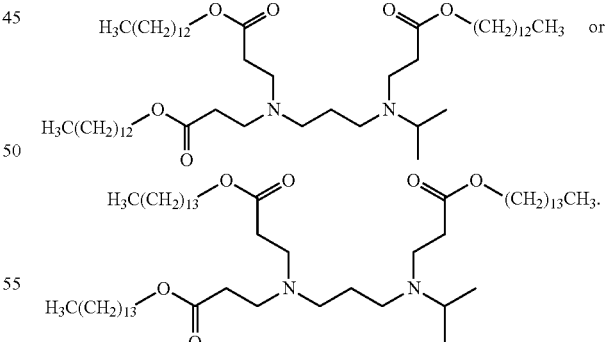

In certain embodiments, an inventive lipidoid is prepared by reacting amine 303 with acrylate $O_{10}$, $O_{11}$, $O_{12}$, $O_{13}$, or $O_{14}$ to form compound $303O_{10}$, $303O_{11}$, $303O_{12}$, $303O_{13}$, or $303O_{14}$. In certain embodiments, an inventive lipidoid is of one of the formulae below:

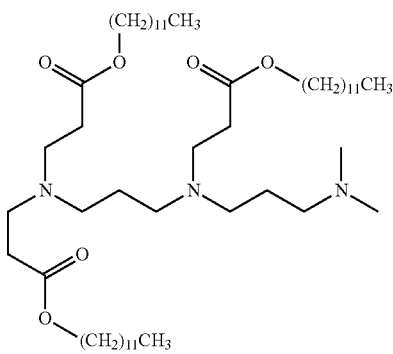

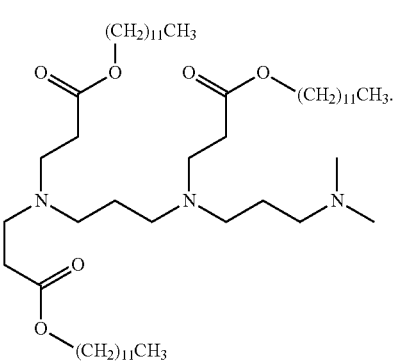

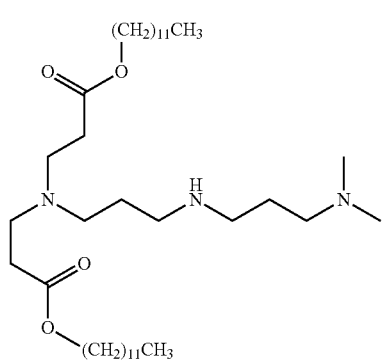

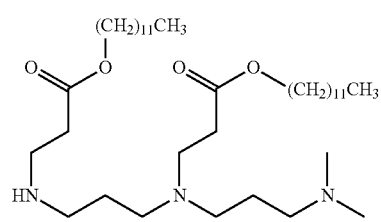

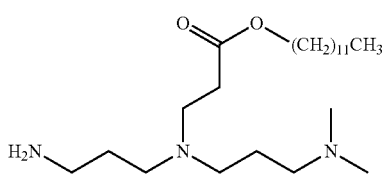

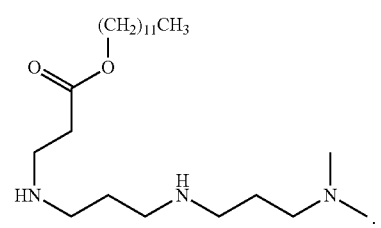

In some embodiments, the present invention provides a composition of one or more of the above lipidoids. In certain embodiments, an inventive lipidoid is of the formula:

In certain embodiments, an inventive lipidoid is prepared by reacting amine 304 with acrylate $O_{10}$, $O_{11}$, $O_{12}$, $O_{13}$, or $O_{14}$ to form compound $304O_{10}$, $304O_{11}$, $304O_{12}$, $304O_{13}$, or $304O_{14}$. In certain embodiments, an inventive lipidoid is of one of the formulae below:

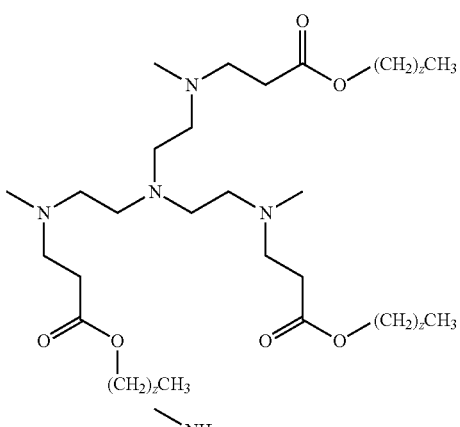

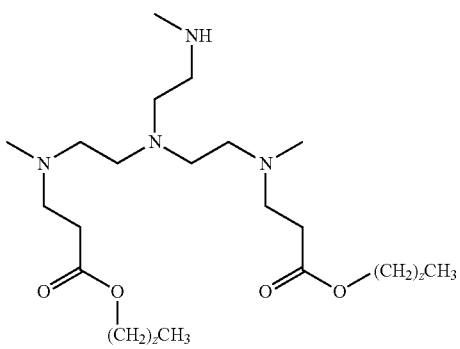

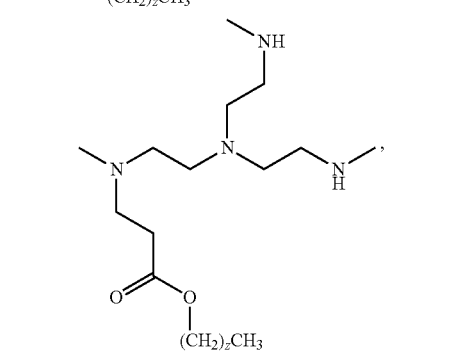

wherein z is 11 or 12.

In some embodiments, the present invention provides a composition of one or more of the above lipidoids. In certain embodiments, an inventive lipidoid is of the formula:

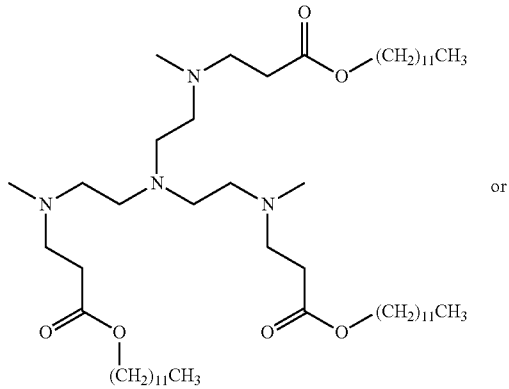

or

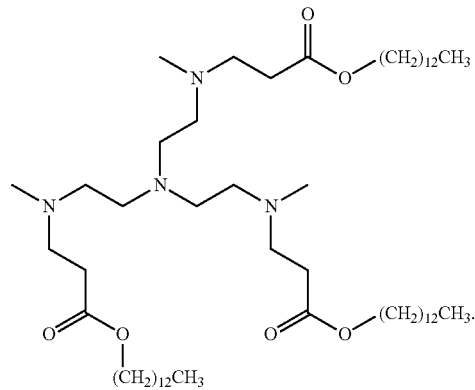

In certain embodiments, an inventive lipidoid is prepared by reacting amine 305 with acrylate $O_{10}$, $O_{11}$, $O_{12}$, $O_{13}$, or $O_{14}$ to form compound $305O_{10}$, $305O_{11}$, $305O_{12}$, $305O_{13}$, or $305O_{14}$. In certain embodiments, an inventive lipidoid is of one of the formulae below:

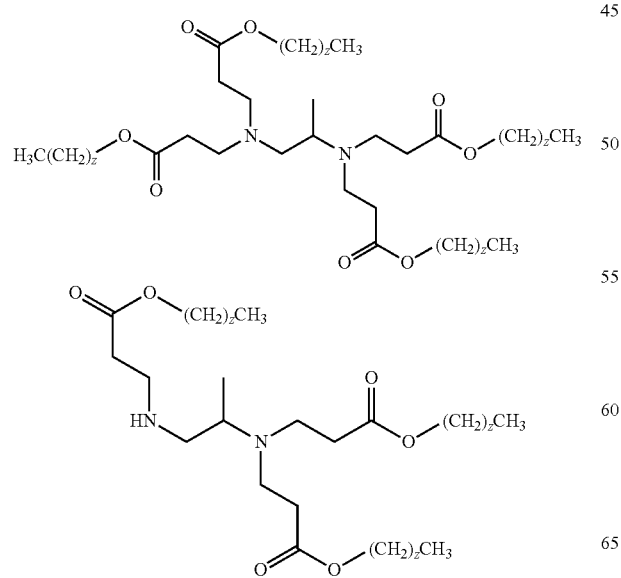

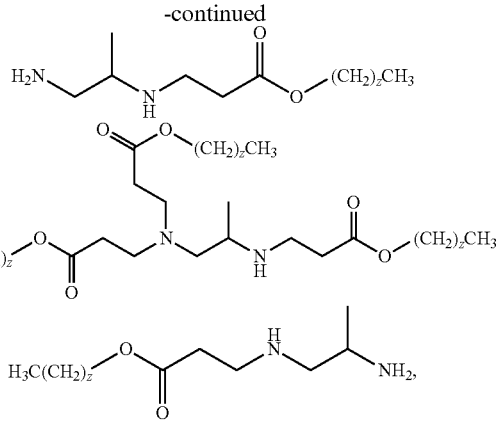

wherein z is 9, 10, 11, 12, or 13.

In some embodiments, the present invention provides a composition of one or more of the above lipidoids. In certain embodiments, an inventive lipidoid is of the formula:

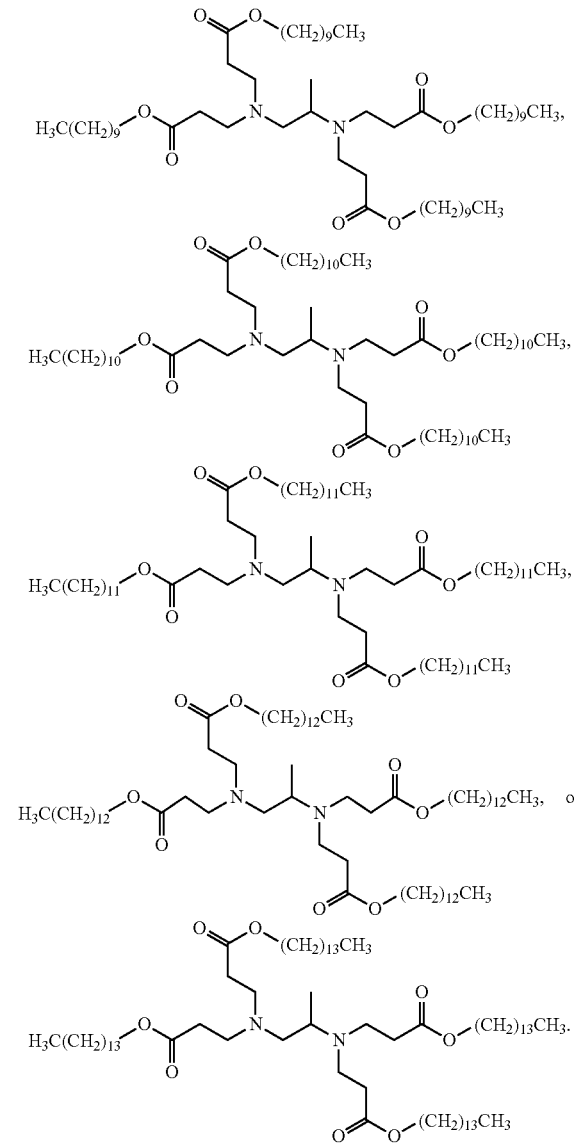

In certain embodiments, an inventive lipidoid is prepared by reacting amine 306 with acrylate $O_{10}$, $O_{11}$, $O_{12}$, $O_{13}$, or $O_{14}$ to form compound $306O_{10}$, $306O_{11}$, $306O_{12}$, $306O_{13}$, or $306O_{14}$. In certain embodiments, an inventive lipidoid is of one of the formulae below:

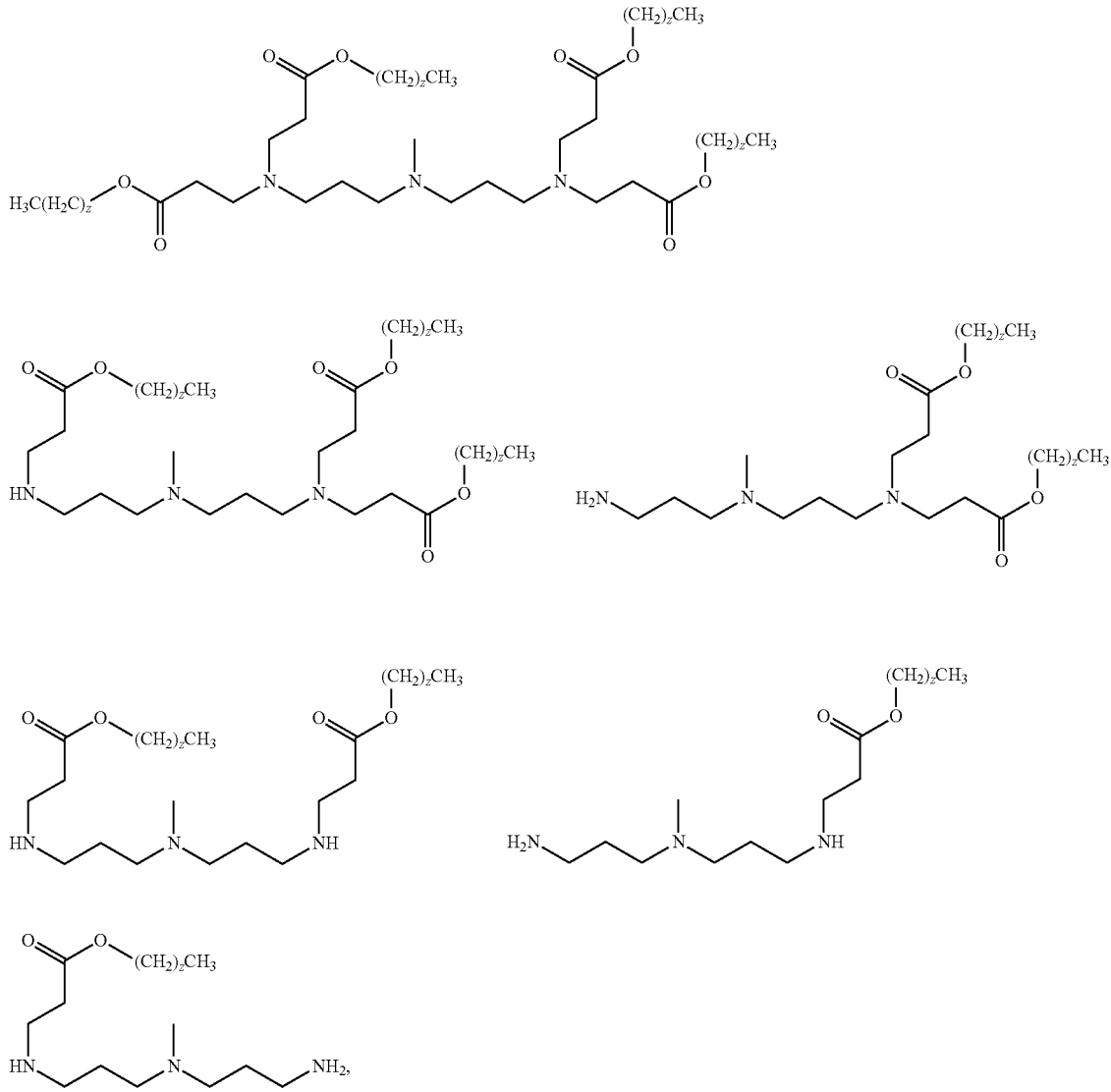

wherein z is 9, 10, 11, 12, or 13.

In some embodiments, the present invention provides a composition of one or more of the above lipidoids. In certain embodiments, an inventive lipidoid is of the formula:

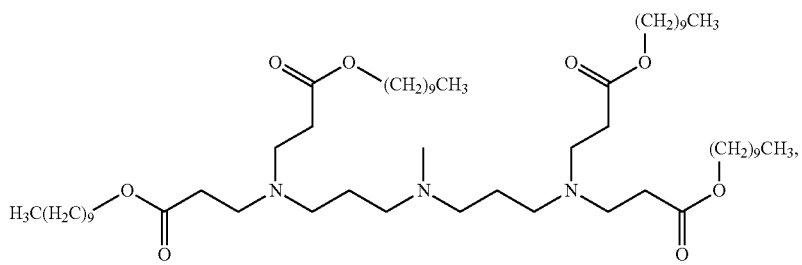

-continued
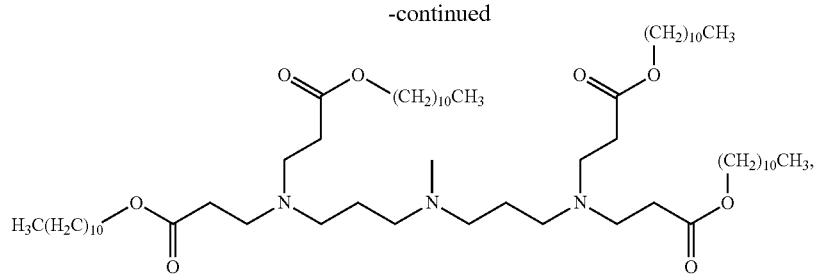
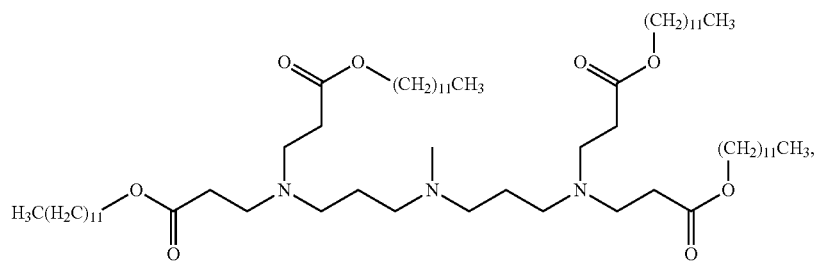
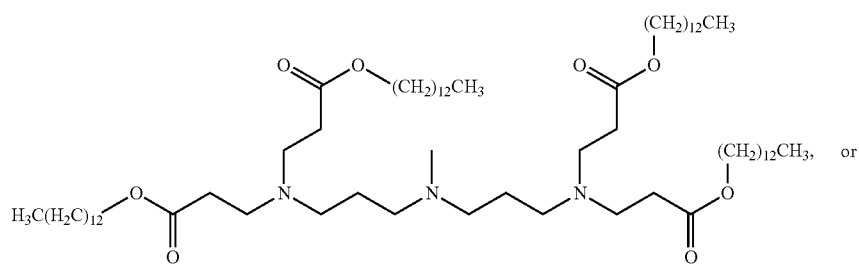
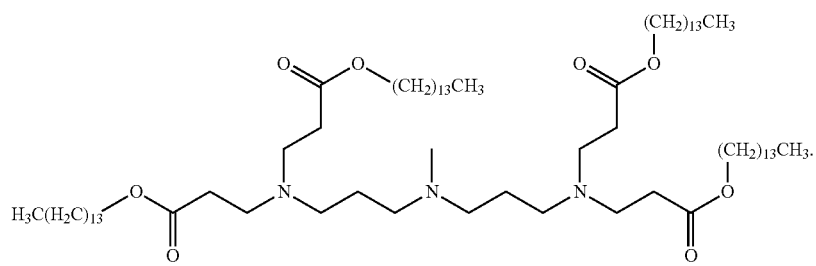
In certain embodiments, an inventive lipidoid is prepared by reacting amine 313 with acrylate $O_{10}$, $O_{11}$, $O_{12}$, $O_{13}$, or $O_{14}$ to form compound $313O_{10}$, $313O_{11}$, $313O_{12}$, $313O_{13}$, or $313O_{14}$. In certain embodiments, an inventive lipidoid is of one of the formulae below:
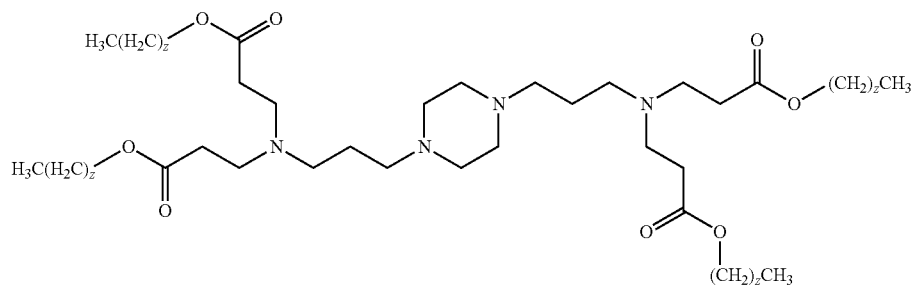

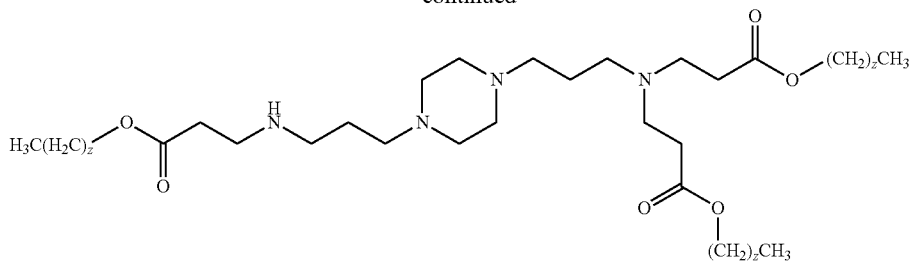
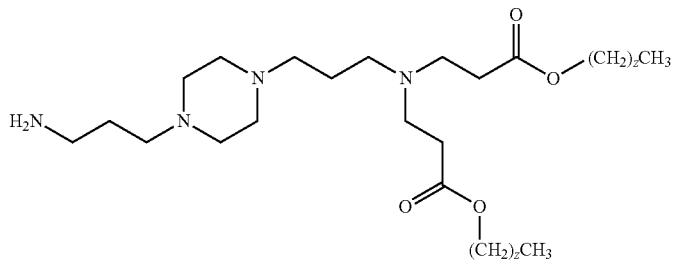
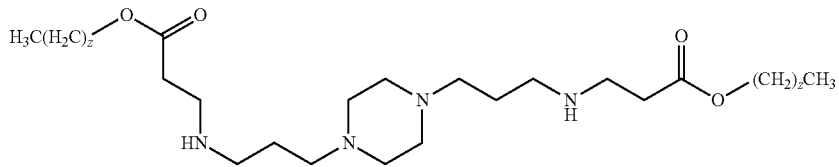
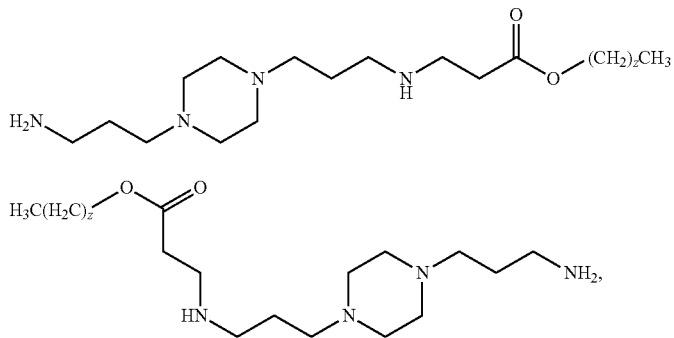
wherein z is 9, 10, 11, or 12.
In some embodiments, the present invention provides a composition of one or more of the above lipidoids. In certain embodiments, an inventive lipidoid is of the formula:
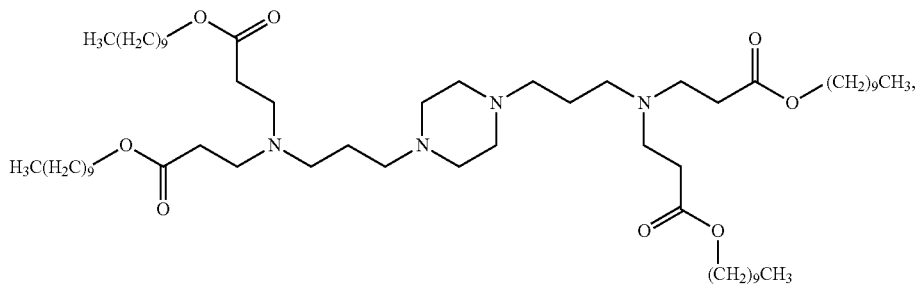

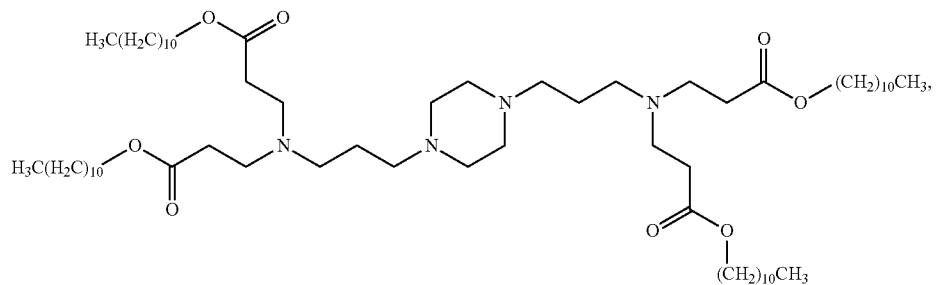
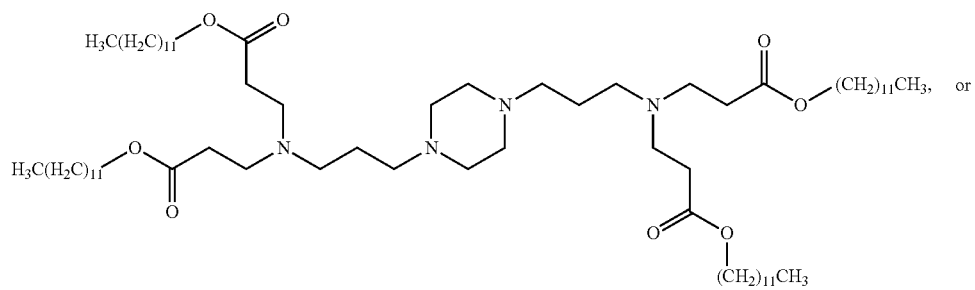
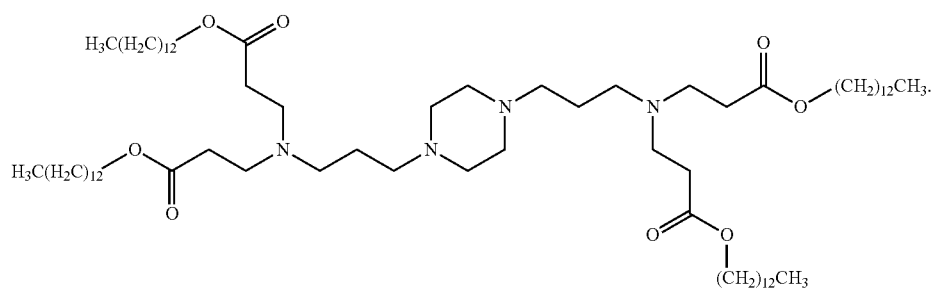
In certain embodiments, an inventive lipidoid is prepared by reacting amine 315 with acrylate $O_{10}$, $O_{11}$, $O_{12}$, $O_{13}$, or $O_{14}$ to form compound $315O_{10}$, $315O_{11}$, $315O_{12}$, $315O_{13}$, or $315O_{14}$. In certain embodiments, an inventive lipidoid is of one of the formulae below:
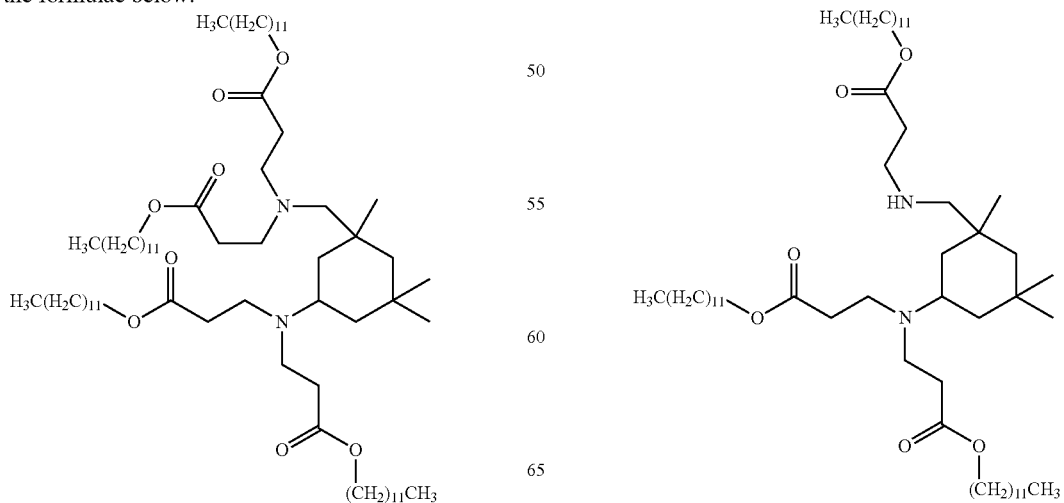

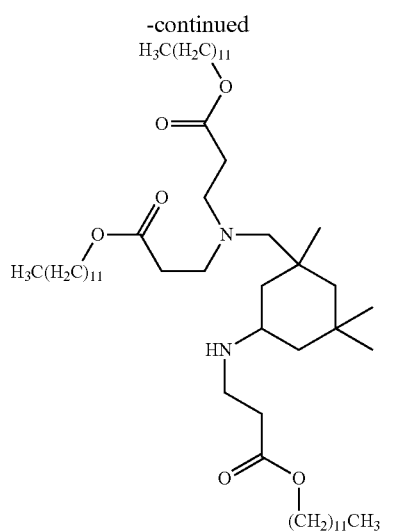
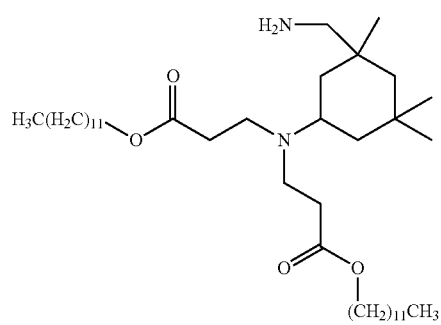
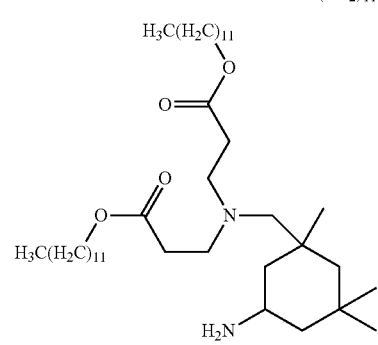
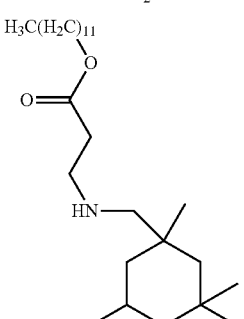
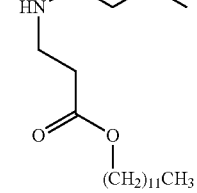

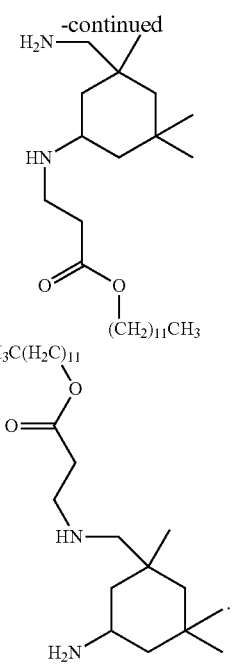

In some embodiments, the present invention provides a composition of one or more of the above lipidoids. In certain embodiments, an inventive lipidoid is of the formula:

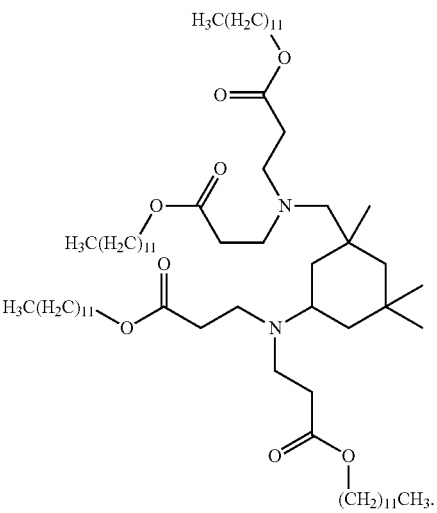

In certain embodiments, an inventive lipidoid is prepared by reacting amine 347 with acrylate $O_{10}$, $O_{11}$, $O_{12}$, $O_{13}$, or $O_{14}$ to form compound $347O_{10}$, $347O_{11}$, $347O_{12}$, $347O_{13}$, or $347O_{14}$. In certain embodiments, an inventive lipidoid is of one of the formulae below:

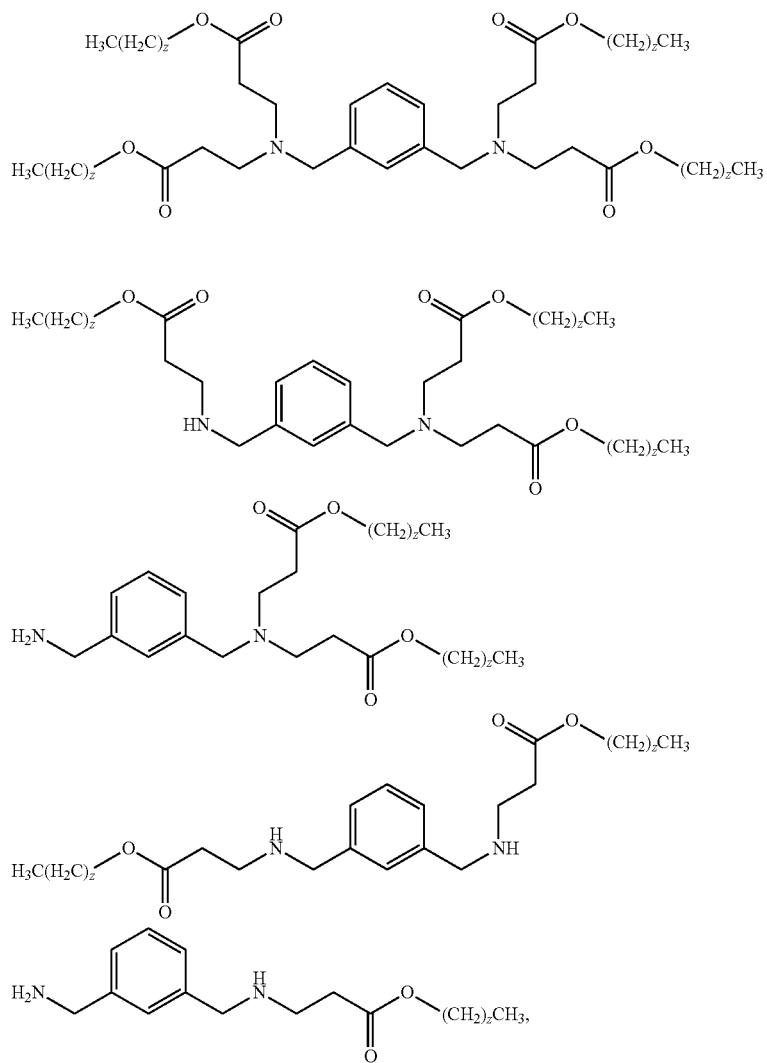
wherein z is 11 or 13.
In some embodiments, the present invention provides a composition of one or more of the above lipidoids. In certain embodiments, an inventive lipidoid is of the formula:
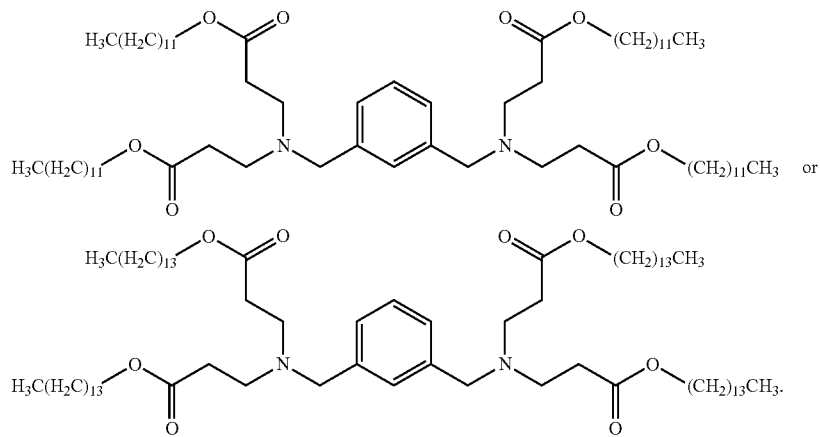

In certain embodiments, an inventive lipidoid is prepared by reacting amine 366 with acrylate $O_{10}$, $O_{11}$, $O_{12}$, $O_{13}$, or $O_{14}$ to form compound $366O_{10}$, $366O_{11}$, $366O_{12}$, $366O_{13}$, or $366O_{14}$. In certain embodiments, an inventive lipidoid is of one of the formulae below:

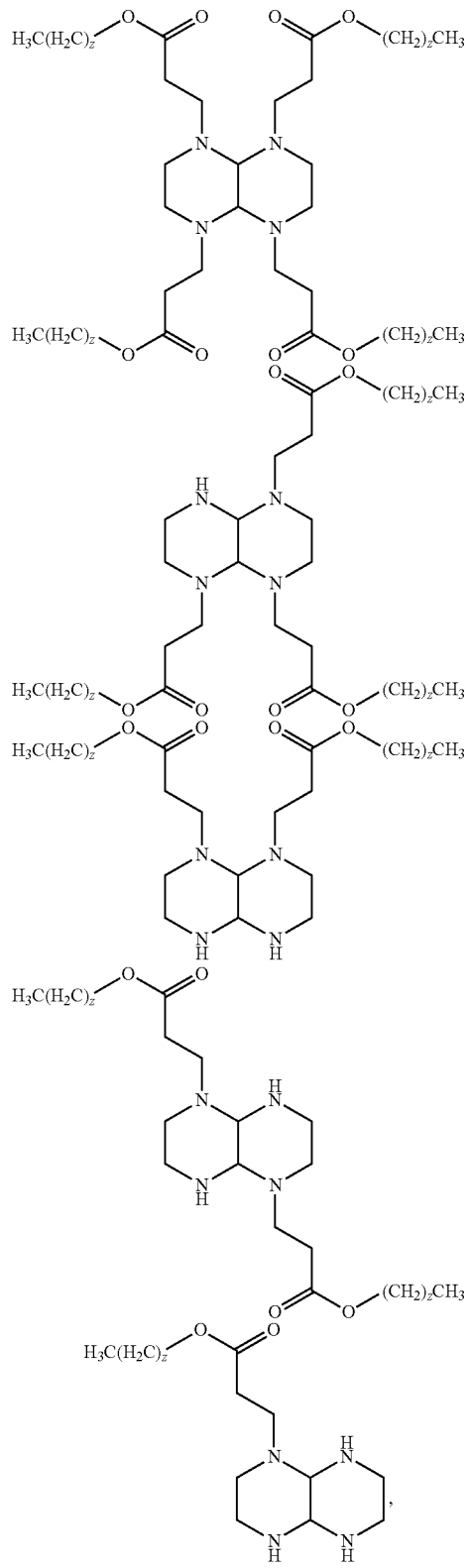

wherein z is 10 or 11.

In some embodiments, the present invention provides a composition of one or more of the above lipidoids. In certain embodiments, an inventive lipidoid is of the formula:

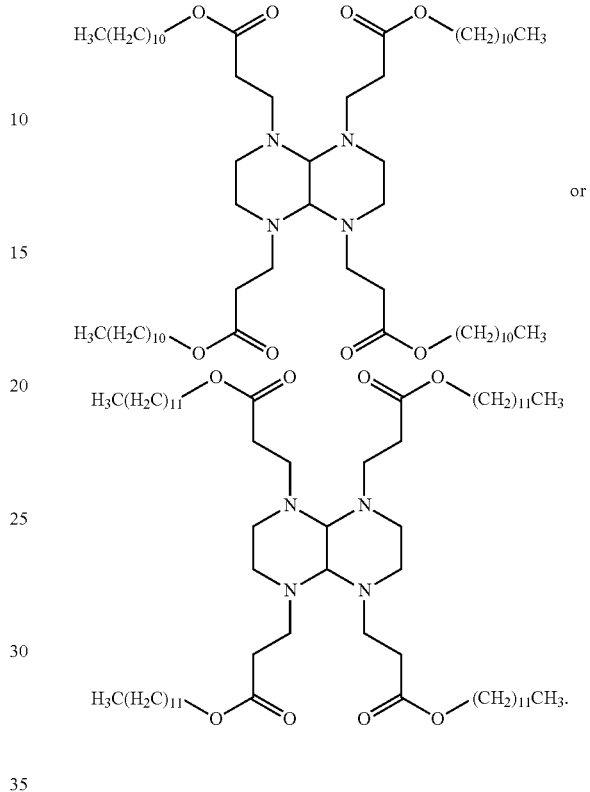

or

In certain embodiments, an inventive lipidoid is prepared by reacting amine 371 with acrylate $O_{10}$, $O_{11}$, $O_{12}$, $O_{13}$, or $O_{14}$ to form compound $371O_{10}$, $371O_{11}$, $371O_{12}$, $371O_{13}$, or $371O_{14}$. In certain embodiments, an inventive lipidoid is of one of the formulae below:

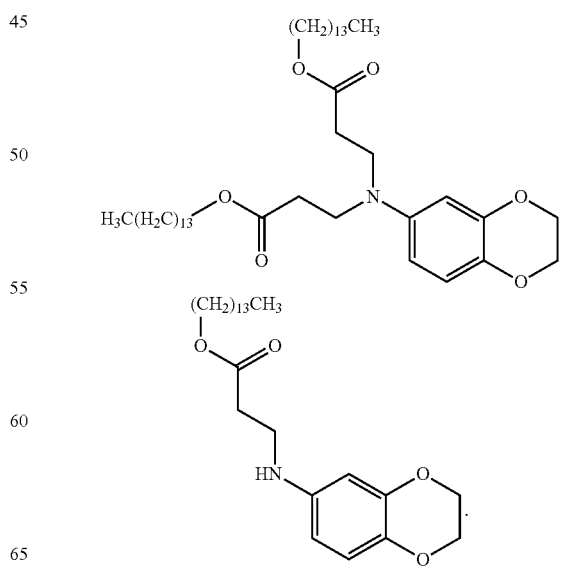

In some embodiments, the present invention provides a composition of one or more of the above lipidoids. In certain embodiments, an inventive lipidoid is of the formula:

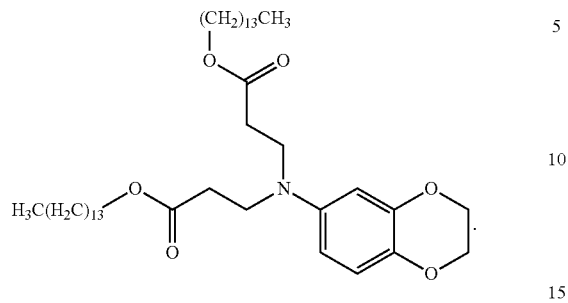

In certain embodiments, an inventive lipidoid is prepared by reacting amine 500 with acrylate $O_{10}$, $O_{11}$, $O_{12}$, $O_{13}$, or $O_{14}$ to form compound $500O_{10}$, $500O_{11}$, $500O_{12}$, $500O_{13}$, or $500O_{14}$. In certain embodiments, an inventive lipidoid is of one of the formulae below:

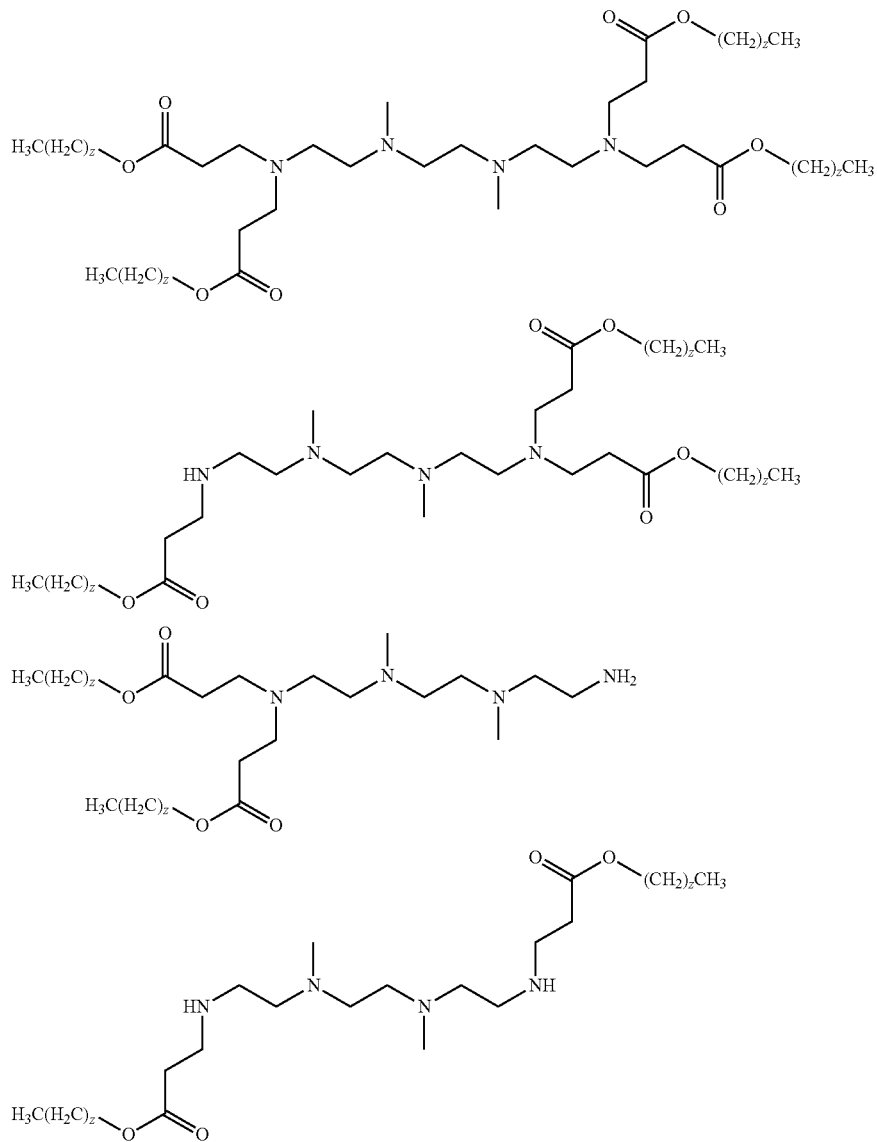

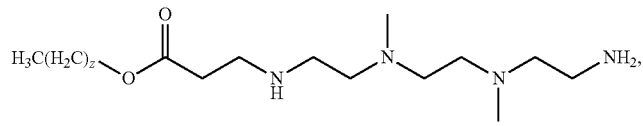
wherein z is 9, 10, 11, 12, or 13.
In some embodiments, the present invention provides a composition of one or more of the above lipidoids. In certain embodiments, an inventive lipidoid is of the formula:
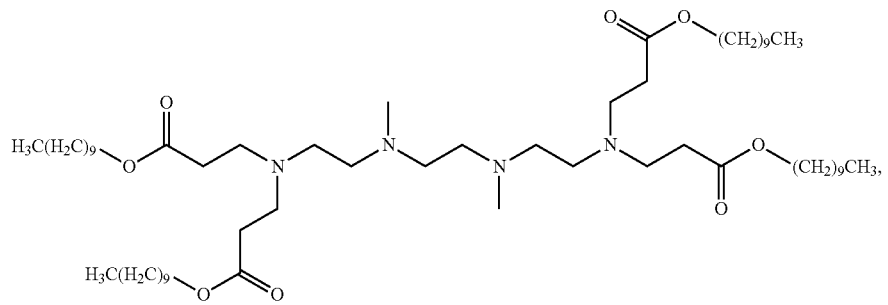
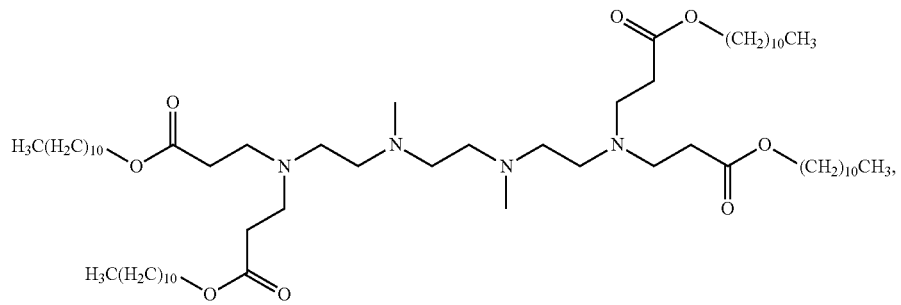
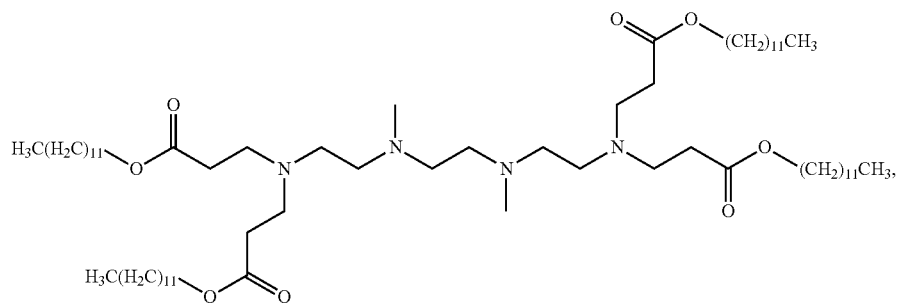
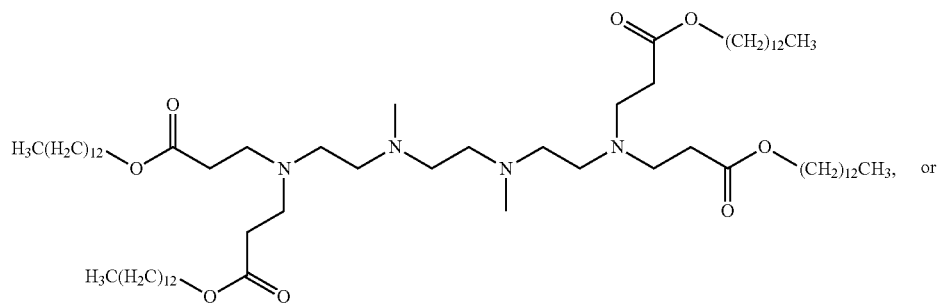

-continued
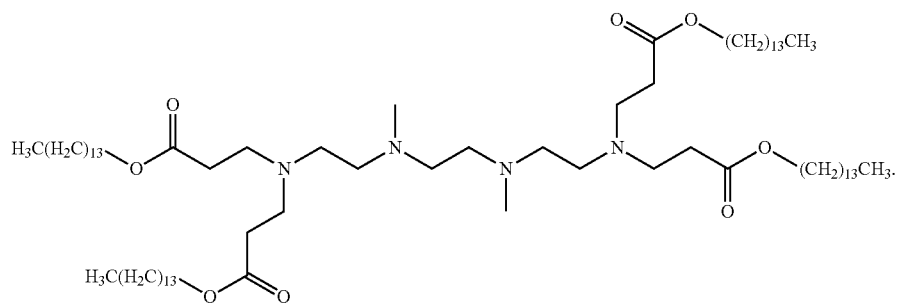
In certain embodiments, an inventive lipidoid is prepared by reacting amine 501 with acrylate $O_{10}$, $O_{11}$, $O_{12}$, $O_{13}$, or $O_{14}$ to form compound $501O_{10}$, $501O_{11}$, $501O_{12}$, $501O_{13}$, or $501O_{14}$. In certain embodiments, an inventive lipidoid is of one of the formulae below:
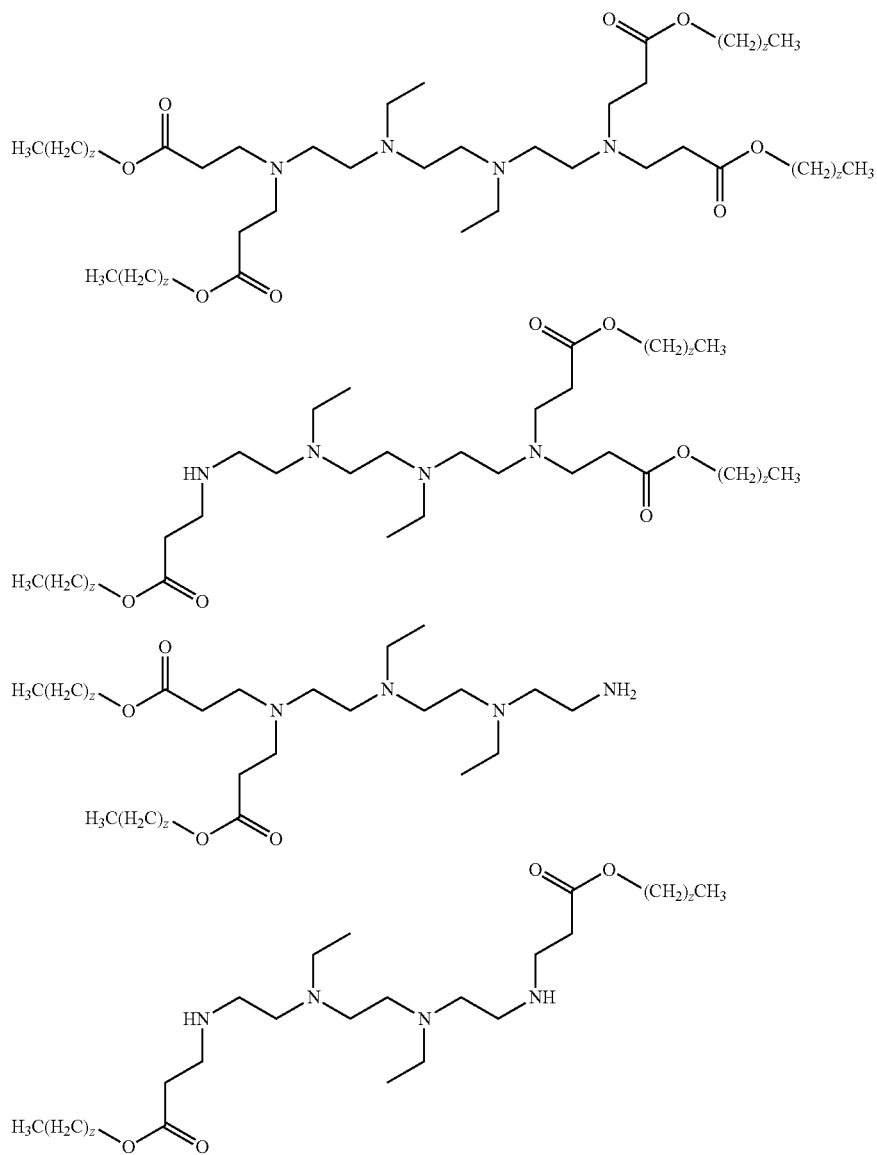

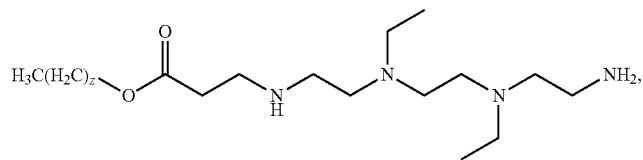
wherein z is 9, 10, 11, 12, or 13.
In some embodiments, the present invention provides a composition of one or more of the above lipidoids. In certain embodiments, an inventive lipidoid is of the formula:
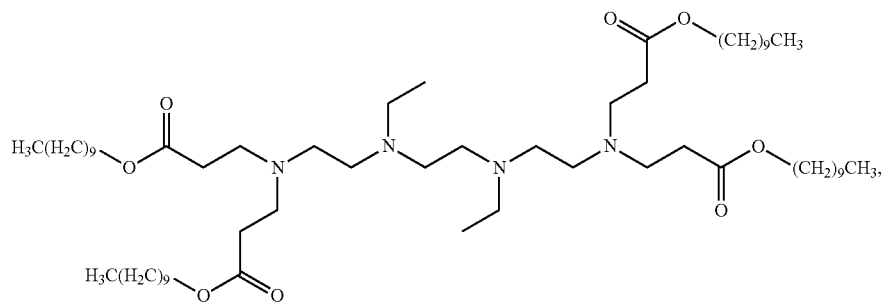
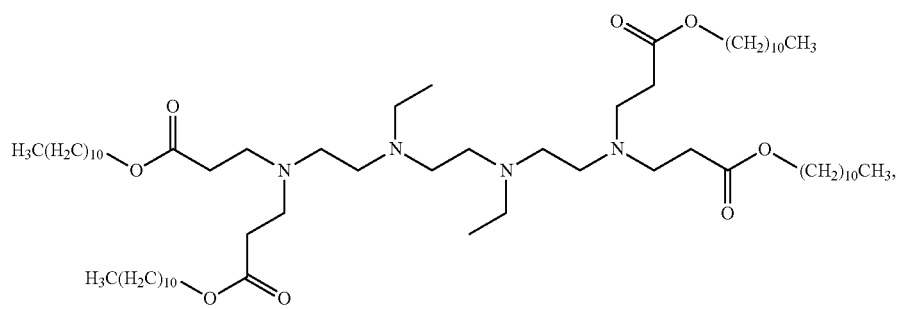
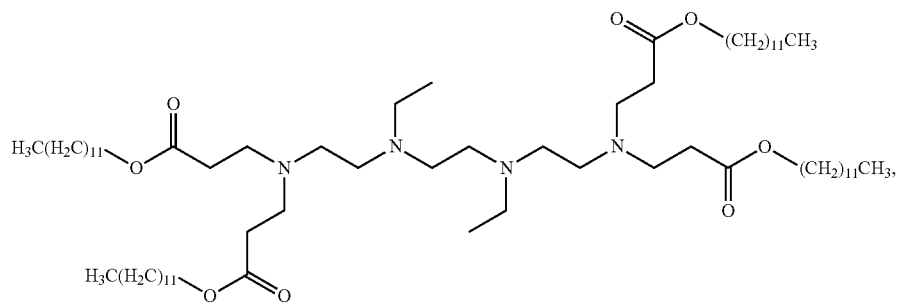
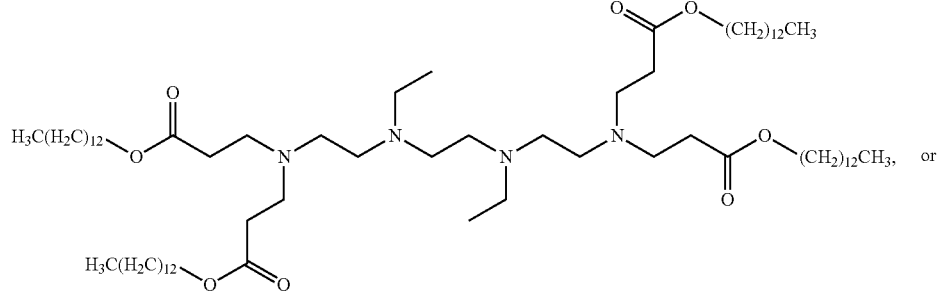

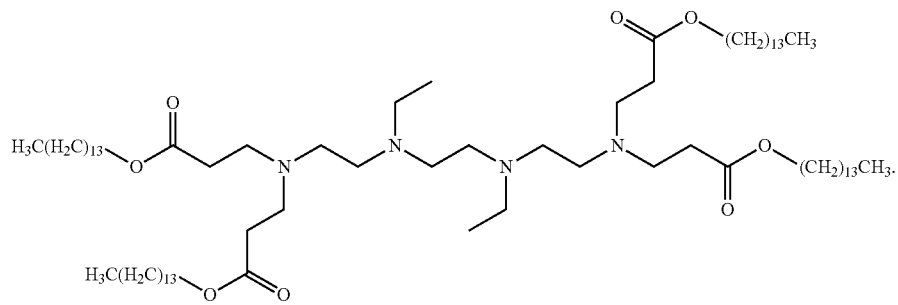
In certain embodiments, an inventive lipidoid is prepared by reacting amine 502 with acrylate $O_{10}$, $O_{11}$, $O_{12}$, $O_{13}$, or $O_{14}$ to form compound $502O_{10}$, $502O_{11}$, $502O_{12}$, $502O_{13}$, or $502O_{14}$. In certain embodiments, an inventive lipidoid is of one of the formulae below:
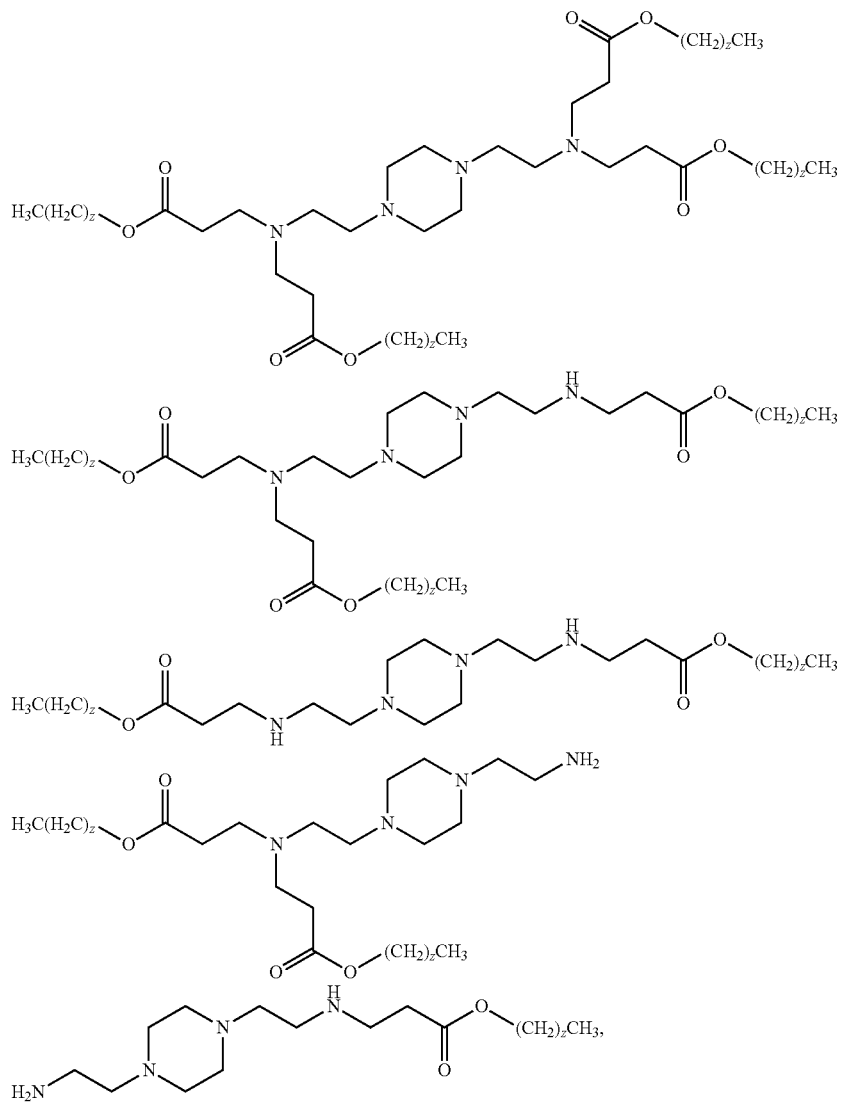
wherein z is 9, 10, 11, 12, or 13.

In some embodiments, the present invention provides a composition of one or more of the above lipidoids. In certain embodiments, an inventive lipidoid is of the formula:
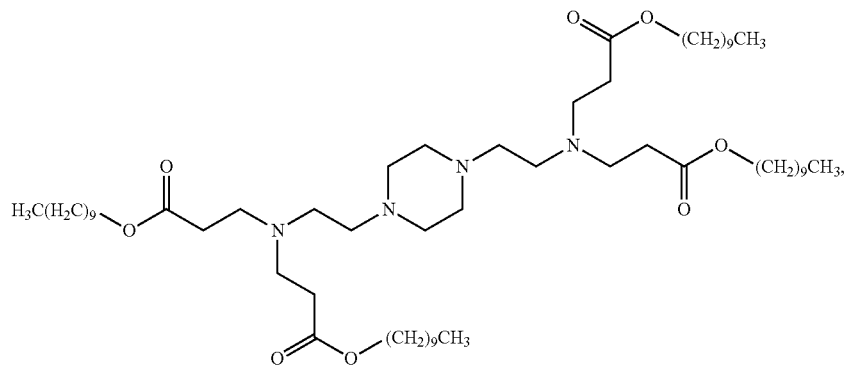
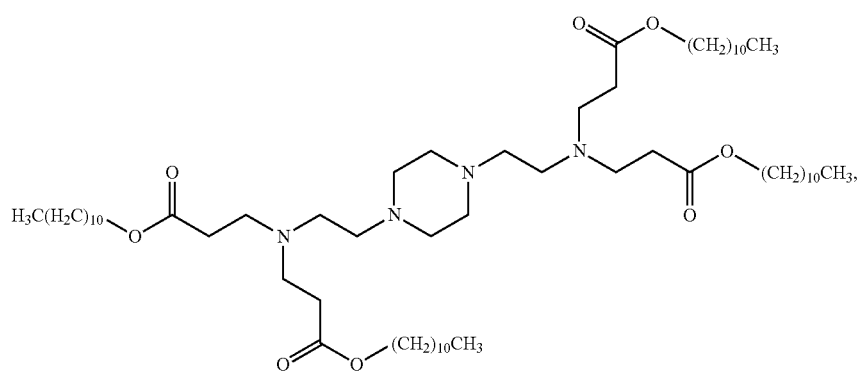
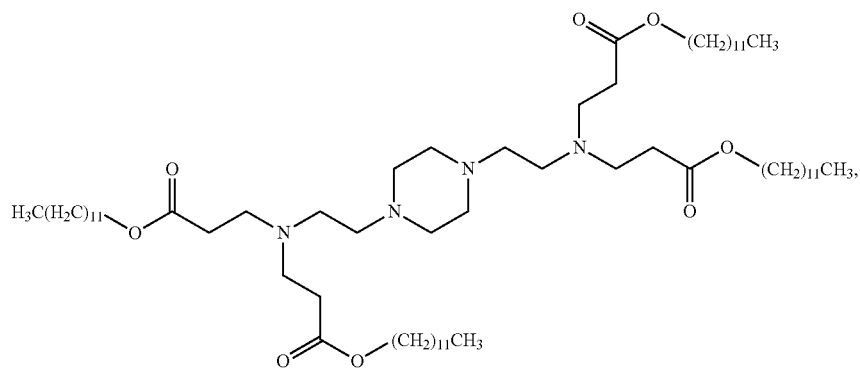
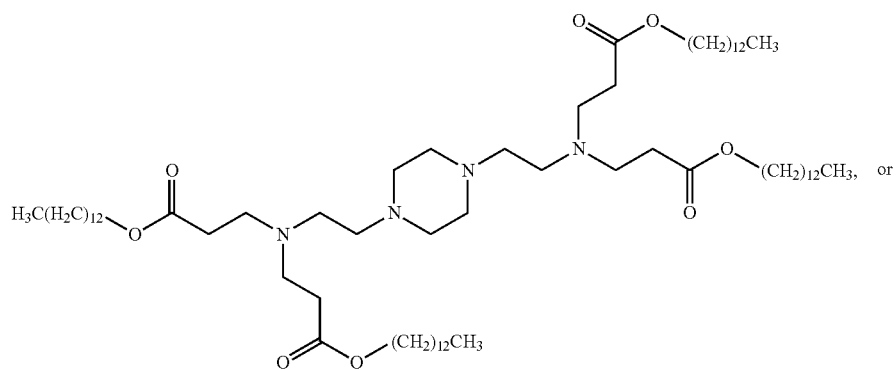

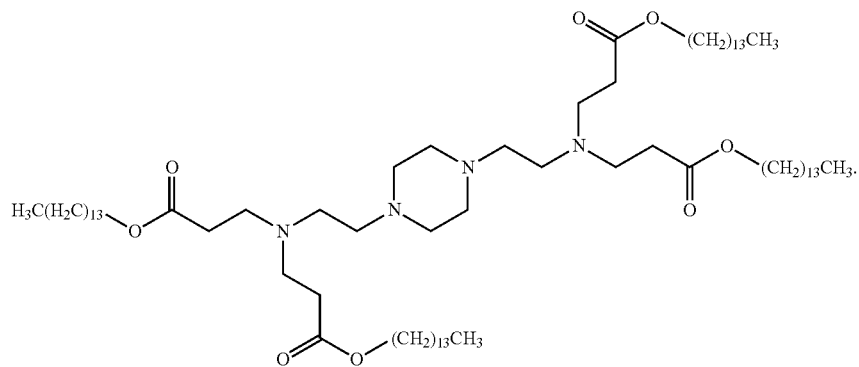

In certain embodiments, an inventive lipidoid is prepared by reacting amine 503 with acrylate $O_{10}$, $O_{11}$, $O_{12}$, $O_{13}$, or $O_{14}$ to form compound $503O_{10}$, $503O_{11}$, $503O_{12}$, $503O_{13}$, or $503O_{14}$. In certain embodiments, an inventive lipidoid is of one of the formulae below:

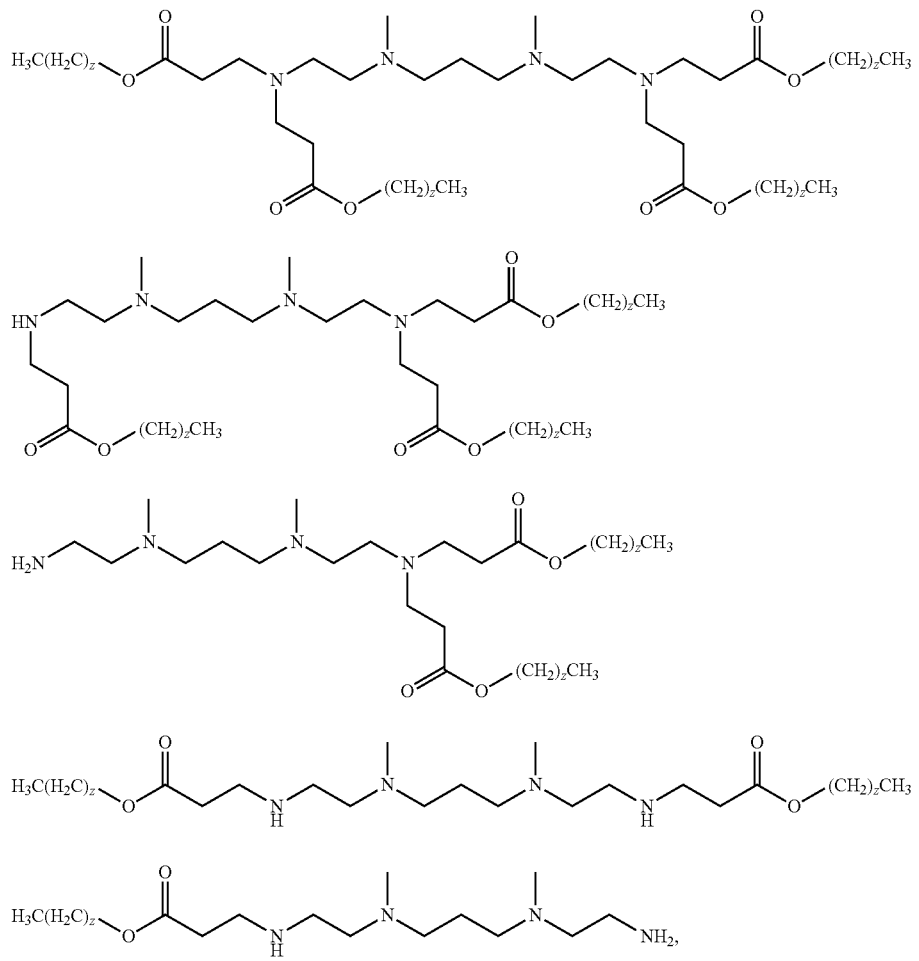

wherein z is 9, 10, 11, 12, or 13.

In some embodiments, the present invention provides a composition of one or more of the above lipidoids. In certain embodiments, an inventive lipidoid is of the formula:

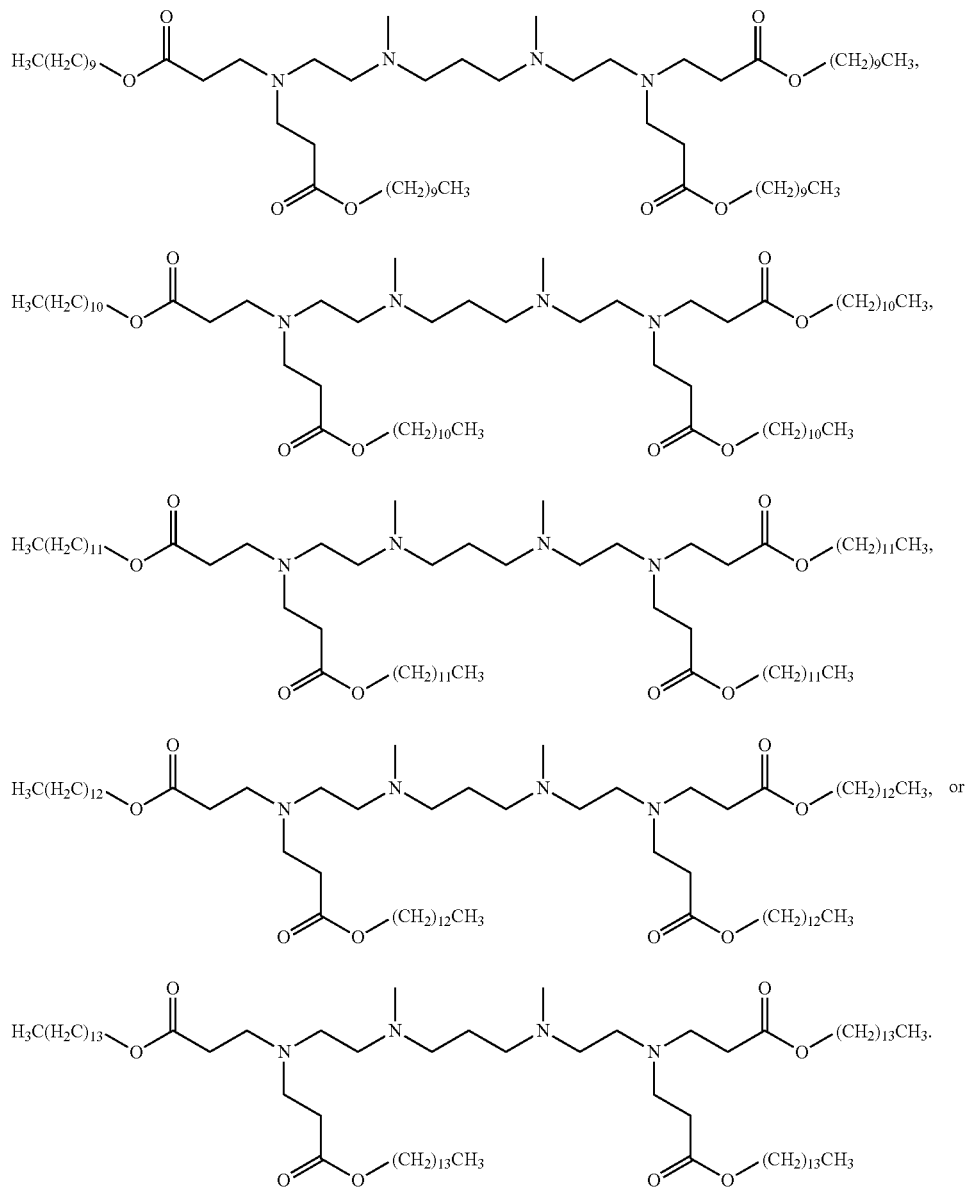
In certain embodiments, an inventive lipidoid is prepared by reacting amine 504 with acrylate $O_{10}$, $O_{11}$, $O_{12}$, $O_{13}$, or $O_{14}$ to form compound $504O_{10}$, $504O_{11}$, $504O_{12}$, $504O_{13}$, or $504O_{14}$. In certain embodiments, an inventive lipidoid is of one of the formulae below:
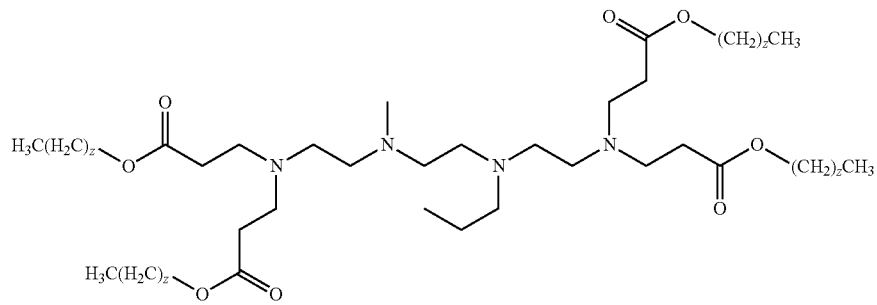

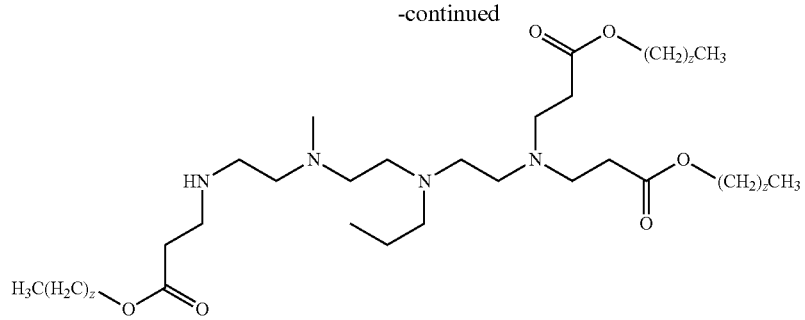
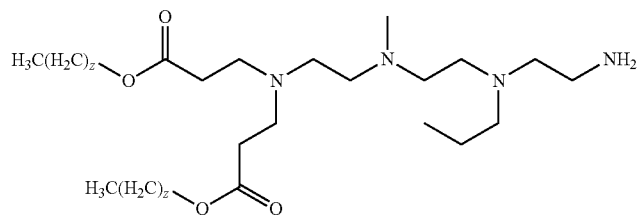
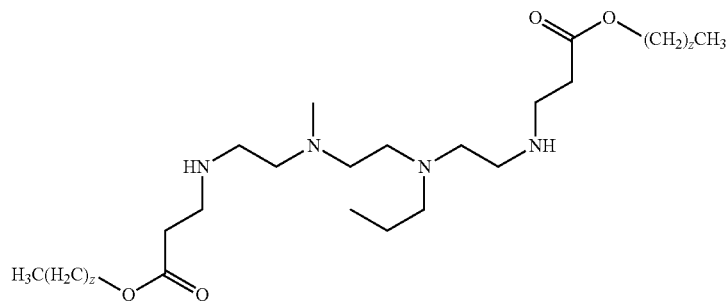
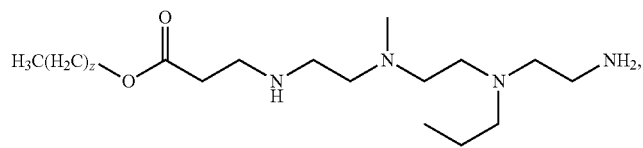
wherein z is 9, 10, 11, 12, or 13.
In some embodiments, the present invention provides a composition of one or more of the above lipidoids. In certain embodiments, an inventive lipidoid is of the formula:
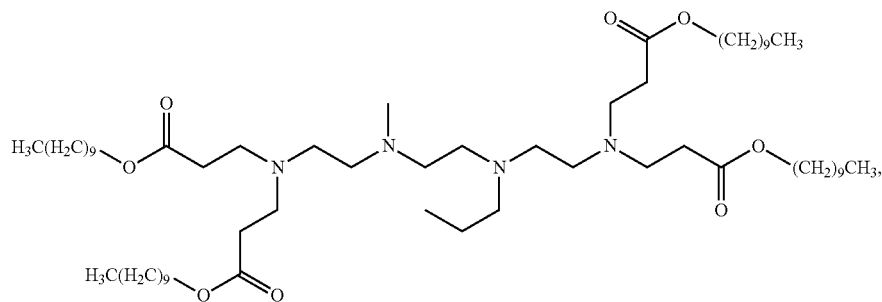

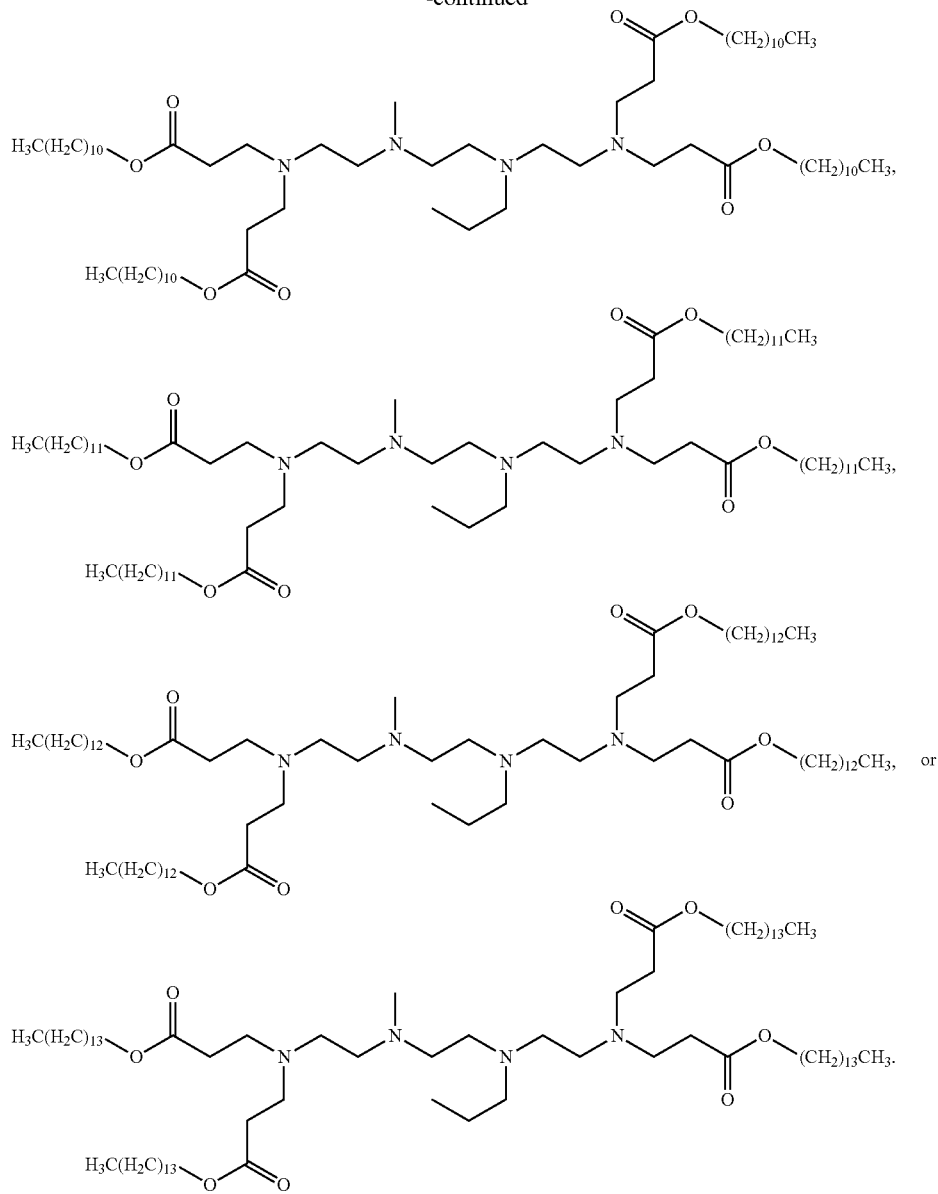
In certain embodiments, an inventive lipidoid is prepared by reacting amine 505 with acrylate $O_{10}$, $O_{11}$, $O_{12}$, $O_{13}$, or $O_{14}$ to form compound $505O_{10}$, $505O_{11}$, $505O_{12}$, $505O_{13}$, or $505O_{14}$. In certain embodiments, an inventive lipidoid is of one of the formulae below:
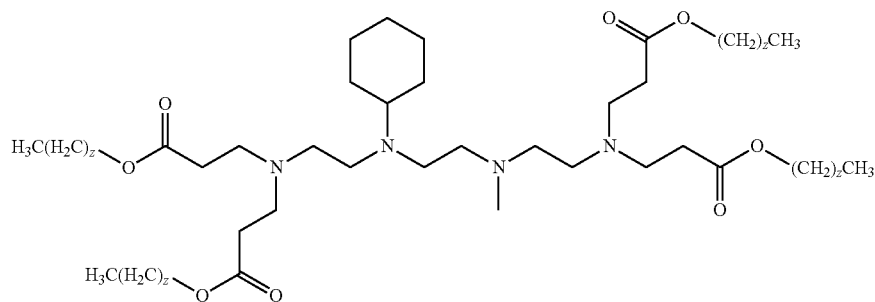

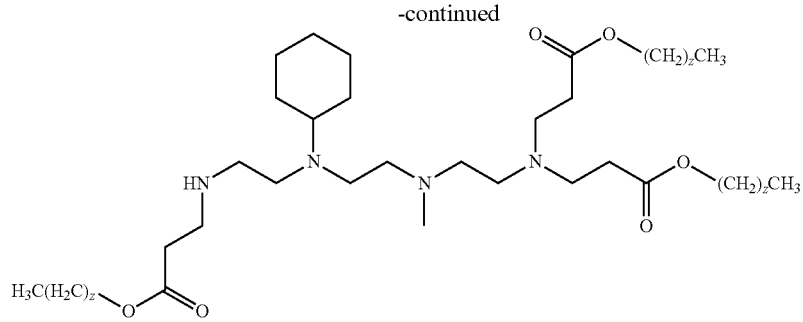
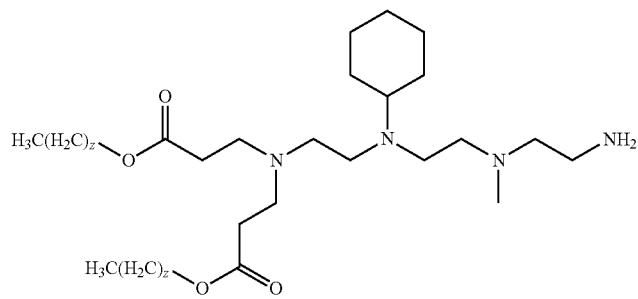
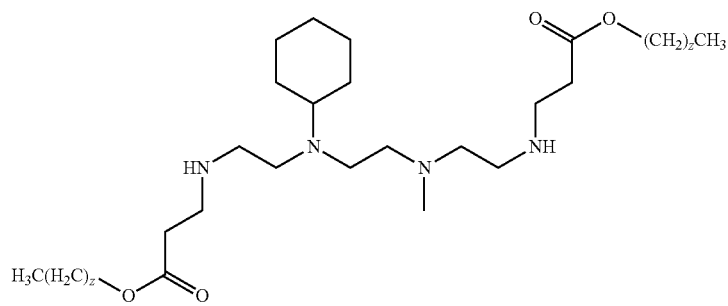
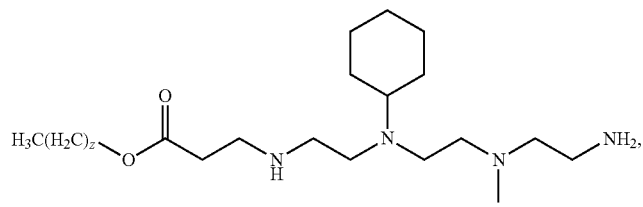
wherein z is 9, 10, 11, 12, or 13.
In some embodiments, the present invention provides a composition of one or more of the above lipidoids. In certain embodiments, an inventive lipidoid is of the formula:
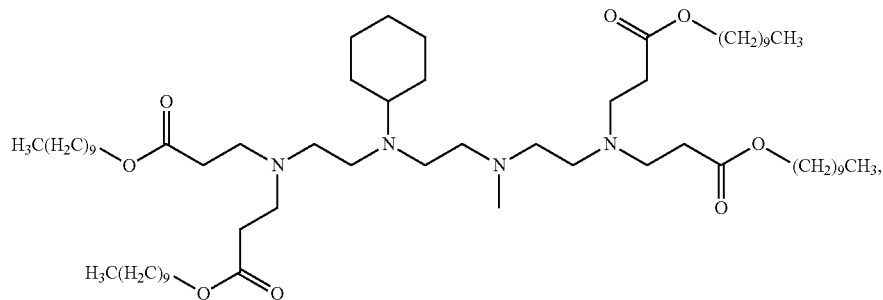

-continued
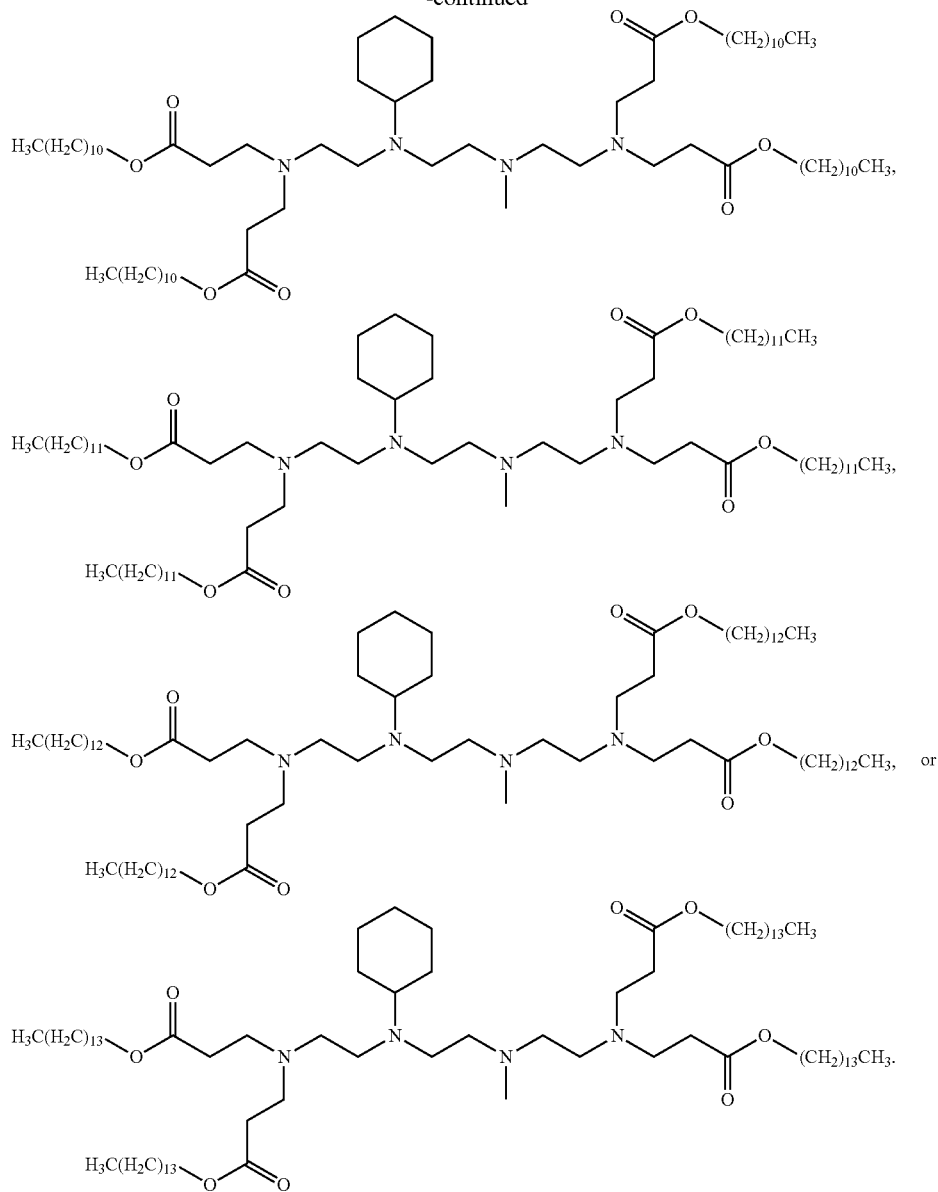
In certain embodiments, an inventive lipidoid is prepared by reacting amine 506 with acrylate $O_{10}$, $O_{11}$, $O_{12}$, $O_{13}$, or $O_{14}$ to form compound $506O_{10}$, $506O_{11}$, $506O_{12}$, $506O_{13}$, or $506O_{14}$. In certain embodiments, an inventive lipidoid is of one of the formulae below:
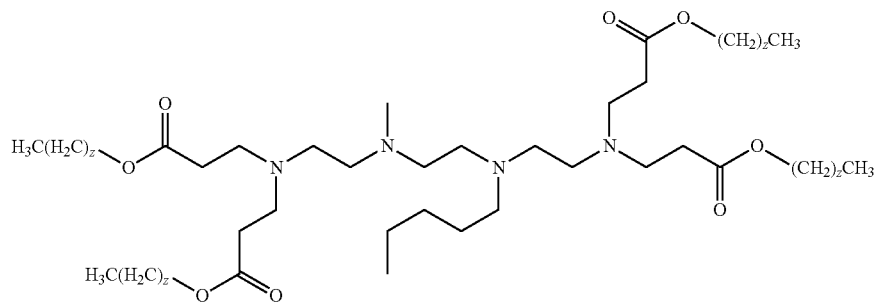

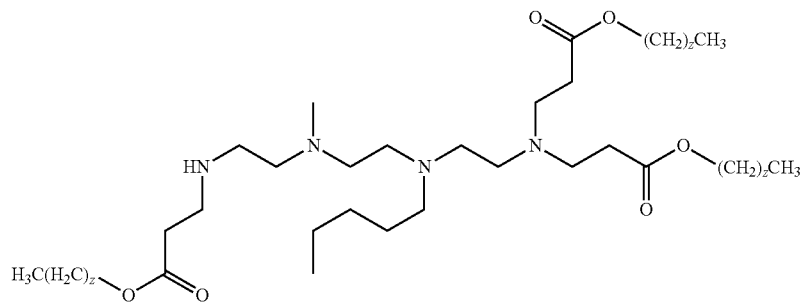
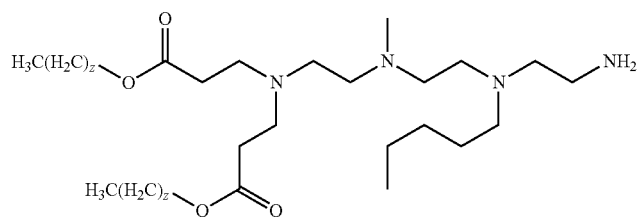
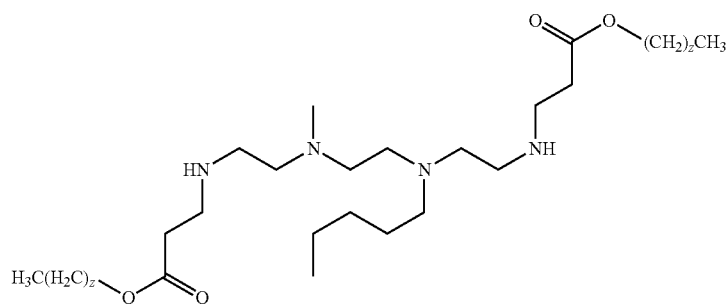
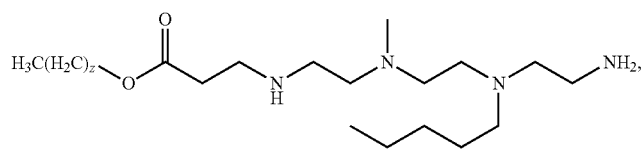
wherein z is 9, 10, 11, 12, or 13.
In some embodiments, the present invention provides a composition of one or more of the above lipidoids. In certain embodiments, an inventive lipidoid is of the formula:
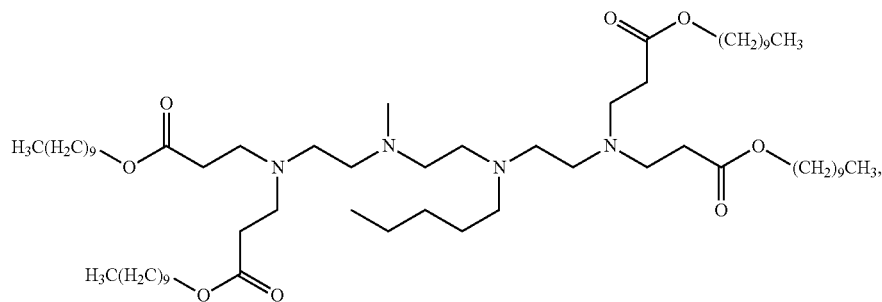

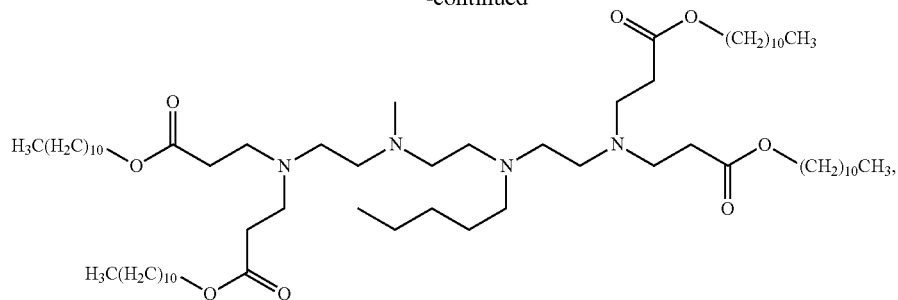
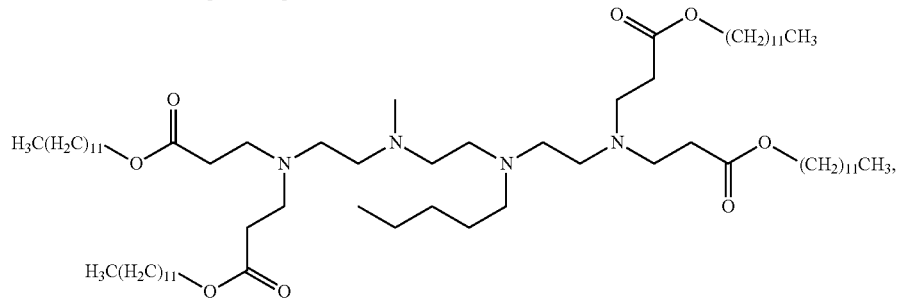
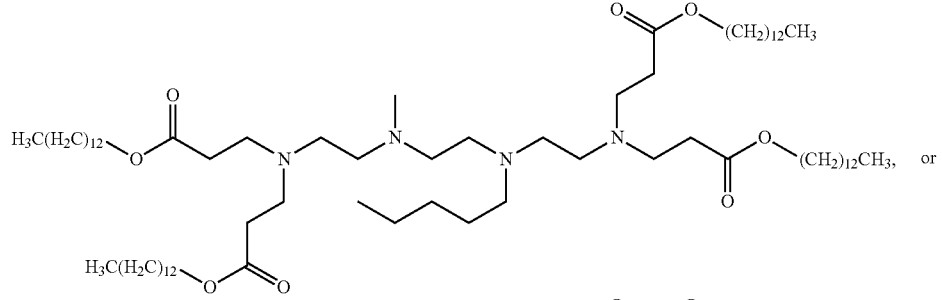
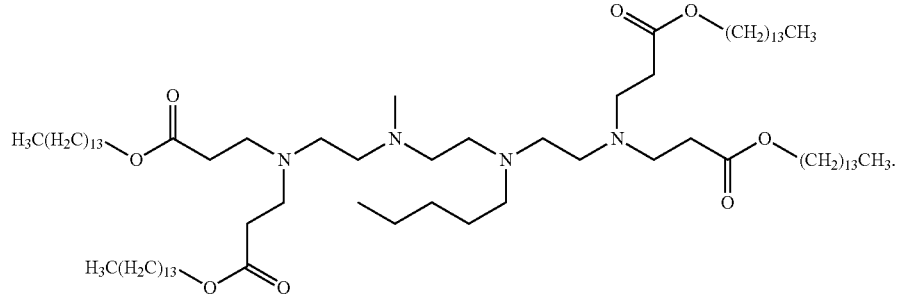
In certain embodiments, an inventive lipidoid is prepared by reacting amine 507 with acrylate $O_{10}$, $O_{11}$, $O_{12}$, $O_{13}$, or $O_{14}$ to form compound $507O_{10}$, $507O_{11}$, $507O_{12}$, $507O_{13}$, or $507O_{14}$. In certain embodiments, an inventive lipidoid is of one of the formulae below:
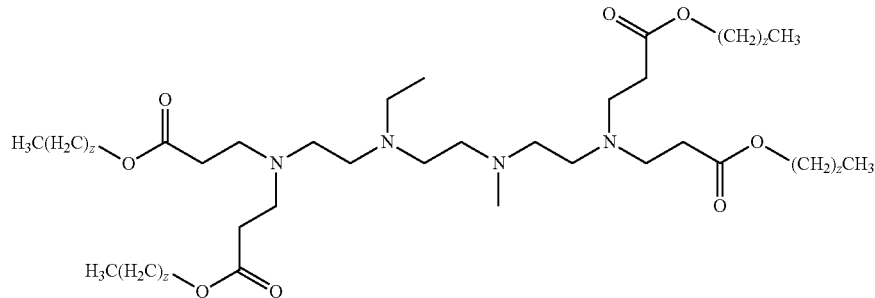

-continued
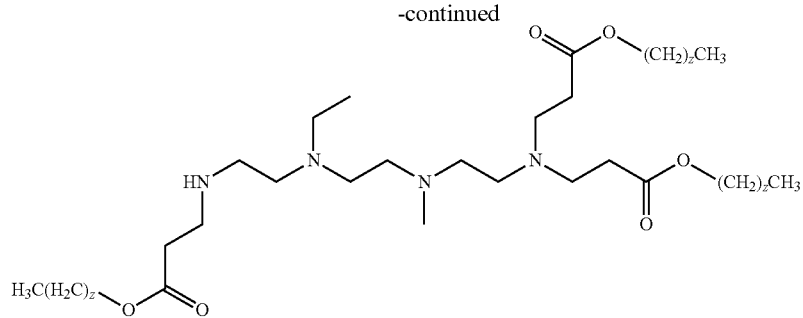
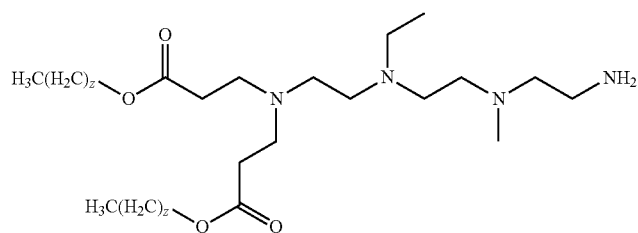
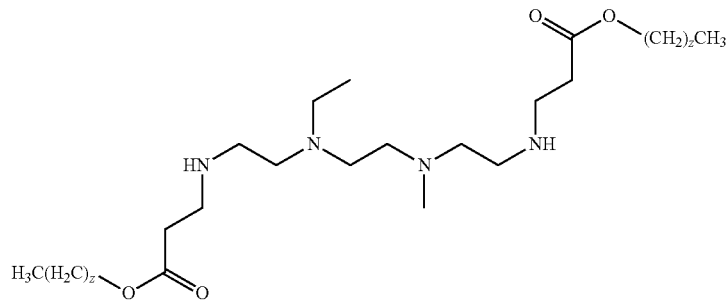
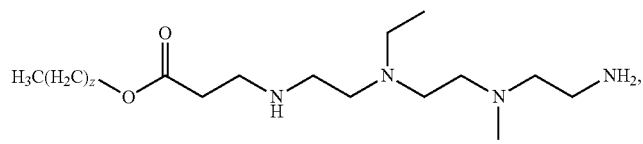
wherein z is 9, 10, 11, 12, or 13.
In some embodiments, the present invention provides a composition of one or more of the above lipidoids. In certain embodiments, an inventive lipidoid is of the formula:
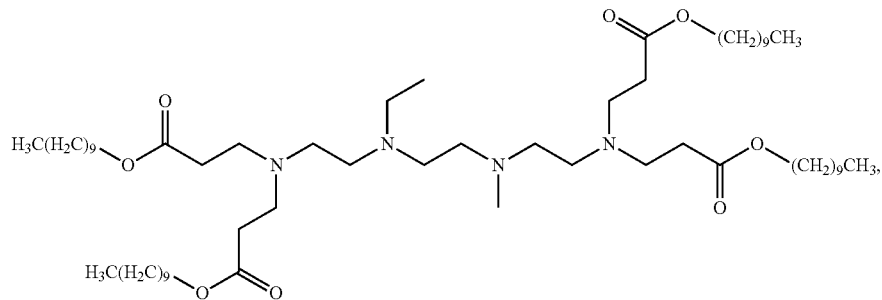

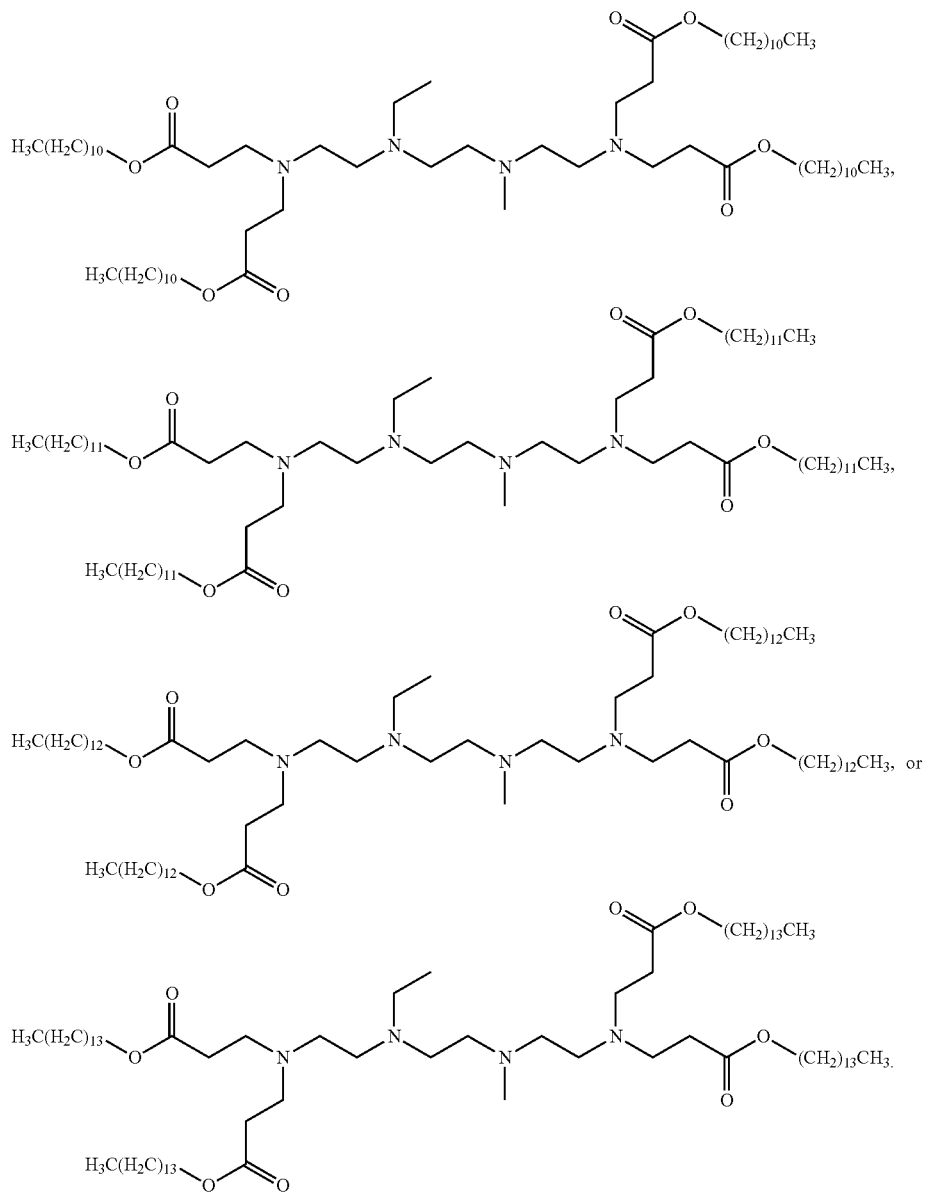
In certain embodiments, an inventive lipidoid is prepared by reacting amine 508 with acrylate $O_{10}$, $O_{11}$, $O_{12}$, $O_{13}$, or $O_{14}$ to form compound $508O_{10}$, $508O_{11}$, $508O_{12}$, $508O_{13}$, or $508O_{14}$. In certain embodiments, an inventive lipidoid is of one of the formulae below:
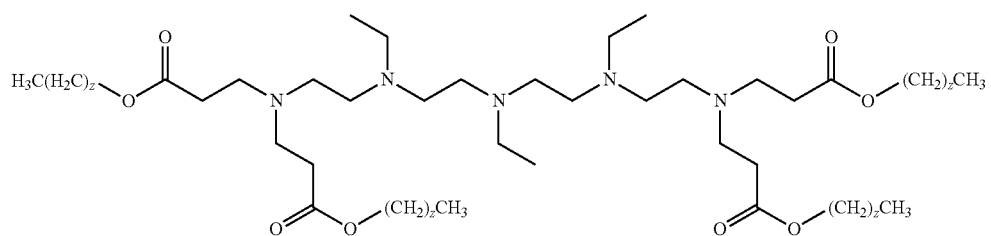

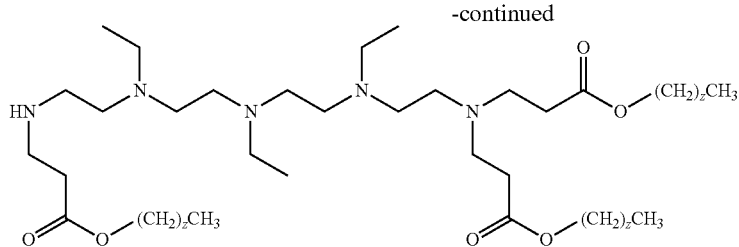
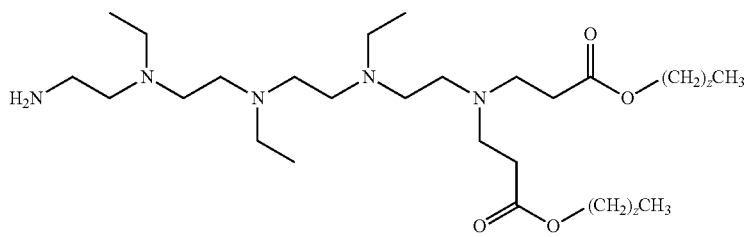
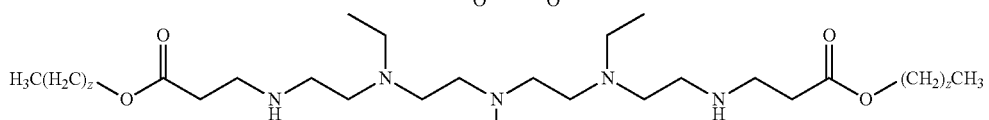
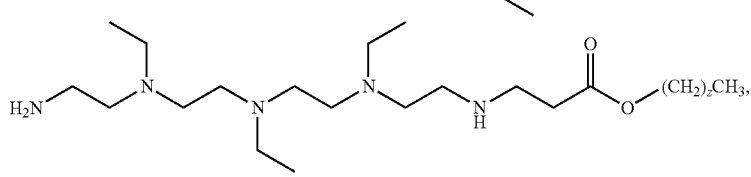
wherein z is 9, 10, 11, 12, or 13.
In some embodiments, the present invention provides a composition of one or more of the above lipidoids. In certain embodiments, an inventive lipidoid is of the formula:
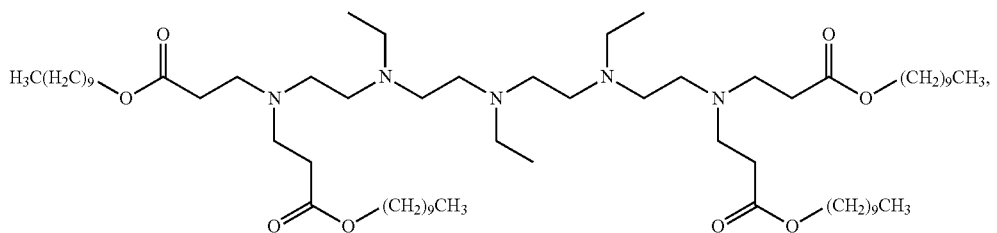
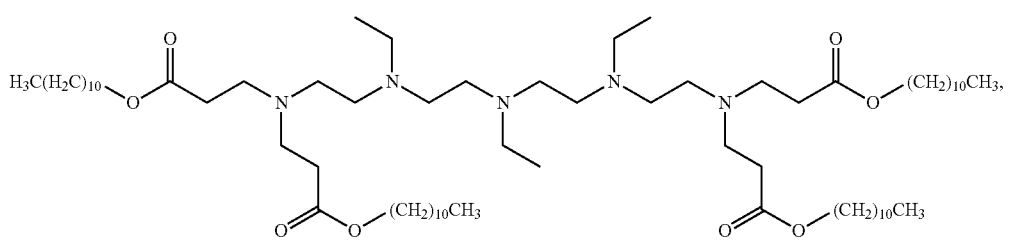
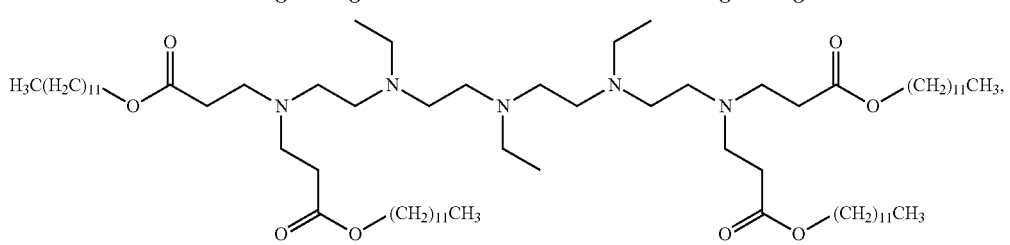

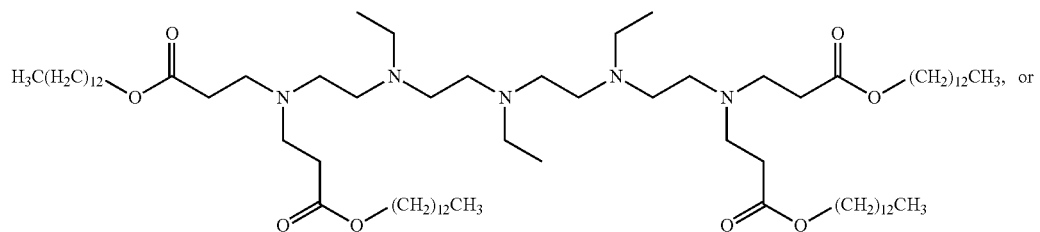
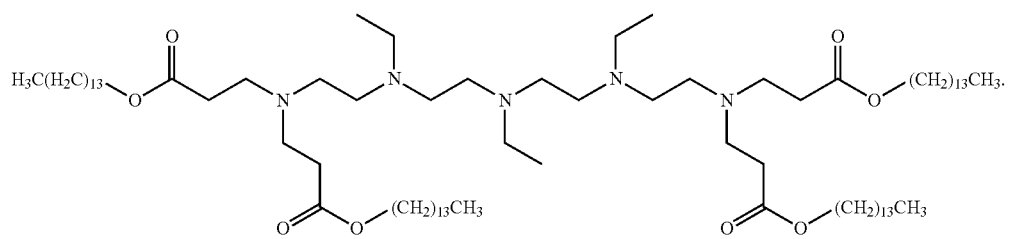
In certain embodiments, an inventive lipidoid is prepared by reacting amine 509 with acrylate $O_{10}$, $O_{11}$, $O_{12}$, $O_{13}$, or $O_{14}$ to form compound $509O_{10}$, $509O_{11}$, $509O_{12}$, $509O_{13}$, or $509O_{14}$. In certain embodiments, an inventive lipidoid is of one of the formulae below:
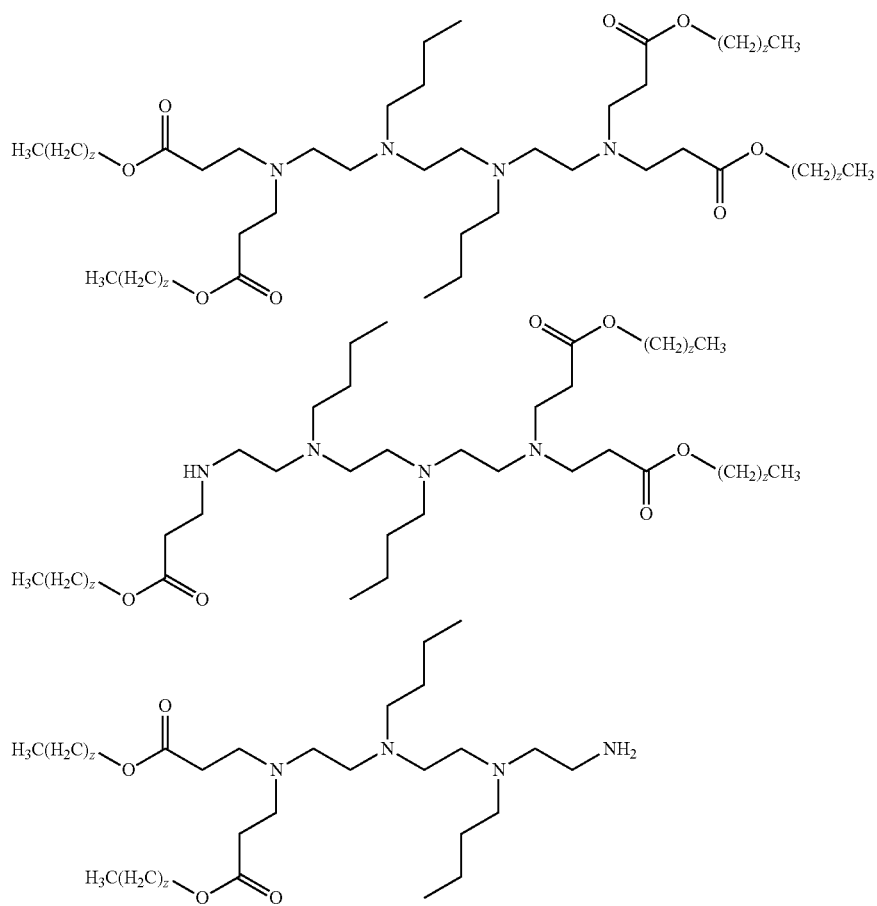

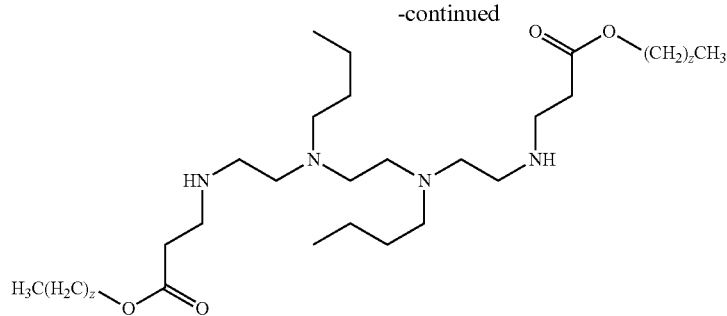
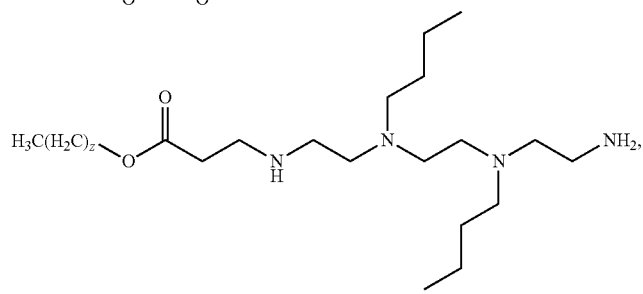
wherein z is 9, 10, 11, 12, or 13.
In some embodiments, the present invention provides a composition of one or more of the above lipidoids. In certain embodiments, an inventive lipidoid is of the formula:
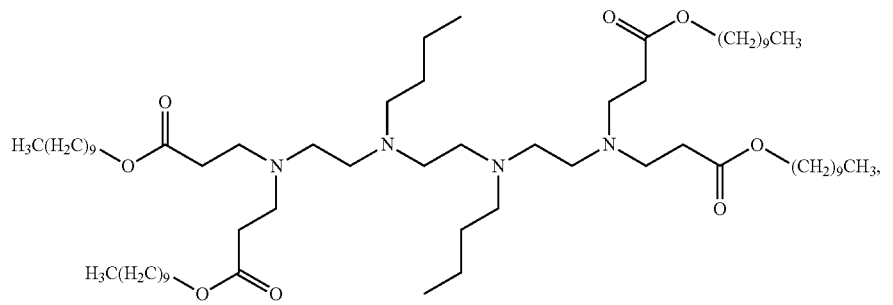
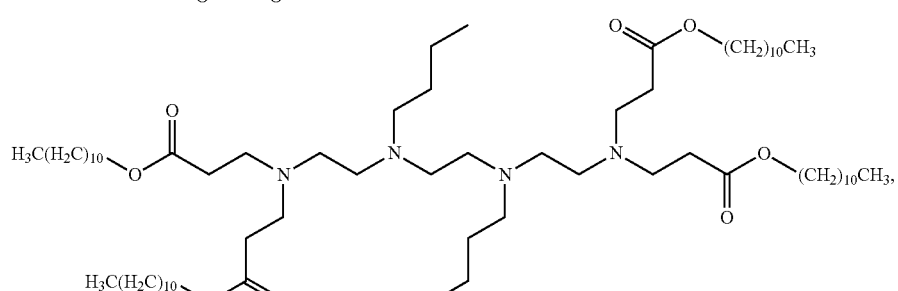
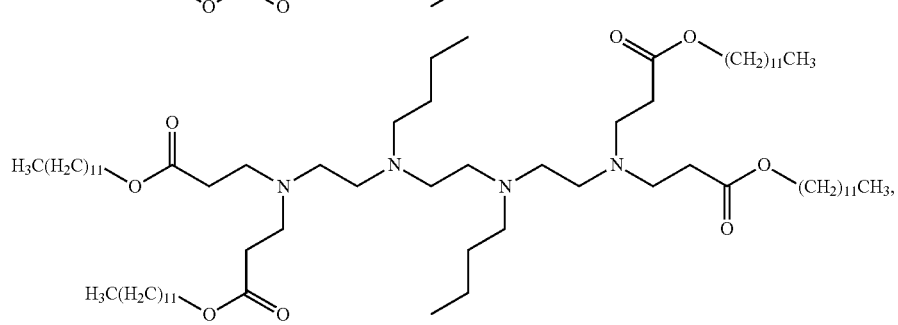

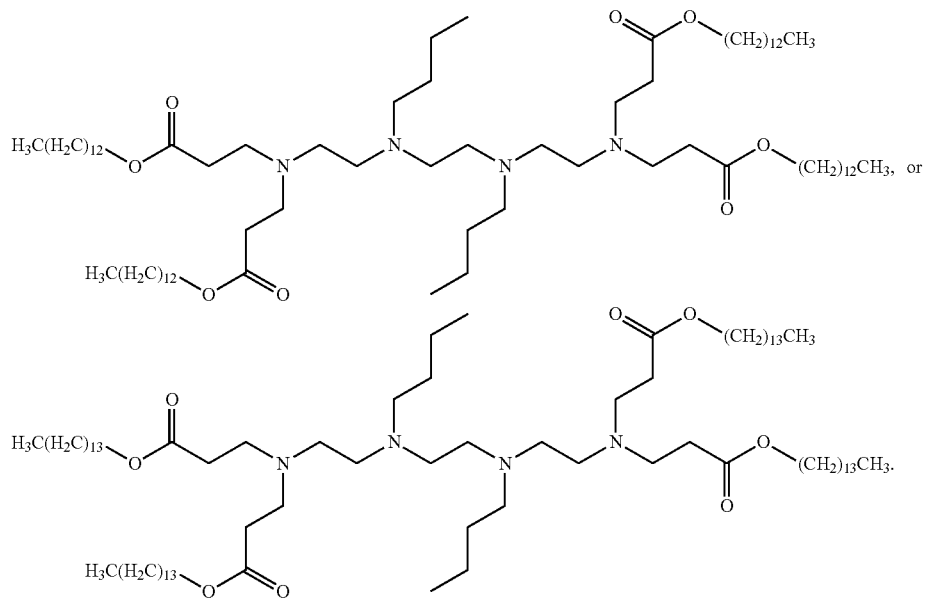
In certain embodiments, an inventive lipidoid is prepared by reacting amine 510 with acrylate $O_{10}$, $O_{11}$, $O_{12}$, $O_{13}$, or $O_{14}$ to form compound $510O_{10}$, $510O_{11}$, $510O_{12}$, $510O_{13}$, or $510O_{14}$. In certain embodiments, an inventive lipidoid is of one of the formulae below:
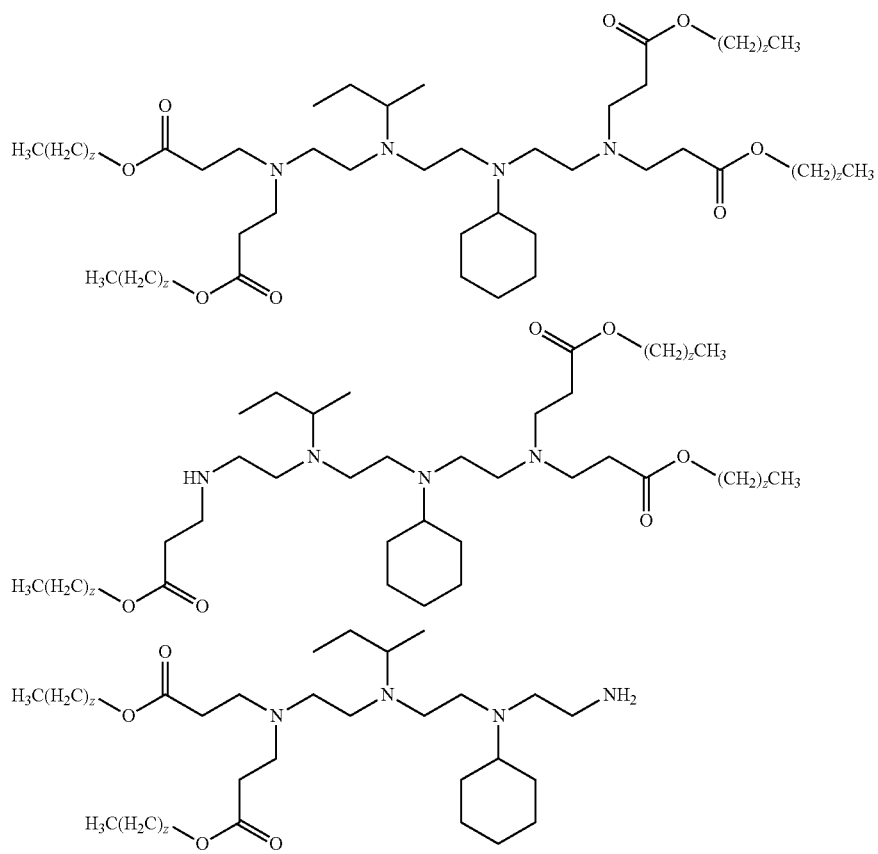

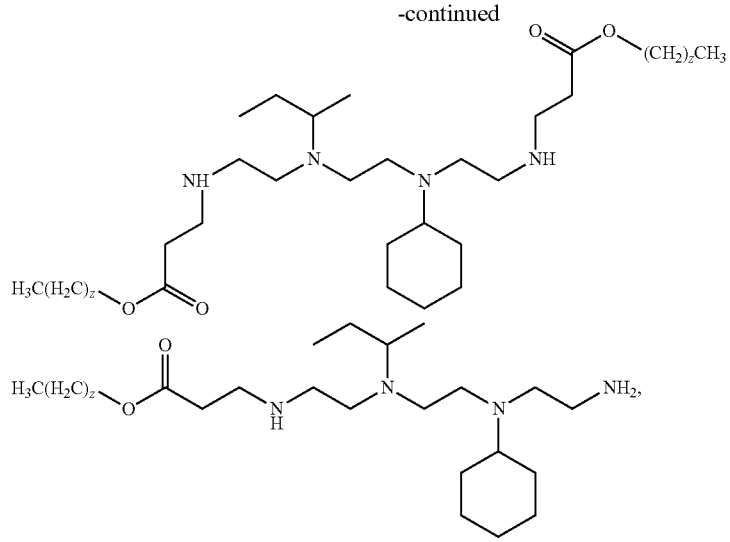
wherein z is 9, 10, 11, 12, or 13.
In some embodiments, the present invention provides a composition of one or more of the above lipidoids. In certain embodiments, an inventive lipidoid is of the formula:
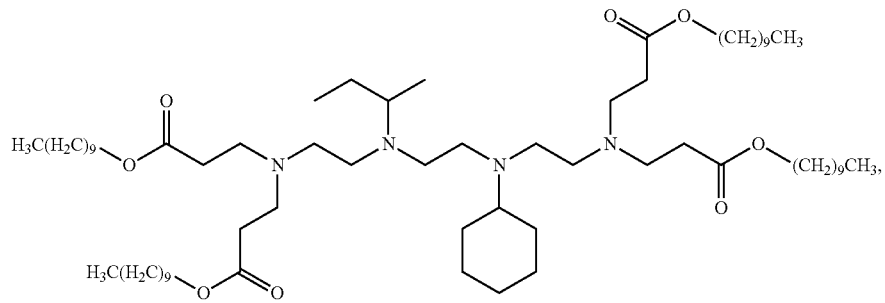
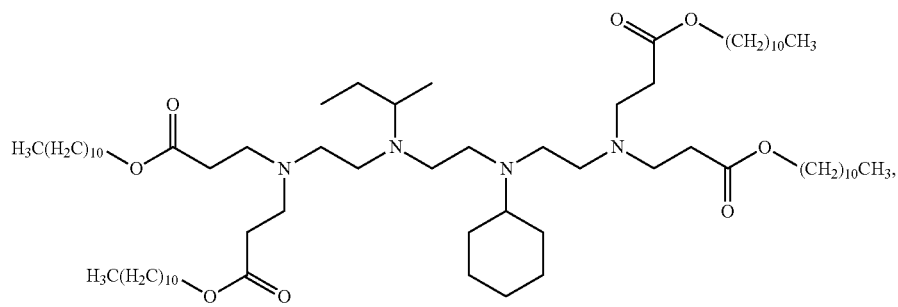
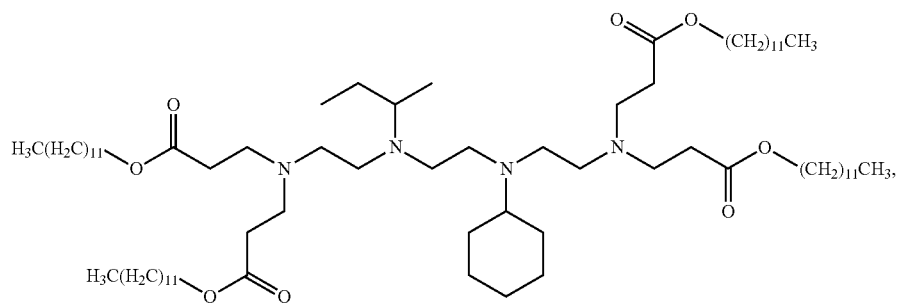

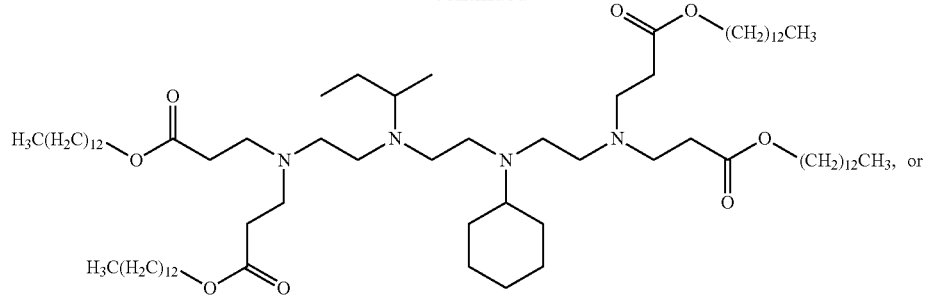
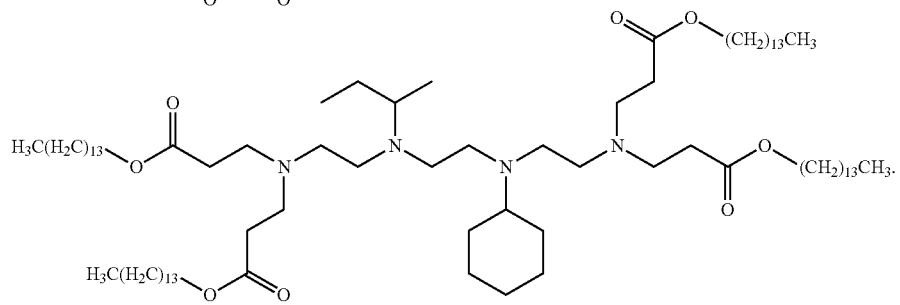
In certain embodiments, an inventive lipidoid is prepared by reacting amine 511 with acrylate $O_{10}$, $O_{11}$, $O_{12}$, $O_{13}$, or $O_{14}$ to form compound $511O_{10}$, $511O_{11}$, $511O_{12}$, $511O_{13}$, or $511O_{14}$. In certain embodiments, an inventive lipidoid is of one of the formulae below:
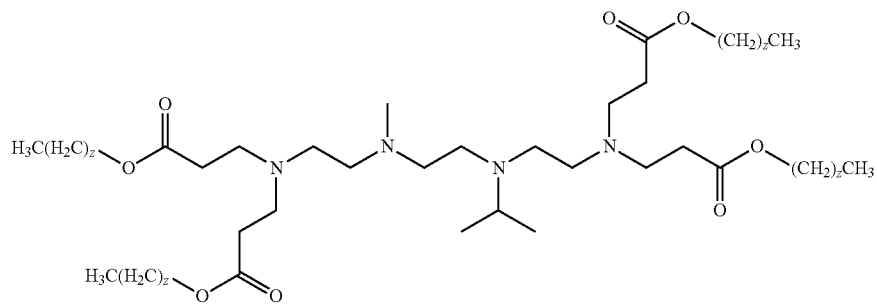
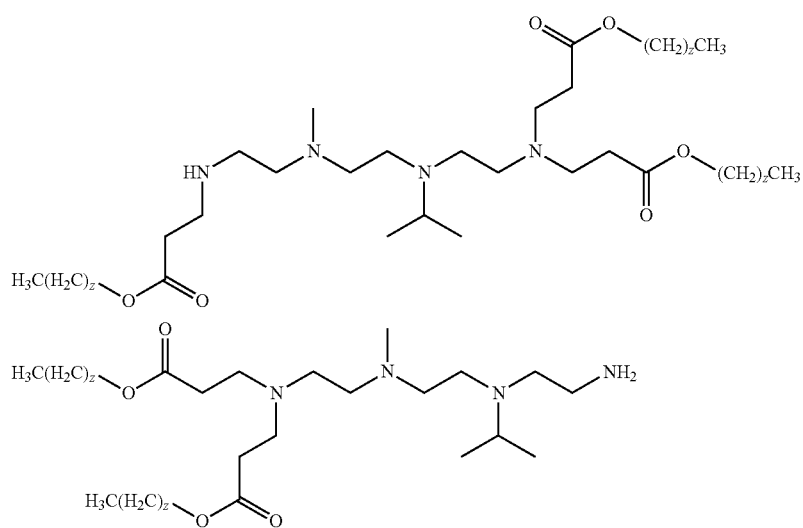

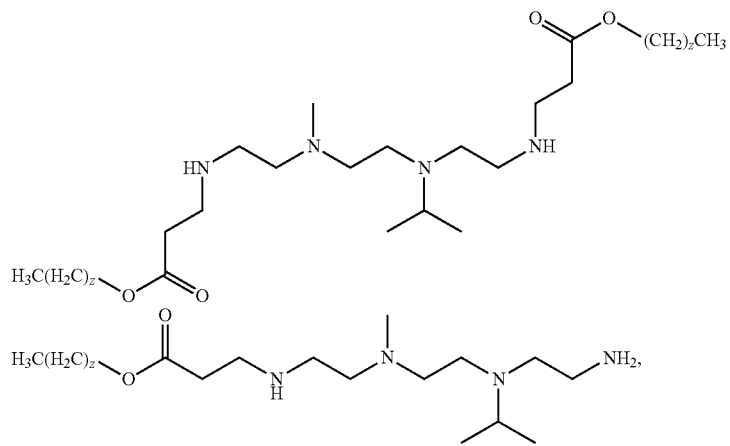
wherein z is 9, 10, 11, 12, or 13.
In some embodiments, the present invention provides a composition of one or more of the above lipidoids. In certain embodiments, an inventive lipidoid is of the formula:
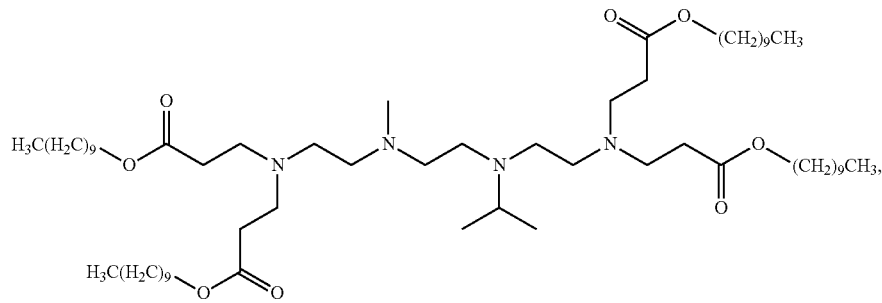
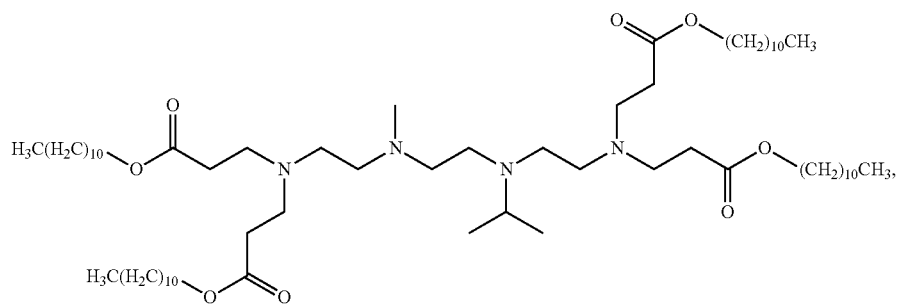
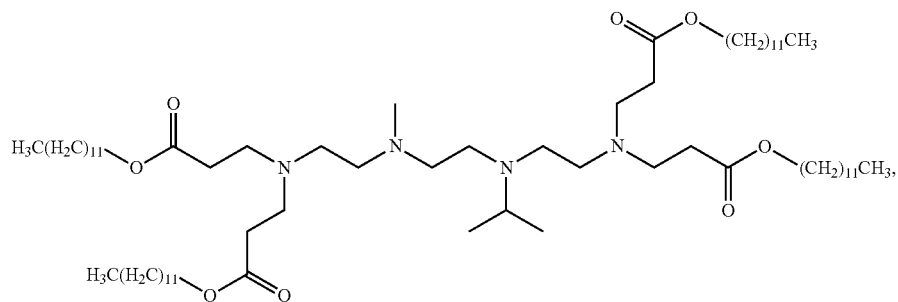

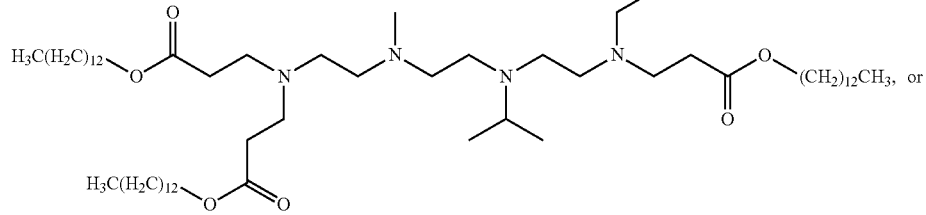
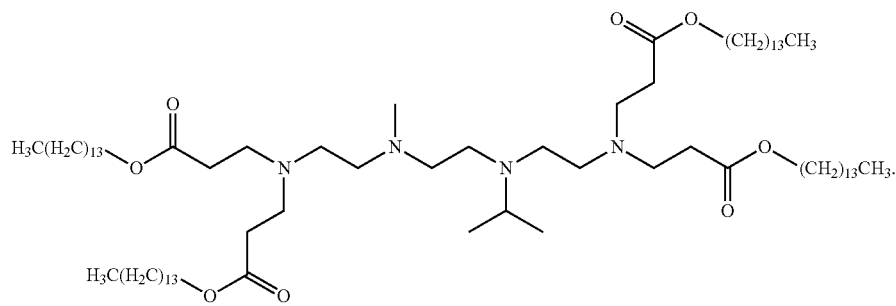
In certain embodiments, an inventive lipidoid is prepared by reacting amine 512 with acrylate $O_{10}$, $O_{11}$, $O_{12}$, $O_{13}$, or $O_{14}$ to form compound $512O_{10}$, $512O_{11}$, $512O_{12}$, $512O_{13}$, or $512O_{14}$. In certain embodiments, an inventive lipidoid is of one of the formulae below:
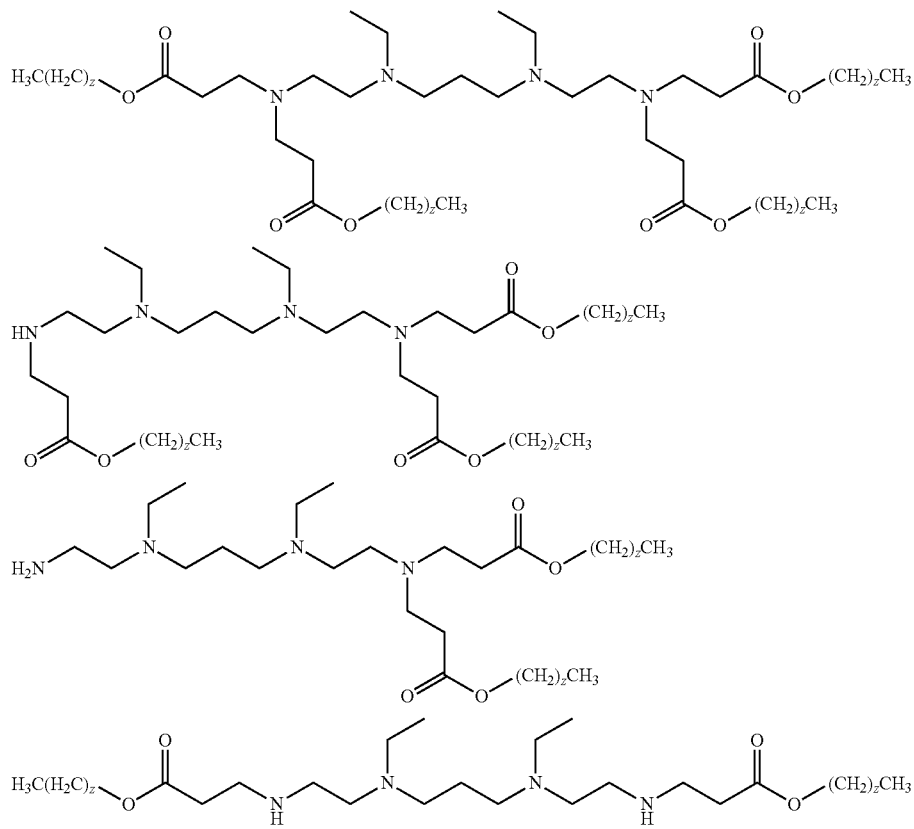

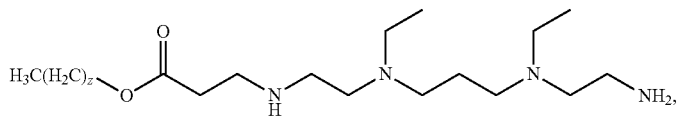

wherein z is 9, 10, 11, 12, or 13.

In some embodiments, the present invention provides a composition of one or more of the above lipidoids. In certain embodiments, an inventive lipidoid is of the formula:

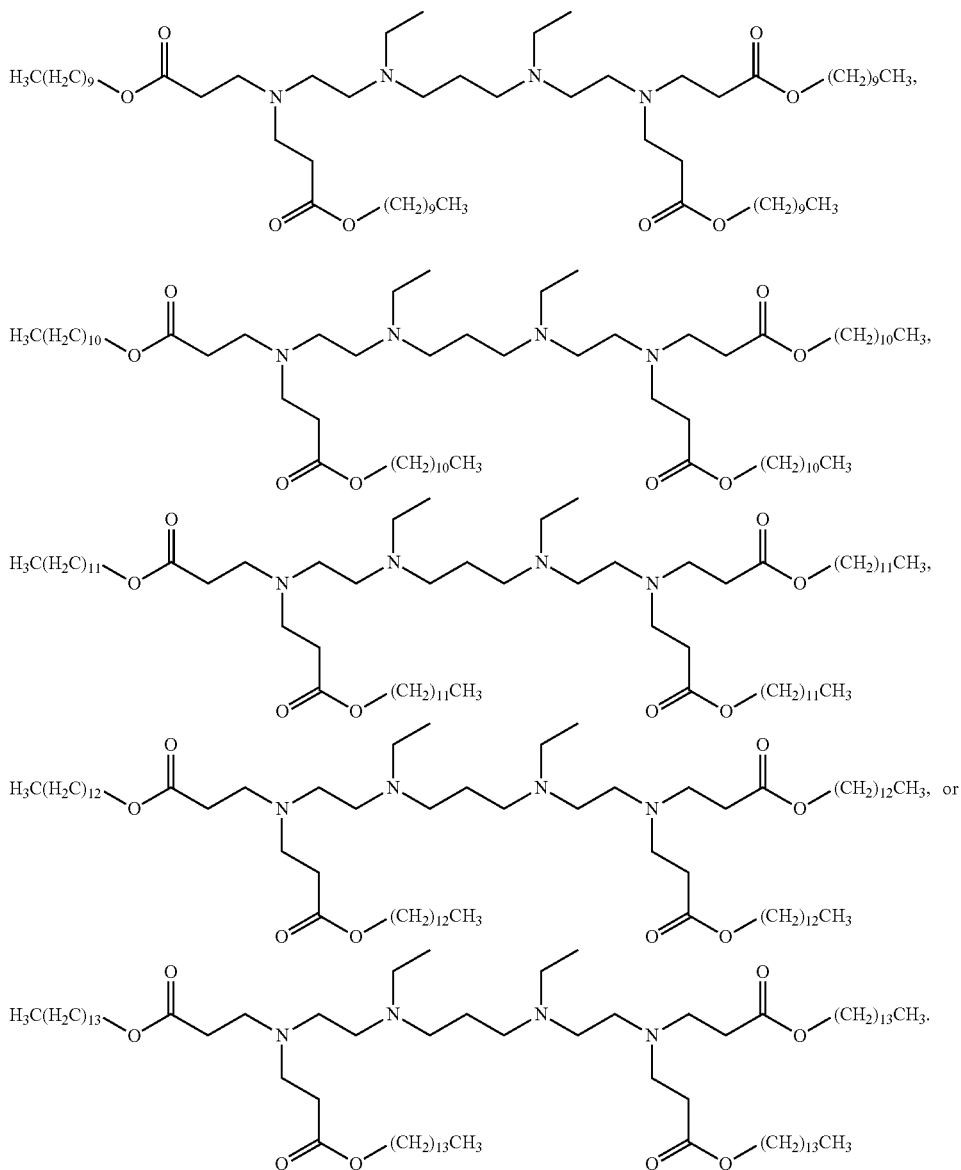

In certain embodiments, an inventive lipidoid is prepared by reacting amine 513 with acrylate $O_{10}$, $O_{11}$, $O_{12}$, $O_{13}$, or $O_{14}$ to form compound $513O_{10}$, $513O_{11}$, $513O_{12}$, $513O_{13}$, or $513O_{14}$. In certain embodiments, an inventive lipidoid is of one of the formulae below:

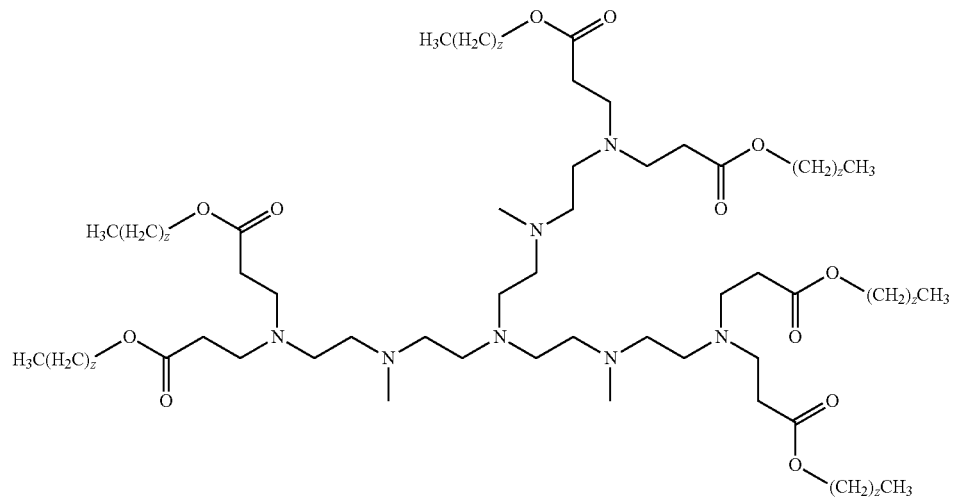
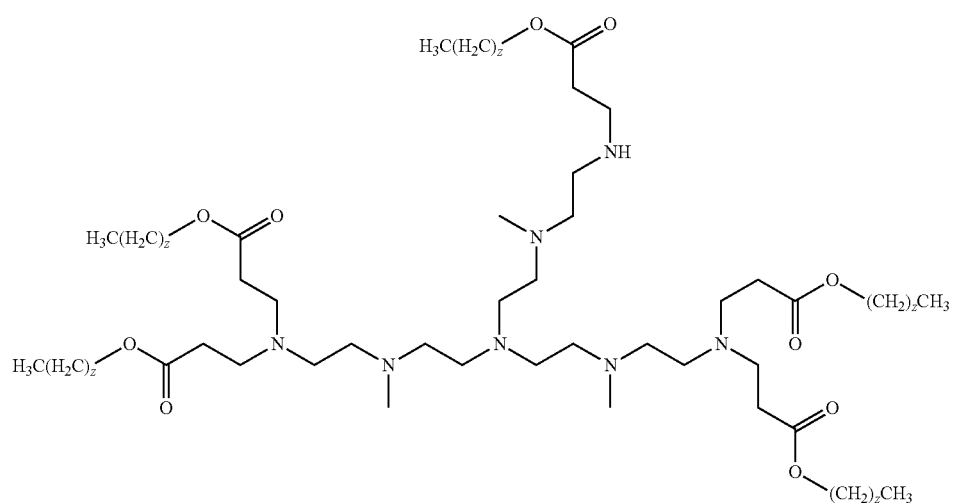
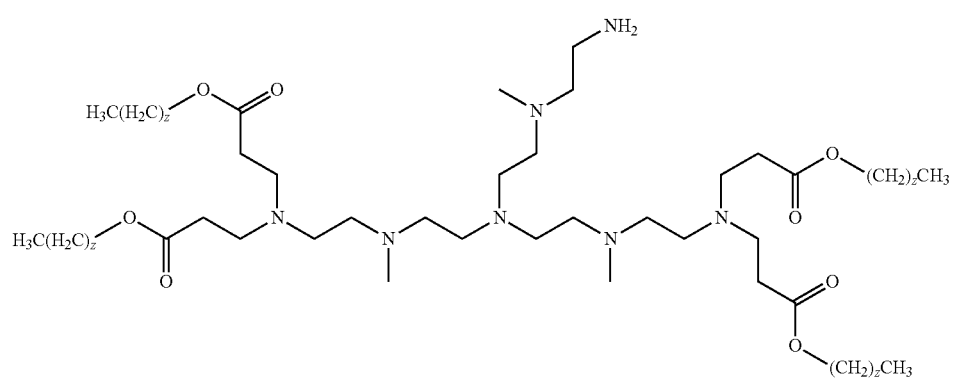

-continued
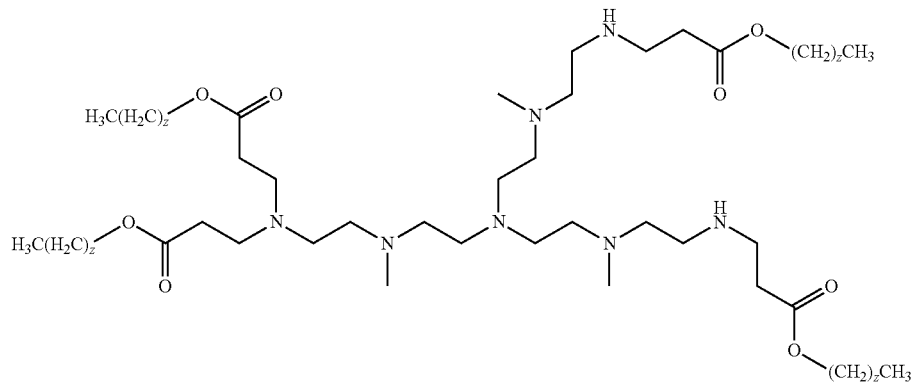
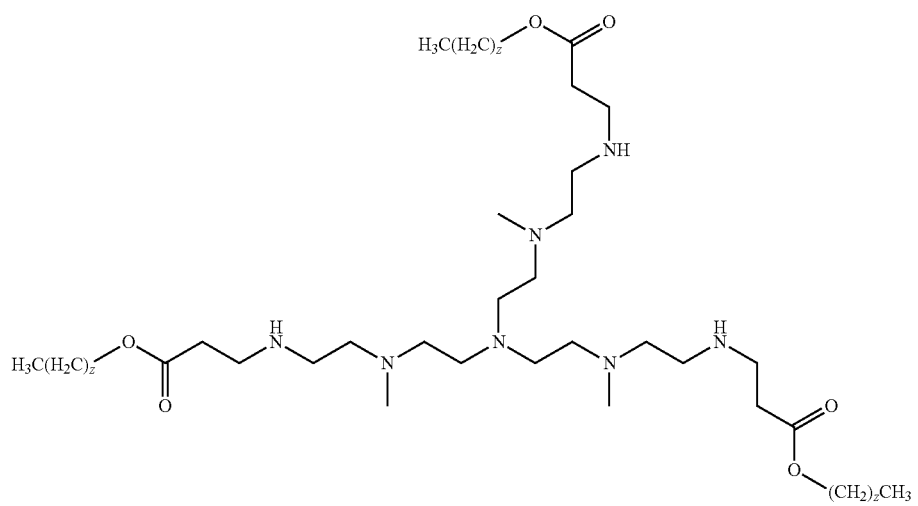
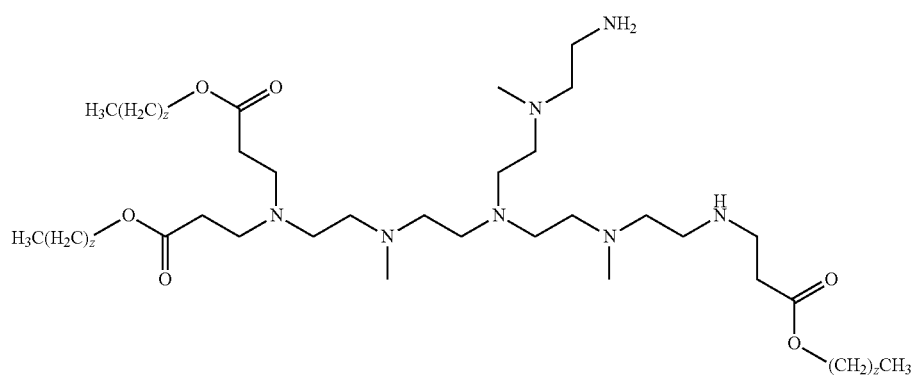
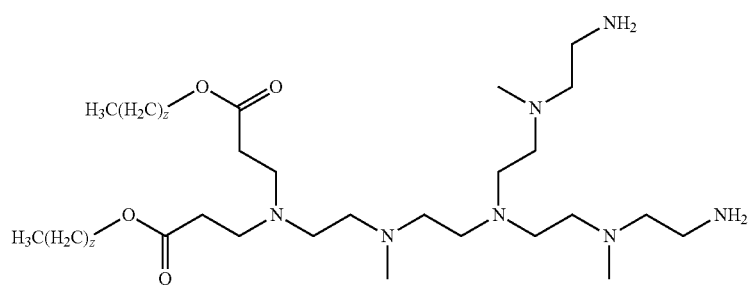

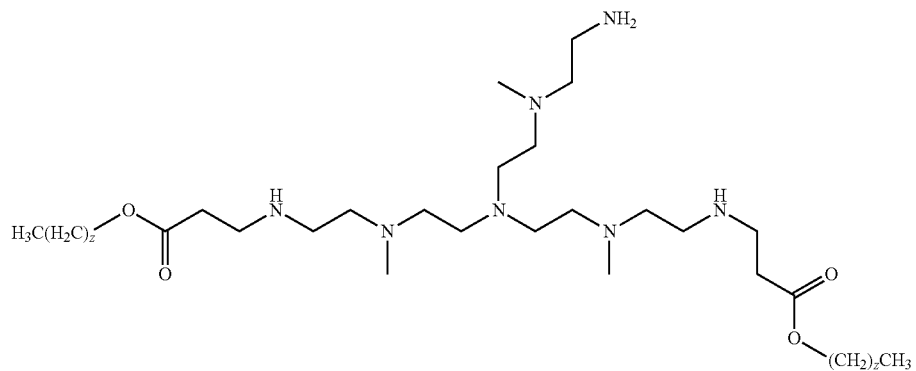
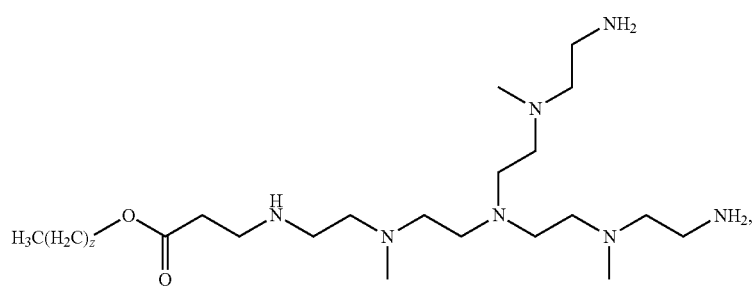
wherein z is 9, 10, 11, 12, or 13.
In some embodiments, the present invention provides a composition of one or more of the above lipidoids. In certain embodiments, an inventive lipidoid is of the formula:
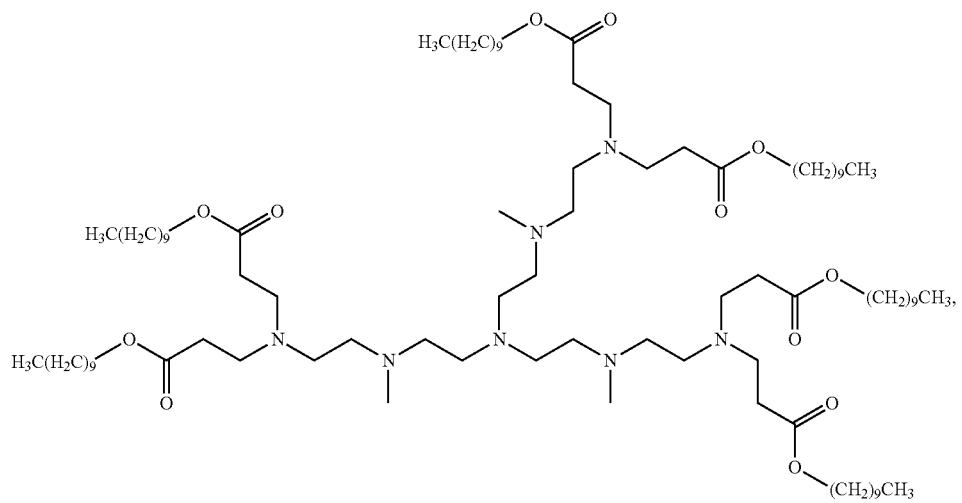

-continued
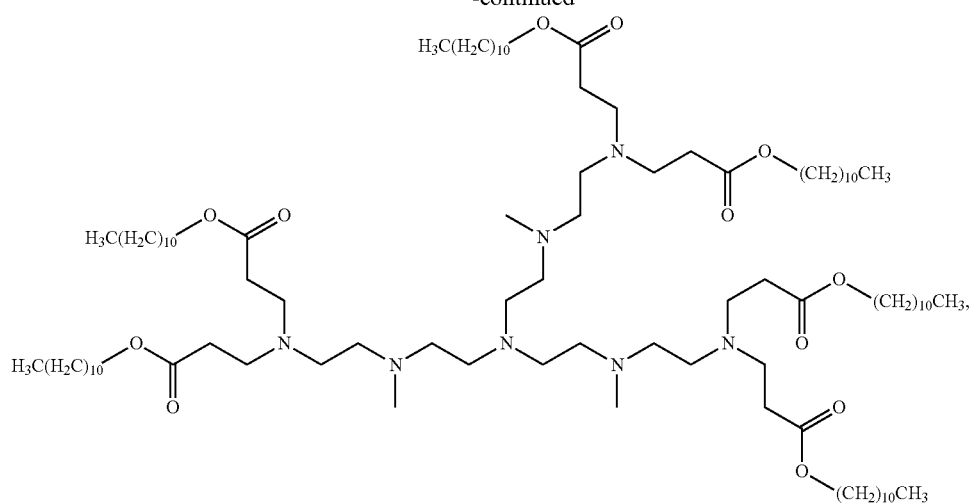
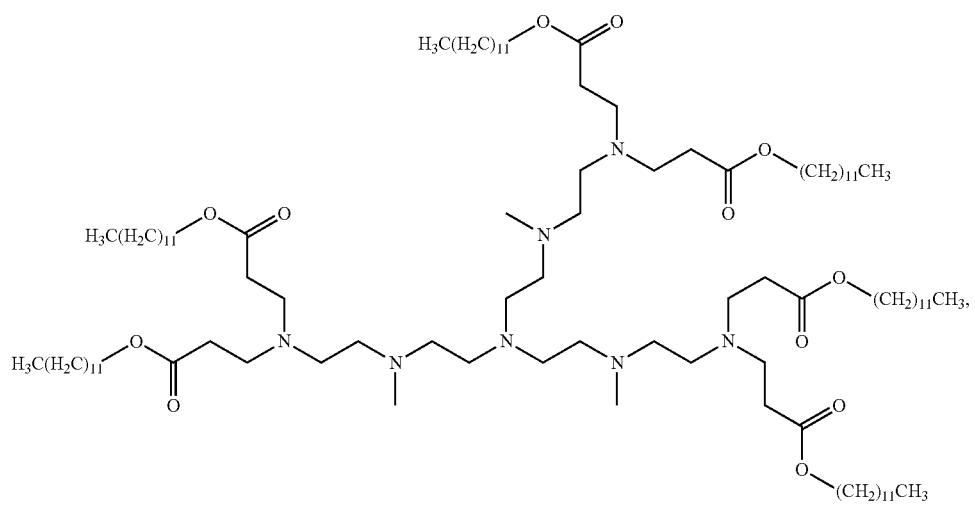
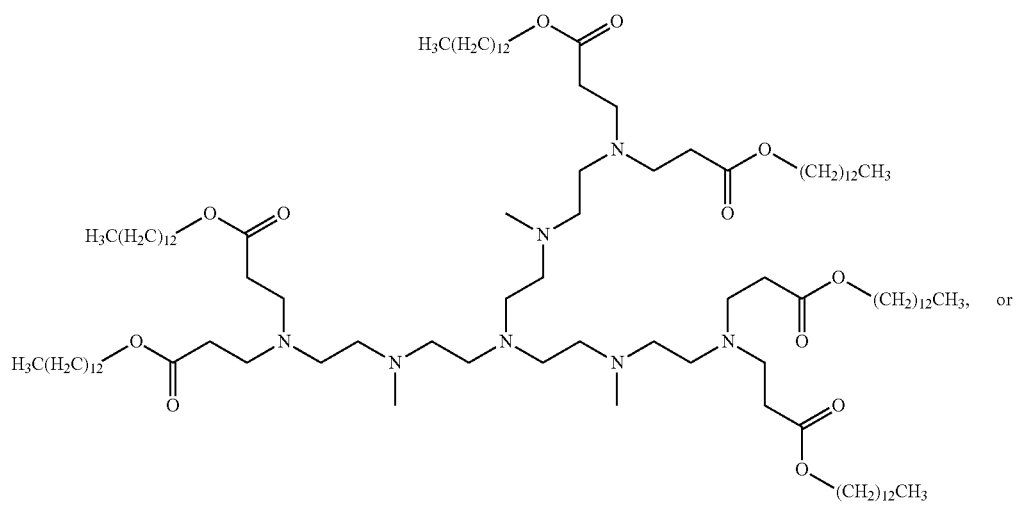
or

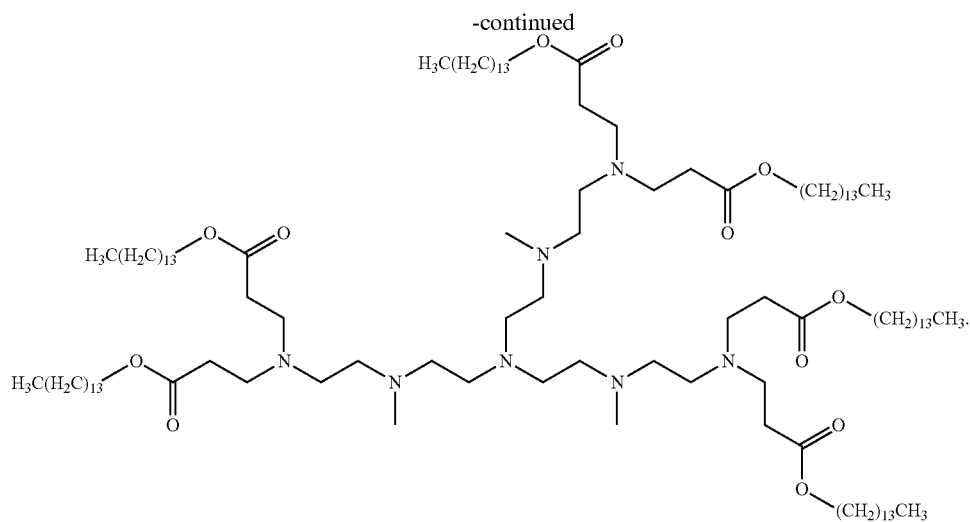
In certain embodiments, an inventive lipidoid is prepared by reacting amine 514 with acrylate $O_{10}$, $O_{11}$, $O_{12}$, $O_{13}$, or $O_{14}$ to form compound $514O_{10}$, $514O_{11}$, $514O_{12}$, $514O_{13}$, or $514O_{14}$. In certain embodiments, an inventive lipidoid is of one of the formulae below:
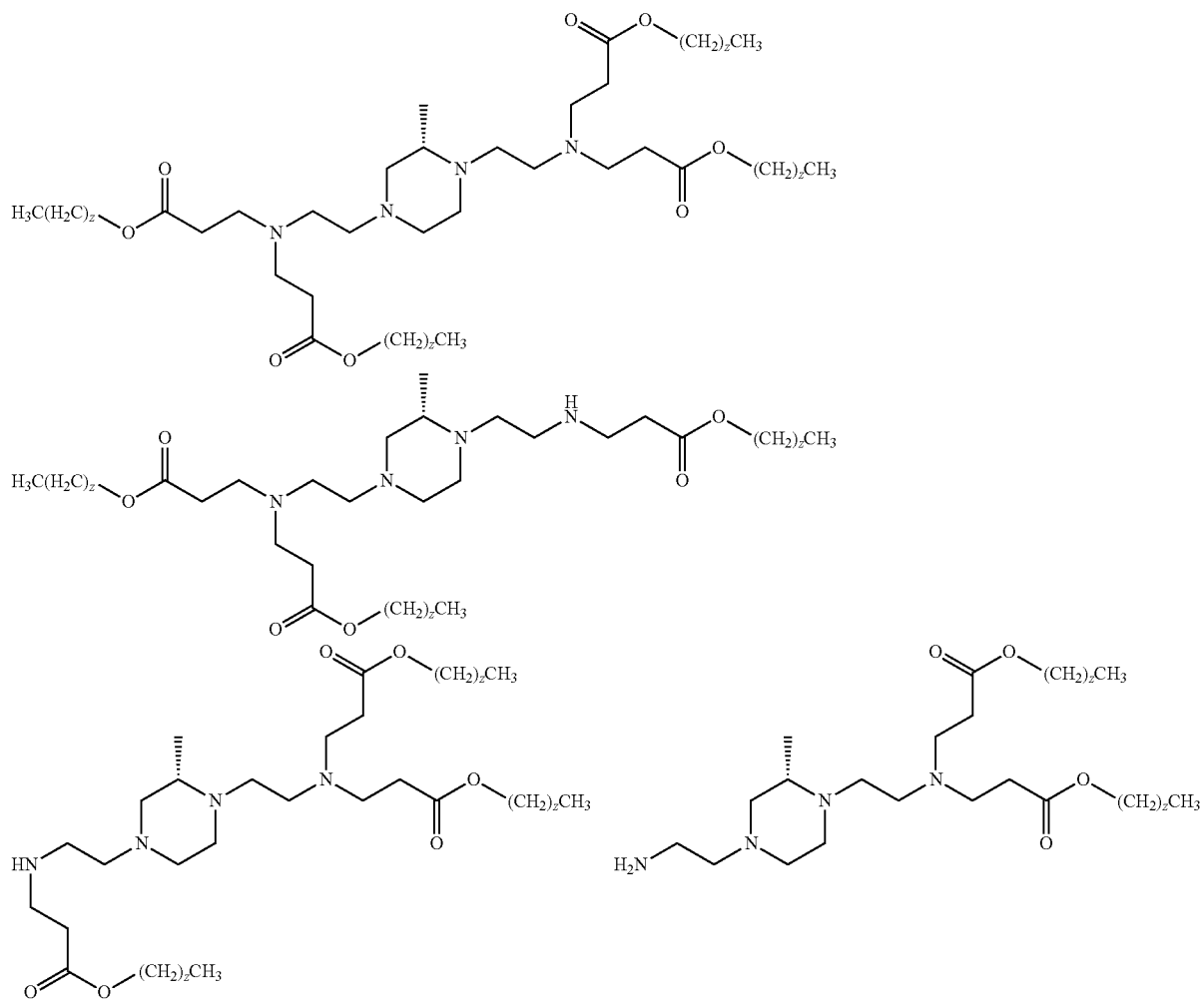

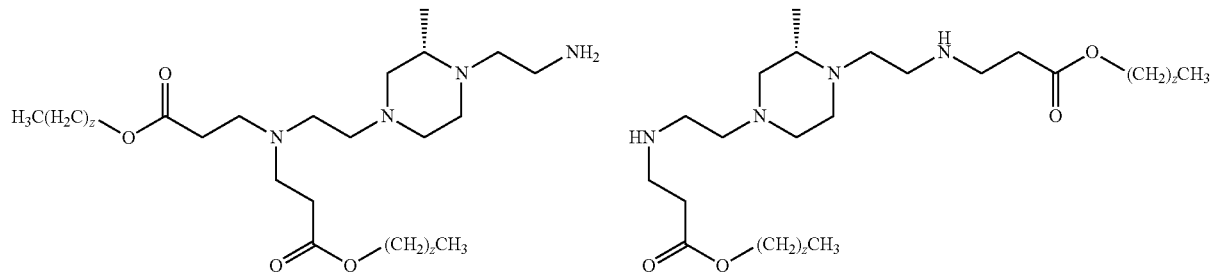
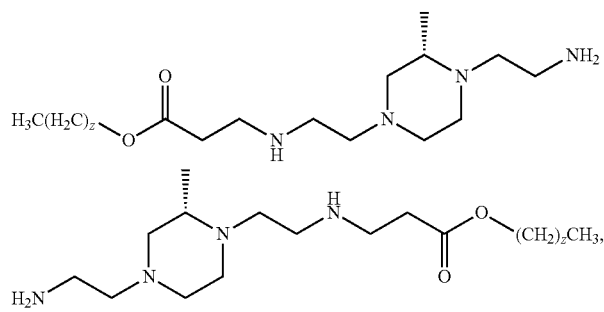
wherein z is 9, 10, 11, 12, or 13.
In some embodiments, the present invention provides a composition of one or more of the above lipidoids. In certain embodiments, an inventive lipidoid is of the formula:
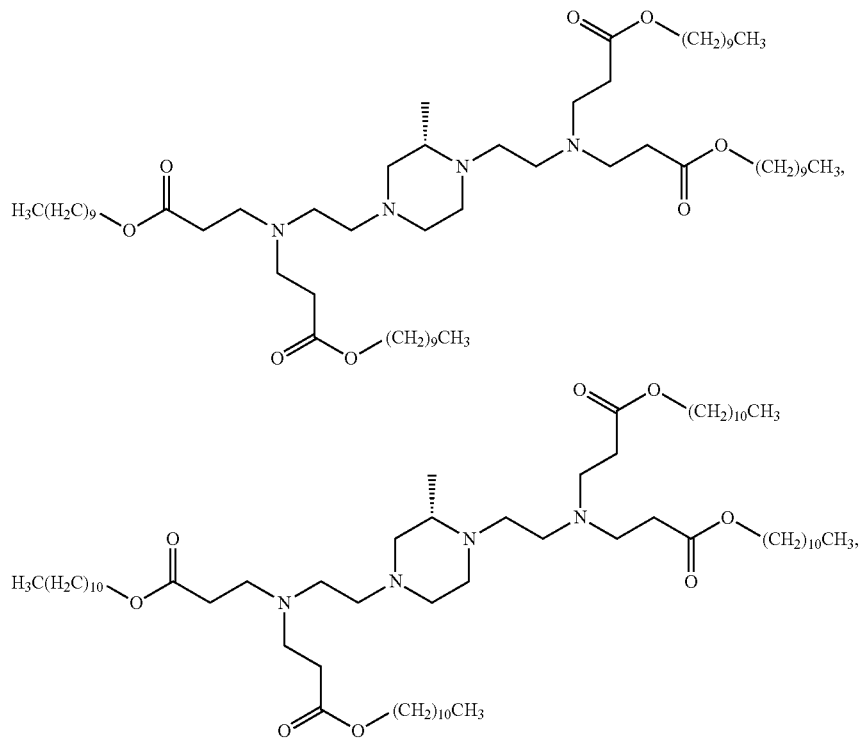

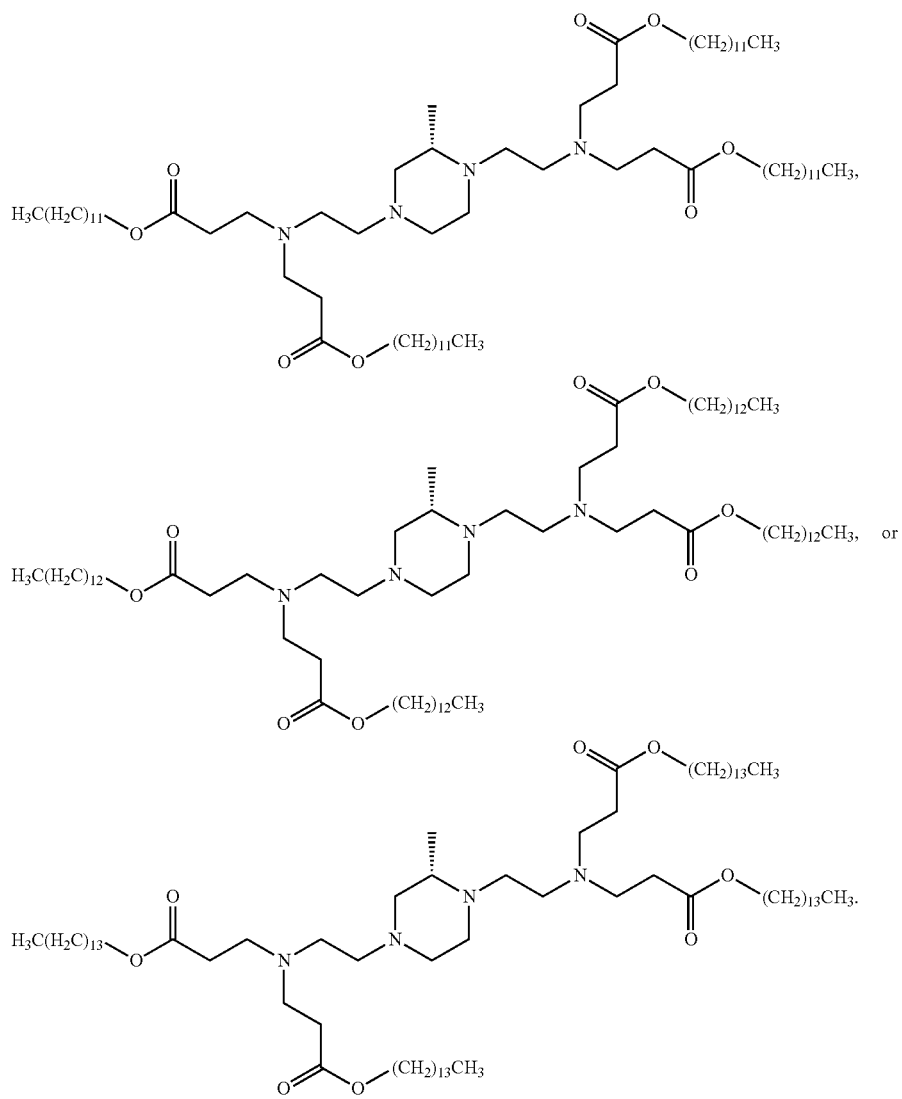
In certain embodiments, an inventive lipidoid is prepared by reacting amine 515 with acrylate $O_{10}$, $O_{11}$, $O_{12}$, $O_{13}$, or $O_{14}$ to form compound $515O_{10}$, $515O_{11}$, $515O_{12}$, $515O_{13}$, or $515O_{14}$. In certain embodiments, an inventive lipidoid is of one of the formulae below:
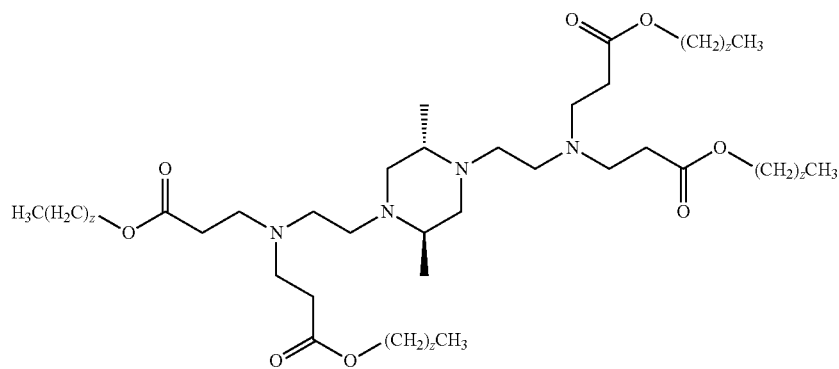

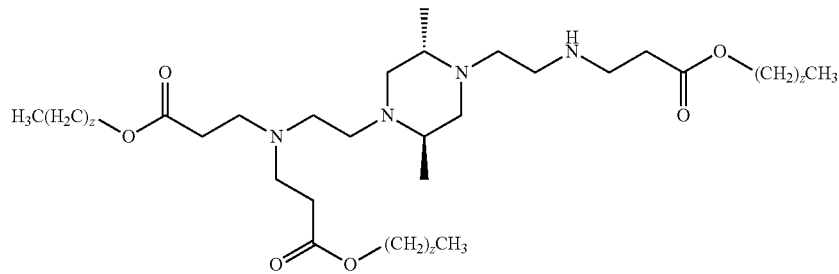
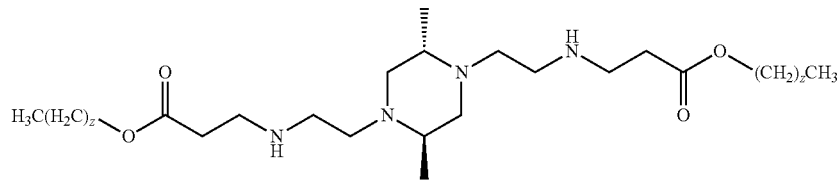
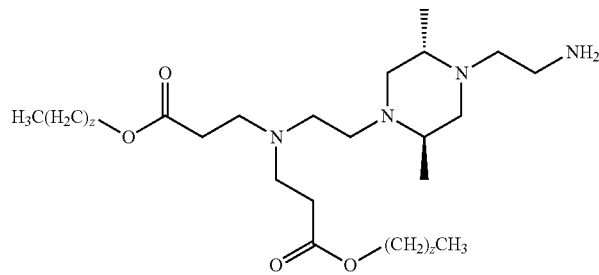
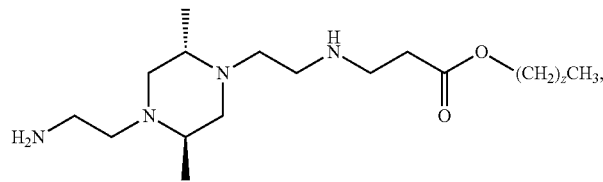
wherein z is 9, 10, 11, 12, or 13.
In some embodiments, the present invention provides a composition of one or more of the above lipidoids. In certain embodiments, an inventive lipidoid is of the formula:
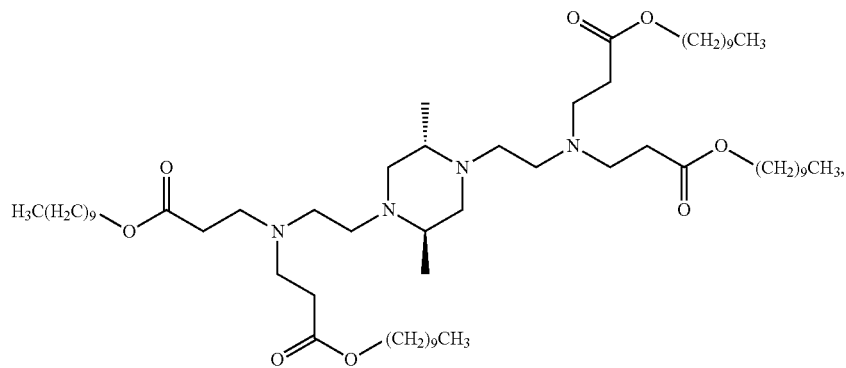

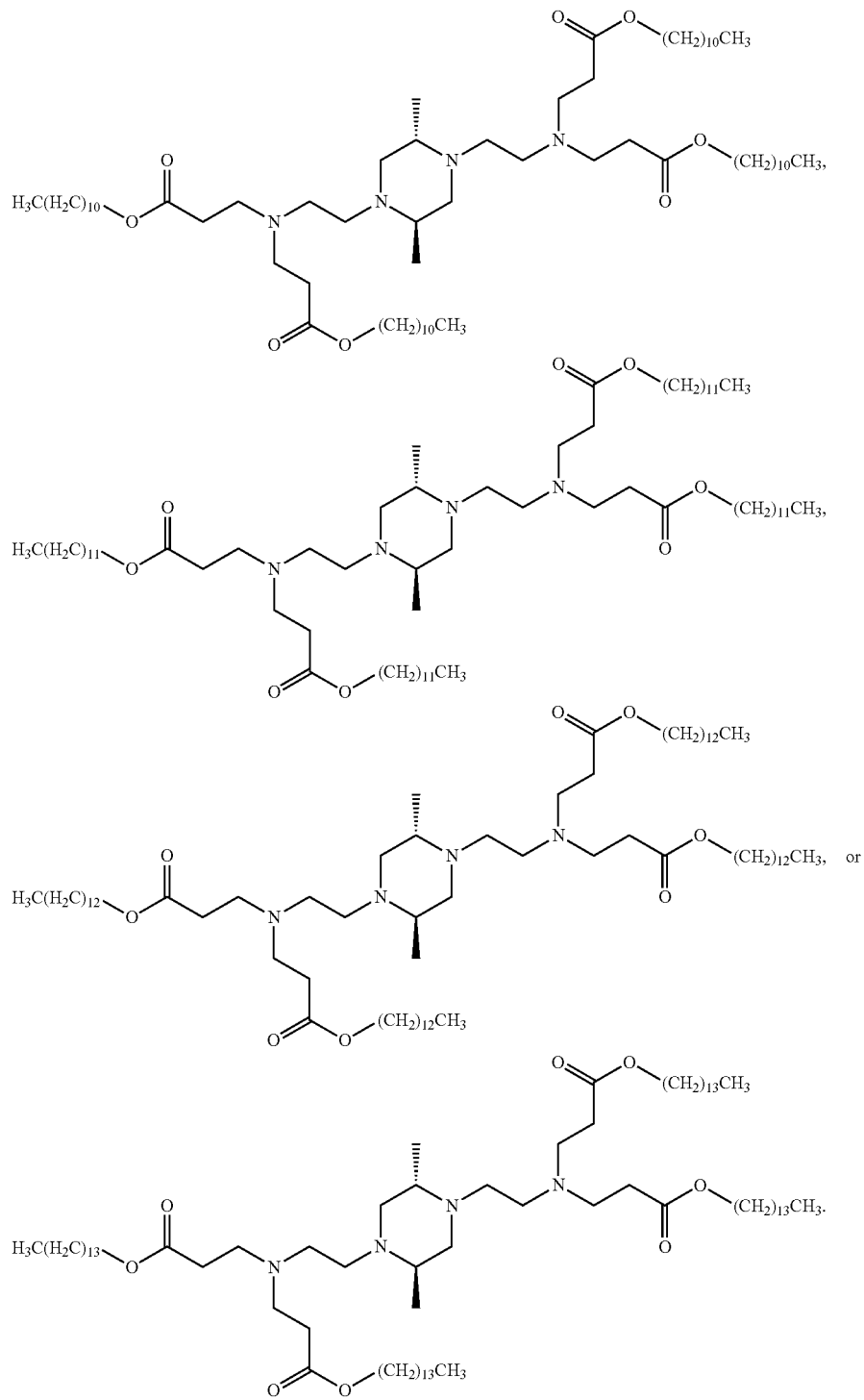

Synthesis of Lipids

Lipidoids described herein may be prepared by any method known in the art. In certain embodiments, inventive lipidoids are prepared via the conjugate addition of primary or secondary amines to acrylates. Such syntheses are described in detail in U.S. Publication No. 2011/0009641, incorporated herein by reference. In certain embodiments, inventive lipidoids are prepared from commercially available starting materials, such acrylates and amines. In other embodiments, inventive lipidoids are prepared from easily and/or inexpensively prepared starting materials. As would be appreciated by one of skill in the art, the lipidoids described herein can be prepared by total synthesis starting from commercially available starting materials. A particular lipidoid may be the desired final product of the synthesis, or a mixture of lipidoids may be the desired final product.

Polynucleotide Complexes

The ability of cationic compounds to interact with negatively charged polynucleotides through electrostatic interactions is well known. Cationic lipids such as Lipofectamine have been prepared and studied for their ability to complex and transfect polynucleotides. The interaction of the lipid with the polynucleotide is thought to at least partially prevent the degradation of the polynucleotide. By neutralizing the charge on the backbone of the polynucleotide, the neutral or slightly-positively-charged complex is also able to more easily pass through the hydrophobic membranes (e.g., cytoplasmic, lysosomal, endosomal, nuclear) of the cell. In certain embodiments, the complex is slightly positively charged. In certain embodiments, the complex has a positive ζ-potential. In certain embodiments, the ζ-potential is between +1 and +30.

In certain embodiments, lipidoids of the present invention possess tertiary amines. Although these amines are hindered, they are available to interact with a polynucleotide (e.g., DNA, RNA, synthetic analogs of DNA and/or RNA, DNA/RNA hydrids, etc.). In certain embodiments, polynucleotides or derivatives thereof are contacted with the inventive lipidoids under conditions suitable to form polynucleotide/lipidoid complexes. In certain embodiments, the lipidoid is at least partially protonated so as to form a complex with the negatively charged polynucleotide. In certain embodiments, the polynucleotide/lipidoid complexes form nanoparticles that are useful in the delivery of polynucleotides to cells. In certain embodiments, multiple lipidoid molecules may be associated with a polynucleotide molecule. The complex may include 1-100 lipidoid molecules, 1-1000 lipidoid molecules, 10-1000 lipidoid molecules, or 100-10,000 lipidoid molecules. In certain embodiments, the complex may form a nanoparticle. In certain embodiments, the diameter of the nanoparticles ranges from 10-500 nm, from 10-1200 nm, or from 50-150 nm. In certain embodiments, nanoparticles may be associated with a targeting agent as described below.

Polynucleotide

A polynucleotide to be complexed, encapsulated by the inventive lipidoids, or included in a composition with the inventive lipidoids may be any nucleic acid including but not limited to RNA and DNA. In certain embodiments, the polynucleotide is DNA. In other embodiments, the polynucleotide is RNA. In certain embodiments, the polynucleotide is an siRNA. In certain embodiments, the polynucleotide is an shRNA. In certain embodiments, the polynucleotide is an mRNA. In certain embodiments, the polynucleotide is a dsRNA. In certain embodiments, the polynucleotide is an miRNA. In certain embodiments, the polynucleotide is an antisense RNA. The polynucleotides may be of any size or sequence, and they may be single- or double-stranded. In certain embodiments, the polynucleotide is greater than 100 base pairs long. In certain other embodiments, the polynucleotide is greater than 1000 base pairs long and may be greater than 10,000 base pairs long. In certain embodiments, the polynucleotide is purified and substantially pure. In certain embodiments, the polynucleotide is greater than 50% pure, greater than 75% pure, or greater than 95% pure. The polynucleotide may be provided by any means known in the art. In certain preferred embodiments, the polynucleotide has been engineered using recombinant techniques (for a more detailed description of these techniques, please see Ausubel et al. *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989); each of which is incorporated herein by reference). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides are preferably prepared using synthetic chemistry in vitro. The polynucleotides to be delivered may be in any form. For example, the polynucleotide may be a circular plasmid, a linearized plasmid, a cosmid, a viral genome, a modified viral genome, an artificial chromosome, etc.

The polynucleotide may be of any sequence. In certain preferred embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In other particularly preferred embodiments, the polynucleotide is not intended to encode a protein. For example, the polynucleotide may be used to fix an error in the genome of the cell being transfected.

The polynucleotide may also be provided as an antisense agent or RNA interference (RNAi) (Fire et al. *Nature* 391: 806-811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" *Biochim. Biophys. Acta* 1489(1):31-44, 1999; Crooke "Evaluating the mechanism of action of antiproliferative antisense drugs" *Antisense Nucleic Acid Drug Dev.*

10(2):123-126, discussion 127, 2000; *Methods in Enzymology* volumes 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al. *J. Mol. Med.* 75(4):267-282, 1997; incorporated herein by reference).

In certain embodiments, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection. The polynucleotide of these vaccines may be combined with interleukins, interferon, cytokines, and adjuvants such as cholera toxin, alum, Freund's adjuvant, etc. A large number of adjuvant compounds are known; a useful compendium of many such compounds is prepared by the National Institutes of Health and can be found on the internet (http://www.niaid.nih.gov/daids/vaccine/pdf/compendium.pdf, incorporated herein by reference; see also Allison *Dev. Biol. Stand.* 92:3-11, 1998; Unkeless et al. *Annu. Rev. Immunol.* 6:251-281, 1998; and Phillips et al. *Vaccine* 10:151-158, 1992, each of which is incorporated herein by reference).

An antigenic protein or peptides encoded by a polynucleotide may be derived from such bacterial organisms as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

Microparticles and Nanoparticles

The lipidoids of the present invention may also be used to form drug delivery devices. Inventive lipidoids may be used to encapsulate agents including polynucleotides, small molecules, proteins, peptides, metals, organometallic compounds, etc. Lipidoids described herein have several properties that make them particularly suitable in the preparation of drug delivery devices. These include 1) the ability of the lipid to complex and "protect" labile agents; 2) the ability to buffer the pH in the endosome; 3) the ability to act as a "proton sponge" and cause endosomolysis; and 4) the ability to neutralize the charge on negatively charged agents. In certain embodiments, the diameter of the particles range from between 1 micrometer to 1,000 micrometers. In certain embodiments, the diameter of the particles range from between from 1 micrometer to 100 micrometers. In certain embodiments, the diameter of the particles range from between from 1 micrometer to 10 micrometers. In certain embodiments, the diameter of the particles range from between from 10 micrometer to 100 micrometers. In certain embodiments, the diameter of the particles range from between from 100 micrometer to 1,000 micrometers. In certain embodiments, the particles range from 1-5 micrometers. In certain embodiments, the diameter of the particles range from between 1 nm to 1,000 nm. In certain embodiments, the diameter of the particles range from between from 1 nm to 100 nm. In certain embodiments, the diameter of the particles range from between from 1 nm to 10 nm. In certain embodiments, the diameter of the particles range from between from 10 nm to 100 nm. In certain embodiments, the diameter of the particles range from between from 100 nm to 1,000 nm. In certain embodiments, the diameter of the particles range from between from 20 nm to 2,000 nm. In certain embodiments, the particles range from 1-5 nm. In certain embodiments, the diameter of the particles range from between 1 pm to 1,000 pm. In certain embodiments, the diameter of the particles range from between from 1 pm to 100 pm. In certain embodiments, the diameter of the particles range from between from 1 pm to 10 pm. In certain embodiments, the diameter of the particles range from between from 10 pm to 100 pm. In certain embodiments, the diameter of the particles range from between 100 pm to 1,000 pm. In certain embodiments, the particles range from 1-5 pm.

The inventive particles may be prepared using any method known in this art. These include, but are not limited to, spray drying, single and double emulsion solvent evaporation, solvent extraction, phase separation, simple and complex coacervation, and other methods well known to those of ordinary skill in the art. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the matrix. Methods developed for making particles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988; each of which is incorporated herein by reference).

If the particles prepared by any of the above methods have a size range outside of the desired range, the particles can be sized, for example, using a sieve. The particle may also be coated. In certain embodiments, the particles are coated with a targeting agent. In other embodiments, the particles are coated to achieve desirable surface properties (e.g., a particular charge).

In certain embodiments, the present invention provides a nanoparticle comprising an inventive lipidoid and one or more agents to be delivered. In certain embodiments, the agent is a polynucleotide, drug, protein or peptide, small molecule, or gas. In certain embodiments, the agent is RNA (e.g. mRNA, RNAi, dsRNA, siRNA, shRNA, miRNA, or antisense RNA). In certain embodiments, the nanoparticle further comprises cholesterol or a derivative thereof, such as 3β-[N—(N',N'-dimethylaminoethane)-carbamoyl]cholesterol (DC-cholesterol). In certain embodiments, the nanoparticle further comprises a PEG-based material. In certain embodiments, the PEG-based material is PEG-ceramide, PEG-DMG, PEG-PE, poloxamer, or DSPE carboxy PEG. For instance, in certain embodiments, the PEG-based material is C14 PEG2000 DMG, C15 PEG2000 DMG, C16 PEG2000 DMG, C18 PEG2000 DMG, C14 PEG 2000 ceramide, C15 PEG2000 ceramide, C16 PEG2000 ceramide, C18 PEG2000 ceramide, C14 PEG2000 PE, C15 PEG2000 PE, C16 PEG2000 PE, C18 PEG2000 PE, C14 PEG350 PE, C14 PEG5000 PE, poloxamer F-127, poloxamer F-68, poloxamer L-64, or DSPE carboxy PEG. In certain embodiments, the nanoparticle further comprises a lipid. For example, in certain embodiments, the nanoparticle further comprises DSPC, DOPC, or DOPE. In certain embodiments, the nanoparticle comprises a lipidoid, an agent (e.g., RNA), a lipid, cholesterol or a derivative thereof, and a PEG-based material.

Micelles, Liposomes, and Lipoplexes

Lipidoids described herein may also be used to prepare micelles or liposomes. In addition, any agent may be included in a micelle or liposome. Micelles and liposomes are particularly useful in delivering hydrophobic agents such as hydrophobic small molecules. When the micelle or liposome is complexed with (e.g., encapsulates or covers) a polynucleotide it is referred to as a "lipoplex." Many techniques for preparing micelles, liposomes, and lipoplexes are known in the art, and any method may be used with the inventive lipidoids to make micelles and liposomes.

In certain embodiments, liposomes (lipid vesicles) are formed through spontaneous assembly. In other embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these particles have formed, reducing the size of the particle can be modified through input of sonic energy (sonication) or mechanical energy (extrusion). See Walde, P. "Preparation of Vesicles (Liposomes)" In *Encylopedia of Nanoscience and Nanotechnology*; Nalwa, H. S. Ed. American Scientific Publishers Los Angeles, 2004; Vol. 9, pp. 43-79; Szoka et al. "Comparative Properties and Methods of Preparation of Lipid Vesicles (Liposomes)" *Ann. Rev. Biophys. Bioeng.* 9:467-508, 1980; each of which is incorporated herein. The preparation of lipsomes involves preparing the lipid for hydration, hydrating the lipid with agitation, and sizing the vesicles to achieve a homogenous distribution of liposomes. Lipids are first dissolved in an organic solvent to assure a homogeneous mixture of lipids. The solvent is then removed to form a lipid film. This film is thoroughly dried to remove residual organic solvent by placing the vial or flask on a vaccuum pump overnight. Hydration of the lipid film/cake is accomplished by adding an aqueous medium to the container of dry lipid and agitating the mixture. Disruption of LMV suspensions using sonic energy typically produces small unilamellar vesicles (SUV) with diameters in the range of 15-50 nm. Lipid extrusion is a technique in which a lipid suspension is forced through a polycarbonate filter with a defined pore size to yield particles having a diameter near the pore size of the filter used. Extrusion through filters with 100 nm pores typically yields large, unilamellar vesicles (LUV) with a mean diameter of 120-140 nm.

In certain embodiments, liposomes are formed comprising an inventive lipid, a PEG-based material, cholesterol or a derivative thereof, and a polynucleotide. In certain embodiments, the polynucleotide is an RNA molecule (e.g., an siRNA). In other embodiments, the polynucleotide is a DNA molecule. In certain embodiments, the amount of lipidoid in the liposome ranges from 30-80 mol %, 40-70 mol %, or 60-70 mol %. In certain embodiments, the liposome comprises a PEG-based material. In certain embodiments, the amount of PEG-based material in the liposomes ranges from 5-20 mol %, 10-15 mol %, or 10 mol %. In certain embodiments, the liposome comprises cholesterol or a derivative thereof. In certain embodiments, the amount of cholesterol in the liposome ranges from 5-25 mol %, 10-20 mol %, or 15 mol %. In certain embodiments, the amount of cholesterol in the liposome is approximately 20 mol %. These liposomes may be prepared using any method known in the art. In certain embodiments (e.g., liposomes containing RNAi molecules), the liposomes are prepared by lipid extrusion.

Certain lipidoids can spontaneously self assemble around certain molecules, such as DNA and RNA, to form liposomes. In some embodiments, the application is the delivery of polynucleotides. Use of these lipidoids allows for simple assembly of liposomes without the need for additional steps or devices such as an extruder.

The following scientific papers described other methods for preparing liposomes and micelles: Narang et al. "Cationic Lipids with Increased DNA Binding Affinity for Nonviral Gene Transfer in Dividing and Nondividing Cells" *Bioconjugate Chem.* 16:156-68, 2005; Hofland et al. "Formation of stable cationic lipid/DNA complexes for gene transfer" *Proc. Natl. Acad. Sci. USA* 93:7305-7309, July 1996; Byk et al. "Synthesis, Activity, and Structure—Activity Relationship Studies of Novel Cationic Lipids for DNA Transfer" *J. Med. Chem.* 41(2):224-235, 1998; Wu et al. "Cationic Lipid Polymerization as a Novel Approach for Constructing New DNA Delivery Agents" *Bioconjugate Chem.* 12:251-57, 2001; Lukyanov et al. "Micelles from lipid derivatives of water-soluble polymers as delivery systems for poorly soluble drugs" *Advanced Drug Delivery Reviews* 56:1273-1289, 2004; Tranchant et al. "Physicochemical optimisation of plasmid delivery by cationic lipids" *J. Gene Med.* 6:S24-S35, 2004; van Balen et al. "Liposome/Water Lipophilicity: Methods, Information Content, and Pharmaceutical Applications" *Medicinal Research Rev.* 24(3):299-324, 2004; each of which is incorporated herein by reference.

Agent

The agents to be delivered by the system of the present invention may be therapeutic, diagnostic, or prophylactic agents. Any chemical compound to be administered to an individual may be delivered using the inventive inventive complexes, picoparticles, nanoparticles, microparticles, micelles, or liposomes. The agent may be a small molecule, organometallic compound, nucleic acid, protein, peptide, polynucleotide, targeting agent, an isotopically labeled chemical compound, drug, vaccine, immunological agent, etc. In certain embodiments, the agents are organic compounds with pharmaceutical activity. In another embodiment of the invention, the agent is a clinically used drug. In a particularly preferred embodiment, the drug is an antibiotic, chemotherapeutic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

In certain embodiments, the agent to be delivered may be a mixture of agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials. Prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Targeting Agents

The inventive lipidoids, and the complexes, liposomes, micelles, microparticles, picoparticles and nanoparticles prepared therefrom, may be modified to include targeting agents since it is often desirable to target a particular cell, collection of cells, or tissue. A variety of targeting agents that direct pharmaceutical compositions to particular cells are known in the art (see, for example, Cotten et al. *Methods Enzym.* 217: 618, 1993; incorporated herein by reference). The targeting agents may be included throughout the particle or may be only on the surface. The targeting agent may be a protein, peptide, carbohydrate, glycoprotein, lipid, small molecule, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, etc. If the targeting agent is included throughout the particle, the targeting agent may be included in the mixture that is used to form the particles. If the targeting agent is only on the surface, the targeting agent may be associated with (i.e., by covalent, hydrophobic, hydrogen bonding, van der Waals, or other interactions) the formed particles using standard chemical techniques.

Compositions

In certain embodiments, an inventive lipidoid is a component of a composition which may be useful in a variety of medical and non-medical applications. For example, pharmaceutical compositions comprising an inventive lipidoid may be useful in the delivery of an effective amount of an agent to a subject in need thereof. Nutraceutical compositions comprising an inventive lipidoid may be useful in the delivery of an effective amount of a nutraceutical, e.g., a dietary supplement, to a subject in need thereof. Cosmetic compositions comprising an inventive lipidoid may be formulated as a cream, ointment, balm, paste, film, or liquid, etc., and may be useful in the application of make-up, hair products, and materials useful for personal hygiene, etc.

In certain embodiments, the composition comprises one or more lipidoids of the present invention. "One or more lipidoids" refers to one or more different types of lipidoids included in the composition, and encompasses 1, 2, 3, 4, 5, 6, 7, 8, 9, 10 or more different types of lipidoids.

In certain embodiments, the inventive lipidoids are useful in compositions, either for delivery of an effective amount of an agent to a subject in need thereof (e.g., a pharmaceutical composition, a cosmetic composition) or for use as an excipient. For example, cosmetic compositions may further use the inventive lipidoids as excipients rather than as a delivery system encapsulating an agent to be delivered. In certain embodiments, the composition is a pharmaceutical composition. In certain embodiments, the composition is a cosmetic composition.

In certain embodiments, the composition further comprises an agent, as described herein. For example, in certain embodiments, the agent is a small molecule, organometallic compound, nucleic acid, protein, peptide, polynucleotide, metal, targeting agent, an isotopically labeled chemical compound, drug, vaccine, or immunological agent. In certain embodiments, the agent is a polynucleotide. In certain embodiments, the polynucleotide is DNA or RNA. In certain embodiments, the RNA is mRNA, RNAi, dsRNA, siRNA, shRNA, miRNA, or antisense RNA.

In certain embodiments, the polynucleotide and the one or more lipidoids are not covalently attached.

In certain embodiments, the one or more lipidoids are in the form of a particle. In certain embodiments, the particle is a nanoparticle or microparticle. In certain embodiments, the one or more conjugated lipidoids are in the form of liposomes or micelles. It is understood that, in certain embodiments, these lipidoids self-assemble to provide a particle, micelle or liposome. In certain embodiments, the particle, liposome, or micelle encapsulates an agent. The agent to be delivered by the particles, liposomes, or micelles may be in the form of a gas, liquid, or solid. The inventive lipidoids may be combined with polymers (synthetic or natural), surfactants, cholesterol, carbohydrates, proteins, lipids etc. to form the particles. These particles may be combined with an excipient to form pharmaceutical and cosmetic compositions.

Once the complexes, micelles, liposomes, or particles have been prepared, they may be combined with one or more excipients to form a composition that is suitable to administer to animals including humans.

As would be appreciated by one of skill in this art, the excipients may be chosen based on the route of administration as described below, the agent being delivered, time course of delivery of the agent, etc.

In certain embodiments, provided is a composition comprising an inventive lipidoids and an excipient. As used herein, the term "excipient" means a non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

Methods of Use

In another aspect, provided are methods of using the inventive lipidoids, e.g., for the treatment of a disease, disorder or condition from which a subject suffers. It is contemplated that the inventive lipidoids will be useful in the treatment of a variety of diseases, disorders or conditions, especially as a system for delivering agents useful in the treatment of that particular disease, disorder or condition.

For example, in one aspect, provided is a method of treating cancer comprising administering to a subject in need thereof an effective amount of a lipidoid of the present invention, or salt thereof, or a composition thereof. In certain embodiments, the method further comprises administering an anti-cancer agent. In certain embodiments, the lipidoid encapsulates the anti-cancer agent. In certain embodiments, the lipidoid and the anti-cancer agent form a particle (e.g., a nanoparticle, a microparticle, a micelle, a liposome, a lipoplex).

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

EXAMPLES

In order that the invention described herein may be more fully understood, the following examples are set forth. It should be understood that these examples are for illustrative purposes only and are not to be construed as limiting this invention in any manner.

Lipidoid Synthesis

Lipidoids were synthesized through the conjugate addition of alkyl-acrylates to amines. Amines were purchased from Sigma Aldrich (St. Louis, Mo.), Alfa Aesar, Acros Organics, and CHESS Organics. Acrylates were purchased from Scientific Polymer Products (Ontario, N.Y.) and Hampford Research, Inc. (Stratford, Conn.). Amines were combined with acrylates stoichiometrically in a glass scintillation vial and were stirred at 90° C. for either for 3 days. In vitro experiments were conducted with crude materials, and in vivo experiments were performed with lipidoids purified via a Teledyne Isco Chromatography system (Lincoln, Nebr.).

Lipidoid Hydrolysis

To a 25 ml round bottom flask was added 3040$_{13}$ (0.250 g, 0.263 mmol, 1 equiv). For acidic hydrolysis, 10 ml of a solution of 6 N HCl was added to the flask to afford a cloudy heterogeneous solution. The reaction was heated to reflux to afford a clear, homogeneous solution and was stirred at reflux for 24 hours. For basic hydrolysis, 10 ml of a solution of KOH in EtOH/H$_2$O (solution=5.61 g KOH in 47.5 ml EtOH w/2.5 ml distilled H$_2$O) was added to the flask to afford a clear colorless solution. The reaction was heated to reflux and stirred for 41 h. Both acidic and basic reactions were cooled to room temperature and TLC analysis showed the presence of tridecanol (17.5% EtOAC/Hexanes) and the consumption of 3040$_{13}$. Reactions were concentrated to dryness under reduced pressure and diluted with CDCl$_3$. The basic reaction was filtered to remove excess KOH. Proton NMR analysis was performed in CDCl$_3$. Proton nuclear magnetic resonance spectra were recorded with a Bruker Avance 400 spectrometer, are depicted in parts per million on the δ scale, and are referenced from the residual protium in the NMR solvent (CDCl$_3$: δ 7.26 (CHCl$_3$).

Formulation of Lipid Nanoparticles

Lipidoids were formulated into nanoparticles for all studies described in the Examples. Nanoparticles were formed by mixing lipidoids, cholesterol (Sigma Aldrich), DSPC (Avanti Polar Lipids, Alabaster, Ala.) and mPEG2000-DMG (MW 2660, gift from Alnylam Pharamceuticals, Cambridge, Mass.) at a molar ratio of 38.5:50:(11.5-X): X in a solution of 90% ethanol and 10% 10 mM sodium citrate (by volume). An siRNA solution was prepared by diluting siRNA in 10 mM sodium citrate such that the final weight ratio of total lipid (lipidoid+cholesterol+DSPC+PEG):siRNA was 10:1. Equal volumes of lipid solution and siRNA solution were rapidly mixed together using either a microfluidic device (Chen, D. et al. *J. Am. Chem. Soc.* 134, 120410134818007 (2012)) or by pipet to form nanoparticles. Particles were diluted in phosphate buffered saline (PBS, Invitrogen) and then dialyzed against PBS for 90 minutes in 3500 MWCO cassettes (Pierce/Thermo Scientific, Rockford, Ill.).

In Vitro Transfection of Cell Lines with Lipid Nanoparticles

HeLa cells stably modified to express both firefly and *Renilla* luciferase were maintained at 37° C. in high glucose Dulbecco's Modified Eagles Medium without phenol red (Invitrogen, Carlsbad, Calif.) supplemented with 10% fetal bovine serum (FBS, Invitrogen). 12-16 hours prior to transfection, cells were seeded in white 96-well plates at a density of 15,000 cells per well. Cells were transfected with a 40 nM concentration of anti-firefly luciferase siRNA (Dharmacon, Lafayette, Colo.) that had been formulated with lipidoids into nanoparticles. Firefly luciferase silencing was assessed with a Dual-Glo® Luciferase Assay kit (Promega, Madison, Wis.). *Renilla* luciferase activity served as a control. Data for certain lipidoids are shown in Table 1 below.

TABLE 1

In vitro data

| Amine | Lipid tail | Relative Luciferase Activity | Stdev |
|---|---|---|---|
| 98 | O10 | 0.52 | 0.02 |
|  | O11 | 0.58 | 0.08 |
|  | O12 | 0.63 | 0.06 |
|  | O13 | 0.57 | 0.07 |
|  | O14 | 0.61 | 0.07 |
| 122 | O10 | 0.37 | 0.05 |
|  | O11 | 0.61 | 0.04 |
|  | O12 | 0.68 | 0.02 |
|  | O13 | 0.75 | 0.03 |
|  | O14 | 0.73 | 0.04 |
| 123 | O10 | 0.73 | 0.05 |
|  | O11 | 0.62 | 0.03 |
|  | O12 | 0.70 | 0.03 |
|  | O13 | 0.22 | 0.02 |
|  | O14 | 0.68 | 0.14 |
| 154 | O10 | 0.74 | 0.04 |
|  | O11 | 0.72 | 0.04 |
|  | O12 | 0.33 | 0.12 |
|  | O13 | 0.87 | 0.06 |
|  | O14 | 0.88 | 0.07 |
| 174 | O10 | 0.40 | 0.01 |
|  | O11 | 0.47 | 0.07 |
|  | O12 | 0.69 | 0.05 |
|  | O13 | 0.55 | 0.02 |
|  | O14 | 0.24 | 0.01 |
| 176 | O10 | 0.20 | 0.03 |
|  | O11 | 0.17 | 0.01 |
|  | O12 | 0.90 | 0.03 |
|  | O13 | 0.79 | 0.03 |
|  | O14 | 0.63 | 0.03 |
| 191 | O10 | 0.71 | 0.09 |
|  | O11 | 0.31 | 0.05 |
|  | O12 | 0.32 | 0.03 |
|  | O13 | 0.76 | 0.06 |
|  | O14 | 0.34 | 0.08 |
| 192 | O10 | 0.88 | 0.03 |
|  | O11 | 0.49 | 0.04 |
|  | O12 | 0.37 | 0.04 |
|  | O13 | 0.80 | 0.04 |
|  | O14 | 0.60 | 0.06 |
| 193 | O10 | 0.55 | 0.06 |
|  | O11 | 0.38 | 0.06 |
|  | O12 | 0.28 | 0.03 |
|  | O13 | 0.84 | 0.03 |
|  | O14 | 0.55 | 0.04 |
| 195 | O10 | 0.80 | 0.06 |
|  | O11 | 0.75 | 0.04 |
|  | O12 | 0.43 | 0.03 |
|  | O13 | 0.28 | 0.02 |
|  | O14 | 0.76 | 0.04 |
| 196 | O10 | 0.92 | 0.03 |
|  | O11 | 0.76 | 0.02 |
|  | O12 | 0.85 | 0.09 |
|  | O13 | 0.58 | 0.04 |
|  | O14 | 0.38 | 0.05 |
| 200 | O10 | 0.57 | 0.03 |
|  | O11 | 0.64 | 0.03 |
|  | O12 | 0.41 | 0.03 |
|  | O13 | 0.53 | 0.05 |
|  | O14 | 0.36 | 0.01 |
| 205 | O10 | 0.67 | 0.04 |
|  | O11 | 0.68 | 0.03 |
|  | O12 | 0.53 | 0.05 |
|  | O13 | 0.72 | 0.04 |
|  | O14 | 0.43 | 0.02 |
| 217 | O10 | NA | NA |
|  | O11 | NA | NA |
|  | O12 | 0.22 | 0.03 |
|  | O13 | 0.33 | 0.05 |
|  | O14 | NA | NA |

TABLE 1-continued

In vitro data

| Amine | Lipid tail | Relative Luciferase Activity | Stdev |
|---|---|---|---|
| 218 | O10 | 0.91 | 0.04 |
| | O11 | 0.90 | 0.06 |
| | O12 | 0.80 | 0.03 |
| | O13 | 0.41 | 0.06 |
| | O14 | 0.57 | 0.08 |
| 232 | O10 | 0.92 | 0.05 |
| | O11 | 0.90 | 0.07 |
| | O12 | 0.83 | 0.04 |
| | O13 | 0.39 | 0.05 |
| | O14 | 0.68 | 0.02 |
| 235 | O10 | 0.85 | 0.10 |
| | O11 | 0.85 | 0.08 |
| | O12 | 0.85 | 0.11 |
| | O13 | 0.42 | 0.03 |
| | O14 | 0.72 | 0.03 |
| 302 | O10 | 0.64 | 0.01 |
| | O11 | 0.64 | 0.03 |
| | O12 | 0.64 | 0.03 |
| | O13 | 0.34 | 0.05 |
| | O14 | 0.36 | 0.09 |
| 303 | O10 | 0.07 | 0.01 |
| | O11 | 0.78 | 0.04 |
| | O12 | 0.40 | 0.07 |
| | O13 | 0.89 | 0.05 |
| | O14 | 0.89 | 0.08 |
| 304 | O10 | 0.86 | 0.07 |
| | O11 | 0.45 | 0.02 |
| | O12 | 0.28 | 0.01 |
| | O13 | 0.08 | 0.01 |
| | O14 | 0.53 | 0.01 |
| 306 | O10 | 0.13 | 0.02 |
| | O11 | 0.14 | 0.02 |
| | O12 | 0.09 | 0.01 |
| | O13 | 0.10 | 0.02 |
| | O14 | 0.08 | 0.01 |
| 313 | O10 | 0.37 | 0.02 |
| | O11 | 0.32 | 0.02 |
| | O12 | 0.21 | 0.01 |
| | O13 | 0.23 | 0.04 |
| | O14 | 0.63 | 0.05 |
| 315 | O10 | 0.98 | 0.08 |
| | O11 | 0.89 | 0.09 |
| | O12 | 0.30 | 0.01 |
| | O13 | 0.65 | 0.03 |
| | O14 | 0.80 | 0.04 |
| 347 | O10 | 0.68 | 0.04 |
| | O11 | 0.57 | 0.02 |
| | O12 | 0.17 | 0.06 |
| | O13 | 0.55 | 0.07 |
| | O14 | 0.17 | 0.06 |
| 366 | O10 | 0.50 | 0.09 |
| | O11 | 0.38 | 0.08 |
| | O12 | 0.38 | 0.04 |
| | O13 | 0.59 | 0.08 |
| | O14 | 0.55 | 0.11 |
| 371 | O10 | 0.85 | 0.01 |
| | O11 | 0.40 | 0.01 |
| | O12 | 0.48 | 0.02 |
| | O13 | 0.76 | 0.04 |
| | O14 | 0.39 | 0.01 |
| 500 | O10 | 0.14 | 0.03 |
| | O11 | 0.09 | 0.03 |
| | O12 | 0.06 | 0.01 |
| | O13 | 0.07 | 0.01 |
| | O14 | 0.02 | 0.00 |
| 501 | O10 | 0.37 | 0.02 |
| | O11 | 0.37 | 0.04 |
| | O12 | 0.22 | 0.04 |
| | O13 | 0.24 | 0.03 |
| | O14 | 0.20 | 0.08 |
| 502 | O10 | 0.18 | 0.03 |
| | O11 | 0.12 | 0.01 |
| | O12 | 0.08 | 0.01 |
| | O13 | 0.09 | 0.01 |
| | O14 | 0.08 | 0.02 |
| 503 | O10 | 0.39 | 0.05 |
| | O11 | 0.39 | 0.06 |
| | O12 | 0.33 | 0.07 |
| | O13 | 0.07 | 0.00 |
| | O14 | 0.12 | 0.04 |

In Vivo Gene Silencing

All animal experiments were conducted using institutionally-approved protocols. Female C57BL/6 mice (Charles River Laboratories, Wilmington, Mass.) received injections through the lateral tail vein injections of PBS (negative control), or lipidoid nanoparticles containing either non-targeting siRNA (negative control) or anti-Factor VII siRNA diluted in PBS at a volume of 0.01 ml/g. The sequence of the siFVII, provided by Alnylam Pharmaceuticals, was:

```
                                          (SEQ ID NO.: 1)
sense: 5'-GGAucAucucAAGucuuAcT*T-3'

(SEQ ID NO.: 2)
antisense: 5'-GuAAGAcuuGAGAuGAuccT*T-3'
``` where 2'-fluoro-modified nucleotides are in lower case and phosphorothioate linkages are represented by asterisks. Two days post-injection, a 100 ul blood sample was obtained from mice and centrifuged at 13,000 rpm in serum separator tubes (Becton Dickinson). Serum levels of Factor VII were analyzed using a Biophen FVII assay kit as described previously (Aniara Corporation, Mason, Ohio) Semple, S. C. et al. *Nature Biotechnology* 1-7 (2010). Results shown in Table 2.

TABLE 2

Original Library FVII Activity Data

| Lipidoid | 5 mg/kg | | 2 mg/kg | | 0.5 mg/kg | | 0.1 mg/kg | |
|---|---|---|---|---|---|---|---|---|
| | Relative FVII Activity | Standard Deviation | Relative FVII Activity | Standard Deviation | Relative FVII Activity | Standard Deviation | Relative FVII Activity | Standard Deviation |
| 64O14 | 0.92 | 0.05 | | | | | | |
| 68O10 | 0.91 | 0.20 | | | | | | |
| 68O11 | 1.03 | 0.11 | | | | | | |
| 77O13 | 0.85 | 0.10 | | | | | | |
| 77O14 | 0.74 | 0.02 | | | | | | |
| 80O13 | 0.66 | 0.23 | | | | | | |
| 81O13 | 0.43 | 0.18 | | | | | | |
| 86O12 | 0.87 | 0.07 | | | | | | |
| 87O13 | 0.77 | 0.03 | | | | | | |
| 94O14 | 0.13 | 0.06 | | | | | | |
| 99O11 | 0.53 | 0.07 | | | | | | |
| 109O11 | 0.85 | 0.05 | | | | | | |
| 109O12 | 0.82 | 0.06 | | | | | | |
| 109O13 | 0.38 | 0.09 | | | | | | |
| 110O10 | 0.35 | 0.11 | | | | | | |
| 110O13 | 0.75 | 0.07 | | | | | | |
| 113O10 | 0.15 | 0.06 | | | | | | |
| 113O11 | 0.57 | 0.20 | | | | | | |
| 113O12 | 0.01 | 0.00 | 0.09 | 0.10 | 0.49 | 0.08 | 0.59 | 0.08 |
| 113O13 | 0.00 | 0.00 | 0.00 | 0.00 | 0.04 | 0.11 | 0.48 | 0.12 |
| 113O14 | 0.75 | 0.14 | | | | | | |
| 120O11 | 0.93 | 0.04 | | | | | | |

TABLE 2-continued

Original Library FVII Activity Data

| Lipidoid | 5 mg/kg Relative FVII Activity | 5 mg/kg Standard Deviation | 2 mg/kg Relative FVII Activity | 2 mg/kg Standard Deviation | 0.5 mg/kg Relative FVII Activity | 0.5 mg/kg Standard Deviation | 0.1 mg/kg Relative FVII Activity | 0.1 mg/kg Standard Deviation |
|---|---|---|---|---|---|---|---|---|
| 120O12 | 0.88 | 0.15 | | | | | | |
| 120O13 | 0.92 | 0.08 | | | | | | |
| 120O14 | 0.79 | 0.05 | | | | | | |
| 122O10 | 0.13 | 0.06 | | | | | | |
| 122O12 | 0.82 | 0.06 | | | | | | |
| 123O12 | 0.93 | 0.07 | | | | | | |
| 123O13 | 0.00 | 0.00 | 0.00 | 0.00 | 0.50 | 0.22 | 0.86 | 0.13 |
| 134O13 | 0.89 | 0.16 | | | | | | |
| 144O13 | 0.93 | 0.17 | | | | | | |
| 154O12 | 0.99 | 0.11 | | | | | | |
| 156O11 | 0.77 | 0.09 | | | | | | |
| 156O12 | 1.06 | 0.06 | | | | | | |
| 158O14 | 0.91 | 0.04 | | | | | | |
| 159O14 | 0.80 | 0.01 | | | | | | |
| 161O14 | 0.85 | 0.05 | | | | | | |
| 164O14 | 0.90 | 0.08 | | | | | | |
| 166O10 | 0.99 | 0.03 | | | | | | |
| 166O14 | 0.83 | 0.08 | | | | | | |
| 191O11 | 0.61 | 0.19 | | | | | | |
| 191O12 | 0.80 | 0.19 | | | | | | |
| 191O14 | 0.61 | 0.10 | | | | | | |
| 193O10 | 0.70 | 0.12 | | | | | | |
| 193O11 | 0.61 | 0.13 | | | | | | |
| 193O12 | 0.70 | 0.09 | | | | | | |
| 195O12 | 0.43 | 0.07 | | | | | | |
| 195O13 | 0.56 | 0.04 | | | | | | |
| 196O13 | 0.80 | 0.01 | | | | | | |
| 196O14 | 0.82 | 0.06 | | | | | | |
| 200O10 | 0.56 | 0.17 | | | | | | |
| 200O11 | 0.67 | 0.07 | | | | | | |
| 200O12 | 0.62 | 0.00 | | | | | | |
| 200O13 | 0.40 | 0.10 | | | | | | |
| 200O14 | 0.91 | 0.20 | | | | | | |
| 205O12 | 0.78 | 0.10 | | | | | | |
| 205O14 | 0.83 | 0.09 | | | | | | |
| 217O12 | 0.58 | 0.13 | | | | | | |
| 217O13 | 0.02 | 0.01 | 0.33 | 0.28 | 0.85 | 0.13 | 0.92 | 0.12 |
| 218O13 | 0.73 | 0.16 | | | | | | |
| 219O13 | 0.00 | 0.00 | | | | | | |
| 235O13 | 0.39 | 0.07 | | | | | | |
| 25O13 | 0.25 | 0.23 | | | | | | |
| 302O13 | 1.03 | 0.22 | | | | | | |
| 302O14 | 0.84 | 0.29 | | | | | | |
| 303O10 | 0.95 | 0.26 | | | | | | |
| 303O12 | 0.01 | 0.01 | 0.20 | 0.09 | 0.91 | 0.04 | 0.95 | 0.05 |
| 304O11 | 0.57 | 0.02 | | | | | | |
| 304O12 | 0.81 | 0.24 | | | | | | |
| 304O13 | 0.01 | 0.00 | 0.02 | 0.01 | 0.23 | 0.06 | 0.54 | 0.26 |
| 304O14 | 0.58 | 0.13 | | | | | | |
| 305O12 | 0.75 | 0.11 | | | | | | |
| 305O13 | 0.00 | 0.00 | 0.06 | 0.04 | 0.25 | 0.06 | 0.96 | 0.17 |
| 306O10 | 0.00 | 0.00 | 0.00 | 0.01 | 0.23 | 0.07 | 0.69 | 0.13 |
| 306O11 | 0.02 | 0.01 | 0.00 | 0.00 | 0.40 | 0.15 | 0.59 | 0.17 |
| 306O12 | 0.00 | 0.00 | 0.00 | 0.00 | 0.20 | 0.15 | 0.37 | 0.02 |
| 306O13 | 0.00 | 0.00 | 0.00 | 0.01 | 0.04 | 0.07 | 0.71 | 0.14 |
| 306O14 | 0.85 | 0.05 | | | | | | |
| 313O10 | 0.00 | 0.00 | 0.21 | 0.11 | 0.74 | 0.10 | 1.04 | 0.13 |
| 313O11 | 0.01 | 0.02 | 0.38 | 0.16 | 0.75 | 0.05 | 0.73 | 0.07 |
| 313O12 | 0.01 | 0.04 | 0.52 | 0.25 | 0.89 | 0.33 | 0.95 | 0.26 |
| 313O13 | 0.01 | 0.01 | 0.09 | 0.04 | 0.09 | 0.08 | 0.86 | 0.24 |
| 313O14 | 0.67 | 0.04 | | | | | | |
| 315O12 | 0.99 | 0.39 | | | | | | |
| 31O14 | 0.88 | 0.14 | | | | | | |
| 32O14 | 0.80 | 0.06 | | | | | | |
| 347O10 | 0.92 | 0.08 | | | | | | |
| 347O11 | 0.85 | 0.16 | | | | | | |
| 347O12 | 0.15 | 0.08 | | | | | | |
| 347O13 | 0.67 | 0.22 | | | | | | |
| 36O14 | 0.69 | 0.25 | | | | | | |
| 371O11 | 0.78 | 0.09 | | | | | | |
| 371O12 | 0.78 | 0.06 | | | | | | |
| 371O14 | 0.85 | 0.03 | | | | | | |

Biodistribution and Immunostaining

Female C57BL/6 mice received tail vein injections of lipid nanoparticles containing siRNA that had been labeled with Cy5.5 on the 5' end of the sense strand (provided by Alnylam Pharmaceuticals). Animals were dosed at 1 mg/kg of siRNA and volume of 0.01 ml/g. At one hour post-injection, mice were euthanized and organs were removed. Body-wide biodistribution was assessed by imaging whole organs with an IVIS® Spectrum system (Caliper Life Sciences, Hopkinton, Mass.) at excitation and emission wavelengths of 675 nm and 720 nm, respectively. Cell-specific distribution within hepatocytes was assessed by embedding, sectioning, and staining the whole liver with antibodies. Imaging was conducted on a LSM 700 confocal microscope (Carl Zeiss, Inc., Peabody, Mass.). For Odyssey and confocal imaging, organs were snap frozen on dry ice and embedded in optimal cutting temperature compound (OCT, Life Technologies, Grand Island, N.Y.). Cryostat sections were cut and collected on superfrost plus treated slides. Prepared frozen sections where kept at −20° C. until needed. Odyssey imaging was conducted on 20 µm thick cryosections of tissue at a resolution of 21 µm (Lee, M. J.-E. et al., Rapid Pharmacokinetic and Biodistribution Studies Using Cholorotoxin-Conjugated Iron Oxide Nanoparticles: A Novel Non-Radioactive Method. PLoS ONE 5, e9536-e9536 (2010)).

For confocal imaging, liver tissue was cryosectioned (12 µm) and fixed using 4% paraformaldehyde at room temperature for 30 min. All solutions were prepared in PBS. Sections were washed 2× with PBS, permeabilized for 30 min with 0.1% Triton X100, and blocked for 1 hour with 5% normal goat serum. Sections then incubated for 1 hour in an immunostaining cocktail solution consisting of DAPI (3 µM), Alexa Fluor 488 conjugated anti-mouse F4/80 (1:200 dilution, BioLegend, San Diego, Calif.), Alexa Fluor® 555 Phalloidin (1:200 dilution, Life Technologies), and 5% normal goat serum. Slides were washed 3× with 0.1% Tween 20 and mounted using ProLong® Gold Antifade (Life Technologies). Sections were imaged using an LSM 700 point scanning confocal microscope (Carl Zeiss, Inc, Jena Germany) equipped with a 40× oil immersion objective.

Blood Clearance

Blood clearance experiments were conducted by injecting LNPs containing Cy5.5-labeled siRNA at an siRNA dose of 0.5 mg/kg. Blood samples were collected as a function of time via the retroorbital vein, with the exception of final time points, which were collected via cardiac puncture. Serum, obtained by centrifugation, was diluted 1:30 in PBS and imaged and quantified using an Odyssey CLx imaging system (LI-COR Biosciences, Lincoln, Nebr.).

Histology

Organs were harvested from animals that had received various doses of either $304O_{13}$ or C12-200 lipid nanoparticles (C12-200 is a control non-degradable lipidoid shown below). Organs were fixed overnight in 4% paraformaldehyde and transferred to 70% ethanol prior to paraffin embedding, sectioning, and H & E staining.

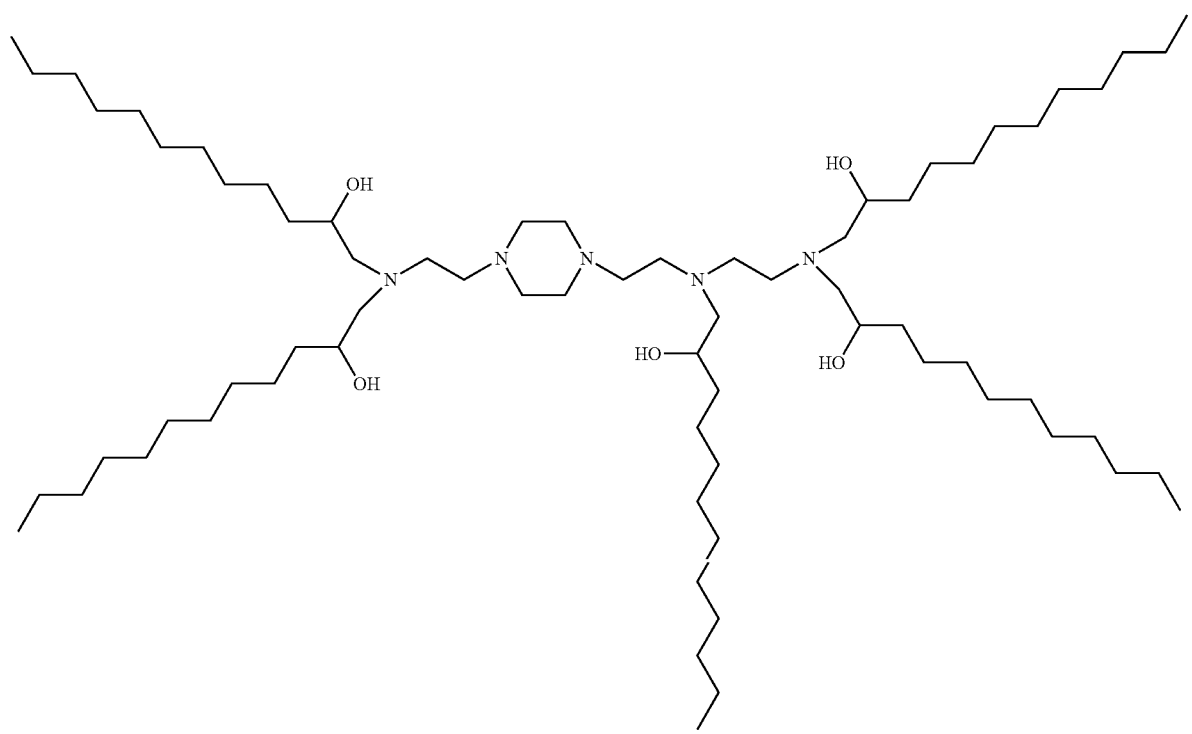

Serum Chemistry and Hematology Analysis

Post-sacrifice, cardiac sticks were immediately performed on animals that had been dosed with either $304O_{13}$ or C12-200 lipid nanoparticles. Blood was centrifuged in serum separator tubes at 5,000 rpm for 10 minutes, and serum was analyzed for various hematological parameters. Serum chemistry was evaluated on a Beckman Olympus AU400 Serum Chemistry Analyzer. Cytokines were analyzed using Bio-Plex Pro Mouse Cytokine 23-Plex Assay kits (Luminex Corporation, Austin, Tex.) on the Bio-Plex 200 system, according to manufacturer instructions.

Cytokine Profiling

Cytokine analysis was done by injecting either $304O_{13}$ or C12-200 nanoparticles at an siRNA dose of 3 mg/kg. Four hours post-injection, blood was harvested via cardiac stick and serum was isolated. Cytokine levels were quantified using an ELISA assay.

Nanoparticle Characterization

Lipid nanoparticles were diluted to an siRNA concentration of ~5 ug/ml in 0.1×PBS, pH 7.3. siRNA entrapment efficiency was determined using the Quant-iT™ RiboGreen® RNA assay (Invitrogen). Particle sizes were measured with a ZETAPals analyzer (Brookhaven Instruments, Holtsville, N.Y.). Sizes reported are the average effective diameter of each LNP. Zeta potential measurements were acquired on a Zetasizer Nano ZS (Malvern, Westborough, Mass.), and reported values were the average of 10-25 runs.

TABLE 3

Characterization Parameters for $304O_{13}$

| | siRNA Entrapment (%) | Diameter (nm) | Zeta Potential (mV) | pKa |
|---|---|---|---|---|
| $304O_{13}$ | 84.2 | 86.0 | 13.7 | 6.8 |
| 306O12 | 79.0 | 98.2 | 12.5 | 6.8 |
| 113O13 | 75.8 | 91.1 | 16.5 | 6.0 |

Results and Discussion

Michael addition chemistry was employed to rapidly synthesize a library of 1400 lipid-like materials with the potential to serve as effective, biodegradable delivery vehicles (FIG. 1). 280 alkyl-amines (FIG. 2) were reacted combinatorially with 5 alkyl-acrylates to form lipidoids consisting of a polar, ionizable core surrounded by hydrophobic carbon tails. Alkyl-amines, which were taken from commercially available supply, were chosen to maximize structural diversity and reactivity within a Michael addition scheme. We chose to work with alkyl-acrylate tails of intermediate length (10-14 carbon chain length), as previous studies indicated that shorter tails often lack efficacy while longer tails may cause insolubility during the nanoparticle formulation process (Akinc, A. et al. Nature Biotechnology 26, 561-569 (2008); Love, K. T. et al. Proc. Natl. Acad. Sci. USA 107, 1864-1869 (2010)).

Figure 11A:
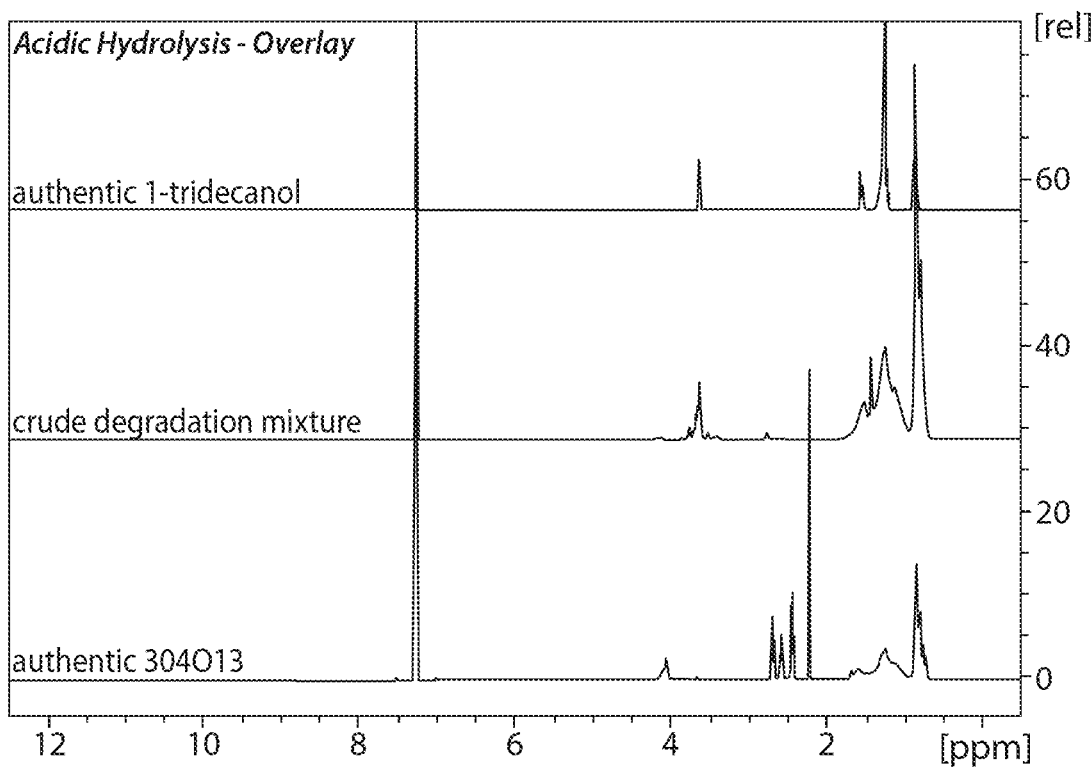
FIGS. 11A and 11B show degradation by hydrolysis of the lipidoid $304O_{13}$. Overlay of $^1H$ NMR spectra of the starting material $304O_{13}$, the crude reaction mixture, and authentic 1-tridecanol demonstrated that the $304O_{13}$ had been consumed and that tridecanol had been formed in significant quantity under both acidic and basic conditions.
Figure 11A:
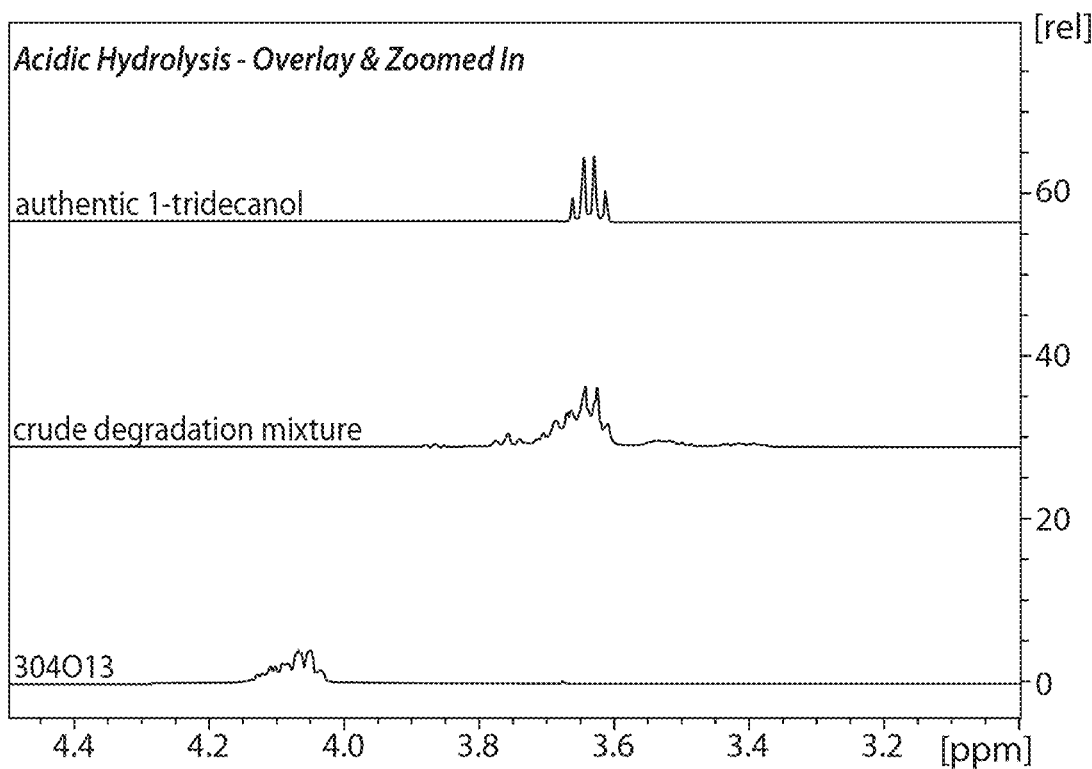
Figure 11B:
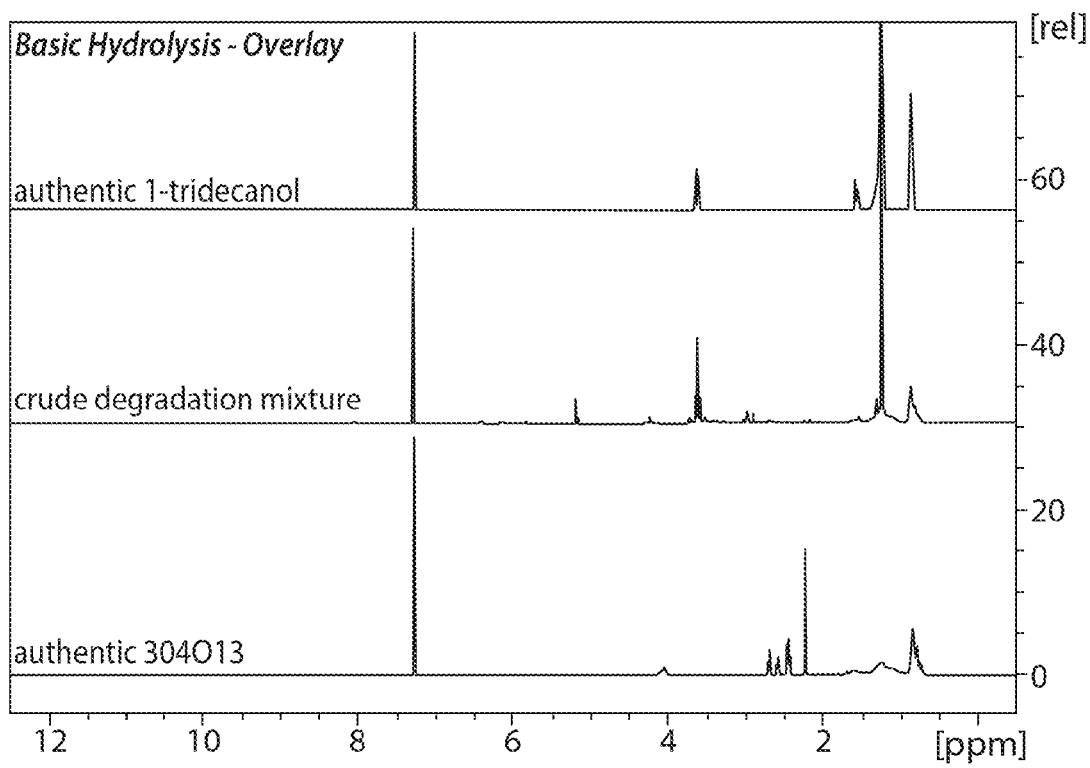
Figure 11B:
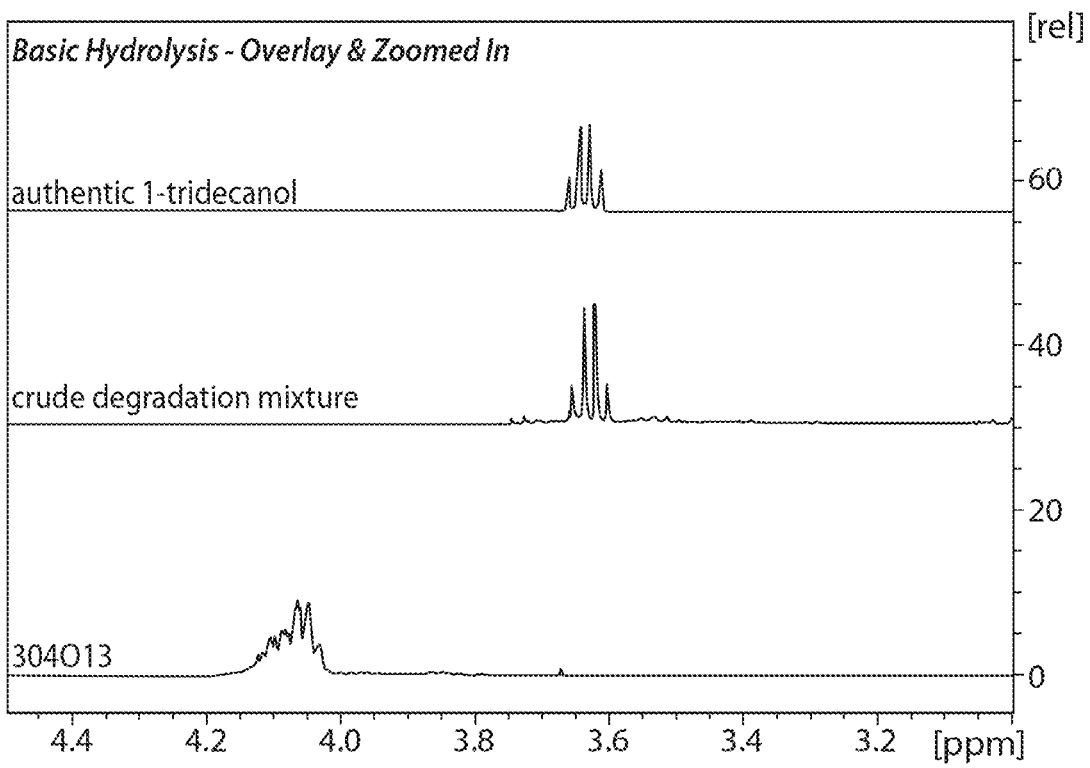

The acrylate-based lipidoids provided herein also contain hydrolysable ester moieties, functional groups which are commonly incorporated into delivery vehicles to promote physiological degradation (Staubli, A., Ron, E. & Langer, R. J. Am. Chem. Soc. 112, 4419-4424 (1990); van Dijkhuizen-Radersma, et al. Biomaterials 23, 4719-4729 (2002); Geng, Y. & Discher, D. E. J. Am. Chem. Soc. 127, 12780-12781 (2005)). Proton NMR analysis indicated that a representative lipidoid, $304O_{13}$, degraded to the anticipated alkyl-alcohol product under hydrolytic conditions (FIGS. 11A and 11B).

Figure 3:
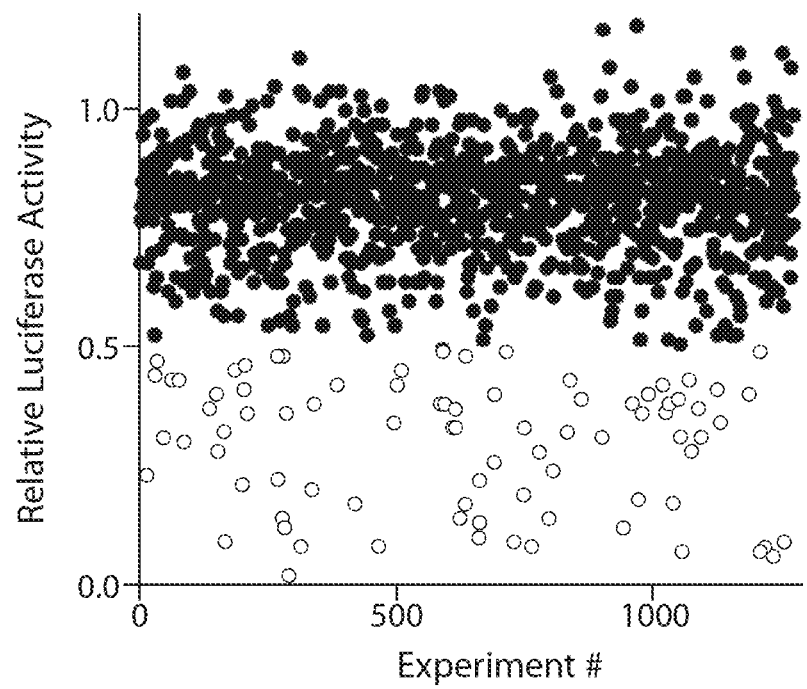
FIG. 3 shows the evaluation of lipidoids for an ability to deliver siRNA to HeLa cells. (a) Relative luciferase activity values (firefly lucifase activity normalized to control Renilla luciferase activity) are shown for 1400 lipidoids. ~7% of the library induced >50% gene silencing (shown in red). The tail length (b), tail substitution number (c) and alkyl-amine composition (d) influenced in vitro activity.
Figure 3:
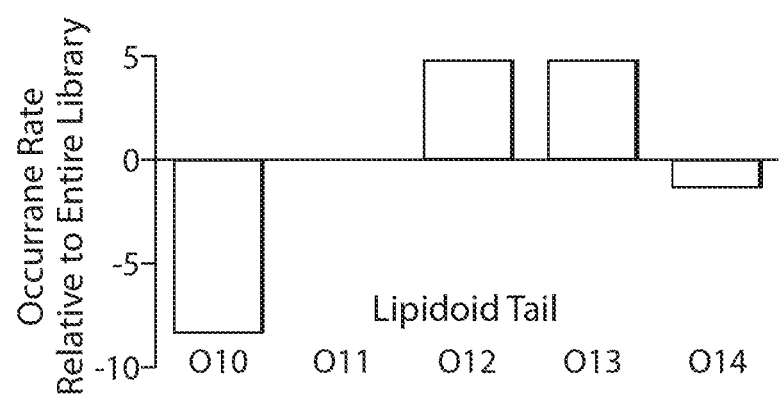
Figure 3:
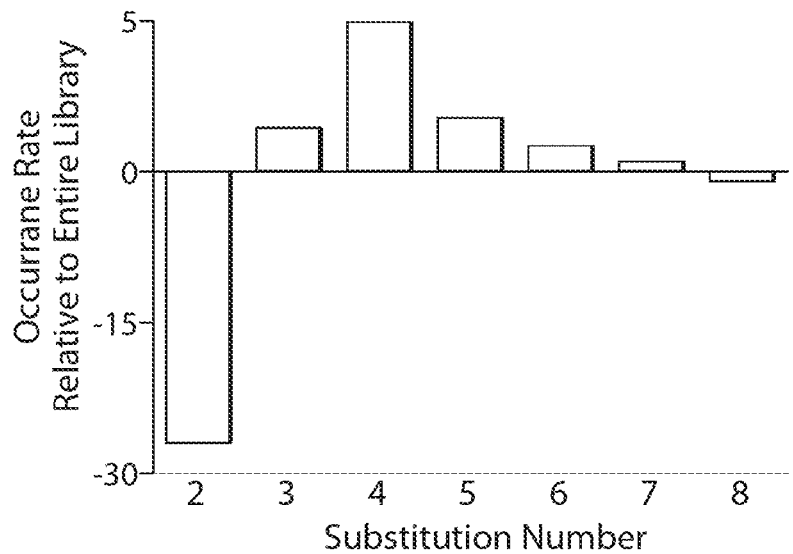
Figure 3:
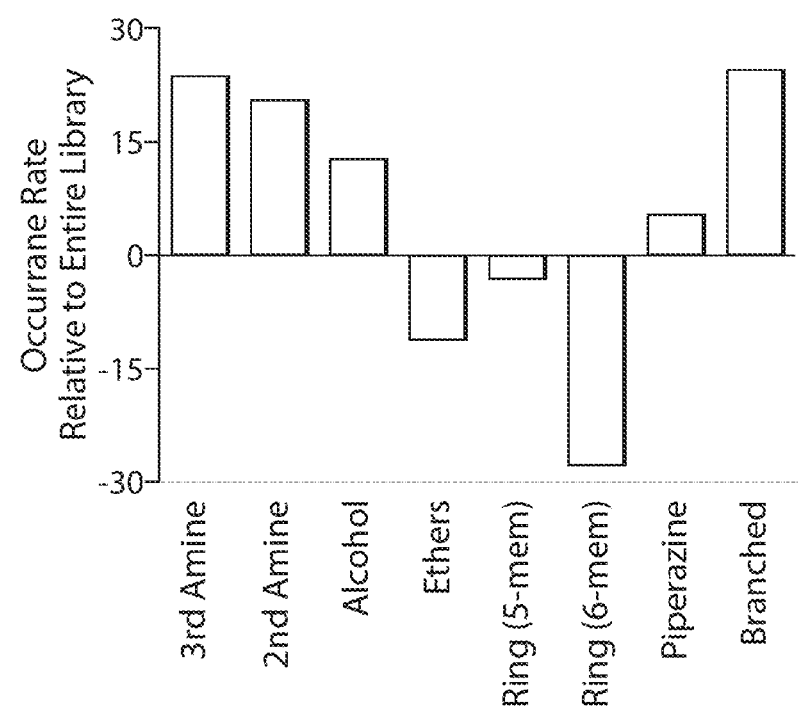

To determine the transfection ability of lipidoids, they were first formulated into lipid nanoparticles (LNPs) containing siRNA, cholesterol and the helper lipids, DSPC and PEG (MW2000)-DMG. The delivery potential of lipidoids was assessed by applying LNPs to HeLa cells that had been genetically modified to stably express two reporter luciferase proteins: firefly and *Renilla*. Firefly luciferase served as the target gene while *Renilla* luciferase served as a built-in control for toxicity and off-targeting effects. Relative luciferase activity, which is the ratio of firefly to *Renilla* activity, is shown in FIG. 3a after treatment with each LNP at an siRNA concentration of 40 nM. Of the 1400 members of the lipidoid library, ~7% mediated target gene silencing of >50% (shown in red circles).

In order to extract structure-function information from the in vitro data, we asked whether various structural properties were more or less common within the group of efficacious lipidoids (red data points) compared to the bulk library. FIG. 3b examines the importance of tail length on transfection. Because there were five tails used in this library, each tail length made up 20% of the library. Of the LNPs that were effective in vitro, however, only 12% contained an $O_{10}$ tail. Occurrence rate (the y-axis value) was calculated as (the occurrence rate in the library)–(the occurrence rate in the group with >50% silencing). Therefore, the occurrence rate for $O_{10}$ is 12%–20%=–8%, indicating that it was significantly underrepresented among materials with transfection potential. On the other hand, $O_{12}$ and $O_{13}$ tails were overrepresented in the efficacious group compared to the library at large, suggesting such tail lengths are associated with efficacious lipidoids. FIG. 3c suggests that lipidoids with the greatest transfection potential were synthesized from alkyl-amines with three or more substitution sites. The effect of various functional groups within the alkyl-amine is analyzed in FIG. 3d. The presence of tertiary and secondary amines, alcohols, and branched or linear chains conferred efficacy, while ethers and rings generally did not. Piperazine rings, however, were an exception, and generally produced efficacious materials.

Figure 4:
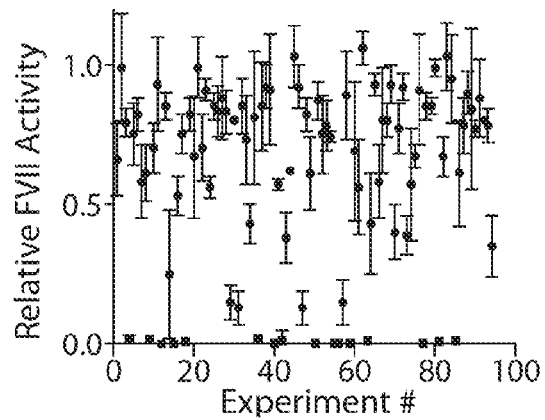
FIG. 4 demonstrates that select lipidoids induced a high degree silencing of multiple targets in mice. (a) Of the ~100 lipidoids tested in vivo, 15 induced complete Factor VII knockdown in mouse hepatocytes at a total siRNA dose of 5 mg/kg (data points in red). (b) The $EC_{50}$ values of these top 15 lipidoids ranged from 0.05 to 1.5 mg/kg under standard formulation conditions. (c) The amount of PEG in the lipid nanoparticle formulation had a dramatic effect on efficacy. Data is shown for the lipidoid $304O_{14}$, which produced the most efficacious formulation of the study when formulated with 0.75% PEG. (d) Dose response and Factor VII activity recovery data for the optimized $304O_{13}$ lipid nanoparticle formulation. $304O_{13}$ also induced CD45 silencing in monocyte and macrophage (CD11b+) populations in the peritoneal cavity (e) as well as in dendritic cells (CD11c+) in the spleen 3 days post-injection. In all panels, error bars represent standard deviation (n=3).
Figure 4:
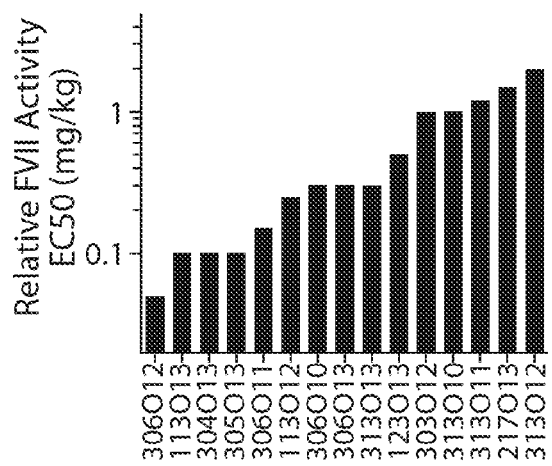
Figure 4:
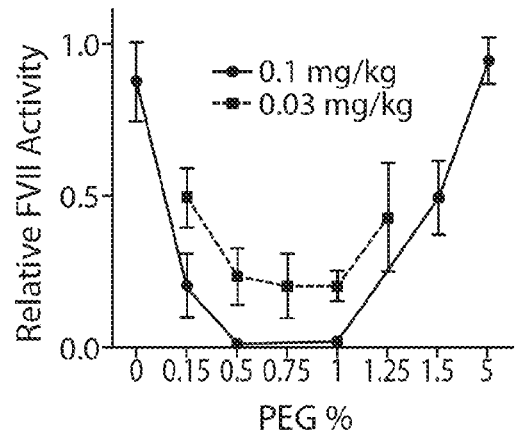
Figure 4:
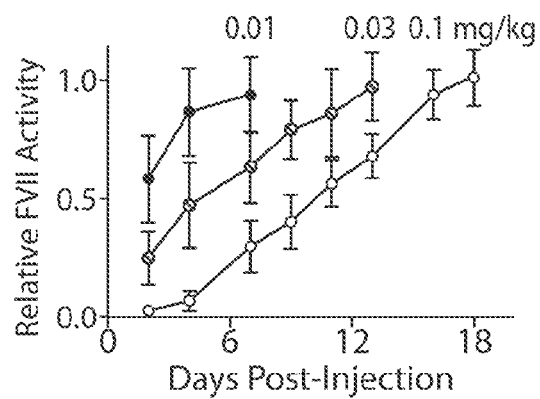
Figure 4:
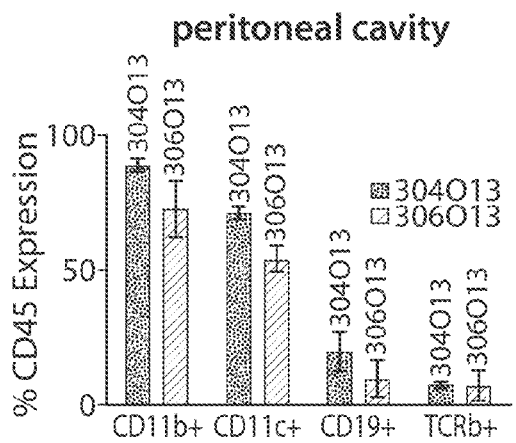
Figure 4:
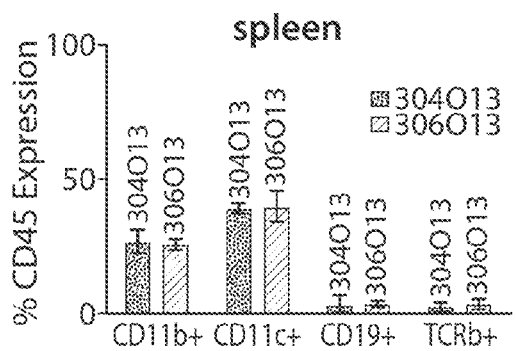
Figure 8:
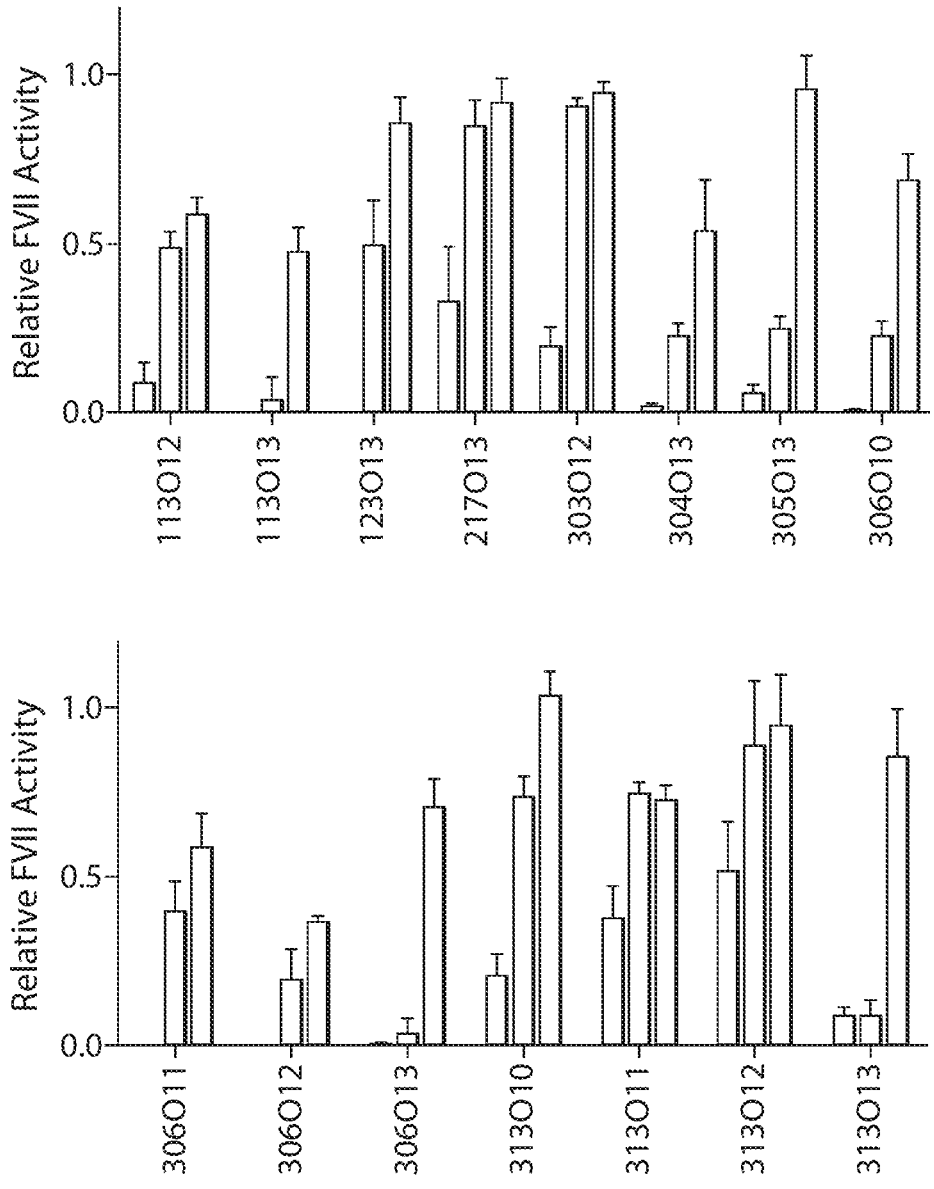
FIG. 8 shows that lipid nanoparticles that induced complete FVII silencing at 5 mg/kg behaved in a dose-dependent manner. Each lipid nanoparticle was evaluated at three additional doses (2, 0.5, and 0.1 mg/kg) shown from left to right. Error bars represent standard deviation (n=3).

Previous studies have indicated that materials capable of conferring >50% luciferase silencing activity in cell culture have the potential to mediate siRNA delivery in vivo (Whitehead, K. A. et al. In Vitro-In VivoTranslation of Lipid Nanoparticles for Hepatocellular siRNA Delivery. ACS Nano 120706143602000 (2012).doi:10.1021/nn301922x). Selected lipidoids (those data points shown in red in FIG. 3a) were analyzed for siRNA delivery to hepatocytes in a murine model of the blood coagulation Factor VII. The Factor VII model, which has been well-validated in the literature (Akinc, A. et al. *Nature Biotechnology* 26, 561-569 (2008); John, M. et al. *Nature* 449, 745-747 (2007); Semple, S. C. et al. *Nature Biotechnology* 1-7 (2010)), allows silencing to be assessed from a few drops of blood using a commercially-available assay. In these experiments, LNPs containing anti-Factor VII siRNA were injected intravenously into mice, and Factor VII activity levels were quantified two days post-injection. Fifteen of the 108 lipidoids analyzed in vivo mediated complete knockdown of Factor VII protein levels at an siRNA dose of 5 mg/kg (FIG. 4a). For these top LNP candidates, control experiments conducted using non-targeting siRNA at 5 mg/kg resulted in no FVII knockdown and suggested that reductions in protein activity were not due to off-targeting or toxicity-mediated gene downregulation. Silencing for these top candidates was dose dependent (FIG. 8), with $EC_{50}$ values ranging from 0.05 to 2 mg/kg when LNPs were formulated at a lipidoid:cholesterol:DSPC:PEG standard testing molar ratio of 50:38.5:10:1.5.

While seeking an optimal molar ratio for the top LNPs (e.g. $306O_{12}$, $113O_{13}$, and $304O_{13}$), the PEG molar percentage was found to have an effect on LNP efficacy. FIG. 4c reveals that, for the lipidoid $304O_{13}$, there is a range of PEG % between 0.5 and 1.0 where optimal hepatocellular delivery is achieved. The optimized $304O_{13}$ formulation (PEG %=0.75) has an EC50 value, 0.01 mg/kg, that is a full order of magnitude lower than when using 1.5% PEG. Optimized $304O_{13}$ behaved in a dose dependent fashion (FIG. 4d), and after a single injection at 0.1 mg/kg, Factor VII levels returned to baseline within 18 days.

Figure 9:
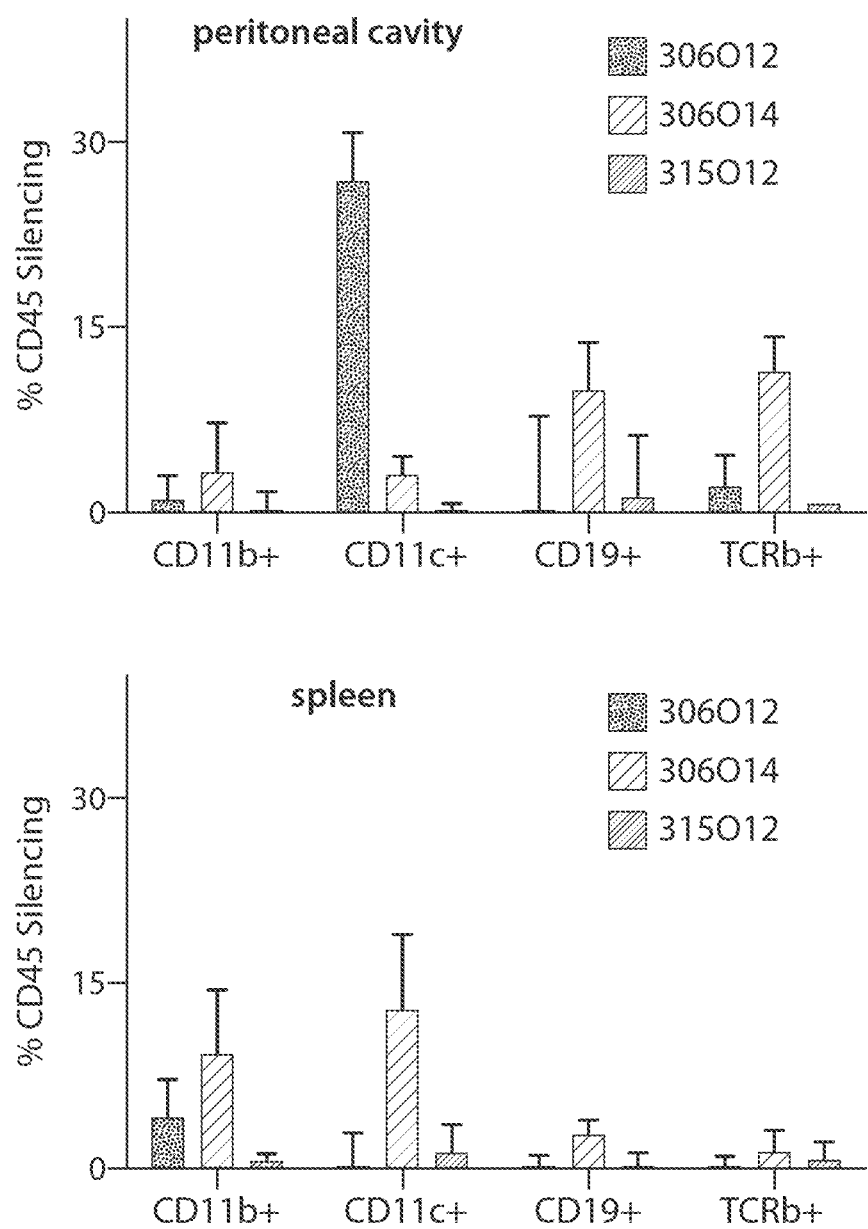
FIG. 9 shows that the lipid nanoparticles $306O_{12}$, $306O_{14}$ and $315O_{12}$ facilitated modest silencing of the surface receptor CD45 in various white blood cell populations harvested from the peritoneal cavity (left) and spleen (right) of B6 mice three days post-injection (dose=2.5 mg/kg total siRNA). Error bars represent standard deviation (n=3).

In addition to examining hepatocellular delivery, we also explored the ability of biodegradable lipidoid materials to deliver siRNA to leukocyte populations in vivo. Immune cells are attractive targets for RNA interference therapy, as they have been implicated in various aspects of disease initiation and progression, including inflammation and autoimmune responses (Geissmann, F. et al. *Science* 327, 656-661 (2010); Grivennikov, et al. *Cell* 140, 883-899 (2010)). Although moderate levels of gene silencing have been achieved recently in leukocytes (Leuschner, F. et al. *Nature Biotechnology* 29, 1005-1010 (2011); Novobrantseva, T. I. et al. *Molecular Therapy—Nucleic Acids* 1, e4 (2012)), it will be important clinically that compounds can be degraded and eliminated from the body. In these experiments, LNPs were formulated with siRNA specific against CD45, which is a tyrosine phosphatase protein found on the surface of all white blood cells. Three days following the intravenous delivery of LNPs in mice, immune cells were harvested from the peritoneal cavity and spleen. Cells were stained with fluorescent antibodies, and CD45 protein silencing was quantified in specific immune cell subsets via flow cytometry analysis. Results were normalized to CD45 levels after delivery of the same LNP containing a non-targeting siRNA. Of the five lipidoid materials evaluated in this model, $304O_{13}$ and $306O_{13}$ mediated the most robust CD45 silencing in immune cells isolated from both the peritoneal cavity and the spleen (FIGS. 4e and *f*). CD11b+ and CD11c+ populations (monocyte/macrophages and dendritic cells, respectively) were subject to high levels of knockdown within the peritoneal cavity (up to 90%) and to a lesser degree within the spleen (up to 40%). The lipidoids $306O_{12}$, $306O_{14}$, and $315O_{12}$ also offered modest CD45 silencing in several immune cell subpopulations (FIG. 9).

Nanoparticle characterization parameters for three of the top LNP candidates were similar (Table 1). Entrapment of siRNA refers to the percentage of siRNA in solution that is incorporated into the nanoparticle during formulation, as measured by an RNA dye-binding assay (Nolan, T., Hands, R. E. & Bustin, S. A. Quantification of mRNA using real-time RT-PCR. Nat. Protoc 1, 1559-1582 (2006)). These results are in keeping with a previous finding that efficacious lipidoid nanoparticles often have entrapment values of approximately 75%17. Zeta potential measurements were conducted under neutral pH conditions. pKa values, which were obtained using a toluene nitrosulphonic acid (TNS) assay, evaluated the pKa of the nanoparticle surface (Heyes, J., Palmer, L., Bremner, K. & MacLachlan, I. Cationic lipid saturation influences intracellular delivery of encapsulated nucleic acids. J Control Release 107, 276-287 (2005)). The pKa values of top LNP candidates corroborate the results of another study in which surface pKa values in the 6-7 range conveyed efficacy in vivo (Jayaraman, M. M. et al., Maximizing the Potency of siRNA Lipid Nanoparticles for Hepatic Gene Silencing In Vivo. Angew. Chem. Int. Ed. 51, 8529-8533 (2012)).

Several analyses were performed to assess the biodistribution of the lead compound, $304O_{13}$, in mice. For these experiments, nanoparticles were formulated with Cy5.5-labeled siRNA. Whole organ IVIS images (FIG. 5a) and Odyssey scans (FIG. 5b) showed that naked siRNA accumulated in the kidneys at 1 hour post-injection, suggesting rapid renal clearance. Quantification of IVIS signal indicated that 14%, 1%, and 71% of naked siRNA signal appeared in the liver, spleen, and kidneys, respectively. In contrast, at 1 hour post injection, $304O_{13}$ localized primarily within the liver (42%) and spleen (24%), with only 18% distributing to the kidneys.

Figure 7:
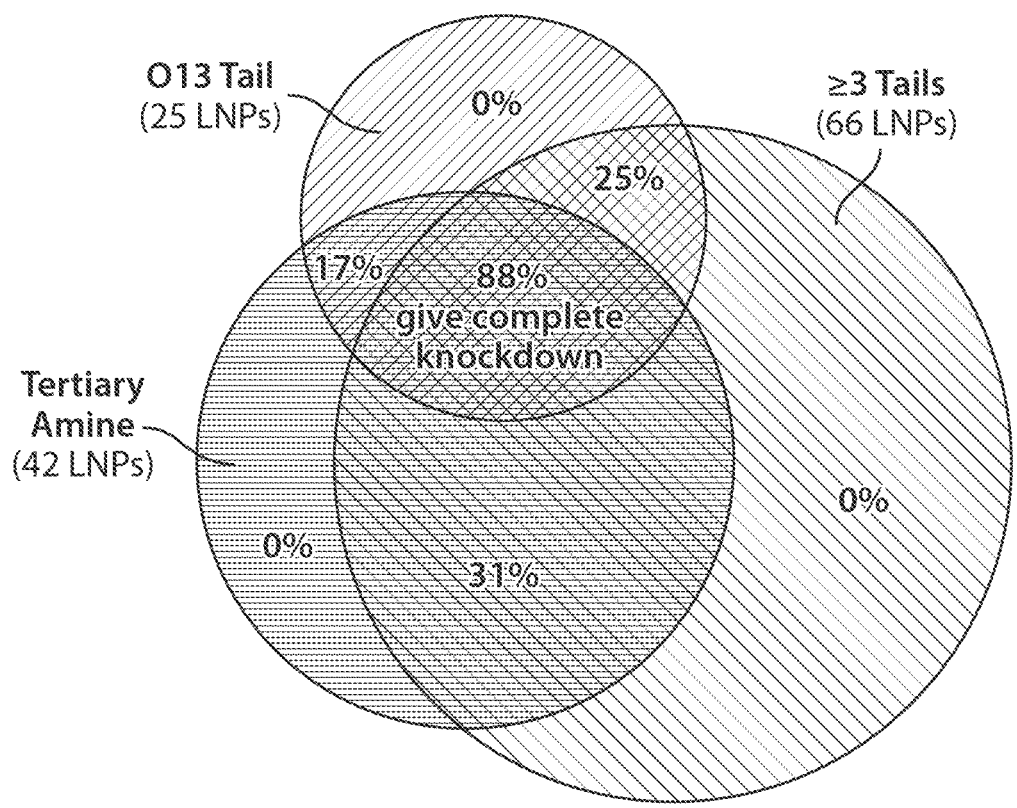
FIG. 7 displays structure-function information of efficacious lipid nanoparticles. (a) Of the 108 lipid nanoparticles tested for siRNA delivery to hepatocytes in mice, 66 had 3 or more tails, 42 had a tertiary amine present in the original alkyl-amine, and 25 had an $O_{13}$ tail length. 88% of the lipid nanoparticles exhibiting all three "efficacy criteria" achieved complete FVII knockdown. The percentage of efficacious lipid nanoparticles decreased precipitously when any criterion were not met. (b) Twelve second generation lipid nanoparticles were made to meet all efficacy criteria by first synthesizing custom alkyl-amines and reacting them with $O_{13}$ tails. (c) 83% of second generation LNPs achieved complete FVII silencing in vivo, and (d) $EC_{50}$s under non-optimized LNP formulating conditions ranged from 0.05 to 1 mg/kg total siRNA. (e) $503O_{13}$ was the most efficacious LNP upon formulation, with an $EC_{50}$ of 0.01 mg/kg. $503O_{13}$ encapsulating control siRNA did not result in FVII knockdown. Error bars represent standard deviation (n=3).
Figure 7:
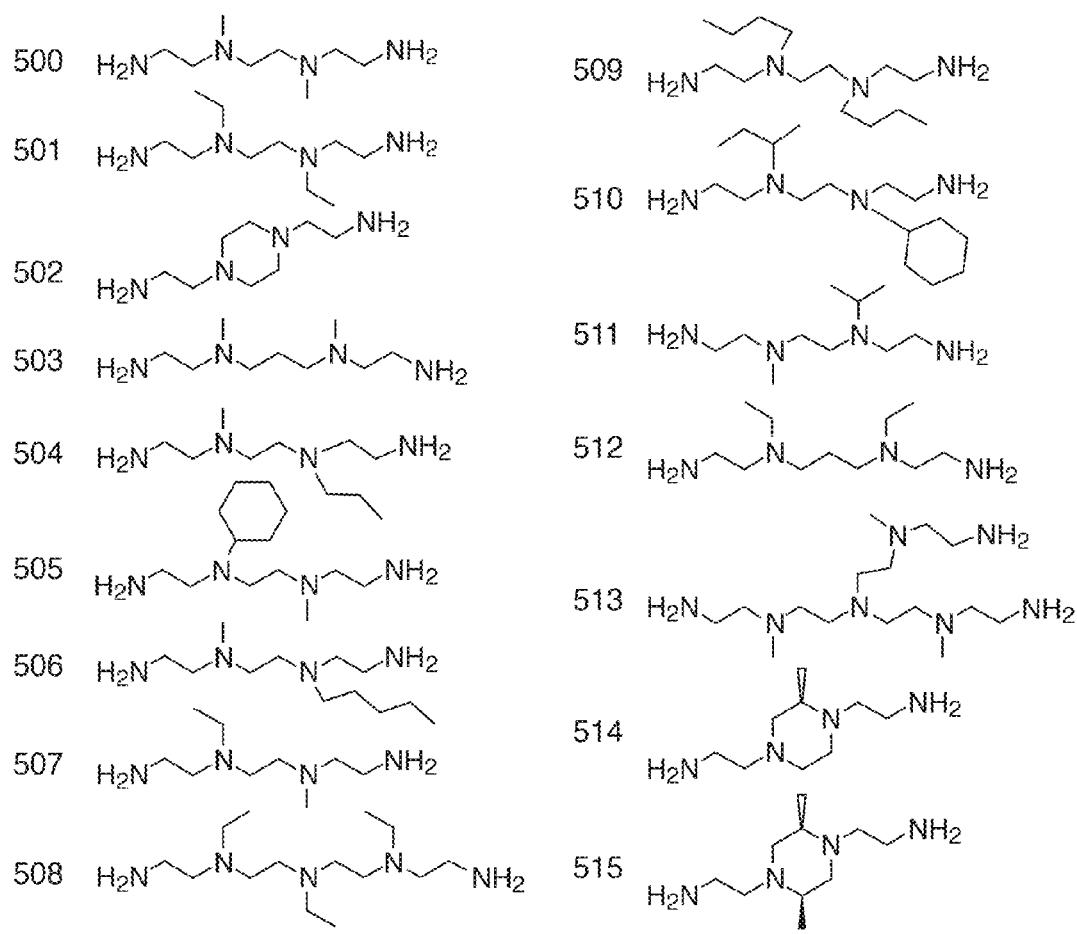
Figure 7:
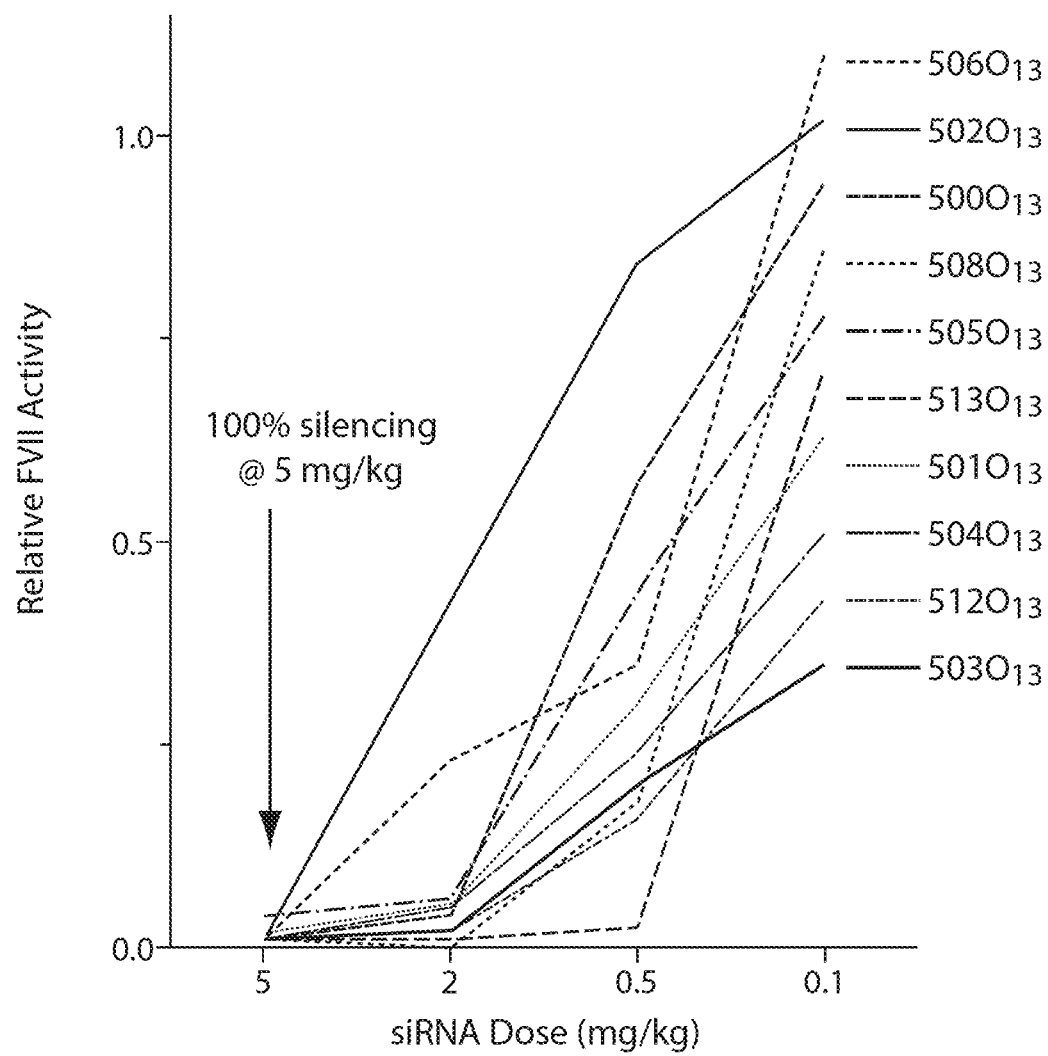
Figure 7:
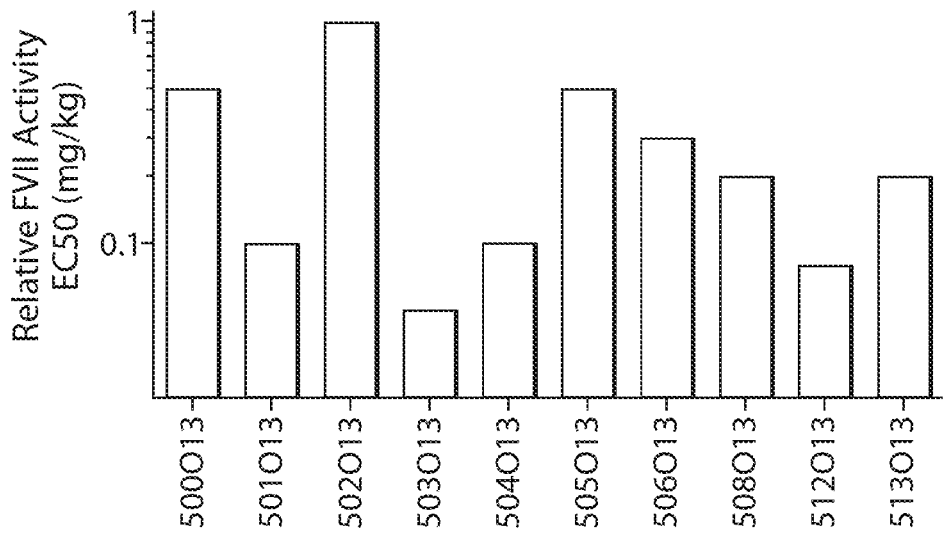
Figure 7:
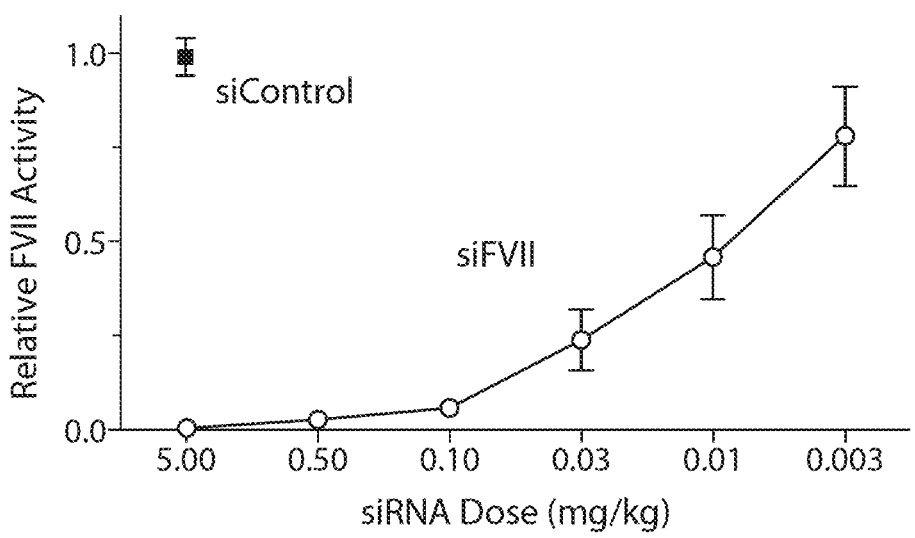

Given their effectiveness for silencing the hepatocellular target, FVII, we examined how $304O_{13}$ nanoparticles were distributing within the liver. Confocal imaging was performed on liver tissues harvested one hour post-injection and stained with nuclear, actin, and macrophage markers (FIG. 7c). Images were taken near the central vein in liver lobules (black void near the center of images). Hepatocytes are outlined in green and macrophages, which appear sporadically, are colored magenta. Only $304O_{13}$ was able to mediate siRNA accumulation throughout nearly all hepatocellular tissue (in red).

Figure 5:
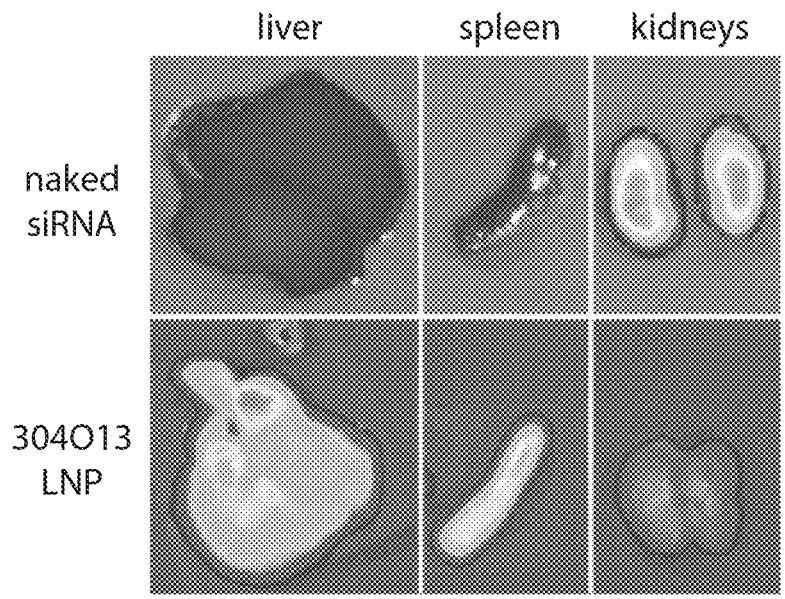
FIG. 5 shows biodistribution images for Cy5.5-labeled siRNA delivered with the lipidoid $304O_{13}$. IVIS (a) and Odyssey (b) imaging show that, while naked siRNA is primarily cleared through the kidneys, $304O_{13}$ mediates accumulation in the liver and spleen. (c) Confocal microscopy of $304O_{13}$-treated liver shows siRNA (red) delivery into nearly all cells, including Kupffer cells and hepatocytes. In contrast, naked siRNA had a limited penetration depth from the blood vessels into hepatocellular tissue. (d) $304O_{13}$ lipid nanoparticles were rapidly eliminated from the bloodstream after tail vein injection. Error bars represent standard deviation (n=3).
Figure 5:
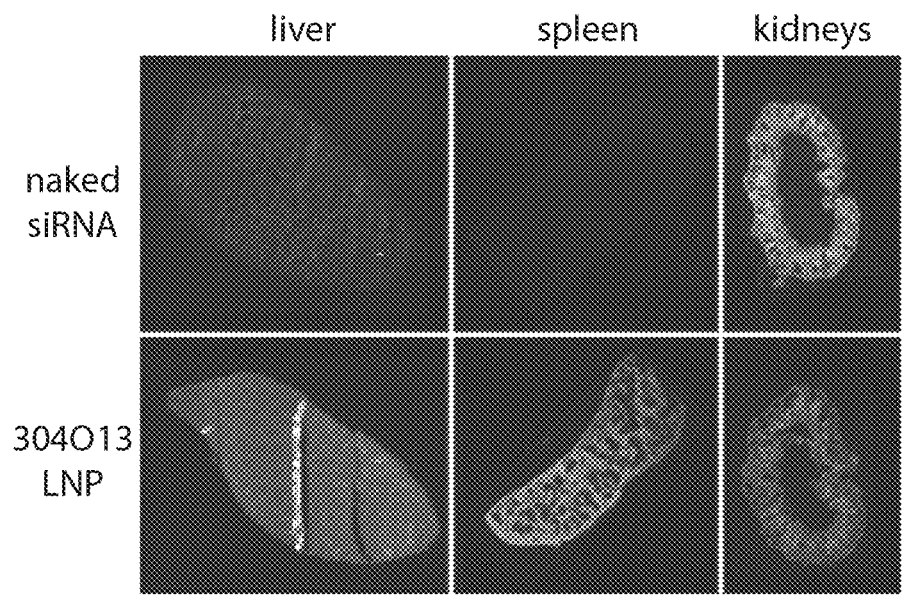
Figure 5:
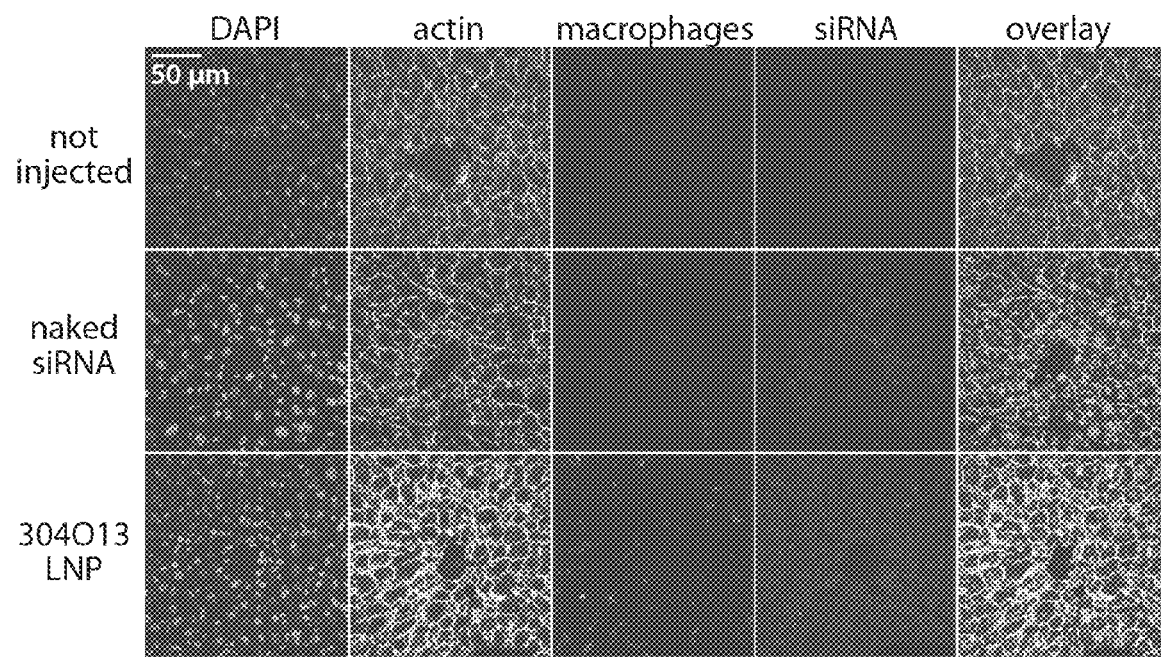
Figure 5:
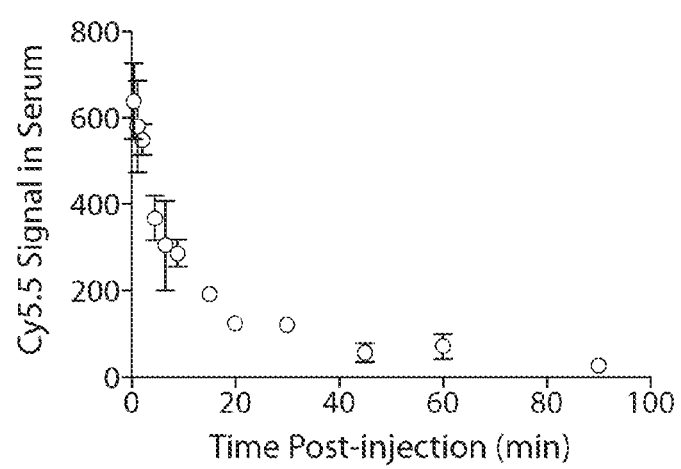

Serum clearance kinetics were assessed by measuring Cy5.5 signal in the mouse bloodstream as a function of time (FIG. 5d). It should be noted that, while the first blood sample was drawn as quickly as possible (20 seconds), maximum signal may have occurred even earlier. Half of the material initially detected at 20 seconds had distributed to tissues by 6 minutes. At 90 minutes post-injection, only 4% of signal remained.

Figure 6:
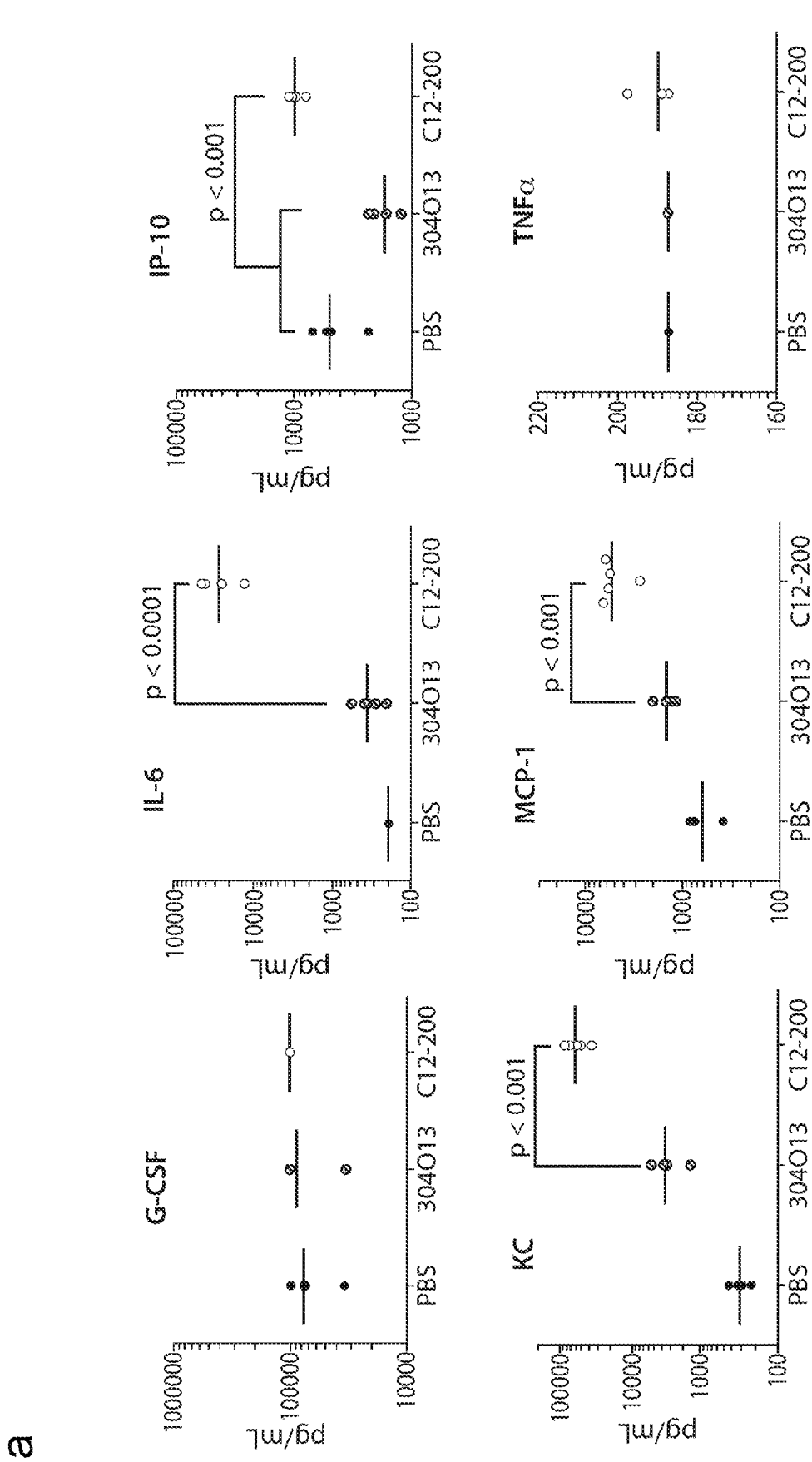
FIG. 6 shows a comparison of (a) cytokine profiles 4 hours post-injection and (b) liver histology sections 72 hours post-injection for degradable ($304O_{13}$) and non-degradable (C12-200) lipid nanoparticles.
Figure 6:
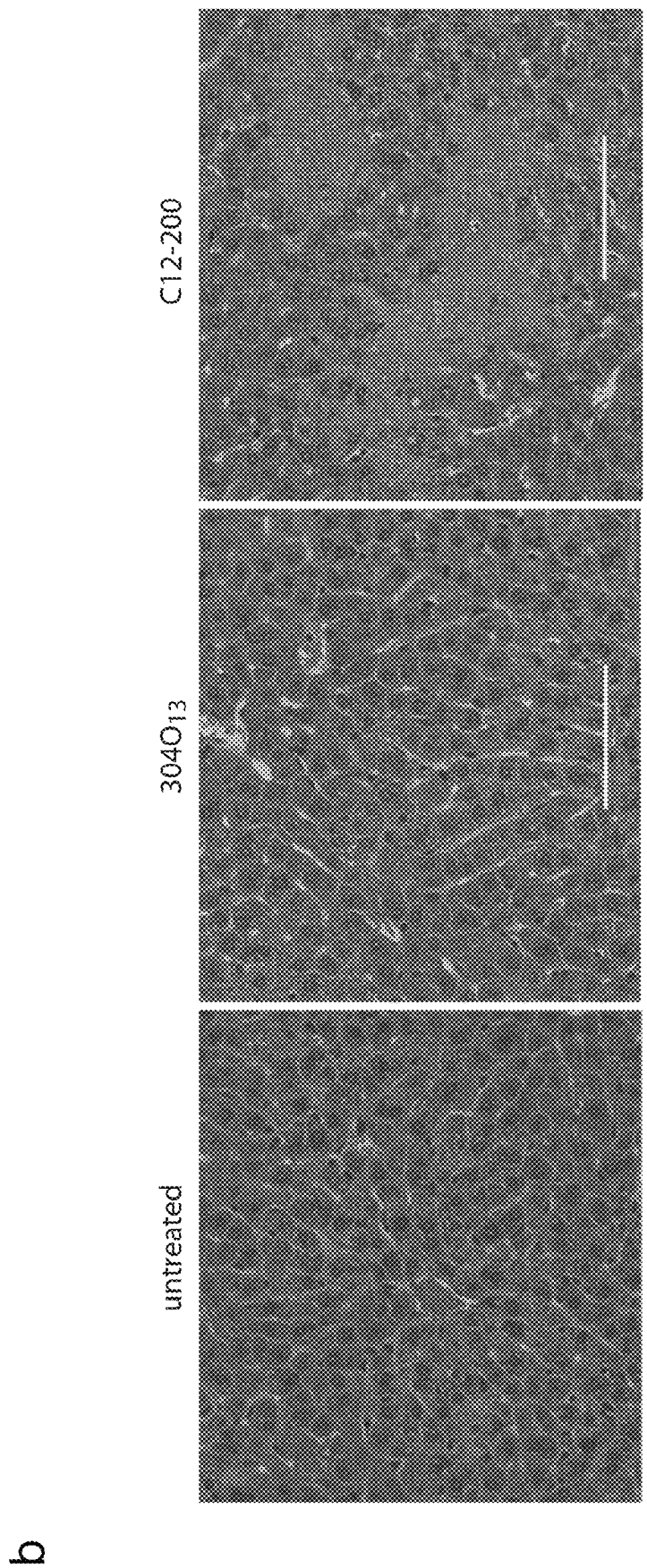
Figure 12:
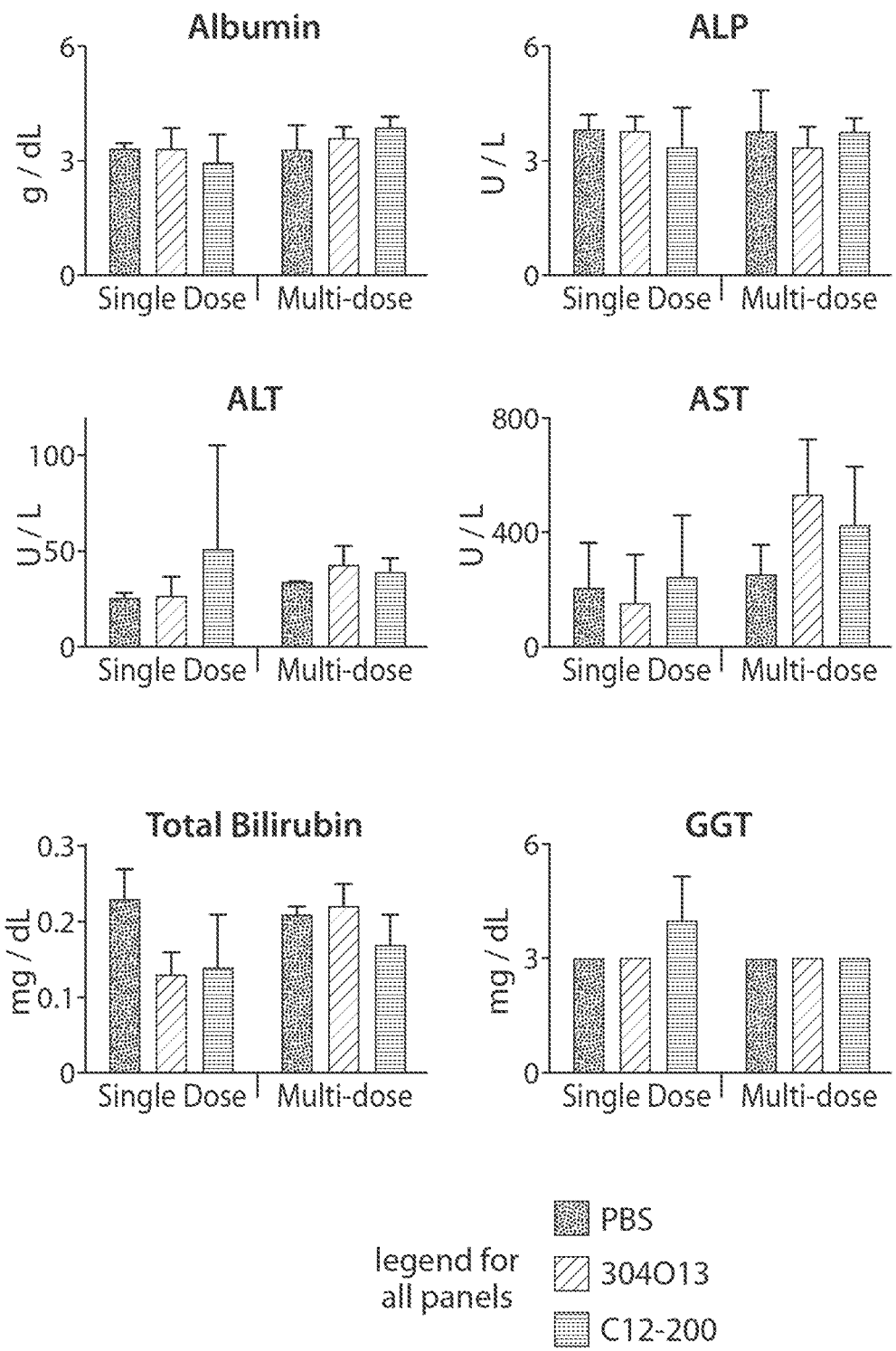
FIG. 12 shows that clinical chemistry parameters were evaluated for negative control (PBS, black), $304O_{13}$ (blue), and C12-200 (red) groups of C57BL/6 mice. The mice had been injected with either a single 3 mg/kg dose of total siRNA or four 3 mg/kg doses (1x per week for four weeks). Blood was drawn for analysis 72 hours post-final injection. There were no statistically significant changes in any of the clinical chemistry parameters for any of the treated groups compared to controls (as evaluated by a student t-test). Error bars represent standard deviation (n=3-5).

A preliminary safety assessment was conducted on the lead LNP, $304O_{13}$, and it was compared to another previously-discovered LNP formulation, C12-200 (Love, K. T. et al. Lipid-like materials for low-dose, in vivo gene silencing. PNAS 107, 1864-1869 (2010)). C12-200 is a 5-tailed, lipidoid that has the same $EC_{50}$ as $304O_{13}$ (0.01 mg/kg). It was chosen for comparison purposes because it does not contain any functional groups that are overtly sensitive to hydrolysis. We chose to examine the effect of doses that were at least 100-fold higher than the $EC_{50}$. Serum cytokine levels for both materials were assessed in mice four hours after a 3 mg/kg IV bolus injection (total siRNA). IL-6, IP-10, KC, and MCP-1 were elevated in the C12-200 group compared to both PBS negative control and $304O_{13}$ groups under these conditions (FIG. 6). Clinical chemistry parameters were evaluated for both materials 72 hours after a single dose of 3 mg/kg and after four once weekly doses of 3 mg/kg each. There were no toxicologically significant increases in albumin, ALT, AST, ALP, total bilirubin, or GGT for either $304O_{13}$ or C12-200 after single or multiple doses (FIG. 12).

Histological analysis was performed through H&E staining on sections from the liver, spleen, kidneys and pancreas. In single-dose studies (0, 1, 2, 3, 5, 7.5, 10 mg/kg), liver necrosis was observed in mice administered ≥7.5 mg/kg of C12-200 and at 10 mg/kg of $304O_{13}$. Pancreatic inflammation and islet cell enlargement were detected at C12-200 doses ≥2 mg/kg. A small amount of apoptosis in splenic red pulp was observed at 10 mg/kg for $304O_{13}$. Multi-dose studies were also conducted in which mice received four injections of 0.3, 1, 2, 3, or 5 mg/kg, once per week for four weeks. Liver necrosis and inflammation were observed in mice administered ≥1 mg/kg of C12-200. There was no sign of liver toxicity in any of the $304O_{13}$ groups up to 5 mg/kg. Based on this limited evaluation, the collective data suggest an improved toxicity profile for $304O_{13}$ compared to C12-200 in mice.

The data from the 108 materials tested in vivo at a total siRNA dose of 5 mg/kg are shown in FIG. 7a. Of the 108 materials tested in mice, 25 of them contained an $O_{13}$ tail, 66 of them had three or more tails, and 42 of them had been synthesized from an alkyl-amine that contained at least one tertiary amine.

Figure 13:
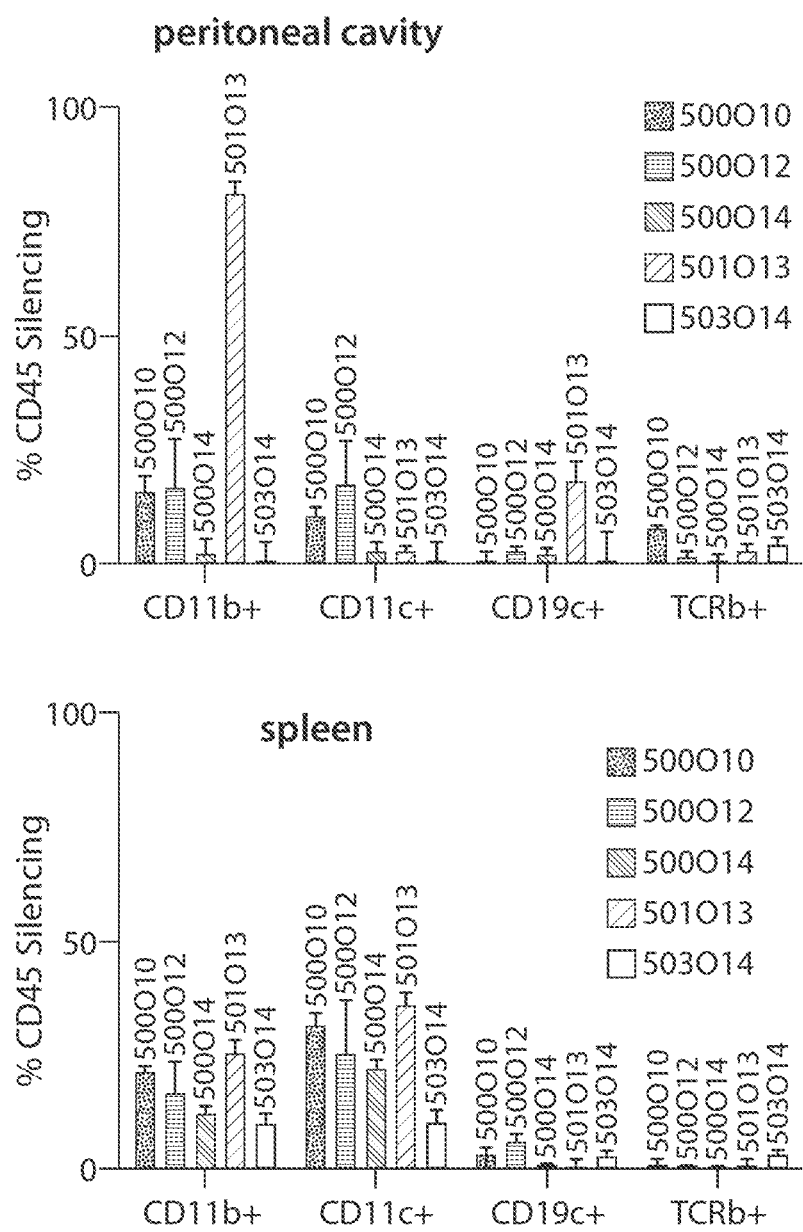
FIG. 13 shows that the second generation lipid nanoparticles (LNPs) facilitated silencing of the surface receptor CD45 in various white blood cell populations harvested from the peritoneal cavity (left) and spleen (right) of B6 mice three days post-injection (dose=2.5 mg/kg total siRNA). Percent silencing was calculated by comparing to an identically defined cell population from animals injected with a non-targeting siRNA formulated with the same LNP. Error bars represent standard deviation (n=3).

FIG. 7b shows a second generation library of lipidoids from certain amines conjugated to an $O_{13}$ tail. When tested in vivo, 10 out of 12 of these materials mediated 100% Factor VII silencing at a dose of 5 mg/kg (FIG. 7c). Knockdown was dose-dependent, with EC50 values varying from 0.05-1 mg/kg (FIG. 7d). Formulation optimization of the best second generation material, $503O_{13}$, markedly decreased the $EC_{50}$ value to 0.01 mg/kg (FIG. 7e). Several second generation materials also facilitated significant CD45 knockdown in monocyte, macrophage, dendritic cell, and B cell populations (FIG. 13).

Figure 10:
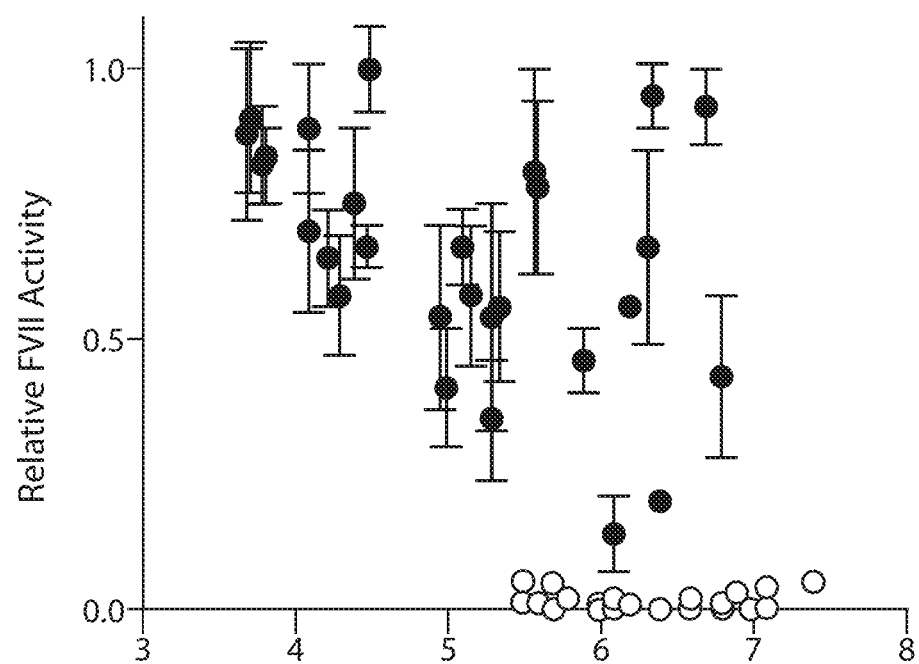
FIG. 10 shows that pKa values significantly influence delivery efficacy to hepatocytes in vivo. All lipidoid nanoparticles capable of mediating complete Factor VII gene silencing had pKa values greater or equal to 5.5.

Since the ability of materials to take on a positive charge with decreasing pH has been shown to confer transfection efficacy (Zhang, J. J., Fan, H. H., Levorse, D. A. D. & Crocker, L. S. L. Ionization behavior of amino lipids for siRNA delivery: determination of ionization constants, SAR, and the impact of lipid pKa on cationic lipid-biomembrane interactions. Langmuir 27, 1907-1914 (2011)), the surface pKa values of 59 distinct lipidoid nanoparticles were measured. The data in FIG. 10 indicate that pKa values play a decisive role in this LNP delivery system, with a critical pKa value of approximately 5.5. Materials demonstrating considerable in vivo efficacy (red data points) had surface pKa values of approximately 5.5 or higher. For values less than approximately 5.5, average efficacy decreased monotonically with pKa. Therefore, surface pKa can be used as an indicator of in vivo potency, improving our predictive capability for this data set.

Other Embodiments

All patents, patent applications, and literature references cited herein are incorporated herein by reference.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function. Use of terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound of Formula (I):

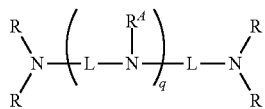

or a salt thereof,
wherein
each L is, independently, branched or unbranched $C_{1-6}$ alkylene, wherein L is optionally substituted with one or more fluorine radicals;
each $R^A$ is, independently, branched or unbranched $C_{1-6}$ alkyl, $C_{3-7}$ cycloalkyl, or branched or unbranched $C_{4-12}$ cycloalkylalkyl, wherein $R^A$ is optionally substituted with one or more fluorine radicals;
each R is, independently, hydrogen, or —$CH_2CH_2C(=O)OR^B$, provided that at least three R groups are —$CH_2CH_2C(=O)OR^B$;
each $R^B$ is, independently, $C_{10-14}$ alkyl, wherein $R^B$ is optionally substituted with one or more fluorine radicals; and
q is 1, 2, or 3;
provided that the compound is not

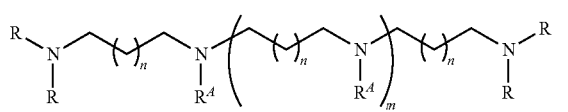

2. The compound of claim 1, wherein the compound is of the Formula (I-a):

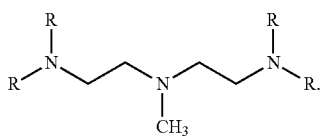

or a salt thereof, wherein
each n is, independently, 0, 1, or 2; and
m is 0, 1, or 2.

3. The compound of claim 1, wherein L is unbranched $C_{1-6}$ alkylene.

4. The compound of claim 1, wherein the compound is of the formula

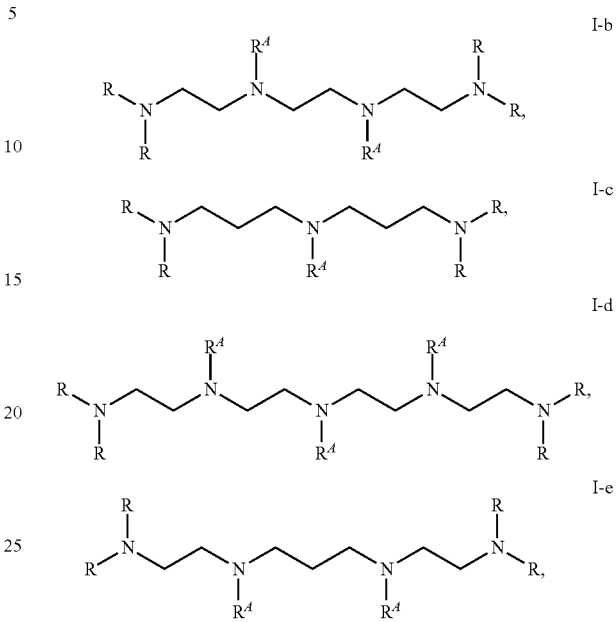

or a salt thereof.

5. The compound of claim 1, wherein the compound is of the formula:

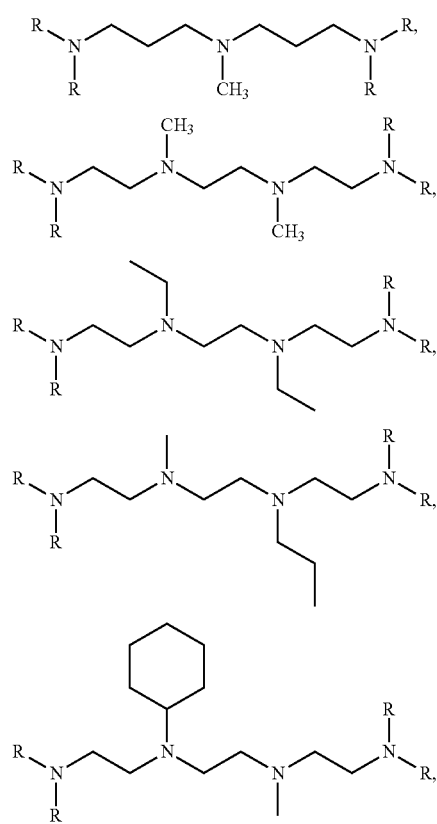

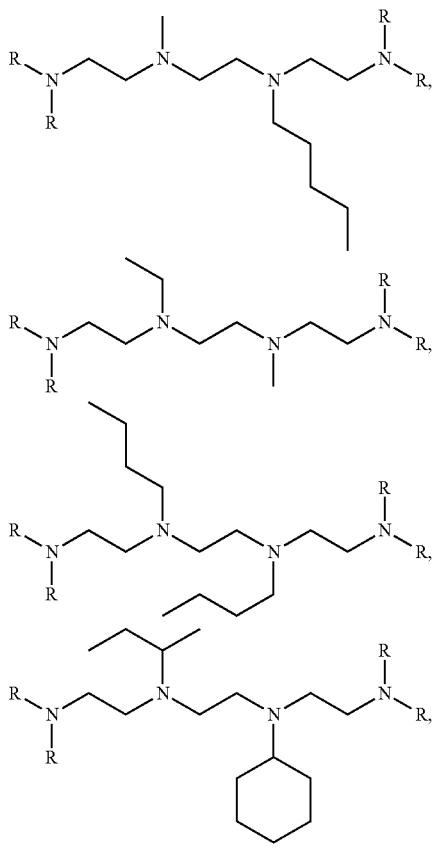
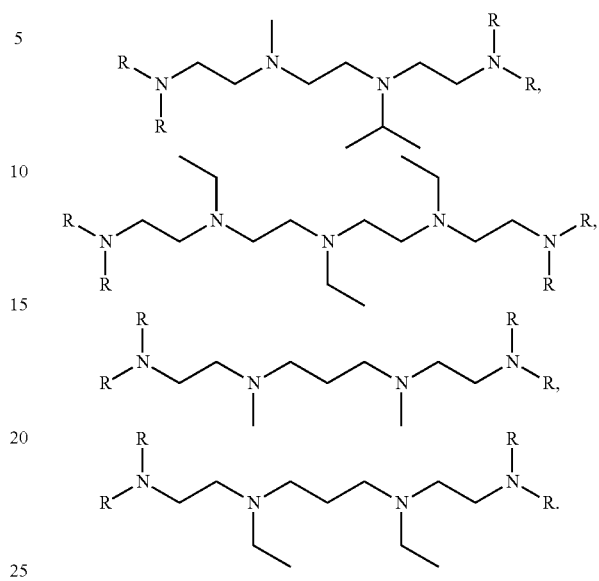
or a salt thereof.
6. The compound of claim 1, wherein all R groups are —CH$_2$CH$_2$C(=O)OR$^B$.
7. The compound of claim 1, wherein all R$^B$ groups are the same.
8. The compound of claim 1, wherein R$^B$ is C$_{10}$ alkyl, C$_{11}$ alkyl, C$_{12}$ alkyl, C$_{13}$ alkyl, or C$_{14}$ alkyl.
9. A compound selected from the group consisting of:
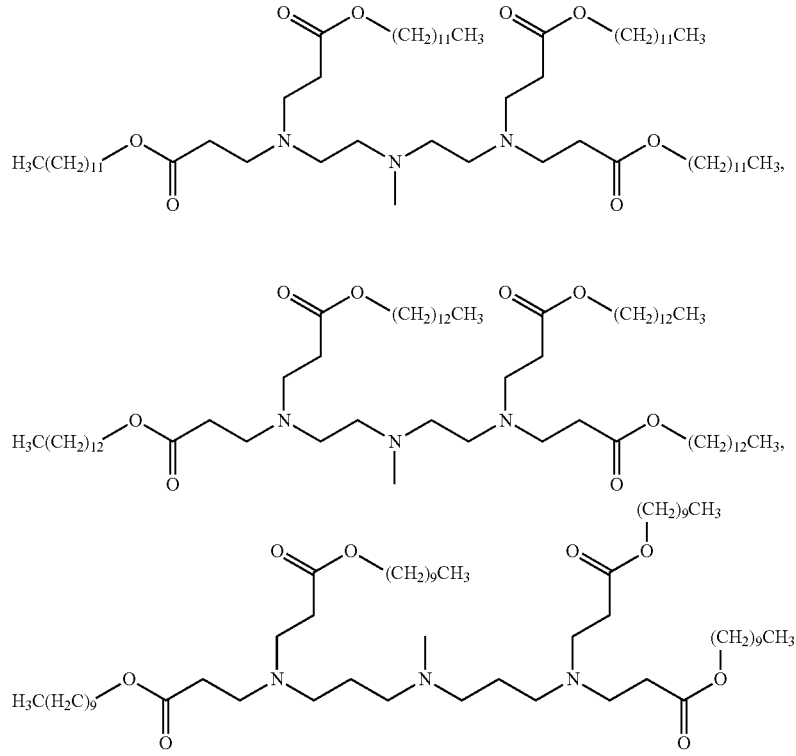

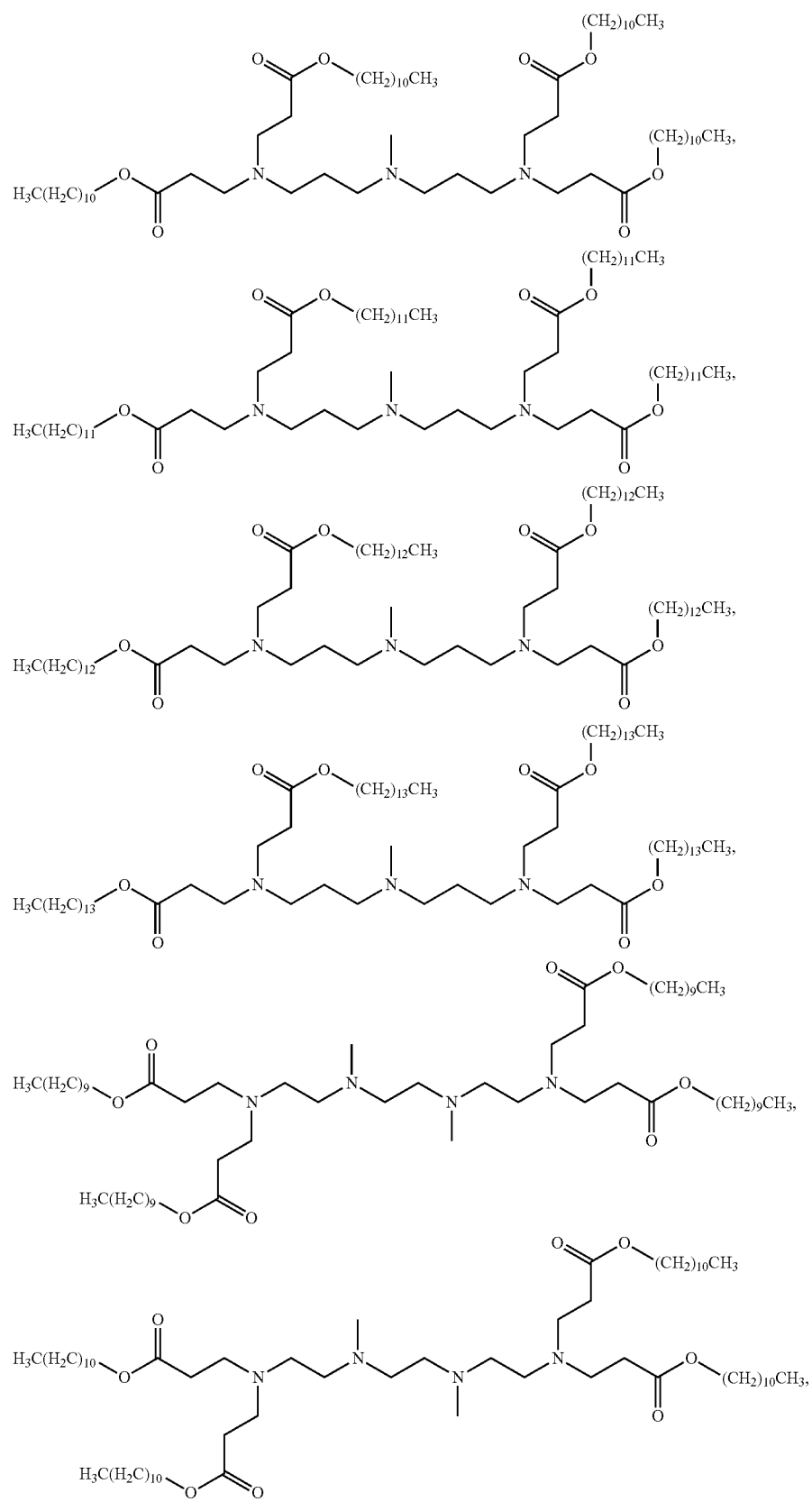

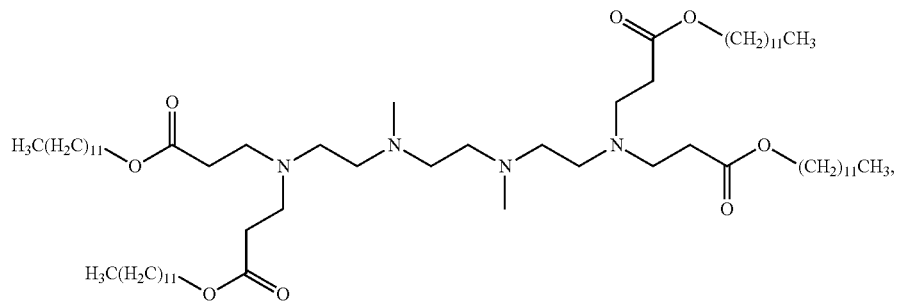
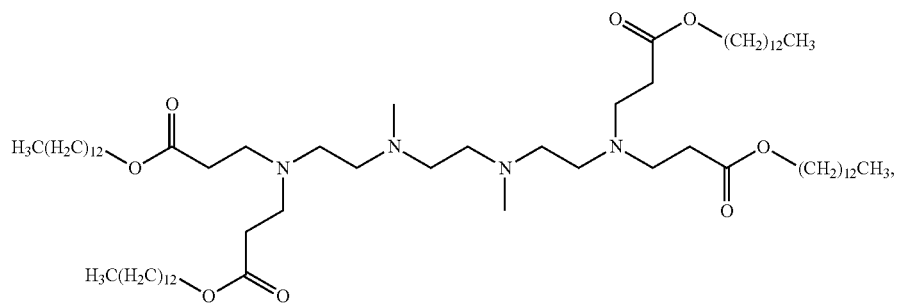
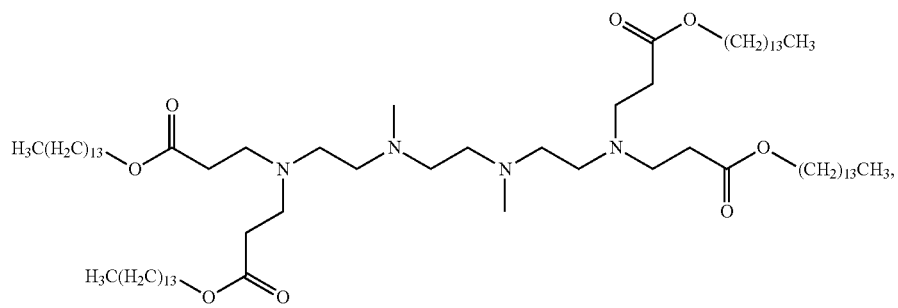
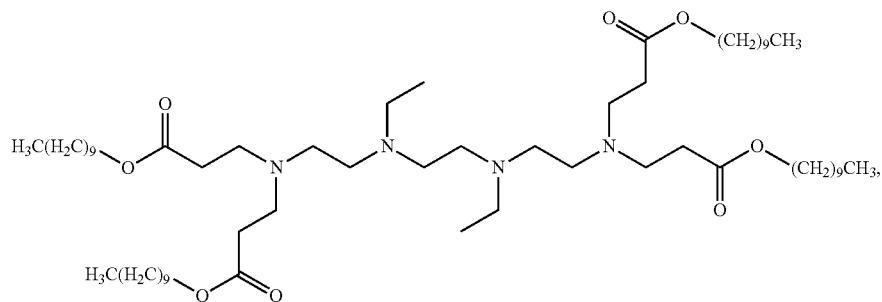
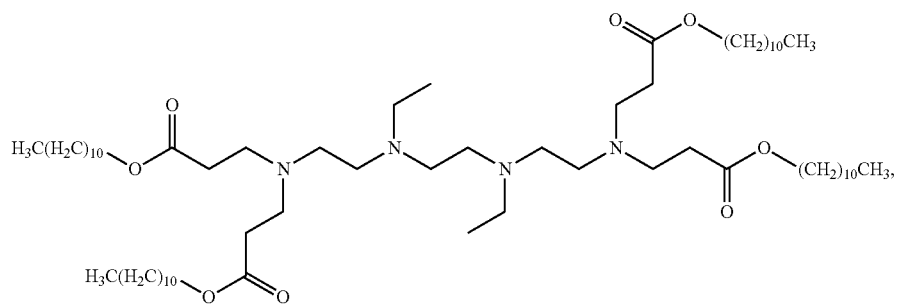

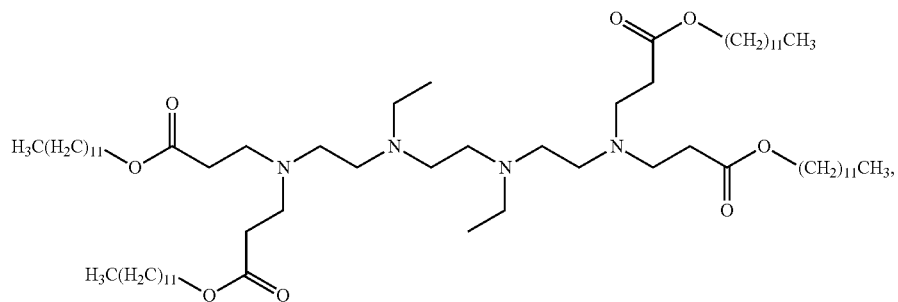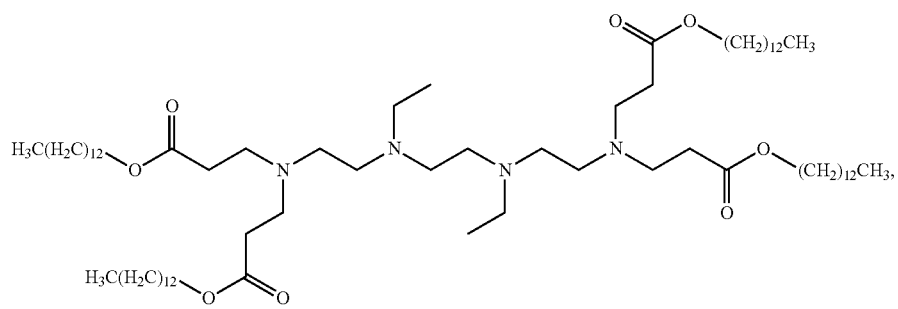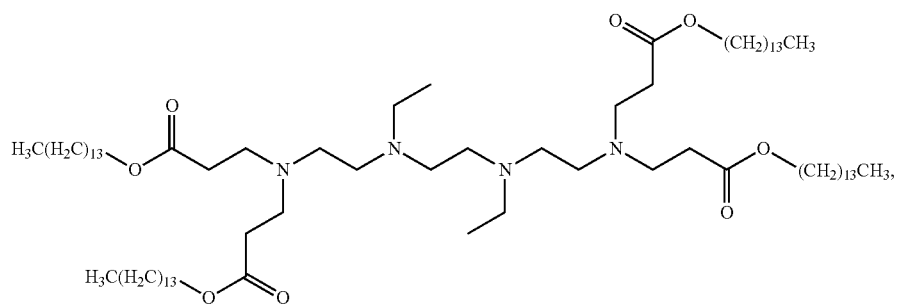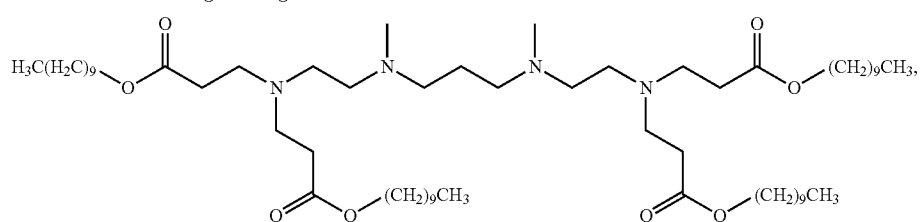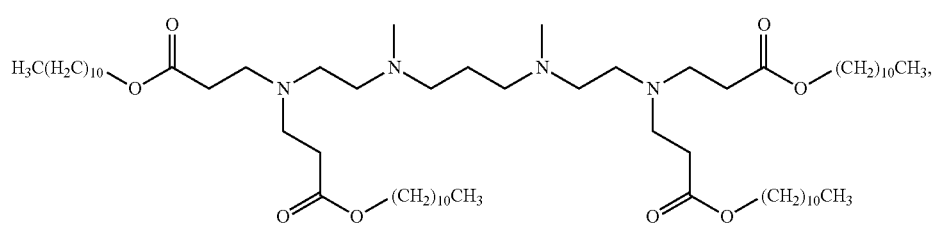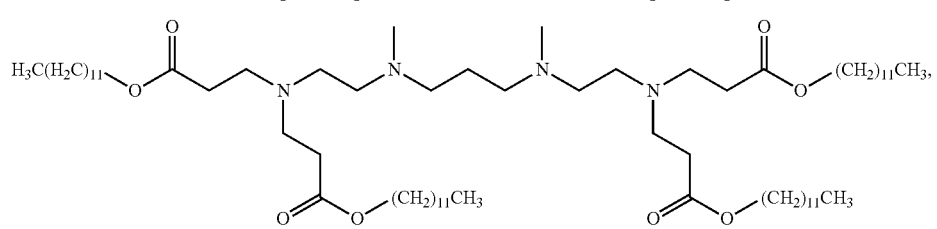

-continued
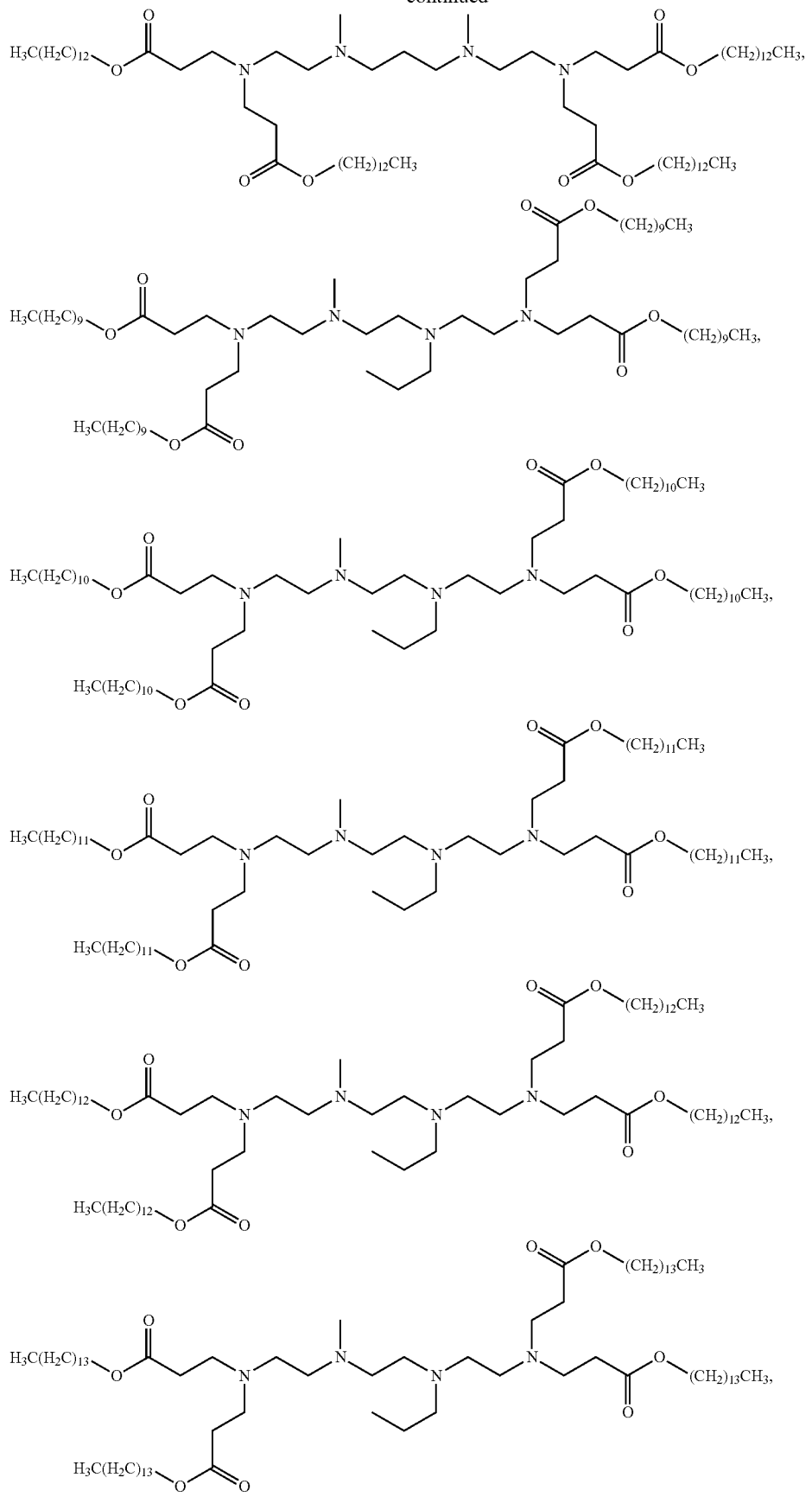

-continued
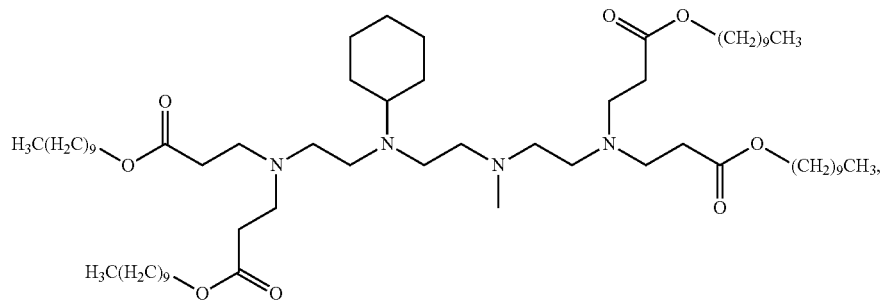
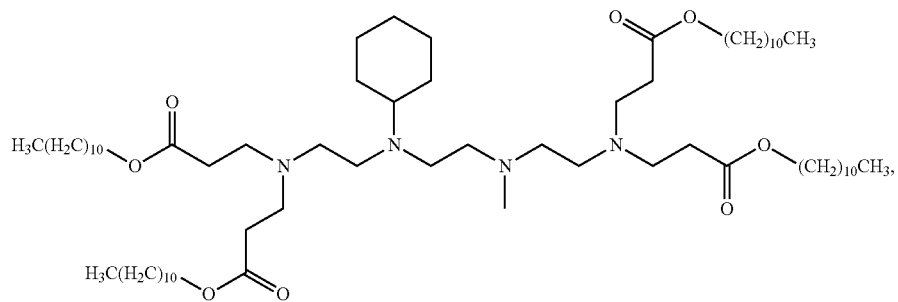
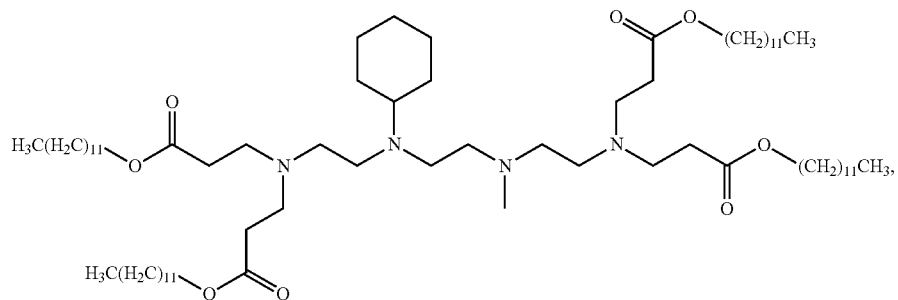
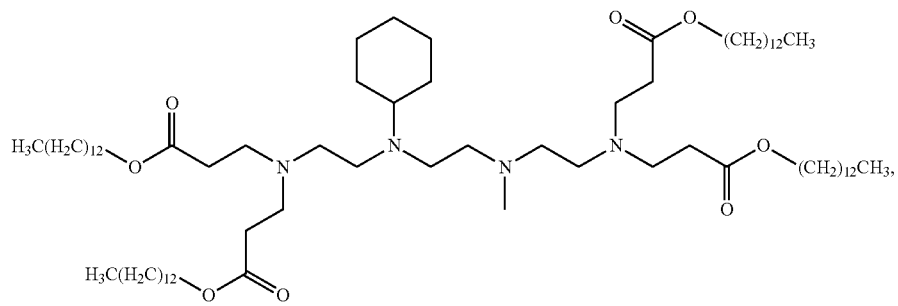
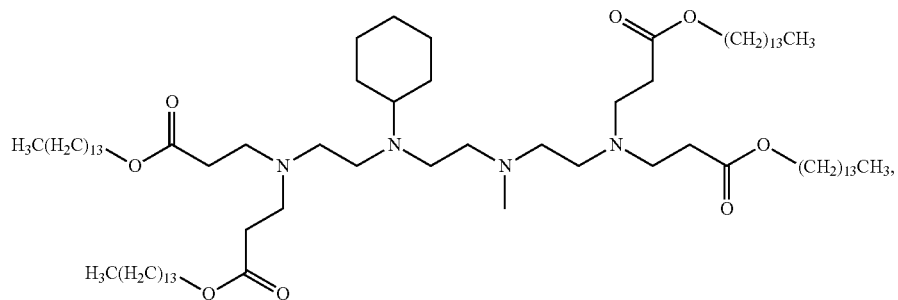

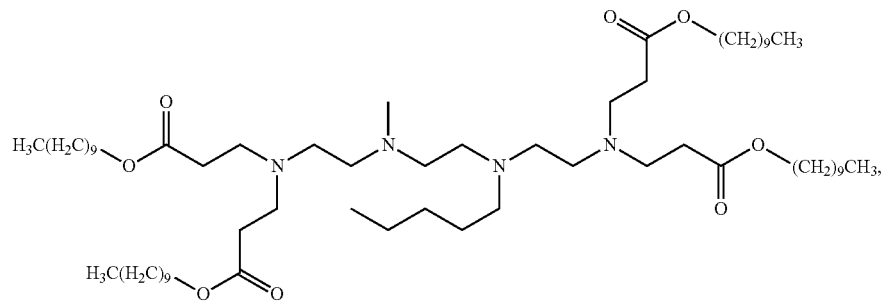
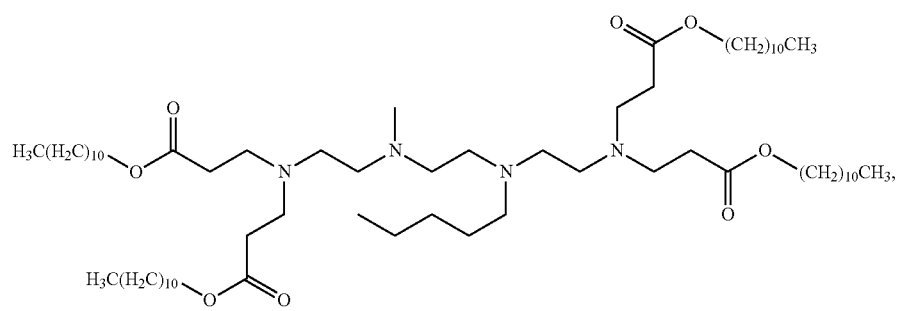
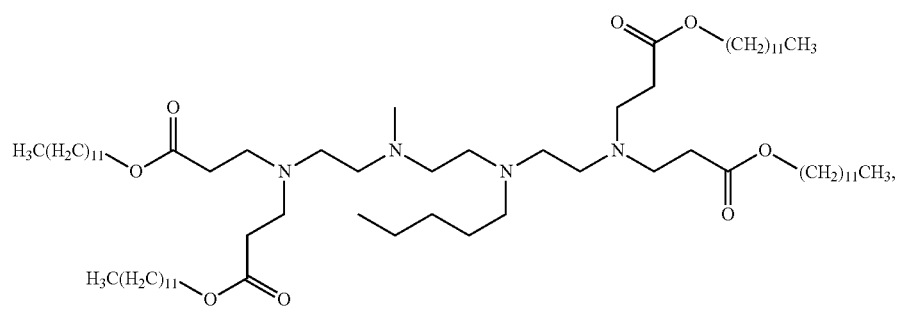
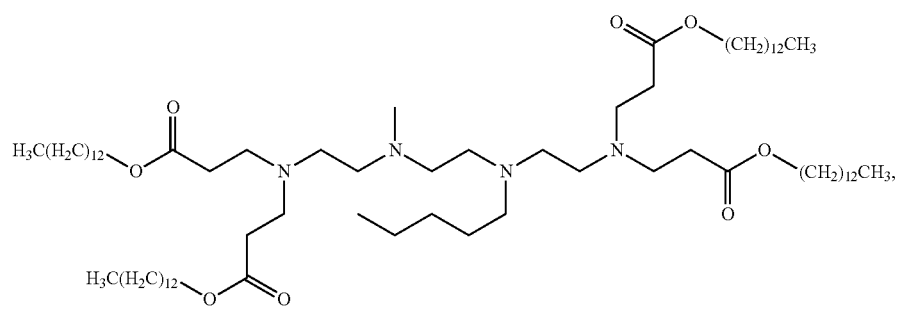
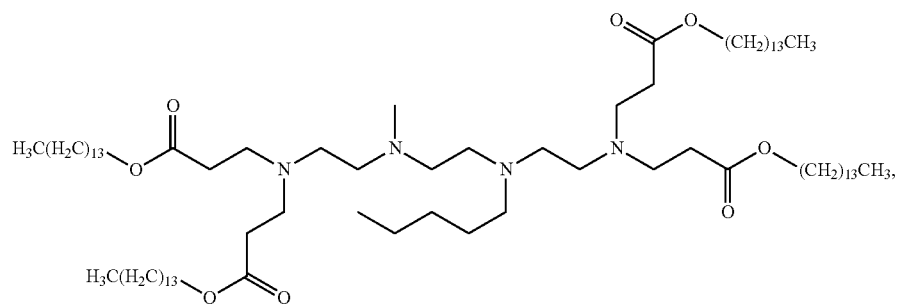

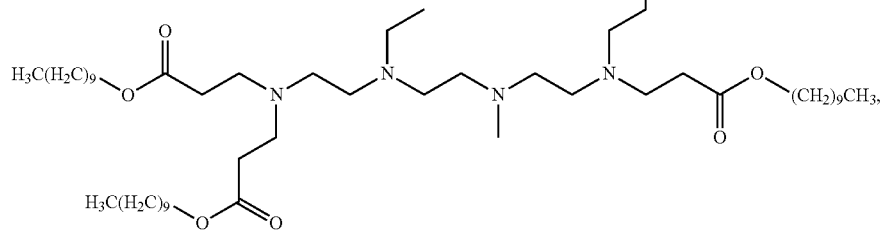
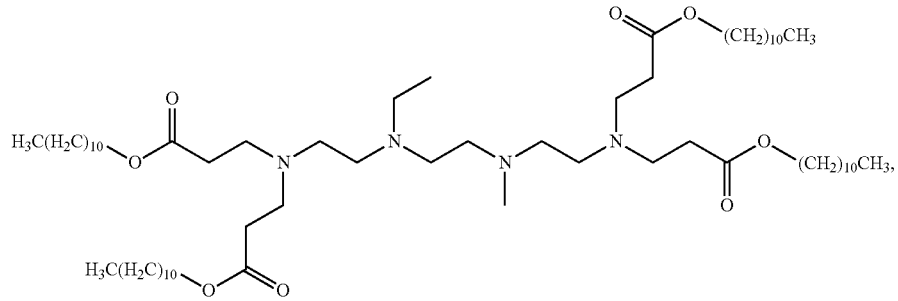
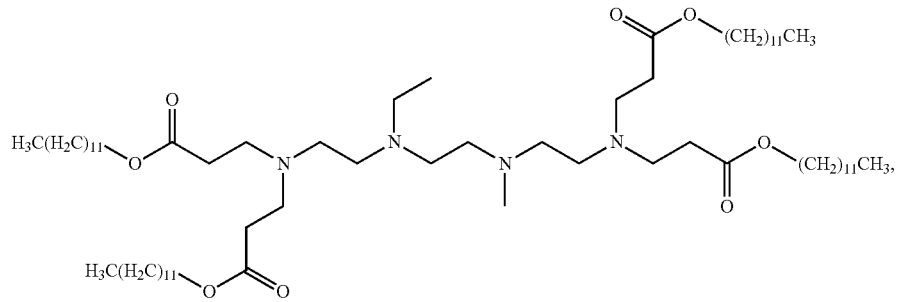
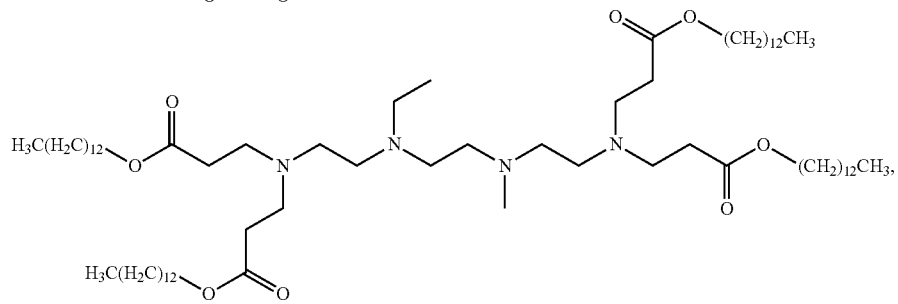
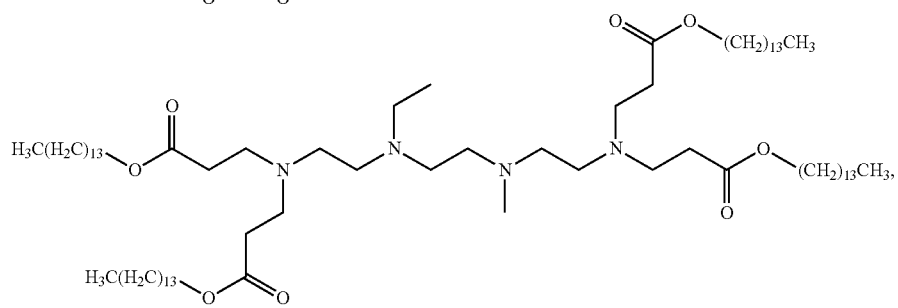
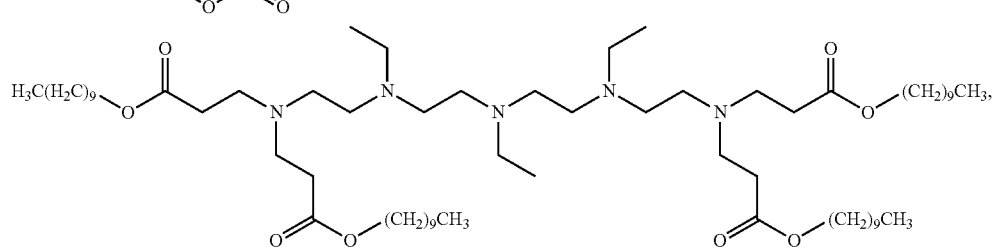

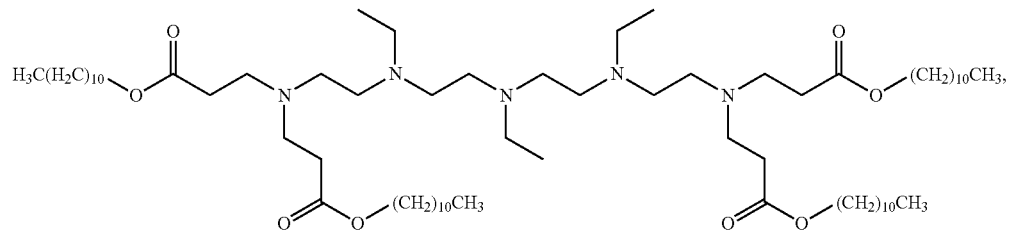
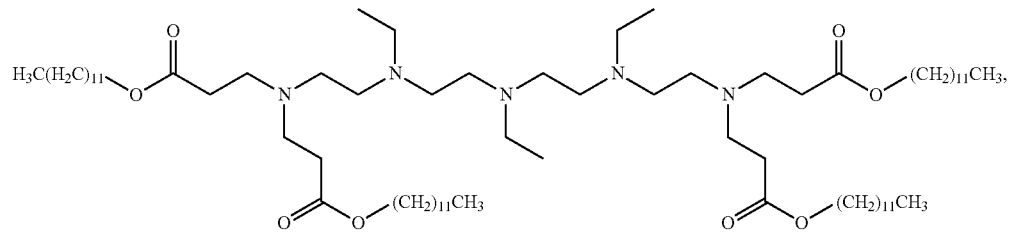
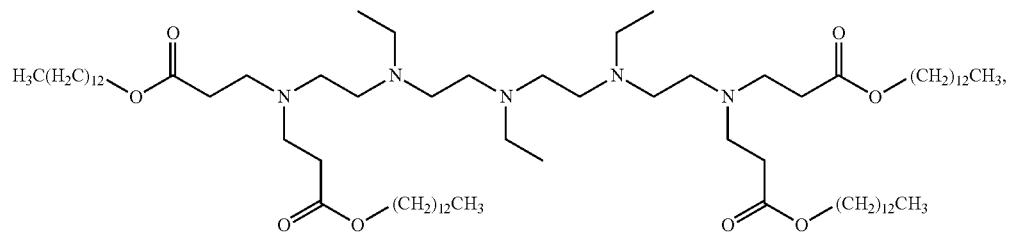
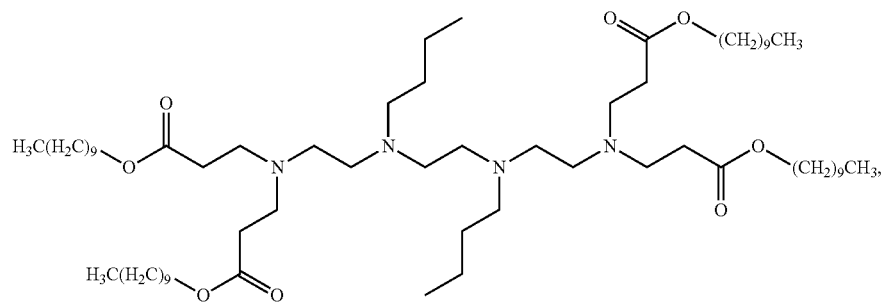
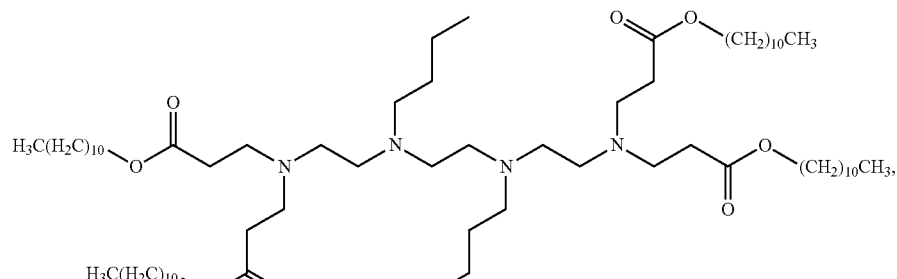
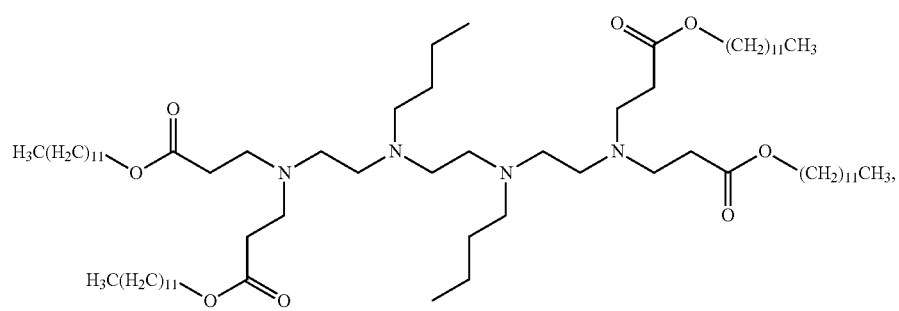

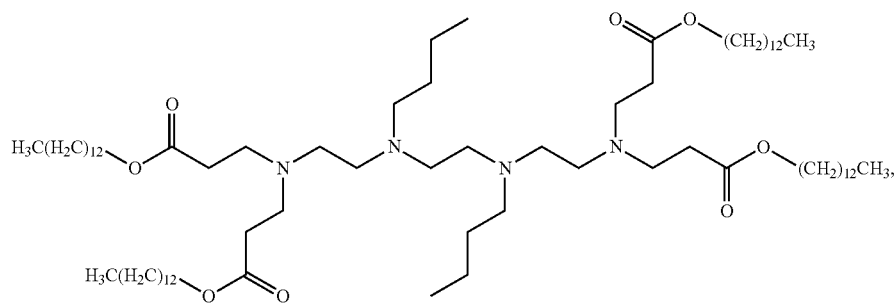
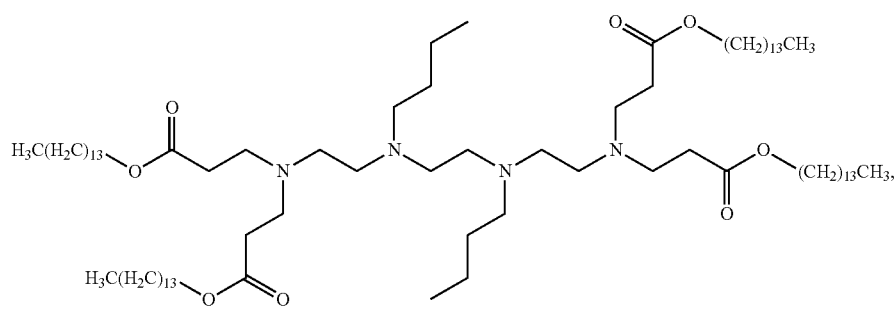
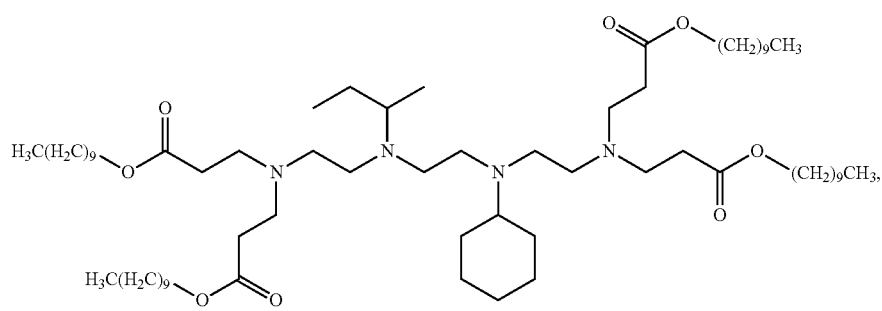
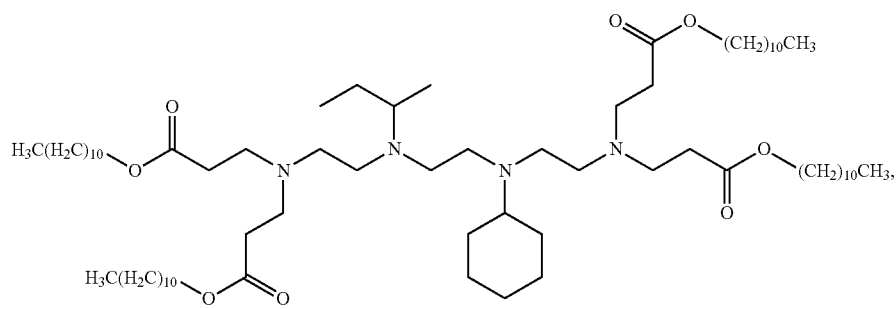
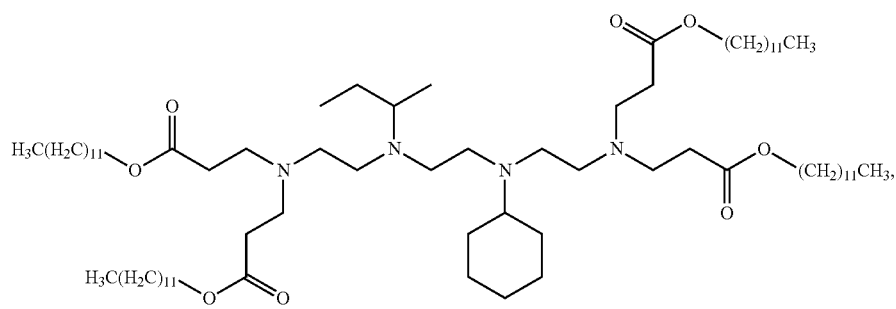

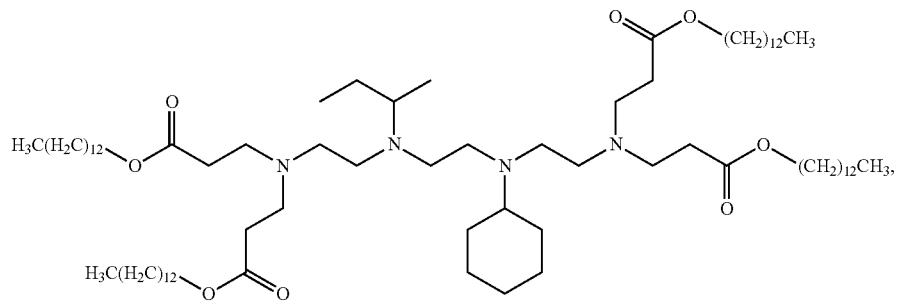
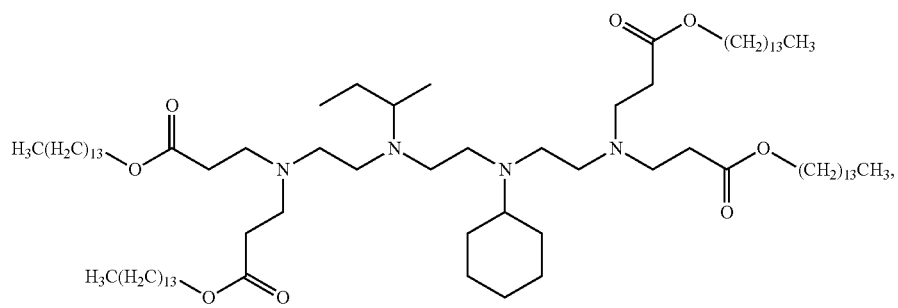
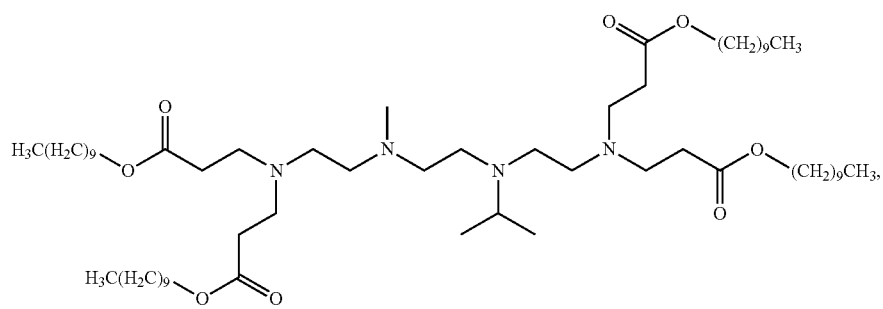
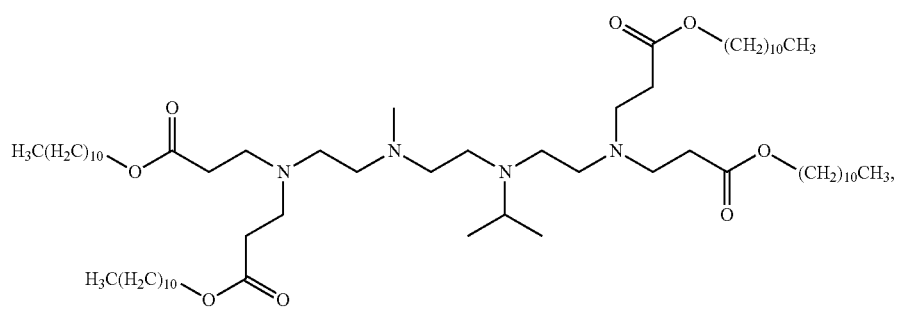
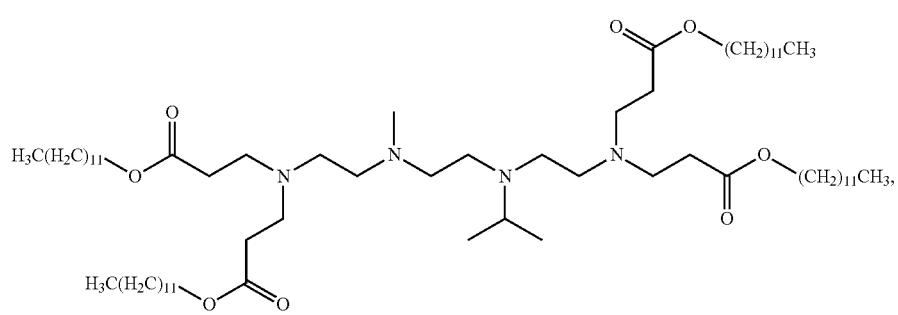

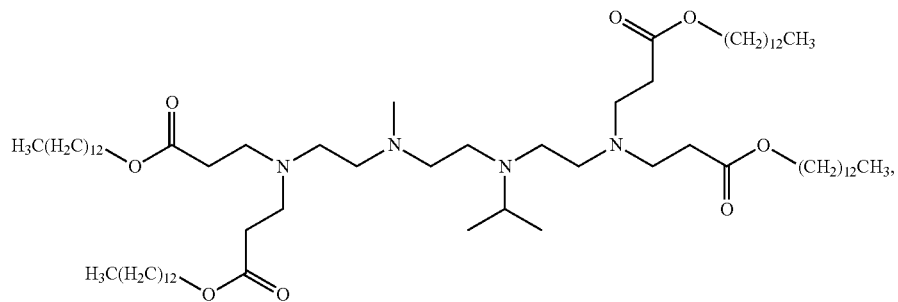
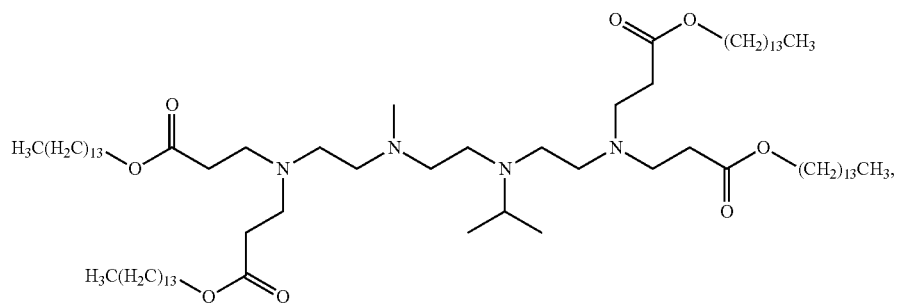
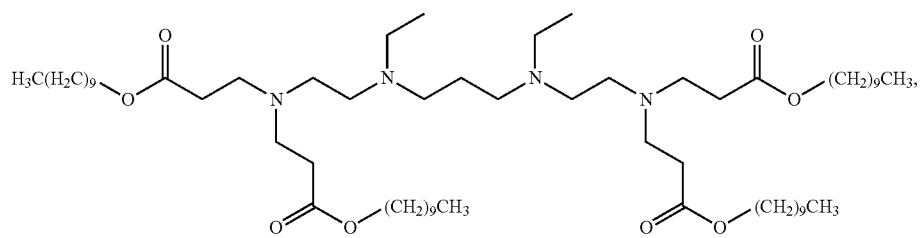
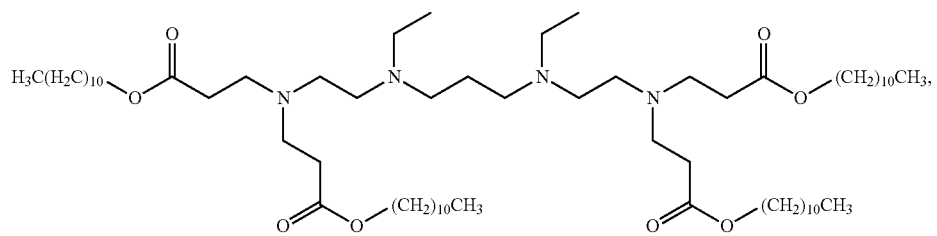
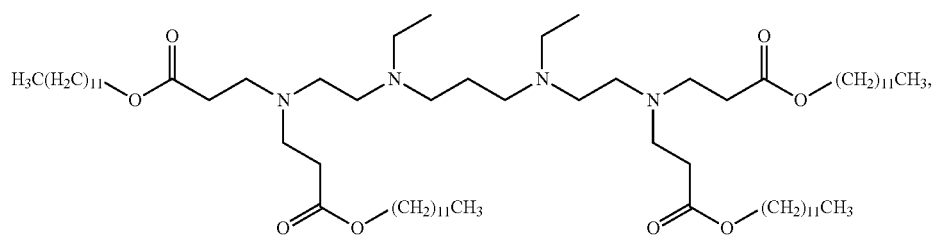
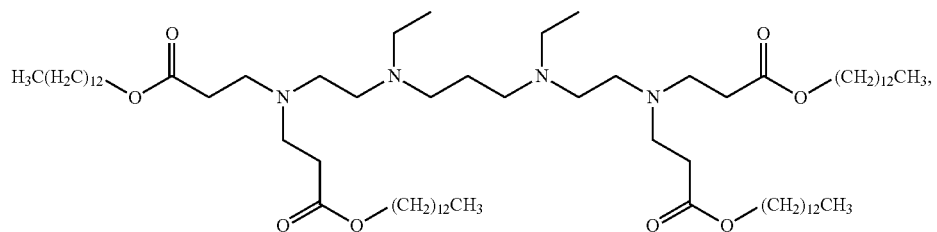

-continued

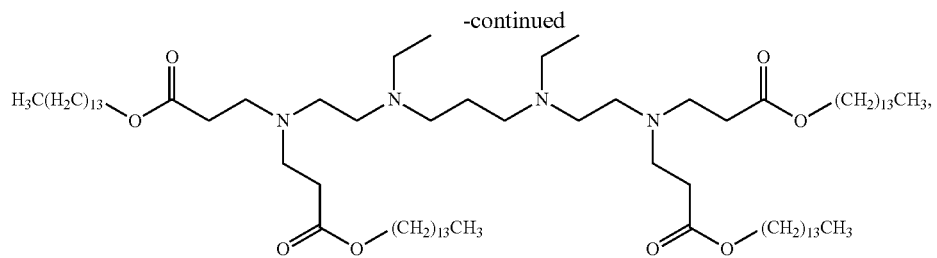

and salts thereof.

10. A nanoparticle comprising a compound of claim 1 and one or more agents to be delivered.

11. The nanoparticle of claim 10, wherein the one or more agents is a polynucleotide, drug, protein, peptide, a small molecule, or gas.

12. A composition comprising one or more compounds of claim 1, and an excipient.

13. The composition of claim 12, wherein the composition further comprises an agent selected from the group consisting of an organic molecule, inorganic molecule, nucleic acid, protein, peptide, polynucleotide, targeting agent, an isotopically labeled chemical compound, vaccine, and an immunological agent.

14. A method of administering an agent, the method comprising:
administering to a subject in need thereof a therapeutically effective amount of a composition comprising a compound of claim 1 and an agent to be delivered.

15. The compound of claim 1, wherein L is ethylene.

16. The compound of claim 1, wherein L is propylene.

17. The compound of claim 1, wherein q is 1.

18. The compound of claim 1, wherein q is 2.

19. The compound of claim 1, wherein q is 3.

20. The compound of claim 1, wherein $R^4$ is branched or unbranched $C_{1-6}$ alkyl.

21. The compound of claim 1, wherein $R^4$ is methyl, ethyl, or propyl.

22. The compound of claim 1, wherein $R^4$ is $C_{3-7}$ cycloalkyl.

23. The nanoparticle of claim 11, wherein the one or more agents is a polynucleotide, and the polynucleotide is RNA.

24. The composition of claim 13, wherein the agent is a polynucleotide, and the polynucleotide is DNA.

25. The composition of claim 13, wherein the agent is a polynucleotide, and the polynucleotide is RNA.

26. The composition of claim 25, wherein the RNA is mRNA, dsRNA, siRNA, shRNA, miRNA, or antisense RNA.

27. The composition of claim 13, wherein the agent is a polynucleotide, and the polynucleotide encodes a protein or peptide.

* * * * *